US007297536B2

(12) United States Patent
Harms et al.

(10) Patent No.: US 7,297,536 B2
(45) Date of Patent: Nov. 20, 2007

(54) INDUCIBLE PROTEIN EXPRESSION SYSTEM

(75) Inventors: Jerome S. Harms, Madison, WI (US); Gary A. Splitter, Brooklyn, WI (US); Kurt A. Eakle, Prairie du Sac, WI (US); Robert D. Bremel, Hillpoint, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 476 days.

(21) Appl. No.: 10/763,976

(22) Filed: Jan. 23, 2004

(65) Prior Publication Data

US 2005/0026288 A1 Feb. 3, 2005

Related U.S. Application Data

(60) Provisional application No. 60/442,103, filed on Jan. 23, 2003.

(51) Int. Cl.

*C12N 15/85* (2006.01)
*C12N 15/864* (2006.01)
*C12N 15/861* (2006.01)
*C12N 15/867* (2006.01)
*C12N 15/48* (2006.01)
*C12N 15/49* (2006.01)
*A61K 48/00* (2006.01)

(52) U.S. Cl. .................. 435/320.1; 530/350; 530/327; 530/324; 536/23.1; 536/23.4; 536/23.72; 536/24.1

(58) Field of Classification Search ..................... None
See application file for complete search history.

(56) References Cited

U.S. PATENT DOCUMENTS 6,096,538 A * 8/2000 Kingsman et al. .......... 435/325
6,835,568 B2 * 12/2004 Chang et al. ............... 435/440

OTHER PUBLICATIONS

Choi, Eun-A. et al., "The Role of Poly (A) Tail Stability in the Abilitty of the Woodchuck Hepatitis Virus Posttranscriptional Regulatory Element to Stimulate Gene Experession", American Society of Gene Therapy Abstracts of Scientific Presentations: The 5th Annual meeting of the American Society of Gene Therapy, Jun. 5-9, 2002, Abstract No. 439.

Ketteler, Robin et al., "The Woodchuck Post-Transcriptional Regulatory Element WPRE Can Overcome Restriction in Tetroviral gene Expression in Embryonic Stem Cells", American Society of Gene Therapy Abstracts of Scientific Presentations: The 5th Annual meeting of the American Society of Gene Therapy, Jun. 5-9, 2002, Abstract No. 87.

Daisuke, Nagakubo, et al., "Expression of CCR9 in HTLV-1+ T Cells and ATL Cells Expressing Tax", Int. J. Cancer: 120, 1591-1597 (2007).

Shayakhmetov, D. et al., "Use of the Bovine Leukaemia Virus LTR U3 Promoter for Expressing Antisense Antiviral RNAs and Competitive Inhibition of Viral Infection in Cell Culture", Journal of General Virology (1997), 78, 1941-1948.

Pare, Marie-Eve, et al., "A New Sensitive and Quantitative HTLV-I-Mediated Cell Fusion Assay in T Cells", VIROLOGY 338 (2005) 309-322.

Katoh, Iyoko, et al., "Bovine Leukemia Virus Trans-Activator p38tax Activates Heterologous Promoters with a common sequence Known as a cAMP-Responsive Element or the Binding Site of a Cellular transcription Factor ATF", The EMBO Journal, vol. 8 No. 2, pp. 497-503 (1989).

Brooks, Patricia A. et al., "Activation of BLV Transcription by NF-kB and Tax", Virology 243, 94-98 (1998) Article No. VY989035.

Pankow, Rudiger, et all, "The HTLV-I Tax Protein Transcriptionally Modulates OX40 Antigen Expression", The Journal of Immunology (2000) 165: 263-270.

* cited by examiner

*Primary Examiner*—David Guzo
(74) *Attorney, Agent, or Firm*—Quarles & Brady LLP

(57) ABSTRACT

Inducible gene expression systems and a method thereof. A first inducible gene expression system includes a first vector comprising at least one retroviral promoter and at least one factor to induce the retroviral promoter. At least one gene product is expressed in proportion to retroviral promoter induction. The method includes providing a first vector comprising at least one retroviral promoter and providing at least one factor corresponding to the retroviral promoter. The retroviral promoter is induced with the at least one factor. At least one protein is expressed based on the induction of the retroviral promoter. A second inducing expression system includes a first vector comprising at least one retroviral promoter, an inducer for the retroviral promoter, and at least one protein expressed in proportion to retroviral promoter induction.

13 Claims, 62 Drawing Sheets

Thursday, June 13, 2002 3:34 PM
GD2403 pLNBlv-G .MPD (1 > 7880) Site and Sequence
Enzymes : 36 of 538 enzymes (Filtered)
Settings : Circular, Certain Sites Only, Standard Genetic Code

```
                                                          PstI
GAAACCAGCAGCGGCTATCCGCGCATCCATGCCCCCGAACTGCAGGAGTGGGGAGGCACGATGGCCGCTTTGGTCGAGGC  2800
CTTTGGTCGTCGCCGATAGGCGCGTAGGTACGGGGGCTTGACGTCCTCACCCCTCCGTGCTACCGGCGAAACCAGCTCCG

 BamHI
GGATCCTAGCAGAAAAATAAGACTTGATTCCCCCTTAAAATTACAACTGCTAGAAAATGAATGGCTCTCCCGCCTTTTTT  2880
CCTAGGATCGTCTTTTTATTCTGAACTAAGGGGGAATTTTAATGTTGACGATCTTTTACTTACCGAGAGGGCGGAAAAAA
                            BLV Promoter

                                                      NarI                                  PvuII
GAGGGGGAATCATTTGTATGAAAGATCATGCCGACCTAGGCGCCGCCACCGCCCCGTAAACCAGACAGAGACGTCAGCTG  2960
CTCCCCCTTAGTAAACATACTTTCTAGTACGGCTGGATCCGCGGCGGTGGCGGGGCATTTGGTCTGTCTCTGCAGTCGAC
                            BLV Promoter

                    PvuII
CCAGAAAAGCTGGTGACGGCAGCTGGTGGCTAGAATCCCCGTACCTCCCCAACTTCCCCTTTCCCGAAAAATCCACACCC  3040
GGTCTTTTCGACCACTGCCGTCGACCACCGATCTTAGGGGCATGGAGGGGTTGAAGGGGAAAGGGCTTTTTAGGTGTGGG
                            BLV Promoter

                                                        NaeI
TGAGCTGCTGACCTCACCTGCTGATAAATTAATAAAATGCCGGCCCTGTCGAGTTAGCGGCACCAGAAGCGTTCTTCTCC  3120
ACTCGACGACTGGAGTGGACGACTATTTAATTATTTTACGGCCGGGACAGCTCAATCGCCGTGGTCTTCGCAAGAAGAGG
                            BLV Promoter

                                  XhoI   HindIII
TGAGACCCTCGTGCTCAGCTCTCGGTCCTGCCTCGAGAAGCTTGTTATCACAAGTTTGTACAAAAAAGCTGAACGAGAAA  3200
ACTCTGGGAGCACGAGTCGAGAGCCAGGACGGAGCTCTTCGAACAATAGTGTTCAAACATGTTTTTTCGACTTGCTCTTT
         BLV Promoter                                    Gateway
                                                              att R1
```

FIG. 2

SEQUENCE LISTING -- TAX [Bovine leukemia virus]

LOCUS AAF97920 309 aa
ACCESSION AAF97920

NUCLEOTIDE SEQUENCE (SEQ ID NO:2):

ATG GCA AGT GTT GTT GGT TGG GGG CCC CAC TCT CTA CAT GCC TGC CCG
GCC CTG GTT TTG TCC AAT GAC GTC ACC ATC GAT GCC TGG TGC CCC CTC
TGC GGG CCC CAT GAG CGA CTC CAA TTC GAA AGG ATC GAC ACC ACG CAC
ACC TGC GAG ACC CAC CGT ATC ACC TGG ACC GCC GAT GGA CGA CCT TTC
GGC CTC AAT GGA GCG CTG TTC CCT CGA CTG CAT GTC TCC AGA GAC CCG
GCC CCA AGG GCC CGA CGA CTC TGG ATC AAC TGC CCC CTT CCG GCC GTT
CGC GCT CAG CCC GGC CCG GTT TCA CTT TCC CCC TTC GAG CGG TCC CCC
TTC CAG CCC TAC CAA TGC CAA TTG CCC TCG GCC TCT AGC GAC GGT TGC
CCC GTC ATC GGG CAC GGC CTT CTT CCC TGG AAC AAC TTA GTA ACG CAT
CCT TGT CCT CGG AAA GTC CTT ATA TTA AAT CAA ATG GCC AAT TTT TCC
TTA CTC CCC CCC TTC AAT ACC CTC CTT GTG GAC CCC CTC CGG TTG TCC
GTC TTT GCC CCA GAC ACC AGG GGA GCC ATA CGT TAT CTC TCC ACC CTT
TTG ACG CTA TGC CCA GCT ACT TGT ATT CTA CCC CTC GGC GA GCC CTT
CTC TCC TAA TGT CCC CAT ATG TCG CTT TCC CCG GGA CTC CAA TGA ACC
CCC CCT TTC AGA ATT CGA GCT GCC CCT TAT CCA AAC GCC CGG CCT GTC
TTG GTC TGT CCC CGC GAT CGA CCT ATT CCT AAC CGG CCC CCC TTC CCC
ATG CGA CCG GTT ACA CGT ATG GTC CAG TCC TCA GGC CTT ACA GCG CTT
CCT CCA TGA CCC TAC GCT AAC CTG GTC AGA ATT GGT TGC TAG CAG GAA
ACT AAG ACT TGA TTC ACC CTT AAA ATT ACA ACT GTT AGA AAA TGA ATG
GCT CTC CCG CCT TTT TTG

PROTEIN SEQUENCE (SEQ ID NO:3)

MASVVGWGPHSLHACPALVLSNDVTIDAWCPLCGPHERLQFERIDTTHTCETHRITW
TADGRPFGLNGALFPRLHVSRDPAPRARRLWINCPLPAVRAQPGPVSLSPFERSPF
QPYQCQLPSASSDGCPVIGHGLLPWNNLVTHPCPRKVLILNQMANFSLLPPFNTLLV
DPLRLSVFAPDTRGAIRYLSTLLTLCPATCILPLGEPFSPNVPICRFPRDSNEPPLSEF
ELPLIQTPGLSWSVPAIDLFLTGPPSPCDRLHVWSSPQALQRFLHDPTLTW
SELVASRKLR LDSPLKLQLLENEWLSRLF

FIG. 3

SEQUENCE LISTING -- HTLV-1 Promoter sequence (SEQ ID NO:6)

```
  1  TGACAATGAC CATGAGCCCC AAATATCCCC CGGGGGCTTA GAGCCTCTCA GTGAAAAACA
 61  TTTCCGTGAA ACAGAAGTCT GAGAAGGTCA GGGCCCAGAA TAAGGCTCTG ACGTCTCCCC
121  CCGGAGGACA GCTCAGCACC AGCTCAGGCT AGGCCCTGAC GTGTCCCCCT AAAGACAAAT
181  CATAAGCTCA GACCTCCGGG AAGCCACCGG GAACCACCCA TTTCCTCCCC ATGTTTGTCA
241  AGCCGTCCTC AGGCGTTGAC GACAACCCCT CACCTCAAAA AACTTTTCAT GGCACGCATA
301  CGGCTCAATA AAATAACAGG AGTCTATAAA AGCGTGGGGA CAGTTCAGGA GGG
```

FIG. 4

SEQUENCE LISTING -- HTLV1 Tax Nucleic Acid (SEQ ID NO:4) and

Protein sequence (SEQ ID NO:5)

```
  1  ATG GCC CAC TTC CCA GGG TTT GGA CAG AGT CTT CTT TTC GGA TAC   45
  1  Met Ala His Phe Pro Gly Phe Gly Gln Ser Leu Leu Phe Gly Tyr   15

 46  CCA GTC TAC GTG TTT GGA GAC TGT GTA CAA GGC GAC TGG TGC CCC   90
 16  Pro Val Tyr Val Phe Gly Asp Cys Val Gln Gly Asp Trp Cys Pro   30

 91  ATC TCT GGG GGA CTA TGT TCG GCC CGC CTA CAT CGT CAC GCC CTA  135
 31  Ile Ser Gly Gly Leu Cys Ser Ala Arg Leu His Arg His Ala Leu   45

136  CTG GCC ACC TGT CCA GAG CAT CAG ATC ACC TGG GAC CCC ATT GAT  180
 46  Leu Ala Thr Cys Pro Glu His Gln Ile Thr Trp Asp Pro Ile Asp   60

181  GGA CGC GTT ATC GGC TCA GCT CTA CAG TTC CTT ATC CCT CGA CTC  225
 61  Gly Arg Val Ile Gly Ser Ala Leu Gln Phe Leu Ile Pro Arg Leu   75

226  CCC TCC TTC CCC ACC CAG AGA ACC TCT AAG ACC CTC AAG GTC CTT  270
 76  Pro Ser Phe Pro Thr Gln Arg Thr Ser Lys Thr Leu Lys Val Leu   90

271  ACC CCG CCA ATC ACT CAT ACA ACC CCC AAC ATT CCA CCC TCC TTC  315
 91  Thr Pro Pro Ile Thr His Thr Thr Pro Asn Ile Pro Pro Ser Phe  105

316  CTC CAG GCC ATG CGC AAA TAC TCC CCC TTC CGA AAT GGA TAC ATG  360
106  Leu Gln Ala Met Arg Lys Tyr Ser Pro Phe Arg Asn Gly Tyr Met  120

361  GAA CCC ACC CTT GGG CAG CAC CTC CCA ACC CTG TCT TTT CCA GAC  405
121  Glu Pro Thr Leu Gly Gln His Leu Pro Thr Leu Ser Phe Pro Asp  135

406  CCC GGA CTC CGG CCC CAA AAC CTG TAC ACC CTC TGG GGA GGC TCC  450
136  Pro Gly Leu Arg Pro Gln Asn Leu Tyr Thr Leu Trp Gly Gly Ser  150

451  GTT GTC TGC ATG TAC CTC TAC CAG CTT TCC CCC CCC ATC ACC TGG  495
151  Val Val Cys Met Tyr Leu Tyr Gln Leu Ser Pro Pro Ile Thr Trp  165

496  CCC CTC CTG CCC CAC GTG ATT TTT TGC CAC CCC GGC CAG CTC GGG  540
166  Pro Leu Leu Pro His Val Ile Phe Cys His Pro Gly Gln Leu Gly  180

541  GCC TTC CTC ACC AAT GTT CCG TAC AAG CGA ATA GAA GAA CTC CTC  585
181  Ala Phe Leu Thr Asn Val Pro Tyr Lys Arg Ile Glu Glu Leu Leu  195

586  TAT AAA ATT TCC CTT ACC ACA GGG GCC CTA ATA ATT CTA CCC GAA  630
196  Tyr Lys Ile Ser Leu Thr Thr Gly Ala Leu Ile Ile Leu Pro Glu  210

631  GAC TGT TTG CCC ACC ACC CTT TTC CAG CCT GTT AGG GCA CCC GTC  675
211  Asp Cys Leu Pro Thr Thr Leu Phe Gln Pro Val Arg Ala Pro Val  225

676  ACG CTA ACA GCC TGG CAA AAC GGC CTC CTT CCG TTC CAC TCA ACC  720
226  Thr Leu Thr Ala Trp Gln Asn Gly Leu Leu Pro Phe His Ser Thr  240

721  CTC ACC ACT CCA GGC CTT ATT TGG ACA TTT ACC GAT GGC ACG CCT  765
241  Leu Thr Thr Pro Gly Leu Ile Trp Thr Phe Thr Asp Gly Thr Pro  255
```

FIG. 5

```
766   ATG ATT TCC GGG CCC TGC CCT AAA GAT GGC CAG CCA TCT TTA GTA   810
256   Met Ile Ser Gly Pro Cys Pro Lys Asp Gly Gln Pro Ser Leu Val   270

811   CTA CAG TCC TCC TCC TTT ATA TTT CAC AAA TTT CAA ACC AAG GCC   855
271   Leu Gln Ser Ser Ser Phe Ile Phe His Lys Phe Gln Thr Lys Ala   285

856   TAC CAC CCC TCA TTT CTA CTC TCA CAC GGC CTC ATA CAG TAC TCT   900
286   Tyr His Pro Ser Phe Leu Leu Ser His Gly Leu Ile Gln Tyr Ser   300

901   TCC TTT CAT AAT TTA CAT CTC CTG TTT GAA GAA TAC ACC AAC ATC   945
301   Ser Phe His Asn Leu His Leu Leu Phe Glu Glu Tyr Thr Asn Ile   315

946   CCC ATT TCT CTA CTT TTT AAC GAA AAA GAG GCA GAT GAC AAT GAC   990
316   Pro Ile Ser Leu Leu Phe Asn Glu Lys Glu Ala Asp Asp Asn Asp   330

991   CAT GAG CCC CAA ATA TCC CCC GGG GGC TTA GAG CCT CCC AGT GAA   1035
331   His Glu Pro Gln Ile Ser Pro Gly Gly Leu Glu Pro Pro Ser Glu   345

1036  AAA CAT TTC CGC GAA ACA GAA GTC TGA   1070
346   Lys His Phe Arg Glu Thr Glu Val TRM   354
```

FIG. 5 (Cont.)

SEQUENCE LISTING -- HIV Promoter sequence (SEQ ID NO:7)

```
  1  CTGGAAGGGC TAATTTGGTC CCAAAGAAGA CAAGAGATCC TTGATCTGTG GATCTACCAC
 61  ACACAAGGCT ACTTCCCTGA TTGGCAGAAT TACACACCAG GGCCAGGGAT CAGATATCCA
121  CTGACCTTTG GATGGTGCTT CAAGCTAGTA CCAGTTGAGC CAGAGAAGGT AGAAGAGGCC
181  AATGAAGGAG AGAACAACAG CTTGTTACAC CCTATGAGCC TGCATGGGAT GGAGGACGCG
241  GAGAAAGAAG TGTTAGTGTG GAGGTTTGAC AGCAAACTAG CATTTCATCA CATGGCCCGA
301  GAGCTGCATC CGGAGTACTA CAAAGACTGC TGACATCGAG CTTTCTACAA GGGACTTTCC
361  GCTGGGGACT TTCCAGGGAG GCGTGGCCTG GGCGGGACTG GGGAGTGGCG TCCCTCAGAT
421  GCTGCATATA AGCAGCTGCT TTTTGCCTGT ACTGGG
```

FIG. 6

SEQUENCE LISTING -- HIV Tat nucleic acid (SEQ ID NO:8) and amino acid (SEQ ID NO:9) of HIV Tat.

```
  1  ATG GAG CCA GTA GAT CCT AAT CTA GAG CCC TGG AAG CAT CCA GGA   45
  1  Met Glu Pro Val Asp Pro Asn Leu Glu Pro Trp Lys His Pro Gly   15

 46  AGT CAG CCT AGG ACT GCT TGT AAC AAT TGC TAT TGT AAA AAG TGT   90
 16  Ser Gln Pro Arg Thr Ala Cys Asn Asn Cys Tyr Cys Lys Lys Cys   30

 91  TGC TTT CAT TGC TAC GCG TGT TTC ACA AGA AAA GGC TTA GGC ATC  135
 31  Cys Phe His Cys Tyr Ala Cys Phe Thr Arg Lys Gly Leu Gly Ile   45

136  TCC TAT GGC AGG AAG AAG CGG AGA CAG CGA CGA AGA GCT CCT CAG  180
 46  Ser Tyr Gly Arg Lys Lys Arg Arg Gln Arg Arg Arg Ala Pro Gln   60

181  GAC AGT CAG ACT CAT CAA GCT TCT CTA TCA AAG CAA CCC GCC TCC  225
 61  Asp Ser Gln Thr His Gln Ala Ser Leu Ser Lys Gln Pro Ala Ser   75

226  CAG TCC CGA GGG GAC CCG ACA GGC CCG ACG GAA TCG AAG AAG AAG  270
 76  Gln Ser Arg Gly Asp Pro Thr Gly Pro Thr Glu Ser Lys Lys Lys   90

271  GTG GAG AGA GAG ACA GAG ACA GAT CCG TTC GAT TAG   306
 91  Val Glu Arg Glu Thr Glu Thr Asp Pro Phe Asp TRM   102
```

FIG. 7

Friday, November 15, 2002 12:30 PM
pLBC-BTaxW Map.MPD (1 > 7685) Site and Sequence
Enzymes : 35 of 538 enzymes (Filtered)
Settings : Circular, Certain Sites Only, Standard Genetic Code

FIG. 10 (cont)

Friday, November 15, 2002 12:30 PM
pLBC-BTaxW Map.MPD (1 > 7685) Site and Sequence

```
SacI                                      AscI                                      SmaI    KpnI
TCAATAAAAGAGCCCACAACCCCTCACTCGGCGCGCCAGTCTTCCGATAGACTGCGTCGCCCGGGTACCCGTATTCCCAA 640
AGTTATTTTCTCGGGTGTTGGGGAGTGAGCCGCGCGGTCAGAAGGCTATCTGACGCAGCGGGCCCATGGGCATAAGGGTT
5' LTR
5' LTR (MoMSV)

TAAAGCCTCTTGCTGTTTGCATCCGAATCGTGGTCTCGCTGTTCCTTGGGAGGGTCTCCTCTGAGTGATTGACTACCCAC 720
ATTTCGGAGAACGACAAACGTAGGCTTAGCACCAGAGCGACAAGGAACCCTCCCAGAGGAGACTCACTAACTGATGGGTG
5' LTR
5' LTR (MoMSV)

GACGGGGGTCTTTCATTTGGGGGCTCGTCCGGGATTTGGAGACCCCTGCCCAGGGACCACCGACCCACCACCGGGAGGTA 800
CTGCCCCCAGAAAGTAAACCCCCGAGCAGGCCCTAAACCTCTGGGGACGGGTCCCTGGTGGCTGGGTGGTGGCCCTCCAT
5' LTR
5' LTR (MoMSV)

                                                                                SpeI
AGCTGGCCAGCAACTTATCTGTGTCTGTCCGATTGTCTAGTGTCTATGTTTGATGTTATGCGCCTGCGTCTGTACTAGTT 880
TCGACCGGTCGTTGAATAGACACAGACAGGCTAACAGATCACAGATACAAACTACAATACGCGGACGCAGACATGATCAA
Pkg Rgn
Extended Packaging Region

AGCTAACTAGCTCTGTATCTGGCGGACCCGTGGTGGAACTGACGAGTTCTGAACACCCGGCCGCAACCCTGGGAGACGTC 960
TCGATTGATCGAGACATAGACCGCCTGGGCACCACCTTGACTGCTCAAGACTTGTGGGCCGGCGTTGGGACCCTCTGCAG
Pkg Rgn
Extended Packaging Region

CCAGGGACTTTGGGGGCCGTTTTTGTGGCCCGACCTGAGGAAGGGAGTCGATGTGGAATCCGACCCCGTCAGGATATGTG 1040
GGTCCCTGAAACCCCCGGCAAAAACACCGGGCTGGACTCCTTCCCTCAGCTACACCTTAGGCTGGGGCAGTCCTATACAC
Pkg Rgn
Extended Packaging Region

GTTCTGGTAGGAGACGAGAACCTAAAACAGTTCCCGCCTCCGTCTGAATTTTTGCTTTCGGTTTGGAACCGAAGCCGCGC 1120
CAAGACCATCCTCTGCTCTTGGATTTTGTCAAGGGCGGAGGCAGACTTAAAAACGAAAGCCAAACCTTGGCTTCGGCGCG
Pkg Rgn
Extended Packaging Region

               PstI      PstI
GTCTTGTCTGCTGCAGCGCTGCAGCATCGTTCTGTGTTGTCTCTGTCTGACTGTGTTTCTGTATTTGTCTGAAAATTAGG 1200
CAGAACAGACGACGTCGCGACGTCGTAGCAAGACACAACAGAGACAGACTGACACAAAGACATAAACAGACTTTTAATCC
Pkg Rgn
Extended Packaging Region
```

Friday, November 15, 2002 12:30 PM
pLBC-BTaxW Map.MPD (1 > 7685) Site and Sequence
Pkg Rgn
Extended Packaging Region
PstI
NarI
EcoRI
BclI
NcoI
EM7
EM7 promoter
Met Ala Lys
BLAST
Pro Leu Ser Gln Glu Glu Ser Thr Leu Ile Glu Arg Ala Thr Ala Thr Ile Asn Ser Ile Pro Ile Ser Glu Asp Tyr

FIG. 10 (cont)

Friday, November 15, 2002 12:30 PM
pLBC-BTaxW Map.MPD (1 > 7685) Site and Sequence

```
GCGTCGCCAGCGCAGCTCTCTCTAGCGACGGCCGCATCTTCACTGGTGTCAATGTATATCATTTTACTGGGGGACCTTGT
---------+---------+---------+---------+---------+---------+---------+---------+ 1920
CGCAGCGGTCGCGTCGAGAGAGATCGCTGCCGGCGTAGAAGTGACCACAGTTACATATAGTAAAATGACCCCCTGGAACA
Ser Val Ala Ser Ala Ala Leu Ser Ser Asp Gly Arg Ile Phe Thr Gly Val Asn Val Tyr His Phe Thr Gly Gly Pro Cys
BLAST

                                                                                  NruI PvuI
GCAGAACTCGTGGTGCTGGGCACTGCTGCTGCTGCGGCAGCTGGCAACCTGACTTGTATCGTCGCGATCGGAAATGAGAA
---------+---------+---------+---------+---------+---------+---------+---------+ 2000
CGTCTTGAGCACCACGACCCGTGACGACGACGACGCCGTCGACCGTTGGACTGAACATAGCAGCGCTAGCCTTTACTCTT
Ala Glu Leu Val Val Leu Gly Thr Ala Ala Ala Ala Ala Ala Gly Asn Leu Thr Cys Ile Val Ala Ile Gly Asn Glu Asn
BLAST

                              SalI
CAGGGGCATCTTGAGCCCCTGCGGACGGTGTCGACAGGTGCTTCTCGATCTGCATCCTGGGATCAAAGCGATAGTGAAGG
---------+---------+---------+---------+---------+---------+---------+---------+ 2080
GTCCCCGTAGAACTCGGGGACGCCTGCCACAGCTGTCCACGAAGAGCTAGACGTAGGACCCTAGTTTCGCTATCACTTCC
Arg Gly Ile Leu Ser Pro Cys Gly Arg Cys Arg Gln Val Leu Leu Asp Leu His Pro Gly Ile Lys Ala Ile Val Lys
BLAST

ACAGTGATGGACAGCCGACGGCAGTTGGGATTCGTGAATTGCTGCCCTCTGGTTATGTGTGGGAGGGCTAAGCACTTCGT
---------+---------+---------+---------+---------+---------+---------+---------+ 2160
TGTCACTACCTGTCGGCTGCCGTCAACCCTAAGCACTTAACGACGGGAGACCAATACACACCCTCCCGATTCGTGAAGCA
Asp Ser Asp Gly Gln Pro Thr Ala Val Gly Ile Arg Glu Leu Leu Pro Ser Gly Tyr Val Trp Glu Gly
BLAST

GGCCGAGGAGCAGGACTGACACGTGCTACGAGATTTCGATTCCACCGCCGCCTTCTATGAAAGGTTGGGCTTCGGAATCG
---------+---------+---------+---------+---------+---------+---------+---------+ 2240
CCGGCTCCTCGTCCTGACTGTGCACGATGCTCTAAAGCTAAGGTGGCGGCGGAAGATACTTTCCAACCCGAAGCCTTAGC

TTTTCCGGGACGCCGATCCGGCCATTAGCCATATTATTCATTGGTTATATAGCATAAATCAATATTGGCTATTGGCCATT
---------+---------+---------+---------+---------+---------+---------+---------+ 2320
AAAAGGCCCTGCGGCTAGGCCGGTAATCGGTATAATAAGTAACCAATATATCGTATTTAGTTATAACCGATAACCGGTAA
CMV Pro
hCMV Promoter

GCATACGTTGTATCCATATCATAATATGTACATTTATATTGGCTCATGTCCAACATTACCGCCATGTTGACATTGATTAT
---------+---------+---------+---------+---------+---------+---------+---------+ 2400
CGTATGCAACATAGGTATAGTATTATACATGTAAATATAACCGAGTACAGGTTGTAATGGCGGTACAACTGTAACTAATA
CMV Pro
hCMV Promoter

   SpeI
TGACTAGTTATTAATAGTAATCAATTACGGGGTCATTAGTTCATAGCCCATATATGGAGTTCCGCGTTACATAACTTACG
---------+---------+---------+---------+---------+---------+---------+---------+ 2480
ACTGATCAATAATTATCATTAGTTAATGCCCCAGTAATCAAGTATCGGGTATATACCTCAAGGCGCAATGTATTGAATGC
CMV Pro
hCMV Promoter
```

FIG. 10 (cont)

Friday, November 15, 2002 12:30 PM
pLBC-BTaxW Map.MPD (1 > 7685) Site and Sequence

```
GTAAATGGCCCGCCTGGCTGACCGCCCAACGACCCCCGCCCATTGACGTCAATAATGACGTATGTTCCCATAGTAACGCC
-------------------------------------------------------------------------------- 2560
CATTTACCGGGCGGACCGACTGGCGGGTTGCTGGGGGCGGGTAACTGCAGTTATTACTGCATACAAGGGTATCATTGCGG
                                     CMV Pro
                                 hCMV Promoter

                                                                               NdeI
AATAGGGACTTTCCATTGACGTCAATGGGTGGAGTATTTACGGTAAACTGCCCACTTGGCAGTACATCAAGTGTATCATA
-------------------------------------------------------------------------------- 2640
TTATCCCTGAAAGGTAACTGCAGTTACCCACCTCATAAATGCCATTTGACGGGTGAACCGTCATGTAGTTCACATAGTAT
                                     CMV Pro
                                 hCMV Promoter

TGCCAAGTACGCCCCCTATTGACGTCAATGACGGTAAATGGCCCGCCTGGCATTATGCCCAGTACATGACCTTATGGGAC
-------------------------------------------------------------------------------- 2720
ACGGTTCATGCGGGGGATAACTGCAGTTACTGCCATTTACCGGGCGGACCGTAATACGGGTCATGTACTGGAATACCCTG
                                     CMV Pro
                                 hCMV Promoter

                                       NcoI
TTTCCTACTTGGCAGTACATCTACGTATTAGTCATCGCTATTACCATGGTGATGCGGTTTTGGCAGTACATCAATGGGCG
-------------------------------------------------------------------------------- 2800
AAAGGATGAACCGTCATGTAGATGCATAATCAGTAGCGATAATGGTACCACTACGCCAAAACCGTCATGTAGTTACCCGC
                                     CMV Pro
                                 hCMV Promoter

TGGATAGCGGTTTGACTCACGGGGATTTCCAAGTCTCCACCCCATTGACGTCAATGGGAGTTTGTTTTGGCACCAAAATC
-------------------------------------------------------------------------------- 2880
ACCTATCGCCAAACTGAGTGCCCCTAAAGGTTCAGAGGTGGGGTAACTGCAGTTACCCTCAAACAAAACCGTGGTTTTAG
                                     CMV Pro
                                 hCMV Promoter

AACGGGACTTTCCAAAATGTCGTAACAACTCCGCCCCATTGACGCAAATGGGCGGTAGGCATGTACGGTGGGAGGTCTAT
-------------------------------------------------------------------------------- 2960
TTGCCCTGAAAGGTTTTACAGCATTGTTGAGGCGGGGTAACTGCGTTTACCCGCCATCCGTACATGCCACCCTCCAGATA
                                     CMV Pro
                                 hCMV Promoter

          SacI
ATAAGCAGAGCTCGTTTAGTGAACCGTCAGATCGCCTGGAGACGCCATCCACGCTGTTTTGACCTCCATAGAAGACACCG
-------------------------------------------------------------------------------- 3040
TATTCGTCTCGAGCAAATCACTTGGCAGTCTAGCGGACCTCTGCGGTAGGTGCGACAAAACTGGAGGTATCTTCTGTGGC
                                     CMV Pro
                                 hCMV Promoter
```

Friday, November 15, 2002 12:30 PM
pLBC-BTaxW Map.MPD (1 > 7685) Site and Sequence

FIG. 10 (cont)

Friday, November 15, 2002 12:30 PM
pLBC-BTaxW Map.MPD (1 > 7685) Site and Sequence NdeI CTCCACCCTTTTGACGCTATGCCCGGCTACTTGTATTCTACCCCTAGGCGAGCCCTTCTCTCCTAATGTCCCCATATGCC 3760
GAGGTGGGAAAACTGCGATACGGGCCGATGAACATAAGATGGGGATCCGCTCGGGAAGAGAGGATTACAGGGGTATACGG
Ser Thr Leu Leu Thr Leu Cys Pro Ala Thr Cys Ile Leu Pro Leu Gly Glu Pro Phe Ser Pro Asn Val Pro Ile Cys
BTax SmaI EcoRI GCTTTCCCCGGGACTCCAATGAACCCCCCCTTTCAGAATTCGAGCTGCCCCTTATCCAAACGCCCGGCCTGTCTTGGTCT 3840
CGAAAGGGGCCCTGAGGTTACTTGGGGGGGAAAGTCTTAAGCTCGACGGGGAATAGGTTTGCGGGCCGGACAGAACCAGA
Arg Phe Pro Arg Asp Ser Asn Glu Pro Pro Leu Ser Glu Phe Glu Leu Pro Leu Ile Gln Thr Pro Gly Leu Ser Trp Ser
BTax PvuI GTCCCCGCGATCGACCTATTCCTAACCGGTCCCCCTTCCCCATGCGACCGGTTACACGTATGGTCCAGTCCTCAGGCCTT 3920
CAGGGGCGCTAGCTGGATAAGGATTGGCCAGGGGGAAGGGGTACGCTGGCCAATGTGCATACCAGGTCAGGAGTCCGGAA
Val Pro Ala Ile Asp Leu Phe Leu Thr Gly Pro Pro Ser Pro Cys Asp Arg Leu His Val Trp Ser Ser Pro Gln Ala Leu
BTax BspHI NheI ACAGCGCTTCCTTCATGACCCTACGCTAACCTGGTCCGAATTAGTTGCTAGCAGAAAAATAAGACTTGATTCCCCCTTAA 4000
TGTCGCGAAGGAAGTACTGGGATGCGATTGGACCAGGCTTAATCAACGATCGTCTTTTTATTCTGAACTAAGGGGGAATT
Gln Arg Phe Leu His Asp Pro Thr Leu Thr Trp Ser Glu Leu Val Ala Ser Arg Lys Ile Arg Leu Asp Ser Pro Leu
BTax ClaI AATTACAACTGCTAGAAAATGAATGGCTCTCCCGCCTTTTTTGAGACCCAGCTTTCTTGTACAAAGTGGTGATAACATCG 4080
TTAATGTTGACGATCTTTTACTTACCGAGAGGGCGGAAAAAACTCTGGGTCGAAAGAACATGTTTCACCACTATTGTAGC
Lys Leu Gln Leu Leu Glu Asn Glu Trp Leu Ser Arg Leu Phe •
BTax attB2

ATAATCAACCTCTGGATTACAAAATTTGTGAAAGATTGACTGGTATTCTTAACTATGTTGCTCCTTTTACGCTATGTGGA 4160
TATTAGTTGGAGACCTAATGTTTTAAACACTTTCTAACTGACCATAAGAATTGATACAACGAGGAAAATGCGATACACCT
WPRE
WPRE

TACGCTGCTTTAATGCCTTTGTATCATGCTATTGCTTCCCGTATGGCTTTCATTTTCTCCTCCTTGTATAAATCCTGGTT 4240
ATGCGACGAAATTACGGAAACATAGTACGATAACGAAGGGCATACCGAAAGTAAAAGAGGAGGAACATATTTAGGACCAA
WPRE
WPRE

FIG. 10 (cont)

Friday, November 15, 2002 12:30 PM
pLBC-BTaxW Map.MPD (1 > 7685) Site and Sequence

```
GCTGTCTCTTTATGAGGAGTTGTGGCCCGTTGTCAGGCAACGTGGCGTGGTGTGCACTGTGTTTGCTGACGCAACCCCCA
---------+---------+---------+---------+---------+---------+---------+---------+ 4320
CGACAGAGAAATACTCCTCAACACCGGGCAACAGTCCGTTGCACCGCACCACACGTGACACAAACGACTGCGTTGGGGGT
WPRE
WPRE

CTGGTTGGGGCATTGCCACCACCTGTCAGCTCCTTTCCGGGACTTTCGCTTTCCCCCTCCCTATTGCCACGGCGGAACTC
---------+---------+---------+---------+---------+---------+---------+---------+ 4400
GACCAACCCCGTAACGGTGGTGGACAGTCGAGGAAAGGCCCTGAAAGCGAAAGGGGGAGGGATAACGGTGCCGCCTTGAG
WPRE
WPRE

ATCGCCGCCTGCCTTGCCCGCTGCTGGACAGGGGCTCGGCTGTTGGGCACTGACAATTCCGTGGTGTTGTCGGGGAAATC
---------+---------+---------+---------+---------+---------+---------+---------+ 4480
TAGCGGCGGACGGAACGGGCGACGACCTGTCCCCGAGCCGACAACCCGTGACTGTTAAGGCACCACAACAGCCCCTTTAG
WPRE
WPRE

ATCGTCCTTTCCTTGGCTGCTCGCCTGTGTTGCCACCTGGATTCTGCGCGGGACGTCCTTCTGCTACGTCCCTTCGGCCC
---------+---------+---------+---------+---------+---------+---------+---------+ 4560
TAGCAGGAAAGGAACCGACGAGCGGACACAACGGTGGACCTAAGACGCGCCCTGCAGGAAGACGATGCAGGGAAGCCGGG
WPRE
WPRE

                          SacII      NaeI
TCAATCCAGCGGACCTTCCTTCCCGCGGCCTGCTGCCGGCTCTGCGGCCTCTTCCGCGTCTTCGCCTTCGCCCTCAGACG
---------+---------+---------+---------+---------+---------+---------+---------+ 4640
AGTTAGGTCGCCTGGAAGGAAGGGCGCCGGACGACGGCCGAGACGCCGGAGAAGGCGCAGAAGCGGAAGCGGGAGTCTGC
WPRE
WPRE

                                    ClaI
AGTCGGATCTCCCTTTGGGCCGCCTCCCCGCCTGATCGATAAAATAAAAGATTTTATTTAGTCTCCAGAAAAAGGGGGGA
---------+---------+---------+---------+---------+---------+---------+---------+ 4720
TCAGCCTAGAGGGAAACCCGGCGGAGGGGCGGACTAGCTATTTTATTTTCTAAAATAAATCAGAGGTCTTTTTCCCCCCT
WPRE
WPRE

                              NheI
ATGAAAGACCCCACCTGTAGGTTTGGCAAGCTAGCTTAAGTAACGCCATTTTGCAAGGCATGGAAAAATACATAACTGAG
---------+---------+---------+---------+---------+---------+---------+---------+ 4800
TACTTTCTGGGGTGGACATCCAAACCGTTCGATCGAATTCATTGCGGTAAAACGTTCCGTACCTTTTTATGTATTGACTC
3' LTR
3' LTR (MoMLV)
```

FIG. 10 (cont)

Friday, November 15, 2002 12:30 PM
pLBC-BTaxW Map.MPD (1 > 7685) Site and Sequence EcoRV AATAGAGAAGTTCAGATCAAGGTCAGGAACAGATGGAACAGCTGAATATGGGCCAAACAGGATATCTGTGGTAAGCAGTT 4880
TTATCTCTTCAAGTCTAGTTCCAGTCCTTGTCTACCTTGTCGACTTATACCCGGTTTGTCCTATAGACACCATTCGTCAA 3' LTR
3' LTR (MoMLV)

EcoRV

CCTGCCCCGGCTCAGGGCCAAGAACAGATGGAACAGCTGAATATGGGCCAAACAGGATATCTGTGGTAAGCAGTTCCTGC 4960
GGACGGGGCCGAGTCCCGGTTCTTGTCTACCTTGTCGACTTATACCCGGTTTGTCCTATAGACACCATTCGTCAAGGACG

3' LTR
3' LTR (MoMLV)

XbaI

CCCGGCTCAGGGCCAAGAACAGATGGTCCCCAGATGCGGTCCAGCCCTCAGCAGTTTCTAGAGAACCATCAGATGTTTCC 5040
GGGCCGAGTCCCGGTTCTTGTCTACCAGGGGTCTACGCCAGGTCGGGAGTCGTCAAAGATCTCTTGGTAGTCTACAAAGG

3' LTR
3' LTR (MoMLV)

AGGGTGCCCCAAGGACCTGAAATGACCCTGTGCCTTATTTGAACTAACCAATCAGTTCGCTTCTCGCTTCTGTTCGCGCG 5120
TCCCACGGGGTTCCTGGACTTTACTGGGACACGGAATAAACTTGATTGGTTAGTCAAGCGAAGAGCGAAGACAAGCGCGC

3' LTR
3' LTR (MoMLV)

SacI NarI SmaI

CTTCTGCTCCCCGAGCTCAATAAAAGAGCCCACAACCCCTCACTCGGGGCGCCAGTCCTCCGATTGACTGAGTCGCCCGG 5200
GAAGACGAGGGGCTCGAGTTATTTTCTCGGGTGTTGGGGAGTGAGCCCCGCGGTCAGGAGGCTAACTGACTCAGCGGGCC

3' LTR
3' LTR (MoMLV)

KpnI

GTACCCGTGTATCCAATAAACCCTCTTGCAGTTGCATCCGACTTGTGGTCTCGCTGTTCCTTGGGAGGGTCTCCTCTGAG 5280
CATGGGCACATAGGTTATTTGGGAGAACGTCAACGTAGGCTGAACACCAGAGCGACAAGGAACCCTCCCAGAGGAGACTC

3' LTR
3' LTR (MoMLV)

TGATTGACTACCCGTCAGCGGGGGTCTTTCATTTTTCCATTGGGGGCTCGTCCGGGATCGGGAGACCCCTGCCCAGGGAC 5360
ACTAACTGATGGGCAGTCGCCCCCAGAAAGTAAAAAGGTAACCCCCGAGCAGGCCCTAGCCCTCTGGGGACGGGTCCCTG

3' LTR
3' LTR (MoMLV)

FIG. 10 (cont)

Friday, November 15, 2002 12:30 PM
pLBC-BTaxW Map.MPD (1 > 7685) Site and Sequence

```
CACCGACCCACCACCGGGAGGTAAGCTGGCTGCCTCGCGCGTTTCGGTGATGACGGTGAAAACCTCTGACACATGCAGCT
-------------------------------------------------------------------------------- 5440
GTGGCTGGGTGGTGGCCCTCCATTCGACCGACGGAGCGCGCAAAGCCACTACTGCCACTTTTGGAGACTGTGTACGTCGA

CCCGGAGACGGTCACAGCTTGTCTGTAAGCGGATGCCGGGAGCAGACAAGCCCGTCAGGGCGCGTCAGCGGGTGTTGGCG
-------------------------------------------------------------------------------- 5520
GGGCCTCTGCCAGTGTCGAACAGACATTCGCCTACGGCCCTCGTCTGTTCGGGCAGTCCCGCGCAGTCGCCCACAACCGC

GGTGTCGGGGCGCAGCCATGACCCAGTCACGTAGCGATAGCGGAGTGTATACTGGCTTAACTATGCGGCATCAGAGCAGA
-------------------------------------------------------------------------------- 5600
CCACAGCCCCGCGTCGGTACTGGGTCAGTGCATCGCTATCGCCTCACATATGACCGAATTGATACGCCGTAGTCTCGTCT

                    NdeI
                    |
TTGTACTGAGAGTGCACCATATGCGGTGTGAAATACCGCACAGATGCGTAAGGAGAAAATACCGCATCAGGCGCTCTTCC
-------------------------------------------------------------------------------- 5680
AACATGACTCTCACGTGGTATACGCCACACTTTATGGCGTGTCTACGCATTCCTCTTTTATGGCGTAGTCCGCGAGAAGG

GCTTCCTCGCTCACTGACTCGCTGCGCTCGGTCGTTCGGCTGCGGCGAGCGGTATCAGCTCACTCAAAGGCGGTAATACG
-------------------------------------------------------------------------------- 5760
CGAAGGAGCGAGTGACTGAGCGACGCGAGCCAGCAAGCCGACGCCGCTCGCCATAGTCGAGTGAGTTTCCGCCATTATGC

GTTATCCACAGAATCAGGGGATAACGCAGGAAAGAACATGTGAGCAAAAGGCCAGCAAAAGGCCAGGAACCGTAAAAAGG
-------------------------------------------------------------------------------- 5840
CAATAGGTGTCTTAGTCCCCTATTGCGTCCTTTCTTGTACACTCGTTTTCCGGTCGTTTTCCGGTCCTTGGCATTTTTCC

CCGCGTTGCTGGCGTTTTTCCATAGGCTCCGCCCCCCTGACGAGCATCACAAAAATCGACGCTCAAGTCAGAGGTGGCGA
-------------------------------------------------------------------------------- 5920
GGCGCAACGACCGCAAAAAGGTATCCGAGGCGGGGGGACTGCTCGTAGTGTTTTTAGCTGCGAGTTCAGTCTCCACCGCT

AACCCGACAGGACTATAAAGATACCAGGCGTTTCCCCCTGGAAGCTCCCTCGTGCGCTCTCCTGTTCCGACCCTGCCGCT
-------------------------------------------------------------------------------- 6000
TTGGGCTGTCCTGATATTTCTATGGTCCGCAAAGGGGGACCTTCGAGGGAGCACGCGAGAGGACAAGGCTGGGACGGCGA

TACCGGATACCTGTCCGCCTTTCTCCCTTCGGGAAGCGTGGCGCTTTCTCATAGCTCACGCTGTAGGTATCTCAGTTCGG
-------------------------------------------------------------------------------- 6080
ATGGCCTATGGACAGGCGGAAAGAGGGAAGCCCTTCGCACCGCGAAAGAGTATCGAGTGCGACATCCATAGAGTCAAGCC

TGTAGGTCGTTCGCTCCAAGCTGGGCTGTGTGCACGAACCCCCCGTTCAGCCCGACCGCTGCGCCTTATCCGGTAACTAT
-------------------------------------------------------------------------------- 6160
ACATCCAGCAAGCGAGGTTCGACCCGACACACGTGCTTGGGGGGCAAGTCGGGCTGGCGACGCGGAATAGGCCATTGATA

CGTCTTGAGTCCAACCCGGTAAGACACGACTTATCGCCACTGGCAGCAGCCACTGGTAACAGGATTAGCAGAGCGAGGTA
-------------------------------------------------------------------------------- 6240
GCAGAACTCAGGTTGGGCCATTCTGTGCTGAATAGCGGTGACCGTCGTCGGTGACCATTGTCCTAATCGTCTCGCTCCAT

TGTAGGCGGTGCTACAGAGTTCTTGAAGTGGTGGCCTAACTACGGCTACACTAGAAGGACAGTATTTGGTATCTGCGCTC
-------------------------------------------------------------------------------- 6320
ACATCCGCCACGATGTCTCAAGAACTTCACCACCGGATTGATGCCGATGTGATCTTCCTGTCATAAACCATAGACGCGAG

TGCTGAAGCCAGTTACCTTCGGAAAAAGAGTTGGTAGCTCTTGATCCGGCAAACAAACCACCGCTGGTAGCGGTGGTTTT
-------------------------------------------------------------------------------- 6400
ACGACTTCGGTCAATGGAAGCCTTTTTCTCAACCATCGAGAACTAGGCCGTTTGTTTGGTGGCGACCATCGCCACCAAAA
```

FIG. 10 (cont)

Friday, November 15, 2002 12:30 PM
pLBC-BTaxW Map.MPD (1 > 7685) Site and Sequence

```
TTTGTTTGCAAGCAGCAGATTACGCGCAGAAAAAAAGGATCTCAAGAAGATCCTTTGATCTTTTCTACGGGGTCTGACGC
-------------------------------------------------------------------------------- 6480
AAACAAACGTTCGTCGTCTAATGCGCGTCTTTTTTTCCTAGAGTTCTTCTAGGAAACTAGAAAAGATGCCCCAGACTGCG

                                    BspHI                                  DraI
TCAGTGGAACGAAAACTCACGTTAAGGGATTTTGGTCATGAGATTATCAAAAAGGATCTTCACCTAGATCCTTTTAAATT
-------------------------------------------------------------------------------- 6560
AGTCACCTTGCTTTTGAGTGCAATTCCCTAAAACCAGTACTCTAATAGTTTTTCCTAGAAGTGGATCTAGGAAAATTTAA

              DraI
AAAAATGAAGTTTTAAATCAATCTAAAGTATATATGAGTAAACTTGGTCTGACAGTTACCAATGCTTAATCAGTGAGGCA
-------------------------------------------------------------------------------- 6640
TTTTTACTTCAAAATTTAGTTAGATTTCATATATACTCATTTGAACCAGACTGTCAATGGTTACGAATTAGTCACTCCGT
                                                                 • Trp His Lys Ile Leu Ser Ala
                                                                 ------------AMP------------

CCTATCTCAGCGATCTGTCTATTTCGTTCATCCATAGTTGCCTGACTCCCCGTCGTGTAGATAACTACGATACGGGAGGG
-------------------------------------------------------------------------------- 6720
GGATAGAGTCGCTAGACAGATAAAGCAAGTAGGTATCAACGGACTGAGGGGCAGCACATCTATTGATGCTATGCCCTCCC
Gly Ile Glu Ala Ile Gln Arg Asn Arg Glu Asp Met Thr Ala Gln Ser Gly Thr Thr Tyr Ile Val Val Ile Arg Ser Pro
-------------------------------------AMP-------------------------------------

CTTACCATCTGGCCCCAGTGCTGCAATGATACCGCGAGACCCACGCTCACCGGCTCCAGATTTATCAGCAATAAACCAGC
-------------------------------------------------------------------------------- 6800
GAATGGTAGACCGGGGTCACGACGTTACTATGGCGCTCTGGGTGCGAGTGGCCGAGGTCTAAATAGTCGTTATTTGGTCG
Lys Gly Asp Pro Gly Leu Ala Ala Ile Ile Gly Arg Ser Gly Arg Glu Gly Ala Gly Ser Lys Asp Ala Ile Phe Trp Gly
-------------------------------------AMP-------------------------------------

CAGCCGGAAGGGCCGAGCGCAGAAGTGGTCCTGCAACTTTATCCGCCTCCATCCAGTCTATTAATTGTTGCCGGGAAGCT
-------------------------------------------------------------------------------- 6880
GTCGGCCTTCCCGGCTCGCGTCTTCACCAGGACGTTGAAATAGGCGGAGGTAGGTCAGATAATTAACAACGGCCCTTCGA
Ala Pro Leu Ala Ser Arg Leu Leu Pro Gly Ala Val Lys Asp Ala Glu Met Trp Asp Ile Leu Gln Gln Arg Ser Ala
-------------------------------------AMP-------------------------------------

                              FspI                      PstI
AGAGTAAGTAGTTCGCCAGTTAATAGTTTGCGCAACGTTGTTGCCATTGCTGCAGGCATCGTGGTGTCACGCTCGTCGTT
-------------------------------------------------------------------------------- 6960
TCTCATTCATCAAGCGGTCAATTATCAAACGCGTTGCAACAACGGTAACGACGTCCGTAGCACCACAGTGCGAGCAGCAA
Leu Thr Leu Leu Glu Gly Thr Leu Leu Lys Arg Leu Thr Thr Ala Met Ala Ala Pro Met Thr Thr Asp Arg Glu Asp Asn
-------------------------------------AMP-------------------------------------

TGGTATGGCTTCATTCAGCTCCGGTTCCCAACGATCAAGGCGAGTTACATGATCCCCCATGTTGTGCAAAAAAGCGGTTA
-------------------------------------------------------------------------------- 7040
ACCATACCGAAGTAAGTCGAGGCCAAGGGTTGCTAGTTCCGCTCAATGTACTAGGGGGTACAACACGTTTTTTCGCCAAT
Pro Ile Ala Glu Asn Leu Glu Pro Glu Trp Arg Asp Leu Arg Thr Val His Asp Gly Met Asn His Leu Phe Ala Thr Leu
-------------------------------------AMP-------------------------------------
```

FIG. 10 (cont)

Friday, November 15, 2002 12:30 PM
pLBC-BTaxW Map.MPD (1 > 7685) Site and Sequence

```
                          PvuI
GCTCCTTCGGTCCTCCGATCGTTGTCAGAAGTAAGTTGGCCGCAGTGTTATCACTCATGGTTATGGCAGCACTGCATAAT
---------------------------------------------------------------------------------+ 7120
CGAGGAAGCCAGGAGGCTAGCAACAGTCTTCATTCAACCGGCGTCACAATAGTGAGTACCAATACCGTCGTGACGTATTA
Glu Lys Pro Gly Gly Ile Thr Thr Leu Leu Leu Asn Ala Ala Thr Asn Asp Ser Met Thr Ile Ala Ala Ser Cys Leu
-------------------------------------AMP-------------------------------------

TCTCTTACTGTCATGCCATCCGTAAGATGCTTTTCTGTGACTGGTGAGTACTCAACCAAGTCATTCTGAGAATAGTGTAT
---------------------------------------------------------------------------------+ 7200
AGAGAATGACAGTACGGTAGGCATTCTACGAAAAGACACTGACCACTCATGAGTTGGTTCAGTAAGACTCTTATCACATA
Glu Arg Val Thr Met Gly Asp Thr Leu His Lys Glu Thr Val Pro Ser Tyr Glu Val Leu Asp Asn Gln Ser Tyr His Ile
-------------------------------------AMP-------------------------------------

                                                                         DraI
GCGGCGACCGAGTTGCTCTTGCCCGGCGTCAACACGGGATAATACCGCGCCACATAGCAGAACTTTAAAAGTGCTCATCA
---------------------------------------------------------------------------------+ 7280
CGCCGCTGGCTCAACGAGAACGGGCCGCAGTTGTGCCCTATTATGGCGCGGTGTATCGTCTTGAAATTTTCACGAGTAGT
Arg Arg Gly Leu Gln Glu Gln Gly Ala Asp Val Arg Ser Leu Val Ala Gly Cys Leu Leu Val Lys Phe Thr Ser Met Met
-------------------------------------AMP-------------------------------------

TTGGAAAACGTTCTTCGGGGCGAAAACTCTCAAGGATCTTACCGCTGTTGAGATCCAGTTCGATGTAACCCACTCGTGCA
---------------------------------------------------------------------------------+ 7360
AACCTTTTGCAAGAAGCCCCGCTTTTGAGAGTTCCTAGAATGGCGACAACTCTAGGTCAAGCTACATTGGGTGAGCACGT
Pro Phe Arg Glu Glu Pro Arg Phe Ser Glu Leu Ile Lys Gly Ser Asn Leu Asp Leu Glu Ile Tyr Gly Val Arg Ala
-------------------------------------AMP-------------------------------------

CCCAACTGATCTTCAGCATCTTTTACTTTCACCAGCGTTTCTGGGTGAGCAAAAACAGGAAGGCAAAATGCCGCAAAAAA
---------------------------------------------------------------------------------+ 7440
GGGTTGACTAGAAGTCGTAGAAAATGAAAGTGGTCGCAAAGACCCACTCGTTTTTGTCCTTCCGTTTTACGGCGTTTTTT
Gly Leu Gln Asp Glu Ala Asp Lys Val Lys Val Leu Thr Glu Pro His Ala Phe Val Pro Leu Cys Phe Ala Ala Phe Phe
-------------------------------------AMP-------------------------------------

GGGAATAAGGGCGACACGGAAATGTTGAATACTCATACTCTTCCTTTTTCAATATTATTGAAGCATTTATCAGGGTTATT
---------------------------------------------------------------------------------+ 7520
CCCTTATTCCCGCTGTGCCTTTACAACTTATGAGTATGAGAAGGAAAAAGTTATAATAACTTCGTAAATAGTCCCAATAA
Pro Ile Leu Ala Val Arg Phe His Gln Ile Ser Met
-----------------AMP-----------------

    BspHI
GTCTCATGAGCGGATACATATTTGAATGTATTTAGAAAAATAAACAAATAGGGGTTCCGCGCACATTTCCCCGAAAAGTG
---------------------------------------------------------------------------------+ 7600
CAGAGTACTCGCCTATGTATAAACTTACATAAATCTTTTTATTTGTTTATCCCCAAGGCGCGTGTAAAGGGGCTTTTCAC

                                BspHI
CCACCTGACGTCTAAGAAACCATTATTATCATGACATTAACCTATAAAAATAGGCGTATCACGAGGCCCTTTCGTCTTCA
---------------------------------------------------------------------------------+ 7680
GGTGGACTGCAGATTCTTTGGTAATAATAGTACTGTAATTGGATATTTTTATCCGCATAGTGCTCCGGGAAAGCAGAAGT

AGAAT
-----> 7685
TCTTA
```

FIG. 12

Thursday, June 13, 2002 3:55 PM
GD2415 (pLNBlv-M4W).MPD (1 > 7428) Site and Sequence
Enzymes : 35 of 538 enzymes (Filtered)
Settings : Circular, Certain Sites Only, Standard Genetic Code XmnI GAATTAATTCATACCAGATCACCGAAAACTGTCCTCCAAATGTGTCCCCCTCACACTCCCAAATTCGCGGGCTTCTGCCT 80
CTTAATTAAGTATGGTCTAGTGGCTTTTGACAGGAGGTTTACACAGGGGGAGTGTGAGGGTTTAAGCGCCCGAAGACGGA SacII CTTAGACCACTCTACCCTATTCCCCACACTCACCGGAGCCAAAGCCGCGGCCCTTCCGTTTCTTTGCTTTTGAAAGACCC 160
GAATCTGGTGAGATGGGATAAGGGGTGTGAGTGGCCTCGGTTTCGGCGCCGGGAAGGCAAAGAAACGAAAACTTTCTGGG
5' LTR
MoMSV 5' LTR NheI CACCCGTAGGTGGCAAGCTAGCTTAAGTAACGCCACTTTGCAAGGCATGGAAAAATACATAACTGAGAATAGAAAAGTTC 240
GTGGGCATCCACCGTTCGATCGAATTCATTGCGGTGAAACGTTCCGTACCTTTTTATGTATTGACTCTTATCTTTTCAAG
5' LTR
MoMSV 5' LTR AGATCAAGGTCAGGAACAAAGAAACAGCTGAATACCAAACAGGATATCTGTGGTAAGCGGTTCCTGCCCCGGCTCAGGGC 320
TCTAGTTCCAGTCCTTGTTTCTTTGTCGACTTATGGTTTGTCCTATAGACACCATTCGCCAAGGACGGGGCCGAGTCCCG
5' LTR
MoMSV 5' LTR CAAGAACAGATGAGACAGCTGAGTGATGGGCCAAACAGGATATCTGTGGTAAGCAGTTCCTGCCCCGGCTCGGGGCCAAG 400
GTTCTTGTCTACTCTGTCGACTCACTACCCGGTTTGTCCTATAGACACCATTCGTCAAGGACGGGGCCGAGCCCCGGTTC
5' LTR
MoMSV 5' LTR AACAGATGGTCCCCAGATGCGGTCCAGCCCTCAGCAGTTTCTAGTGAATCATCAGATGTTTCCAGGGTGCCCCAAGGACC 480
TTGTCTACCAGGGGTCTACGCCAGGTCGGGAGTCGTCAAAGATCACTTAGTAGTCTACAAAGGTCCCACGGGGTTCCTGG
5' LTR
MoMSV 5' LTR TGAAAATGACCCTGTACCTTATTTGAACTAACCAATCAGTTCGCTTCTCGCTTCTGTTCGCGCGCTTCCGCTCTCCGAGC 560
ACTTTTACTGGGACATGGAATAAACTTGATTGGTTAGTCAAGCGAAGAGCGAAGACAAGCGCGCGAAGGCGAGAGGCTCG
5' LTR
MoMSV 5' LTR SacI AscI SmaI KpnI TCAATAAAAGAGCCCACAACCCCTCACTCGGCGCGCCAGTCTTCCGATAGACTGCGTCGCCCGGGTACCCGTATTCCCAA 640
AGTTATTTTCTCGGGTGTTGGGGAGTGAGCCGCGCGGTCAGAAGGCTATCTGACGCAGCGGGCCCATGGGCATAAGGGTT
5' LTR
MoMSV 5' LTR

FIG. 12 (cont)

Thursday, June 13, 2002 3:55 PM
GD2415 (pLNBlv-M4W).MPD (1 > 7428) Site and Sequence

```
TAAAGCCTCTTGCTGTTTGCATCCGAATCGTGGTCTCGCTGTTCCTTGGGAGGGTCTCCTCTGAGTGATTGACTACCCAC  720
ATTTCGGAGAACGACAAACGTAGGCTTAGCACCAGAGCGACAAGGAACCCTCCCAGAGGAGACTCACTAACTGATGGGTG
5' LTR
MoMSV 5' LTR

GACGGGGGTCTTTCATTTGGGGGCTCGTCCGGGATTTGGAGACCCCTGCCCAGGGACCACCGACCCACCACCGGGAGGTA  800
CTGCCCCCAGAAAGTAAACCCCCGAGCAGGCCCTAAACCTCTGGGGACGGGTCCCTGGTGGCTGGGTGGTGGCCCTCCAT
5' LTR
MoMSV 5' LTR

                                                                           SpeI
AGCTGGCCAGCAACTTATCTGTGTCTGTCCGATTGTCTAGTGTCTATGTTTGATGTTATGCGCCTGCGTCTGTACTAGTT  880
TCGACCGGTCGTTGAATAGACACAGACAGGCTAACAGATCACAGATACAAACTACAATACGCGGACGCAGACATGATCAA
Pkg Rgn
Extended Packaging Region

AGCTAACTAGCTCTGTATCTGGCGGACCCGTGGTGGAACTGACGAGTTCTGAACACCCGGCCGCAACCCTGGGAGACGTC  960
TCGATTGATCGAGACATAGACCGCCTGGGCACCACCTTGACTGCTCAAGACTTGTGGGCCGGCGTTGGGACCCTCTGCAG
Pkg Rgn
Extended Packaging Region

CCAGGGACTTTGGGGGCCGTTTTTGTGGCCCGACCTGAGGAAGGGAGTCGATGTGGAATCCGACCCCGTCAGGATATGTG  1040
GGTCCCTGAAACCCCCGGCAAAAACACCGGGCTGGACTCCTTCCCTCAGCTACACCTTAGGCTGGGGCAGTCCTATACAC
Pkg Rgn
Extended Packaging Region

GTTCTGGTAGGAGACGAGAACCTAAAACAGTTCCCGCCTCCGTCTGAATTTTTGCTTTCGGTTTGGAACCGAAGCCGCGC  1120
CAAGACCATCCTCTGCTCTTGGATTTTGTCAAGGGCGGAGGCAGACTTAAAAACGAAAGCCAAACCTTGGCTTCGGCGCG
Pkg Rgn
Extended Packaging Region

                  PstI      PstI
GTCTTGTCTGCTGCAGCGCTGCAGCATCGTTCTGTGTTGTCTCTGTCTGACTGTGTTTCTGTATTTGTCTGAAAATTAGG  1200
CAGAACAGACGACGTCGCGACGTCGTAGCAAGACACAACAGAGACAGACTGACACAAAGACATAAACAGACTTTTAATCC
Pkg Rgn
Extended Packaging Region

GCCAGACTGTTACCACTCCCTTAAGTTTGACCTTAGGTCACTGGAAAGATGTCGAGCGGATCGCTCACAACCAGTCGGTA  1280
CGGTCTGACAATGGTGAGGGAATTCAAACTGGAATCCAGTGACCTTTCTACAGCTCGCCTAGCGAGTGTTGGTCAGCCAT
Pkg Rgn
Extended Packaging Region
```

FIG. 12 (cont)

Thursday, June 13, 2002 3:55 PM
GD2415 (pLNBlv-M4W).MPD (1 > 7428) Site and Sequence

```
                                         PstI
GATGTCAAGAAGAGACGTTGGGTTACCTTCTGCTCTGCAGAATGGCCAACCTTTAACGTCGGATGGCCGCGAGACGGCAC  1360
CTACAGTTCTTCTCTGCAACCCAATGGAAGACGAGACGTCTTACCGGTTGGAAATTGCAGCCTACCGGCGCTCTGCCGTG
                                    Pkg Rgn
                           Extended Packaging Region

CTTTAACCGAGACCTCATCACCCAGGTTAAGATCAAGGTCTTTTCACCTGGCCCGCATGGACACCCAGACCAGGTCCCCT  1440
GAAATTGGCTCTGGAGTAGTGGGTCCAATTCTAGTTCCAGAAAAGTGGACCGGGCGTACCTGTGGGTCTGGTCCAGGGGA
                                    Pkg Rgn
                           Extended Packaging Region

ACATCGTGACCTGGGAAGCCTTGGCTTTTGACCCCCCTCCCTGGGTCAAGCCCTTTGTACACCCTAAGCCTCCGCCTCCT  1520
TGTAGCACTGGACCCTTCGGAACCGAAAACTGGGGGGAGGGACCCAGTTCGGGAAACATGTGGGATTCGGAGGCGGAGGA
                                    Pkg Rgn
                           Extended Packaging Region

CTTCCTCCATCCGCCCCGTCTCTCCCCCTTGAACCTCCTCGTTCGACCCCGCCTCGATCCTCCCTTTATCCAGCCCTCAC  1600
GAAGGAGGTAGGCGGGGCAGAGAGGGGGAACTTGGAGGAGCAAGCTGGGGCGGAGCTAGGAGGGAAATAGGTCGGGAGTG
                                    Pkg Rgn
                           Extended Packaging Region

          NarI  EcoRI       BclI
TCCTTCTCTAGGCGCCGGAATTCCGATCTGATCAAGAGACAGGATGAGGATCGTTTCGCATGATTGAACAAGATGGATTG  1680
AGGAAGAGATCCGCGGCCTTAAGGCTAGACTAGTTCTCTGTCCTACTCCTAGCAAAGCGTACTAACTTGTTCTACCTAAC
  Pkg Rgn                                                    Met Ile Glu Gln Asp Gly Leu
- Extended Packaging                                         Neomycin Phosphotransfer-

CACGCAGGTTCTCCGGCCGCTTGGGTGGAGAGGCTATTCGGCTATGACTGGGCACAACAGACAATCGGCTGCTCTGATGC  1760
GTGCGTCCAAGAGGCCGGCGAACCCACCTCTCCGATAAGCCGATACTGACCCGTGTTGTCTGTTAGCCGACGAGACTACG
 His Ala Gly Ser Pro Ala Ala Trp Val Glu Arg Leu Phe Gly Tyr Asp Trp Ala Gln Gln Thr Ile Gly Cys Ser Asp Ala
                          Neomycin Phosphotransferase

                              NarI
CGCCGTGTTCCGGCTGTCAGCGCAGGGGCGCCCGGTTCTTTTTGTCAAGACCGACCTGTCCGGTGCCCTGAATGAACTGC  1840
GCGGCACAAGGCCGACAGTCGCGTCCCCGCGGGCCAAGAAAAACAGTTCTGGCTGGACAGGCCACGGGACTTACTTGACG
 Ala Val Phe Arg Leu Ser Ala Gln Gly Arg Pro Val Leu Phe Val Lys Thr Asp Leu Ser Gly Ala Leu Asn Glu Leu
                          Neomycin Phosphotransferase

 PstI                                            FspI
AGGACGAGGCAGCGCGGCTATCGTGGCTGGCCACGACGGGCGTTCCTTGCGCAGCTGTGCTCGACGTTGTCACTGAAGCG  1920
TCCTGCTCCGTCGCGCCGATAGCACCGACCGGTGCTGCCCGCAAGGAACGCGTCGACACGAGCTGCAACAGTGACTTCGC
Gln Asp Glu Ala Ala Arg Leu Ser Trp Leu Ala Thr Thr Gly Val Pro Cys Ala Ala Val Leu Asp Val Val Thr Glu Ala
                          Neomycin Phosphotransferase
```

FIG. 12 (cont)

Thursday, June 13, 2002 3:55 PM
GD2415 (pLNBIv-M4W).MPD (1 > 7428) Site and Sequence

```
GGAAGGGACTGGCTGCTATTGGGCGAAGTGCCGGGGCAGGATCTCCTGTCATCTCACCTTGCTCCTGCCGAGAAAGTATC
---------+---------+---------+---------+---------+---------+---------+---------+ 2000
CCTTCCCTGACCGACGATAACCCGCTTCACGGCCCCGTCCTAGAGGACAGTAGAGTGGAACGAGGACGGCTCTTTCATAG
 Gly Arg Asp Trp Leu Leu Leu Gly Glu Val Pro Gly Gln Asp Leu Leu Ser Ser His Leu Ala Pro Ala Glu Lys Val Ser
 ------------------------------ Neomycin Phosphotransferase ------------------------------

CATCATGGCTGATGCAATGCGGCGGCTGCATACGCTTGATCCGGCTACCTGCCCATTCGACCACCAAGCGAAACATCGCA
---------+---------+---------+---------+---------+---------+---------+---------+ 2080
GTAGTACCGACTACGTTACGCCGCCGACGTATGCGAACTAGGCCGATGGACGGGTAAGCTGGTGGTTCGCTTTGTAGCGT
 Ile Met Ala Asp Ala Met Arg Arg Leu His Thr Leu Asp Pro Ala Thr Cys Pro Phe Asp His Gln Ala Lys His Arg
 ------------------------------ Neomycin Phosphotransferase ------------------------------

TCGAGCGAGCACGTACTCGGATGGAAGCCGGTCTTGTCGATCAGGATGATCTGGACGAAGAGCATCAGGGGCTCGCGCCA
---------+---------+---------+---------+---------+---------+---------+---------+ 2160
AGCTCGCTCGTGCATGAGCCTACCTTCGGCCAGAACAGCTAGTCCTACTAGACCTGCTTCTCGTAGTCCCCGAGCGCGGT
Ile Glu Arg Ala Arg Thr Arg Met Glu Ala Gly Leu Val Asp Gln Asp Asp Leu Asp Glu Glu His Gln Gly Leu Ala Pro
 ------------------------------ Neomycin Phosphotransferase ------------------------------

                                  SphI                        NcoI
GCCGAACTGTTCGCCAGGCTCAAGGCGCGCATGCCCGACGGCGAGGATCTCGTCGTGACCCATGGCGATGCCTGCTTGCC
---------+---------+---------+---------+---------+---------+---------+---------+ 2240
CGGCTTGACAAGCGGTCCGAGTTCCGCGCGTACGGGCTGCCGCTCCTAGAGCAGCACTGGGTACCGCTACGGACGAACGG
 Ala Glu Leu Phe Ala Arg Leu Lys Ala Arg Met Pro Asp Gly Glu Asp Leu Val Val Thr His Gly Asp Ala Cys Leu Pro
 ------------------------------ Neomycin Phosphotransferase ------------------------------

                                                    NaeI
GAATATCATGGTGGAAAATGGCCGCTTTTCTGGATTCATCGACTGTGGCCGGCTGGGTGTGGCGGACCGCTATCAGGACA
---------+---------+---------+---------+---------+---------+---------+---------+ 2320
CTTATAGTACCACCTTTTACCGGCGAAAAGACCTAAGTAGCTGACACCGGCCGACCCACACCGCCTGGCGATAGTCCTGT
 Asn Ile Met Val Glu Asn Gly Arg Phe Ser Gly Phe Ile Asp Cys Gly Arg Leu Gly Val Ala Asp Arg Tyr Gln Asp
 ------------------------------ Neomycin Phosphotransferase ------------------------------

TAGCGTTGGCTACCCGTGATATTGCTGAAGAGCTTGGCGGCGAATGGGCTGACCGCTTCCTCGTGCTTTACGGTATCGCC
---------+---------+---------+---------+---------+---------+---------+---------+ 2400
ATCGCAACCGATGGGCACTATAACGACTTCTCGAACCGCCGCTTACCCGACTGGCGAAGGAGCACGAAATGCCATAGCGG
Ile Ala Leu Ala Thr Arg Asp Ile Ala Glu Glu Leu Gly Gly Glu Trp Ala Asp Arg Phe Leu Val Leu Tyr Gly Ile Ala
 ------------------------------ Neomycin Phosphotransferase ------------------------------

GCTCCCGATTCGCAGCGCATCGCCTTCTATCGCCTTCTTGACGAGTTCTTCTGAGCGGGACTCTGGGGTTCGAAATGACC
---------+---------+---------+---------+---------+---------+---------+---------+ 2480
CGAGGGCTAAGCGTCGCGTAGCGGAAGATAGCGGAAGAACTGCTCAAGAAGACTCGCCCTGAGACCCCAAGCTTTACTGG
 Ala Pro Asp Ser Gln Arg Ile Ala Phe Tyr Arg Leu Leu Asp Glu Phe Phe  •
 ------------- Neomycin Phosphotransferase -------------

GACCAAGCGACGCCCAACCTGCCATCACGAGATTTCGATTCCACCGCCGCCTTCTATGAAAGGTTGGGCTTCGGAATCGT
---------+---------+---------+---------+---------+---------+---------+---------+ 2560
CTGGTTCGCTGCGGGTTGGACGGTAGTGCTCTAAAGCTAAGGTGGCGGCGGAAGATACTTTCCAACCCGAAGCCTTAGCA

          NaeI                                                   SmaI
TTTCCGGGACGCCGGCTGGATGATCCTCCAGCGCGGGGATCTCATGCTGGAGTTCTTCGCCCACCCCGGGCTCGATCCCC
---------+---------+---------+---------+---------+---------+---------+---------+ 2640
AAAGGCCCTGCGGCCGACCTACTAGGAGGTCGCGCCCCTAGAGTACGACCTCAAGAAGCGGGTGGGGCCCGAGCTAGGGG
```

FIG. 12 (cont)

Thursday, June 13, 2002 3:55 PM
GD2415 (pLNBlv-M4W).MPD (1 > 7428) Site and Sequence NruI

```
TCGCGAGTTGGTTCAGCTGCTGCCTGAGGCTGGACGACCTCGCGGAGTTCTACCGGCAGTGCAAATCCGTCGGCATCCAG 2720
AGCGCTCAACCAAGTCGACGACGGACTCCGACCTGCTGGAGCGCCTCAAGATGGCCGTCACGTTTAGGCAGCCGTAGGTC
```

PstI

```
GAAACCAGCAGCGGCTATCCGCGCATCCATGCCCCCGAACTGCAGGAGTGGGGAGGCACGATGGCCGCTTTGGTCGAGGC 2800
CTTTGGTCGTCGCCGATAGGCGCGTAGGTACGGGGGCTTGACGTCCTCACCCCTCCGTGCTACCGGCGAAACCAGCTCCG
```

BamHI

```
GGATCCTAGCAGAAAAATAAGACTTGATTCCCCCTTAAAATTACAACTGCTAGAAAATGAATGGCTCTCCCGCCTTTTTT 2880
CCTAGGATCGTCTTTTTATTCTGAACTAAGGGGGAATTTTAATGTTGACGATCTTTTACTTACCGAGAGGGCGGAAAAAA
```

Blv Pro
Blv Promoter

NarI

```
GAGGGGGAATCATTTGTATGAAAGATCATGCCGACCTAGGCGCCGCCACCGCCCCGTAAACCAGACAGAGACGTCAGCTG 2960
CTCCCCCTTAGTAAACATACTTTCTAGTACGGCTGGATCCGCGGCGGTGGCGGGGCATTTGGTCTGTCTCTGCAGTCGAC
```

Blv Pro
Blv Promoter

```
CCAGAAAAGCTGGTGACGGCAGCTGGTGGCTAGAATCCCCGTACCTCCCCAACTTCCCCTTTCCCGAAAAATCCACACCC 3040
GGTCTTTTCGACCACTGCCGTCGACCACCGATCTTAGGGGCATGGAGGGGTTGAAGGGGAAAGGGCTTTTTAGGTGTGGG
```

Blv Pro
Blv Promoter

NaeI

```
TGAGCTGCTGACCTCACCTGCTGATAAATTAATAAAATGCCGGCCCTGTCGAGTTAGCGGCACCAGAAGCGTTCTTCTCC 3120
ACTCGACGACTGGAGTGGACGACTATTTAATTATTTTACGGCCGGGACAGCTCAATCGCCGTGGTCTTCGCAAGAAGAGG
```

Blv Pro
Blv Promoter

XhoI HindIII

```
TGAGACCCTCGTGCTCAGCTCTCGGTCCTGCCTCGAGAAGCTTGTTATCACAAGTTTGTACAAAAAAGCAGGCTTCGAAG 3200
ACTCTGGGAGCACGAGTCGAGAGCCAGGACGGAGCTCTTCGAACAATAGTGTTCAAACATGTTTTTTCGTCCGAAGCTTC
```

Blv Pro
Blv Promoter
att B1
att B1

FIG. 12 (cont)

Thursday, June 13, 2002 3:55 PM
GD2415 (pLNBIv-M4W).MPD (1 > 7428) Site and Sequence

```
                 XmnI                       SalI      BamHI    KpnI EcoRI
GAGATAGAACCAATTCTCTAAGGAAATACTTAACGTCGACTGGATCCGGTACCGAATTCGATCCACATGCCTAAAAAACG 3280
CTCTATCTTGGTTAAGAGATTCCTTTATGAATTGCAGCTGACCTAGGCCATGGCTTAAGCTAGGTGTACGGATTTTTTGC
                                                                     Met Pro Lys Lys Arg
                                                                     ---- Brex M4 ----

                                                                  ApaI
ACGGTCCCGAAGACGCCCACAACCGATCATCAGATGGCAAGTGTTGTTGGTTGGGGGCCCCACTCTCTACATGCCTGCCC 3360
TGCCAGGGCTTCTGCGGGTGTTGGCTAGTAGTCTACCGTTCACAACAACCAACCCCCGGGGTGAGAGATGTACGGACGGG
 Arg Ser Arg Arg Arg Pro Gln Pro Ile Ile Arg Trp Gln Val Leu Leu Val Gly Gly Pro Thr Leu Tyr Met Pro Ala
---------------------------------------- Brex M4 ----------------------------------------

                                         ClaI                       ApaI
GGCCCTGGTTTTGTCCAATGATGTCACCATCGATGCCTGGTGCCCCCTCTGCGGGCCCCATGAGCGACTCCAATTCGAAA 3440
CCGGGACCAAAACAGGTTACTACAGTGGTAGCTACGGACCACGGGGGAGACGCCCGGGGTACTCGCTGAGGTTAAGCTTT
Arg Pro Trp Phe Cys Pro Met Met Ser Pro Ser Met Pro Gly Ala Pro Ser Ala Gly Pro Met Ser Asp Ser Asn Ser Lys
---------------------------------------- Brex M4 ----------------------------------------

GGATCGACACCACGCTCACCTGCGAGACCCACCGTATCAACTGGACCGCCGATGGACGACCTTGCGGCCTCAATGGAACG 3520
CCTAGCTGTGGTGCGAGTGGACGCTCTGGGTGGCATAGTTGACCTGGCGGCTACCTGCTGGAACGCCGGAGTTACCTTGC
Gly Ser Thr Pro Arg Ser Pro Ala Arg Pro Thr Val Ser Thr Gly Pro Pro Met Asp Asp Leu Ala Ala Ser Met Glu Arg
---------------------------------------- Brex M4 ----------------------------------------

                                                      ApaI
TTGTTCCCTCGACTGCATGTCTCCGAGACCCGCCCCCAAGGGCCCCGACGACTCTGGATCAACTGCCCCCTTCCGGCCGT 3600
AACAAGGGAGCTGACGTACAGAGGCTCTGGGCGGGGGTTCCCGGGGCTGCTGAGACCTAGTTGACGGGGGAAGGCCGGCA
 Cys Ser Leu Asp Cys Met Ser Pro Arg Pro Ala Pro Lys Gly Pro Asp Asp Ser Gly Ser Thr Ala Pro Phe Arg Pro
---------------------------------------- Brex M4 ----------------------------------------

                               BglII
TCGCGCTCAGCCCGGCCCGGTTAGATCTTCCCCCTTCGAGCGGTCCCCCTTCCAGCCCTACCAATGCCAATTGCCCTCGG 3680
AGCGCGAGTCGGGCCGGGCCAATCTAGAAGGGGGAAGCTCGCCAGGGGGAAGGTCGGGATGGTTACGGTTAACGGGAGCC
Phe Ala Leu Ser Pro Ala Arg Leu Asp Leu Pro Pro Ser Ser Gly Pro Pro Ser Ser Pro Thr Asn Ala Asn Cys Pro Arg
---------------------------------------- Brex M4 ----------------------------------------

CCTCTAGCGACGGTTGCCCCATTATCGGGCACGGCCTTCTTCCCTGGAACAACTTAGTAACGCATCCTGTCCTCAGAAAA 3760
GGAGATCGCTGCCAACGGGGTAATAGCCCGTGCCGGAAGAAGGGACCTTGTTGAATCATTGCGTAGGACAGGAGTCTTTT
 Pro Leu Ala Thr Val Ala Pro Leu Ser Gly Thr Ala Phe Phe Pro Gly Thr Thr •
------------------------------ Brex M4 ------------------------------
```

Thursday, June 13, 2002 3:55 PM
GD2415 (pLNBIv-M4W).MPD (1 > 7428) Site and Sequence

FIG. 12 (cont)

Thursday, June 13, 2002 3:55 PM
GD2415 (pLNBlv-M4W).MPD (1 > 7428) Site and Sequence ClaI ATCTCCCTTTGGGCCGCCTCCCCGCCTGATCGATAAAATAAAAGATTTTATTTAGTCTCCAGAAAAAGGGGGGAATGAAA 4480
TAGAGGGAAACCCGGCGGAGGGGCGGACTAGCTATTTTATTTTCTAAAATAAATCAGAGGTCTTTTTCCCCCCTTACTTT WPRE — 3' LTR — MoMuL -

NheI

GACCCCACCTGTAGGTTTGGCAAGCTAGCTTAAGTAACGCCATTTTGCAAGGCATGGAAAAATACATAACTGAGAATAGA 4560
CTGGGGTGGACATCCAAACCGTTCGATCGAATTCATTGCGGTAAAACGTTCCGTACCTTTTTATGTATTGACTCTTATCT

3' LTR
MoMuLV 3' LTR

GAAGTTCAGATCAAGGTCAGGAACAGATGGAACAGCTGAATATGGGCCAAACAGGATATCTGTGGTAAGCAGTTCCTGCC 4640
CTTCAAGTCTAGTTCCAGTCCTTGTCTACCTTGTCGACTTATACCCGGTTTGTCCTATAGACACCATTCGTCAAGGACGG

3' LTR
MoMuLV 3' LTR

CCGGCTCAGGGCCAAGAACAGATGGAACAGCTGAATATGGGCCAAACAGGATATCTGTGGTAAGCAGTTCCTGCCCCGGC 4720
GGCCGAGTCCCGGTTCTTGTCTACCTTGTCGACTTATACCCGGTTTGTCCTATAGACACCATTCGTCAAGGACGGGGCCG

3' LTR
MoMuLV 3' LTR

XbaI

TCAGGGCCAAGAACAGATGGTCCCCAGATGCGGTCCAGCCCTCAGCAGTTTCTAGAGAACCATCAGATGTTTCCAGGGTG 4800
AGTCCCGGTTCTTGTCTACCAGGGGTCTACGCCAGGTCGGGAGTCGTCAAAGATCTCTTGGTAGTCTACAAAGGTCCCAC

3' LTR
MoMuLV 3' LTR

CCCCAAGGACCTGAAATGACCCTGTGCCTTATTTGAACTAACCAATCAGTTCGCTTCTCGCTTCTGTTCGCGCGCTTCTG 4880
GGGGTTCCTGGACTTTACTGGGACACGGAATAAACTTGATTGGTTAGTCAAGCGAAGAGCGAAGACAAGCGCGCGAAGAC

3' LTR
MoMuLV 3' LTR

SacI NarI SmaI KpnI

CTCCCCGAGCTCAATAAAAGAGCCCACAACCCCTCACTCGGGGCGCCAGTCCTCCGATTGACTGAGTCGCCCGGGTACCC 4960
GAGGGGCTCGAGTTATTTTCTCGGGTGTTGGGGAGTGAGCCCCGCGGTCAGGAGGCTAACTGACTCAGCGGGCCCATGGG

3' LTR
MoMuLV 3' LTR

FIG. 12 (cont)

Thursday, June 13, 2002 3:55 PM
GD2415 (pLNBlv-M4W).MPD (1 > 7428) Site and Sequence

```
GTGTATCCAATAAACCCTCTTGCAGTTGCATCCGACTTGTGGTCTCGCTGTTCCTTGGGAGGGTCTCCTCTGAGTGATTG
-------------------------------------------------------------------------------- 5040
CACATAGGTTATTTGGGAGAACGTCAACGTAGGCTGAACACCAGAGCGACAAGGAACCCTCCCAGAGGAGACTCACTAAC
                                  3' LTR
                              MoMuLV 3' LTR

ACTACCCGTCAGCGGGGGTCTTTCATTTGGGGGCTCGTCCGGGATCGGGAGACCCCTGCCCAGGGACCACCGACCCACCA
-------------------------------------------------------------------------------- 5120
TGATGGGCAGTCGCCCCCAGAAAGTAAACCCCCGAGCAGGCCCTAGCCCTCTGGGGACGGGTCCCTGGTGGCTGGGTGGT
      3' LTR
   MoMuLV 3' LTR

CCGGGAGGTAAGCTGGCTGCCTCGCGCGTTTCGGTGATGACGGTGAAAACCTCTGACACATGCAGCTCCCGGAGACGGTC
-------------------------------------------------------------------------------- 5200
GGCCCTCCATTCGACCGACGGAGCGCGCAAAGCCACTACTGCCACTTTTGGAGACTGTGTACGTCGAGGGCCTCTGCCAG

ACAGCTTGTCTGTAAGCGGATGCCGGGAGCAGACAAGCCCGTCAGGGCGCGTCAGCGGGTGTTGGCGGGTGTCGGGGCGC
-------------------------------------------------------------------------------- 5280
TGTCGAACAGACATTCGCCTACGGCCCTCGTCTGTTCGGGCAGTCCCGCGCAGTCGCCCACAACCGCCCACAGCCCCGCG

AGCCATGACCCAGTCACGTAGCGATAGCGGAGTGTATACTGGCTTAACTATGCGGCATCAGAGCAGATTGTACTGAGAGT
-------------------------------------------------------------------------------- 5360
TCGGTACTGGGTCAGTGCATCGCTATCGCCTCACATATGACCGAATTGATACGCCGTAGTCTCGTCTAACATGACTCTCA

     NdeI
GCACCATATGCGGTGTGAAATACCGCACAGATGCGTAAGGAGAAAATACCGCATCAGGCGCTCTTCCGCTTCCTCGCTCA
-------------------------------------------------------------------------------- 5440
CGTGGTATACGCCACACTTTATGGCGTGTCTACGCATTCCTCTTTTATGGCGTAGTCCGCGAGAAGGCGAAGGAGCGAGT

CTGACTCGCTGCGCTCGGTCGTTCGGCTGCGGCGAGCGGTATCAGCTCACTCAAAGGCGGTAATACGGTTATCCACAGAA
-------------------------------------------------------------------------------- 5520
GACTGAGCGACGCGAGCCAGCAAGCCGACGCCGCTCGCCATAGTCGAGTGAGTTTCCGCCATTATGCCAATAGGTGTCTT

TCAGGGGATAACGCAGGAAAGAACATGTGAGCAAAAGGCCAGCAAAAGGCCAGGAACCGTAAAAAGGCCGCGTTGCTGGC
-------------------------------------------------------------------------------- 5600
AGTCCCCTATTGCGTCCTTTCTTGTACACTCGTTTTCCGGTCGTTTTCCGGTCCTTGGCATTTTTCCGGCGCAACGACCG

GTTTTTCCATAGGCTCCGCCCCCCTGACGAGCATCACAAAAATCGACGCTCAAGTCAGAGGTGGCGAAACCCGACAGGAC
-------------------------------------------------------------------------------- 5680
CAAAAAGGTATCCGAGGCGGGGGGACTGCTCGTAGTGTTTTTAGCTGCGAGTTCAGTCTCCACCGCTTTGGGCTGTCCTG

TATAAAGATACCAGGCGTTTCCCCCTGGAAGCTCCCTCGTGCGCTCTCCTGTTCCGACCCTGCCGCTTACCGGATACCTG
-------------------------------------------------------------------------------- 5760
ATATTTCTATGGTCCGCAAAGGGGGACCTTCGAGGGAGCACGCGAGAGGACAAGGCTGGGACGGCGAATGGCCTATGGAC

TCCGCCTTTCTCCCTTCGGGAAGCGTGGCGCTTTCTCATAGCTCACGCTGTAGGTATCTCAGTTCGGTGTAGGTCGTTCG
-------------------------------------------------------------------------------- 5840
AGGCGGAAAGAGGGAAGCCCTTCGCACCGCGAAAGAGTATCGAGTGCGACATCCATAGAGTCAAGCCACATCCAGCAAGC

CTCCAAGCTGGGCTGTGTGCACGAACCCCCCGTTCAGCCCGACCGCTGCGCCTTATCCGGTAACTATCGTCTTGAGTCCA
-------------------------------------------------------------------------------- 5920
GAGGTTCGACCCGACACACGTGCTTGGGGGGCAAGTCGGGCTGGCGACGCGGAATAGGCCATTGATAGCAGAACTCAGGT
```

FIG. 12 (cont)

Thursday, June 13, 2002 3:55 PM
GD2415 (pLNBlv-M4W).MPD (1 > 7428) Site and Sequence

```
ACCCGGTAAGACACGACTTATCGCCACTGGCAGCAGCCACTGGTAACAGGATTAGCAGAGCGAGGTATGTAGGCGGTGCT
-------------------------------------------------------------------------------- 6000
TGGGCCATTCTGTGCTGAATAGCGGTGACCGTCGTCGGTGACCATTGTCCTAATCGTCTCGCTCCATACATCCGCCACGA

ACAGAGTTCTTGAAGTGGTGGCCTAACTACGGCTACACTAGAAGGACAGTATTTGGTATCTGCGCTCTGCTGAAGCCAGT
-------------------------------------------------------------------------------- 6080
TGTCTCAAGAACTTCACCACCGGATTGATGCCGATGTGATCTTCCTGTCATAAACCATAGACGCGAGACGACTTCGGTCA

TACCTTCGGAAAAAGAGTTGGTAGCTCTTGATCCGGCAAACAAACCACCGCTGGTAGCGGTGGTTTTTTTGTTTGCAAGC
-------------------------------------------------------------------------------- 6160
ATGGAAGCCTTTTTCTCAACCATCGAGAACTAGGCCGTTTGTTTGGTGGCGACCATCGCCACCAAAAAAACAAACGTTCG

AGCAGATTACGCGCAGAAAAAAAGGATCTCAAGAAGATCCTTTGATCTTTTCTACGGGGTCTGACGCTCAGTGGAACGAA
-------------------------------------------------------------------------------- 6240
TCGTCTAATGCGCGTCTTTTTTTCCTAGAGTTCTTCTAGGAAACTAGAAAAGATGCCCCAGACTGCGAGTCACCTTGCTT

                       BspHI                                      DraI
AACTCACGTTAAGGGATTTTGGTCATGAGATTATCAAAAAGGATCTTCACCTAGATCCTTTTAAATTAAAAATGAAGTTT
-------------------------------------------------------------------------------- 6320
TTGAGTGCAATTCCCTAAAACCAGTACTCTAATAGTTTTTCCTAGAAGTGGATCTAGGAAAATTTAATTTTTACTTCAAA

DraI
TAAATCAATCTAAAGTATATATGAGTAAACTTGGTCTGACAGTTACCAATGCTTAATCAGTGAGGCACCTATCTCAGCGA
-------------------------------------------------------------------------------- 6400
ATTTAGTTAGATTTCATATATACTCATTTGAACCAGACTGTCAATGGTTACGAATTAGTCACTCCGTGGATAGAGTCGCT
                                                  • Trp His Lys Ile Leu Ser Ala Gly Ile Glu Ala Ile
                                                  ------------ b-Lactamase ------------

TCTGTCTATTTCGTTCATCCATAGTTGCCTGACTCCCCGTCGTGTAGATAACTACGATACGGGAGGGCTTACCATCTGGC
-------------------------------------------------------------------------------- 6480
AGACAGATAAAGCAAGTAGGTATCAACGGACTGAGGGGCAGCACATCTATTGATGCTATGCCCTCCCGAATGGTAGACCG
 Gln Arg Asn Arg Glu Asp Met Thr Ala Gln Ser Gly Thr Thr Tyr Ile Val Val Ile Arg Ser Pro Lys Gly Asp Pro
------------------------------- b-Lactamase -------------------------------

CCCAGTGCTGCAATGATACCGCGAGACCCACGCTCACCGGCTCCAGATTTATCAGCAATAAACCAGCCAGCCGGAAGGGC
-------------------------------------------------------------------------------- 6560
GGGTCACGACGTTACTATGGCGCTCTGGGTGCGAGTGGCCGAGGTCTAAATAGTCGTTATTTGGTCGGTCGGCCTTCCCG
Gly Leu Ala Ala Ile Ile Gly Arg Ser Gly Arg Glu Gly Ala Gly Ser Lys Asp Ala Ile Phe Trp Gly Ala Pro Leu Ala
------------------------------- b-Lactamase -------------------------------

CGAGCGCAGAAGTGGTCCTGCAACTTTATCCGCCTCCATCCAGTCTATTAATTGTTGCCGGGAAGCTAGAGTAAGTAGTT
-------------------------------------------------------------------------------- 6640
GCTCGCGTCTTCACCAGGACGTTGAAATAGGCGGAGGTAGGTCAGATAATTAACAACGGCCCTTCGATCTCATTCATCAA
Ser Arg Leu Leu Pro Gly Ala Val Lys Asp Ala Glu Met Trp Asp Ile Leu Gln Gln Arg Ser Ala Leu Thr Leu Leu Glu
------------------------------- b-Lactamase -------------------------------

                  FspI                    PstI
CGCCAGTTAATAGTTTGCGCAACGTTGTTGCCATTGCTGCAGGCATCGTGGTGTCACGCTCGTCGTTTGGTATGGCTTCA
-------------------------------------------------------------------------------- 6720
GCGGTCAATTATCAAACGCGTTGCAACAACGGTAACGACGTCCGTAGCACCACAGTGCGAGCAGCAAACCATACCGAAGT
 Gly Thr Leu Leu Lys Arg Leu Thr Thr Ala Met Ala Ala Pro Met Thr Thr Asp Arg Glu Asp Asn Pro Ile Ala Glu
------------------------------- b-Lactamase -------------------------------
```

FIG. 12 (cont)

Thursday, June 13, 2002 3:55 PM
GD2415 (pLNBlv-M4W).MPD (1 > 7428) Site and Sequence

```
TTCAGCTCCGGTTCCCAACGATCAAGGCGAGTTACATGATCCCCCATGTTGTGCAAAAAAGCGGTTAGCTCCTTCGGTCC
---------+---------+---------+---------+---------+---------+---------+---------+ 6800
AAGTCGAGGCCAAGGGTTGCTAGTTCCGCTCAATGTACTAGGGGGTACAACACGTTTTTTCGCCAATCGAGGAAGCCAGG
Asn Leu Glu Pro Glu Trp Arg Asp Leu Arg Thr Val His Asp Gly Met Asn His Leu Phe Ala Thr Leu Glu Lys Pro Gly
-------------------------------------- b-Lactamase --------------------------------------

    PvuI
TCCGATCGTTGTCAGAAGTAAGTTGGCCGCAGTGTTATCACTCATGGTTATGGCAGCACTGCATAATTCTCTTACTGTCA
---------+---------+---------+---------+---------+---------+---------+---------+ 6880
AGGCTAGCAACAGTCTTCATTCAACCGGCGTCACAATAGTGAGTACCAATACCGTCGTGACGTATTAAGAGAATGACAGT
Gly Ile Thr Thr Leu Leu Leu Asn Ala Ala Thr Asn Asp Ser Met Thr Ile Ala Ala Ser Cys Leu Glu Arg Val Thr Met
-------------------------------------- b-Lactamase --------------------------------------

TGCCATCCGTAAGATGCTTTTCTGTGACTGGTGAGTACTCAACCAAGTCATTCTGAGAATAGTGTATGCGGCGACCGAGT
---------+---------+---------+---------+---------+---------+---------+---------+ 6960
ACGGTAGGCATTCTACGAAAAGACACTGACCACTCATGAGTTGGTTCAGTAAGACTCTTATCACATACGCCGCTGGCTCA
Gly Asp Thr Leu His Lys Glu Thr Val Pro Ser Tyr Glu Val Leu Asp Asn Gln Ser Tyr His Ile Arg Arg Gly Leu
-------------------------------------- b-Lactamase --------------------------------------

                                                        DraI                 XmnI
TGCTCTTGCCCGGCGTCAACACGGGATAATACCGCGCCACATAGCAGAACTTTAAAAGTGCTCATCATTGGAAAACGTTC
---------+---------+---------+---------+---------+---------+---------+---------+ 7040
ACGAGAACGGGCCGCAGTTGTGCCCTATTATGGCGCGGTGTATCGTCTTGAAATTTTCACGAGTAGTAACCTTTTGCAAG
Gln Glu Gln Gly Ala Asp Val Arg Ser Leu Val Ala Gly Cys Leu Leu Val Lys Phe Thr Ser Met Met Pro Phe Arg Glu
-------------------------------------- b-Lactamase --------------------------------------

TTCGGGGCGAAAACTCTCAAGGATCTTACCGCTGTTGAGATCCAGTTCGATGTAACCCACTCGTGCACCCAACTGATCTT
---------+---------+---------+---------+---------+---------+---------+---------+ 7120
AAGCCCCGCTTTTGAGAGTTCCTAGAATGGCGACAACTCTAGGTCAAGCTACATTGGGTGAGCACGTGGGTTGACTAGAA
Glu Pro Arg Phe Ser Glu Leu Ile Lys Gly Ser Asn Leu Asp Leu Glu Ile Tyr Gly Val Arg Ala Gly Leu Gln Asp Glu
-------------------------------------- b-Lactamase --------------------------------------

CAGCATCTTTTACTTTCACCAGCGTTTCTGGGTGAGCAAAAACAGGAAGGCAAAATGCCGCAAAAAAGGGAATAAGGGCG
---------+---------+---------+---------+---------+---------+---------+---------+ 7200
GTCGTAGAAAATGAAAGTGGTCGCAAAGACCCACTCGTTTTTGTCCTTCCGTTTTACGGCGTTTTTTCCCTTATTCCCGC
Ala Asp Lys Val Lys Val Leu Thr Glu Pro His Ala Phe Val Pro Leu Cys Phe Ala Ala Phe Phe Pro Ile Leu Ala
-------------------------------------- b-Lactamase --------------------------------------

                                                                         BspHI
ACACGGAAATGTTGAATACTCATACTCTTCCTTTTTCAATATTATTGAAGCATTTATCAGGGTTATTGTCTCATGAGCGG
---------+---------+---------+---------+---------+---------+---------+---------+ 7280
TGTGCCTTTACAACTTATGAGTATGAGAAGGAAAAAGTTATAATAACTTCGTAAATAGTCCCAATAACAGAGTACTCGCC
Val Arg Phe His Gln Ile Ser Met
------- b-Lactamase -------

ATACATATTTGAATGTATTTAGAAAAATAAACAAATAGGGGTTCCGCGCACATTTCCCCGAAAAGTGCCACCTGACGTCT
---------+---------+---------+---------+---------+---------+---------+---------+ 7360
TATGTATAAACTTACATAAATCTTTTTATTTGTTTATCCCCAAGGCGCGTGTAAAGGGGCTTTTCACGGTGGACTGCAGA
```

FIG. 12 (cont)

Thursday, June 13, 2002 3:55 PM
GD2415 (pLNBlv-M4W).MPD (1 > 7428) Site and Sequence BspHI

```
AAGAAACCATTATTATCATGACATTAACCTATAAAAATAGGCGTATCACGAGGCCCTTTCGTCTTCAA
-------------------------------------------------------------------> 7428
TTCTTTGGTAATAATAGTACTGTAATTGGATATTTTTATCCGCATAGTGCTCCGGGAAAGCAGAAGTT
```

FIG. 14

Thursday, June 13, 2002 3:42 PM
GD2407 pLNBLV-YFP Map.MPD (1 > 7010) Site and Sequence
Enzymes : 36 of 538 enzymes (Filtered)
Settings : Circular, Certain Sites Only, Standard Genetic Code

```
GAATTAATTCATACCAGATCACCGAAAACTGTCCTCCAAATGTGTCCCCCTCACACTCCCAAATTCGCGGCTTCTGCCT
                                                                                  80
CTTAATTAAGTATGGTCTAGTGGCTTTTGACAGGAGGTTTACACAGGGGGAGTGTGAGGGTTTAAGCGCCCGAAGACGGA

                                                                 SacII
CTTAGACCACTCTACCCTATTCCCCACACTCACCGGAGCCAAAGCCGCGGCCCTTCCGTTTCTTTGCTTTTGAAAGACCC
                                                                                  160
GAATCTGGTGAGATGGGATAAGGGGTGTGAGTGGCCTCGGTTTCGGCGCCGGGAAGGCAAAGAAACGAAAACTTTCTGGG
                                                                         5' LTR
                                                                         5' LTR MoMS-

                     NheI
CACCCGTAGGTGGCAAGCTAGCTTAAGTAACGCCACTTTGCAAGGCATGGAAAAATACATAACTGAGAATAGAAAAGTTC
                                                                                  240
GTGGGCATCCACCGTTCGATCGAATTCATTGCGGTGAAACGTTCCGTACCTTTTTATGTATTGACTCTTATCTTTTCAAG
                                    5' LTR
                                 5' LTR MoMSV

                               PvuII                  EcoRV
AGATCAAGGTCAGGAACAAAGAAACAGCTGAATACCAAACAGGATATCTGTGGTAAGCGGTTCCTGCCCCGGCTCAGGGC
                                                                                  320
TCTAGTTCCAGTCCTTGTTTCTTTGTCGACTTATGGTTTGTCCTATAGACACCATTCGCCAAGGACGGGGCCGAGTCCCG
                                    5' LTR
                                 5' LTR MoMSV

                     PvuII                      EcoRV
CAAGAACAGATGAGACAGCTGAGTGATGGGCCAAACAGGATATCTGTGGTAAGCAGTTCCTGCCCCGGCTCGGGGCCAAG
                                                                                  400
GTTCTTGTCTACTCTGTCGACTCACTACCCGGTTTGTCCTATAGACACCATTCGTCAAGGACGGGGCCGAGCCCCGGTTC
                                    5' LTR
                                 5' LTR MoMSV

AACAGATGGTCCCCAGATGCGGTCCAGCCCTCAGCAGTTTCTAGTGAATCATCAGATGTTTCCAGGGTGCCCCAAGGACC
                                                                                  480
TTGTCTACCAGGGGTCTACGCCAGGTCGGGAGTCGTCAAAGATCACTTAGTAGTCTACAAAGGTCCCACGGGGTTCCTGG
                                    5' LTR
                                 5' LTR MoMSV

TGAAAATGACCCTGTACCTTATTTGAACTAACCAATCAGTTCGCTTCTCGCTTCTGTTCGCGCGCTTCCGCTCTCCGAGC
                                                                                  560
ACTTTTACTGGGACATGGAATAAACTTGATTGGTTAGTCAAGCGAAGAGCGAAGACAAGCGCGCGAAGGCGAGAGGCTCG
                                    5' LTR
                                 5' LTR MoMSV
```

FIG. 14 (cont)

Thursday, June 13, 2002 3:42 PM
GD2407 pLNBLV-YFP Map.MPD (1 > 7010) Site and Sequence SacI AscI SmaI KpnI

```
TCAATAAAAGAGCCCACAACCCCTCACTCGGCGCGCCAGTCTTCCGATAGACTGCGTCGCCCGGGTACCCGTATTCCCAA 640
AGTTATTTTCTCGGGTGTTGGGGAGTGAGCCGCGCGGTCAGAAGGCTATCTGACGCAGCGGGCCCATGGGCATAAGGGTT
```

5' LTR
5' LTR MoMSV

```
TAAAGCCTCTTGCTGTTTGCATCCGAATCGTGGTCTCGCTGTTCCTTGGGAGGGTCTCCTCTGAGTGATTGACTACCCAC 720
ATTTCGGAGAACGACAAACGTAGGCTTAGCACCAGAGCGACAAGGAACCCTCCCAGAGGAGACTCACTAACTGATGGGTG
```

5' LTR
5' LTR MoMSV

```
GACGGGGGTCTTTCATTTGGGGGCTCGTCCGGGATTTGGAGACCCCTGCCCAGGGACCACCGACCCACCACCGGGAGGTA 800
CTGCCCCCAGAAAGTAAACCCCCGAGCAGGCCCTAAACCTCTGGGGACGGGTCCCTGGTGGCTGGGTGGTGGCCCTCCAT
```

5' LTR
5' LTR MoMSV

SpeI

```
AGCTGGCCAGCAACTTATCTGTGTCTGTCCGATTGTCTAGTGTCTATGTTTGATGTTATGCGCCTGCGTCTGTACTAGTT 880
TCGACCGGTCGTTGAATAGACACAGACAGGCTAACAGATCACAGATACAAACTACAATACGCGGACGCAGACATGATCAA
```

Pkg Rgn
Extended Packaging Region

```
AGCTAACTAGCTCTGTATCTGGCGGACCCGTGGTGGAACTGACGAGTTCTGAACACCCGGCCGCAACCCTGGGAGACGTC 960
TCGATTGATCGAGACATAGACCGCCTGGGCACCACCTTGACTGCTCAAGACTTGTGGGCCGGCGTTGGGACCCTCTGCAG
```

Pkg Rgn
Extended Packaging Region

```
CCAGGGACTTTGGGGGCCGTTTTTGTGGCCCGACCTGAGGAAGGGAGTCGATGTGGAATCCGACCCCGTCAGGATATGTG 1040
GGTCCCTGAAACCCCCGGCAAAAACACCGGGCTGGACTCCTTCCCTCAGCTACACCTTAGGCTGGGGCAGTCCTATACAC
```

Pkg Rgn
Extended Packaging Region

```
GTTCTGGTAGGAGACGAGAACCTAAAACAGTTCCCGCCTCCGTCTGAATTTTTGCTTTCGGTTTGGAACCGAAGCCGCGC 1120
CAAGACCATCCTCTGCTCTTGGATTTTGTCAAGGGCGGAGGCAGACTTAAAAACGAAAGCCAAACCTTGGCTTCGGCGCG
```

Pkg Rgn
Extended Packaging Region

PstI PstI

```
GTCTTGTCTGCTGCAGCGCTGCAGCATCGTTCTGTGTTGTCTCTGTCTGACTGTGTTTCTGTATTTGTCTGAAAATTAGG 1200
CAGAACAGACGACGTCGCGACGTCGTAGCAAGACACAACAGAGACAGACTGACACAAAGACATAAACAGACTTTTAATCC
```

Pkg Rgn
Extended Packaging Region

FIG. 14 (cont)

Thursday, June 13, 2002 3:42 PM
GD2407 pLNBLV-YFP Map.MPD (1 > 7010) Site and Sequence

```
PstI                                                         FspI PvuII
AGGACGAGGCAGCGCGGCTATCGTGGCTGGCCACGACGGGCGTTCCTTGCGCAGCTGTGCTCGACGTTGTCACTGAAGCG 1920
TCCTGCTCCGTCGCGCCGATAGCACCGACCGGTGCTGCCCGCAAGGAACGCGTCGACACGAGCTGCAACAGTGACTTCGC
Gln Asp Glu Ala Ala Arg Leu Ser Trp Leu Ala Thr Thr Gly Val Pro Cys Ala Ala Val Leu Asp Val Val Thr Glu Ala
Neomycin Phosphotransferase

GGAAGGGACTGGCTGCTATTGGGCGAAGTGCCGGGGCAGGATCTCCTGTCATCTCACCTTGCTCCTGCCGAGAAAGTATC 2000
CCTTCCCTGACCGACGATAACCCGCTTCACGGCCCCGTCCTAGAGGACAGTAGAGTGGAACGAGGACGGCTCTTTCATAG
Gly Arg Asp Trp Leu Leu Leu Gly Glu Val Pro Gly Gln Asp Leu Leu Ser Ser His Leu Ala Pro Ala Glu Lys Val Ser
Neomycin Phosphotransferase

CATCATGGCTGATGCAATGCGGCGGCTGCATACGCTTGATCCGGCTACCTGCCCATTCGACCACCAAGCGAAACATCGCA 2080
GTAGTACCGACTACGTTACGCCGCCGACGTATGCGAACTAGGCCGATGGACGGGTAAGCTGGTGGTTCGCTTTGTAGCGT
Ile Met Ala Asp Ala Met Arg Arg Leu His Thr Leu Asp Pro Ala Thr Cys Pro Phe Asp His Gln Ala Lys His Arg
Neomycin Phosphotransferase

TCGAGCGAGCACGTACTCGGATGGAAGCCGGTCTTGTCGATCAGGATGATCTGGACGAAGAGCATCAGGGGCTCGCGCCA 2160
AGCTCGCTCGTGCATGAGCCTACCTTCGGCCAGAACAGCTAGTCCTACTAGACCTGCTTCTCGTAGTCCCCGAGCGCGGT
Ile Glu Arg Ala Arg Thr Arg Met Glu Ala Gly Leu Val Asp Gln Asp Asp Leu Asp Glu Glu His Gln Gly Leu Ala Pro
Neomycin Phosphotransferase

                                SphI                                NcoI
GCCGAACTGTTCGCCAGGCTCAAGGCGCGCATGCCCGACGGCGAGGATCTCGTCGTGACCCATGGCGATGCCTGCTTGCC 2240
CGGCTTGACAAGCGGTCCGAGTTCCGCGCGTACGGGCTGCCGCTCCTAGAGCAGCACTGGGTACCGCTACGGACGAACGG
Ala Glu Leu Phe Ala Arg Leu Lys Ala Arg Met Pro Asp Gly Glu Asp Leu Val Val Thr His Gly Asp Ala Cys Leu Pro
Neomycin Phosphotransferase

                                                            NaeI
GAATATCATGGTGGAAAATGGCCGCTTTTCTGGATTCATCGACTGTGGCCGGCTGGGTGTGGCGGACCGCTATCAGGACA 2320
CTTATAGTACCACCTTTTACCGGCGAAAAGACCTAAGTAGCTGACACCGGCCGACCCACACCGCCTGGCGATAGTCCTGT
Asn Ile Met Val Glu Asn Gly Arg Phe Ser Gly Phe Ile Asp Cys Gly Arg Leu Gly Val Ala Asp Arg Tyr Gln Asp
Neomycin Phosphotransferase

TAGCGTTGGCTACCCGTGATATTGCTGAAGAGCTTGGCGGCGAATGGGCTGACCGCTTCCTCGTGCTTTACGGTATCGCC 2400
ATCGCAACCGATGGGCACTATAACGACTTCTCGAACCGCCGCTTACCCGACTGGCGAAGGAGCACGAAATGCCATAGCGG
Ile Ala Leu Ala Thr Arg Asp Ile Ala Glu Glu Leu Gly Gly Glu Trp Ala Asp Arg Phe Leu Val Leu Tyr Gly Ile Ala
Neomycin Phosphotransferase

GCTCCCGATTCGCAGCGCATCGCCTTCTATCGCCTTCTTGACGAGTTCTTCTGAGCGGGACTCTGGGGTTCGAAATGACC 2480
CGAGGGCTAAGCGTCGCGTAGCGGAAGATAGCGGAAGAACTGCTCAAGAAGACTCGCCCTGAGACCCCAAGCTTTACTGG
Ala Pro Asp Ser Gln Arg Ile Ala Phe Tyr Arg Leu Leu Asp Glu Phe Phe •
Neomycin Phosphotransferase
```

FIG. 14 (cont)

Thursday, June 13, 2002 3:42 PM
GD2407 pLNBLV-YFP Map.MPD (1 > 7010) Site and Sequence

```
GACCAAGCGACGCCCAACCTGCCATCACGAGATTTCGATTCCACCGCCGCCTTCTATGAAAGGTTGGGCTTCGGAATCGT
-------------------------------------------------------------------------------- 2560
CTGGTTCGCTGCGGGTTGGACGGTAGTGCTCTAAAGCTAAGGTGGCGGCGGAAGATACTTTCCAACCCGAAGCCTTAGCA

          NaeI                                                            SmaI
TTTCCGGGACGCCGGCTGGATGATCCTCCAGCGCGGGGATCTCATGCTGGAGTTCTTCGCCCACCCCGGGCTCGATCCCC
-------------------------------------------------------------------------------- 2640
AAAGGCCCTGCGGCCGACCTACTAGGAGGTCGCGCCCCTAGAGTACGACCTCAAGAAGCGGGTGGGGCCCGAGCTAGGGG

 NruI         PvuII
TCGCGAGTTGGTTCAGCTGCTGCCTGAGGCTGGACGACCTCGCGGAGTTCTACCGGCAGTGCAAATCCGTCGGCATCCAG
-------------------------------------------------------------------------------- 2720
AGCGCTCAACCAAGTCGACGACGGACTCCGACCTGCTGGAGCGCCTCAAGATGGCCGTCACGTTTAGGCAGCCGTAGGTC

                                           PstI
GAAACCAGCAGCGGCTATCCGCGCATCCATGCCCCCGAACTGCAGGAGTGGGGAGGCACGATGGCCGCTTTGGTCGAGGC
-------------------------------------------------------------------------------- 2800
CTTTGGTCGTCGCCGATAGGCGCGTAGGTACGGGGGCTTGACGTCCTCACCCCTCCGTGCTACCGGCGAAACCAGCTCCG

BamHI
GGATCCTAGCAGAAAAATAAGACTTGATTCCCCCTTAAAATTACAACTGCTAGAAAATGAATGGCTCTCCCGCCTTTTTT
-------------------------------------------------------------------------------- 2880
CCTAGGATCGTCTTTTTATTCTGAACTAAGGGGGAATTTTAATGTTGACGATCTTTTACTTACCGAGAGGGCGGAAAAAA
                              BLV Pro
                            BLV Promoter

                                                        NarI                   PvuII
GAGGGGGAATCATTTGTATGAAAGATCATGCCGACCTAGGCGCCGCCACCGCCCCGTAAACCAGACAGAGACGTCAGCTG
-------------------------------------------------------------------------------- 2960
CTCCCCCTTAGTAAACATACTTTCTAGTACGGCTGGATCCGCGGCGGTGGCGGGGCATTTGGTCTGTCTCTGCAGTCGAC
                              BLV Pro
                            BLV Promoter

                      PvuII
CCAGAAAAGCTGGTGACGGCAGCTGGTGGCTAGAATCCCCGTACCTCCCCAACTTCCCCTTTCCCGAAAAATCCACACCC
-------------------------------------------------------------------------------- 3040
GGTCTTTTCGACCACTGCCGTCGACCACCGATCTTAGGGGCATGGAGGGGTTGAAGGGGAAAGGGCTTTTTAGGTGTGGG
                              BLV Pro
                            BLV Promoter

                                                         NaeI
TGAGCTGCTGACCTCACCTGCTGATAAATTAATAAAATGCCGGCCCTGTCGAGTTAGCGGCACCAGAAGCGTTCTTCTCC
-------------------------------------------------------------------------------- 3120
ACTCGACGACTGGAGTGGACGACTATTTAATTATTTTACGGCCGGGACAGCTCAATCGCCGTGGTCTTCGCAAGAAGAGG
                              BLV Pro
                            BLV Promoter
```

FIG. 14 (cont)

Thursday, June 13, 2002 3:42 PM
GD2407 pLNBLV-YFP Map.MPD (1 > 7010) Site and Sequence

```
                                          XhoI     HindIII
TGAGACCCTCGTGCTCAGCTCTCGGTCCTGCCTCGAGAAGCTTGTTATCACAAGTTTGTACAAAAAAGCAGGCTTCGAAG 3200
ACTCTGGGAGCACGAGTCGAGAGCCAGGACGGAGCTCTTCGAACAATAGTGTTCAAACATGTTTTTTCGTCCGAAGCTTC
BLV Pro
BLV Promoter                                                attB1

                                            NcoI
GAGATAGAACCAATTCTCTAAGGAAATACTTAACCATGGTGAGCAAGGGCGAGGAGCTGTTCACCGGGGTGGTGCCCATC 3280
CTCTATCTTGGTTAAGAGATTCCTTTATGAATTGGTACCACTCGTTCCCGCTCCTCGACAAGTGGCCCCACCACGGGTAG
                                           Met Val Ser Lys Gly Glu Glu Leu Phe Thr Gly Val Val Pro Ile
                                           EYFP

CTGGTCGAGCTGGACGGCGACGTAAACGGCCACAAGTTCAGCGTGTCCGGCGAGGGCGAGGGCGATGCCACCTACGGCAA 3360
GACCAGCTCGACCTGCCGCTGCATTTGCCGGTGTTCAAGTCGCACAGGCCGCTCCCGCTCCCGCTACGGTGGATGCCGTT
Leu Val Glu Leu Asp Gly Asp Val Asn Gly His Lys Phe Ser Val Ser Gly Glu Gly Glu Gly Asp Ala Thr Tyr Gly Lys
EYFP

GCTGACCCTGAAGTTCATCTGCACCACCGGCAAGCTGCCCGTGCCCTGGCCCACCCTCGTGACCACCTTCGGCTACGGCC 3440
CGACTGGGACTTCAAGTAGACGTGGTGGCCGTTCGACGGGCACGGGACCGGGTGGGAGCACTGGTGGAAGCCGATGCCGG
Leu Thr Leu Lys Phe Ile Cys Thr Thr Gly Lys Leu Pro Val Pro Trp Pro Thr Leu Val Thr Thr Phe Gly Tyr Gly
EYFP

   PstI
TGCAGTGCTTCGCCCGCTACCCCGACCACATGAAGCAGCACGACTTCTTCAAGTCCGCCATGCCCGAAGGCTACGTCCAG 3520
ACGTCACGAAGCGGGCGATGGGGCTGGTGTACTTCGTCGTGCTGAAGAAGTTCAGGCGGTACGGGCTTCCGATGCAGGTC
Leu Gln Cys Phe Ala Arg Tyr Pro Asp His Met Lys Gln His Asp Phe Phe Lys Ser Ala Met Pro Glu Gly Tyr Val Gln
EYFP

GAGCGCACCATCTTCTTCAAGGACGACGGCAACTACAAGACCCGCGCCGAGGTGAAGTTCGAGGGCGACACCCTGGTGAA 3600
CTCGCGTGGTAGAAGAAGTTCCTGCTGCCGTTGATGTTCTGGGCGCGGCTCCACTTCAAGCTCCCGCTGTGGGACCACTT
Glu Arg Thr Ile Phe Phe Lys Asp Asp Gly Asn Tyr Lys Thr Arg Ala Glu Val Lys Phe Glu Gly Asp Thr Leu Val Asn
EYFP

CCGCATCGAGCTGAAGGGCATCGACTTCAAGGAGGACGGCAACATCCTGGGGCACAAGCTGGAGTACAACTACAACAGCC 3680
GGCGTAGCTCGACTTCCCGTAGCTGAAGTTCCTCCTGCCGTTGTAGGACCCCGTGTTCGACCTCATGTTGATGTTGTCGG
Arg Ile Glu Leu Lys Gly Ile Asp Phe Lys Glu Asp Gly Asn Ile Leu Gly His Lys Leu Glu Tyr Asn Tyr Asn Ser
EYFP

ACAACGTCTATATCATGGCCGACAAGCAGAAGAACGGCATCAAGGTGAACTTCAAGATCCGCCACAACATCGAGGACGGC 3760
TGTTGCAGATATAGTACCGGCTGTTCGTCTTCTTGCCGTAGTTCCACTTGAAGTTCTAGGCGGTGTTGTAGCTCCTGCCG
His Asn Val Tyr Ile Met Ala Asp Lys Gln Lys Asn Gly Ile Lys Val Asn Phe Lys Ile Arg His Asn Ile Glu Asp Gly
EYFP
```

FIG. 14 (cont)

Thursday, June 13, 2002 3:42 PM
GD2407 pLNBLV-YFP Map.MPD (1 > 7010) Site and Sequence

```
AGCGTGCAGCTCGCCGACCACTACCAGCAGAACACCCCCATCGGCGACGGCCCCGTGCTGCTGCCCGACAACCACTACCT
-------------------------------------------------------------------------------- 3840
TCGCACGTCGAGCGGCTGGTGATGGTCGTCTTGTGGGGGTAGCCGCTGCCGGGGCACGACGACGGGCTGTTGGTGATGGA
Ser Val Gln Leu Ala Asp His Tyr Gln Gln Asn Thr Pro Ile Gly Asp Gly Pro Val Leu Leu Pro Asp Asn His Tyr Leu
EYFP

GAGCTACCAGTCCGCCCTGAGCAAAGACCCCAACGAGAAGCGCGATCACATGGTCCTGCTGGAGTTCGTGACCGCCGCCG
-------------------------------------------------------------------------------- 3920
CTCGATGGTCAGGCGGGACTCGTTTCTGGGGTTGCTCTTCGCGCTAGTGTACCAGGACGACCTCAAGCACTGGCGGCGGC
Ser Tyr Gln Ser Ala Leu Ser Lys Asp Pro Asn Glu Lys Arg Asp His Met Val Leu Leu Glu Phe Val Thr Ala Ala
EYFP

NotI XhoI EcoRV XbaI
GGATCACTCTCGGCATGGACGAGCTGTACAAGTAAAGCGGCCGCACTCGAGATATCTAGACCCAGCTTTCTTGTACAAAG
-------------------------------------------------------------------------------- 4000
CCTAGTGAGAGCCGTACCTGCTCGACATGTTCATTTCGCCGGCGTGAGCTCTATAGATCTGGGTCGAAAGAACATGTTTC
Gly Ile Thr Leu Gly Met Asp Glu Leu Tyr Lys •
EYFP                                                        attB2
                                                            attB2

ClaI
TGGTGATAACATCGATAAAATAAAAGATTTTATTTAGTCTCCAGAAAAAGGGGGGAATGAAAGACCCCACCTGTAGGTTT
-------------------------------------------------------------------------------- 4080
ACCACTATTGTAGCTATTTTATTTTCTAAAATAAATCAGAGGTCTTTTTCCCCCCTTACTTTCTGGGGTGGACATCCAAA
att                                                         3' LTR
attB                                                        3' LTR MoMLV

NheI
GGCAAGCTAGCTTAAGTAACGCCATTTTGCAAGGCATGGAAAAATACATAACTGAGAATAGAGAAGTTCAGATCAAGGTC
-------------------------------------------------------------------------------- 4160
CCGTTCGATCGAATTCATTGCGGTAAAACGTTCCGTACCTTTTTATGTATTGACTCTTATCTCTTCAAGTCTAGTTCCAG
3' LTR
3' LTR MoMLV

PvuII EcoRV
AGGAACAGATGGAACAGCTGAATATGGGCCAAACAGGATATCTGTGGTAAGCAGTTCCTGCCCCGGCTCAGGGCCAAGAA
-------------------------------------------------------------------------------- 4240
TCCTTGTCTACCTTGTCGACTTATACCCGGTTTGTCCTATAGACACCATTCGTCAAGGACGGGGCCGAGTCCCGGTTCTT
3' LTR
3' LTR MoMLV

PvuII EcoRV
CAGATGGAACAGCTGAATATGGGCCAAACAGGATATCTGTGGTAAGCAGTTCCTGCCCCGGCTCAGGGCCAAGAACAGAT
-------------------------------------------------------------------------------- 4320
GTCTACCTTGTCGACTTATACCCGGTTTGTCCTATAGACACCATTCGTCAAGGACGGGGCCGAGTCCCGGTTCTTGTCTA
3' LTR
3' LTR MoMLV
```

FIG. 14 (cont)

Thursday, June 13, 2002 3:42 PM
GD2407 pLNBLV-YFP Map.MPD (1 > 7010) Site and Sequence XbaI GGTCCCCAGATGCGGTCCAGCCCTCAGCAGTTTCTAGAGAACCATCAGATGTTTCCAGGGTGCCCCAAGGACCTGAAATG 4400
CCAGGGGTCTACGCCAGGTCGGGAGTCGTCAAAGATCTCTTGGTAGTCTACAAAGGTCCCACGGGGTTCCTGGACTTTAC 3' LTR
3' LTR MoMLV SacI ACCCTGTGCCTTATTTGAACTAACCAATCAGTTCGCTTCTCGCTTCTGTTCGCGCGCTTCTGCTCCCCGAGCTCAATAAA 4480
TGGGACACGGAATAAACTTGATTGGTTAGTCAAGCGAAGAGCGAAGACAAGCGCGCGAAGACGAGGGGCTCGAGTTATTT 3' LTR
3' LTR MoMLV NarI SmaI KpnI AGAGCCCACAACCCCTCACTCGGGGCGCCAGTCCTCCGATTGACTGAGTCGCCCGGGTACCCGTGTATCCAATAAACCCT 4560
TCTCGGGTGTTGGGGAGTGAGCCCCGCGGTCAGGAGGCTAACTGACTCAGCGGGCCCATGGGCACATAGGTTATTTGGGA 3' LTR
3' LTR MoMLV CTTGCAGTTGCATCCGACTTGTGGTCTCGCTGTTCCTTGGGAGGGTCTCCTCTGAGTGATTGACTACCCGTCAGCGGGGG 4640
GAACGTCAACGTAGGCTGAACACCAGAGCGACAAGGAACCCTCCCAGAGGAGACTCACTAACTGATGGGCAGTCGCCCCC 3' LTR
3' LTR MoMLV TCTTTCATTTGGGGGCTCGTCCGGGATCGGGAGACCCCTGCCCAGGGACCACCGACCCACCACCGGGAGGTAAGCTGGCT 4720
AGAAAGTAAACCCCCGAGCAGGCCCTAGCCCTCTGGGGACGGGTCCCTGGTGGCTGGGTGGTGGCCCTCCATTCGACCGA 3' LTR
3' LTR Mo GCCTCGCGCGTTTCGGTGATGACGGTGAAAACCTCTGACACATGCAGCTCCCGGAGACGGTCACAGCTTGTCTGTAAGCG 4800
CGGAGCGCGCAAAGCCACTACTGCCACTTTTGGAGACTGTGTACGTCGAGGGCCTCTGCCAGTGTCGAACAGACATTCGC GATGCCGGGAGCAGACAAGCCCGTCAGGGCGCGTCAGCGGGTGTTGGCGGGTGTCGGGGCGCAGCCATGACCCAGTCACG 4880
CTACGGCCCTCGTCTGTTCGGGCAGTCCCGCGCAGTCGCCCACAACCGCCCACAGCCCCGCGTCGGTACTGGGTCAGTGC NdeI TAGCGATAGCGGAGTGTATACTGGCTTAACTATGCGGCATCAGAGCAGATTGTACTGAGAGTGCACCATATGCGGTGTGA 4960
ATCGCTATCGCCTCACATATGACCGAATTGATACGCCGTAGTCTCGTCTAACATGACTCTCACGTGGTATACGCCACACT AATACCGCACAGATGCGTAAGGAGAAAATACCGCATCAGGCGCTCTTCCGCTTCCTCGCTCACTGACTCGCTGCGCTCGG 5040
TTATGGCGTGTCTACGCATTCCTCTTTTATGGCGTAGTCCGCGAGAAGGCGAAGGAGCGAGTGACTGAGCGACGCGAGCC

FIG. 14 (cont)

Thursday, June 13, 2002 3:42 PM
GD2407 pLNBLV-YFP Map.MPD (1 > 7010) Site and Sequence

```
TCGTTCGGCTGCGGCGAGCGGTATCAGCTCACTCAAAGGCGGTAATACGGTTATCCACAGAATCAGGGGATAACGCAGGA
--------+---------+---------+---------+---------+---------+---------+---------+ 5120
AGCAAGCCGACGCCGCTCGCCATAGTCGAGTGAGTTTCCGCCATTATGCCAATAGGTGTCTTAGTCCCCTATTGCGTCCT

AAGAACATGTGAGCAAAAGGCCAGCAAAAGGCCAGGAACCGTAAAAAGGCCGCGTTGCTGGCGTTTTTCCATAGGCTCCG
--------+---------+---------+---------+---------+---------+---------+---------+ 5200
TTCTTGTACACTCGTTTTCCGGTCGTTTTCCGGTCCTTGGCATTTTTCCGGCGCAACGACCGCAAAAAGGTATCCGAGGC

CCCCCCTGACGAGCATCACAAAAATCGACGCTCAAGTCAGAGGTGGCGAAACCCGACAGGACTATAAAGATACCAGGCGT
--------+---------+---------+---------+---------+---------+---------+---------+ 5280
GGGGGGACTGCTCGTAGTGTTTTTAGCTGCGAGTTCAGTCTCCACCGCTTTGGGCTGTCCTGATATTTCTATGGTCCGCA

TTCCCCCTGGAAGCTCCCTCGTGCGCTCTCCTGTTCCGACCCTGCCGCTTACCGGATACCTGTCCGCCTTTCTCCCTTCG
--------+---------+---------+---------+---------+---------+---------+---------+ 5360
AAGGGGGACCTTCGAGGGAGCACGCGAGAGGACAAGGCTGGGACGGCGAATGGCCTATGGACAGGCGGAAAGAGGGAAGC

GGAAGCGTGGCGCTTTCTCATAGCTCACGCTGTAGGTATCTCAGTTCGGTGTAGGTCGTTCGCTCCAAGCTGGGCTGTGT
--------+---------+---------+---------+---------+---------+---------+---------+ 5440
CCTTCGCACCGCGAAAGAGTATCGAGTGCGACATCCATAGAGTCAAGCCACATCCAGCAAGCGAGGTTCGACCCGACACA

GCACGAACCCCCCGTTCAGCCCGACCGCTGCGCCTTATCCGGTAACTATCGTCTTGAGTCCAACCCGGTAAGACACGACT
--------+---------+---------+---------+---------+---------+---------+---------+ 5520
CGTGCTTGGGGGGCAAGTCGGGCTGGCGACGCGGAATAGGCCATTGATAGCAGAACTCAGGTTGGGCCATTCTGTGCTGA

TATCGCCACTGGCAGCAGCCACTGGTAACAGGATTAGCAGAGCGAGGTATGTAGGCGGTGCTACAGAGTTCTTGAAGTGG
--------+---------+---------+---------+---------+---------+---------+---------+ 5600
ATAGCGGTGACCGTCGTCGGTGACCATTGTCCTAATCGTCTCGCTCCATACATCCGCCACGATGTCTCAAGAACTTCACC

TGGCCTAACTACGGCTACACTAGAAGGACAGTATTTGGTATCTGCGCTCTGCTGAAGCCAGTTACCTTCGGAAAAAGAGT
--------+---------+---------+---------+---------+---------+---------+---------+ 5680
ACCGGATTGATGCCGATGTGATCTTCCTGTCATAAACCATAGACGCGAGACGACTTCGGTCAATGGAAGCCTTTTTCTCA

TGGTAGCTCTTGATCCGGCAAACAAACCACCGCTGGTAGCGGTGGTTTTTTTGTTTGCAAGCAGCAGATTACGCGCAGAA
--------+---------+---------+---------+---------+---------+---------+---------+ 5760
ACCATCGAGAACTAGGCCGTTTGTTTGGTGGCGACCATCGCCACCAAAAAAACAAACGTTCGTCGTCTAATGCGCGTCTT

AAAAAGGATCTCAAGAAGATCCTTTGATCTTTTCTACGGGGTCTGACGCTCAGTGGAACGAAAACTCACGTTAAGGGATT
--------+---------+---------+---------+---------+---------+---------+---------+ 5840
TTTTTCCTAGAGTTCTTCTAGGAAACTAGAAAAGATGCCCCAGACTGCGAGTCACCTTGCTTTTGAGTGCAATTCCCTAA

     BspHI                                    DraI                  DraI
TTGGTCATGAGATTATCAAAAAGGATCTTCACCTAGATCCTTTTAAATTAAAAATGAAGTTTTAAATCAATCTAAAGTAT
--------+---------+---------+---------+---------+---------+---------+---------+ 5920
AACCAGTACTCTAATAGTTTTTCCTAGAAGTGGATCTAGGAAAATTTAATTTTTACTTCAAAATTTAGTTAGATTTCATA

ATATGAGTAAACTTGGTCTGACAGTTACCAATGCTTAATCAGTGAGGCACCTATCTCAGCGATCTGTCTATTTCGTTCAT
--------+---------+---------+---------+---------+---------+---------+---------+ 6000
TATACTCATTTGAACCAGACTGTCAATGGTTACGAATTAGTCACTCCGTGGATAGAGTCGCTAGACAGATAAAGCAAGTA
                        • Trp His Lys Ile Leu Ser Ala Gly Ile Glu Ala Ile Gln Arg Asn Arg Glu Asp
                        L______________________ b-Lactamse ______________________
```

FIG. 14 (cont)

Thursday, June 13, 2002 3:42 PM
GD2407 pLNBLV-YFP Map.MPD (1 > 7010) Site and Sequence

```
CCATAGTTGCCTGACTCCCCGTCGTGTAGATAACTACGATACGGGAGGGCTTACCATCTGGCCCCAGTGCTGCAATGATA
---------+---------+---------+---------+---------+---------+---------+---------+ 6080
GGTATCAACGGACTGAGGGGCAGCACATCTATTGATGCTATGCCCTCCCGAATGGTAGACCGGGGTCACGACGTTACTAT
 Met Thr Ala Gln Ser Gly Thr Thr Tyr Ile Val Val Ile Arg Ser Pro Lys Gly Asp Pro Gly Leu Ala Ala Ile Ile
                                   b-Lactamse

CCGCGAGACCCACGCTCACCGGCTCCAGATTTATCAGCAATAAACCAGCCAGCCGGAAGGGCCGAGCGCAGAAGTGGTCC
---------+---------+---------+---------+---------+---------+---------+---------+ 6160
GGCGCTCTGGGTGCGAGTGGCCGAGGTCTAAATAGTCGTTATTTGGTCGGTCGGCCTTCCCGGCTCGCGTCTTCACCAGG
Gly Arg Ser Gly Arg Glu Gly Ala Gly Ser Lys Asp Ala Ile Phe Trp Gly Ala Pro Leu Ala Ser Arg Leu Leu Pro Gly
                                   b-Lactamse

                                                                                FspI
TGCAACTTTATCCGCCTCCATCCAGTCTATTAATTGTTGCCGGGAAGCTAGAGTAAGTAGTTCGCCAGTTAATAGTTTGC
---------+---------+---------+---------+---------+---------+---------+---------+ 6240
ACGTTGAAATAGGCGGAGGTAGGTCAGATAATTAACAACGGCCCTTCGATCTCATTCATCAAGCGGTCAATTATCAAACG
 Ala Val Lys Asp Ala Glu Met Trp Asp Ile Leu Gln Gln Arg Ser Ala Leu Thr Leu Leu Glu Gly Thr Leu Leu Lys Arg
                                   b-Lactamse

                   PstI
GCAACGTTGTTGCCATTGCTGCAGGCATCGTGGTGTCACGCTCGTCGTTTGGTATGGCTTCATTCAGCTCCGGTTCCCAA
---------+---------+---------+---------+---------+---------+---------+---------+ 6320
CGTTGCAACAACGGTAACGACGTCCGTAGCACCACAGTGCGAGCAGCAAACCATACCGAAGTAAGTCGAGGCCAAGGGTT
 Leu Thr Thr Ala Met Ala Ala Pro Met Thr Thr Asp Arg Glu Asp Asn Pro Ile Ala Glu Asn Leu Glu Pro Glu Trp
                                   b-Lactamse

                                                                      PvuI
CGATCAAGGCGAGTTACATGATCCCCCATGTTGTGCAAAAAAGCGGTTAGCTCCTTCGGTCCTCCGATCGTTGTCAGAAG
---------+---------+---------+---------+---------+---------+---------+---------+ 6400
GCTAGTTCCGCTCAATGTACTAGGGGGTACAACACGTTTTTTCGCCAATCGAGGAAGCCAGGAGGCTAGCAACAGTCTTC
Arg Asp Leu Arg Thr Val His Asp Gly Met Asn His Leu Phe Ala Thr Leu Glu Lys Pro Gly Gly Ile Thr Thr Leu Leu
                                   b-Lactamse

TAAGTTGGCCGCAGTGTTATCACTCATGGTTATGGCAGCACTGCATAATTCTCTTACTGTCATGCCATCCGTAAGATGCT
---------+---------+---------+---------+---------+---------+---------+---------+ 6480
ATTCAACCGGCGTCACAATAGTGAGTACCAATACCGTCGTGACGTATTAAGAGAATGACAGTACGGTAGGCATTCTACGA
 Leu Asn Ala Ala Thr Asn Asp Ser Met Thr Ile Ala Ala Ser Cys Leu Glu Arg Val Thr Met Gly Asp Thr Leu His Lys
                                   b-Lactamse

TTTCTGTGACTGGTGAGTACTCAACCAAGTCATTCTGAGAATAGTGTATGCGGCGACCGAGTTGCTCTTGCCCGGCGTCA
---------+---------+---------+---------+---------+---------+---------+---------+ 6560
AAAGACACTGACCACTCATGAGTTGGTTCAGTAAGACTCTTATCACATACGCCGCTGGCTCAACGAGAACGGGCCGCAGT
 Glu Thr Val Pro Ser Tyr Glu Val Leu Asp Asn Gln Ser Tyr His Ile Arg Arg Gly Leu Gln Glu Gln Gly Ala Asp
                                   b-Lactamse

                                         DraI
ACACGGGATAATACCGCGCCACATAGCAGAACTTTAAAAGTGCTCATCATTGGAAAACGTTCTTCGGGGCGAAAACTCTC
---------+---------+---------+---------+---------+---------+---------+---------+ 6640
TGTGCCCTATTATGGCGCGGTGTATCGTCTTGAAATTTTCACGAGTAGTAACCTTTTGCAAGAAGCCCCGCTTTTGAGAG
Val Arg Ser Leu Val Ala Gly Cys Leu Leu Val Lys Phe Thr Ser Met Met Pro Phe Arg Glu Glu Pro Arg Phe Ser Glu
                                   b-Lactamse
```

FIG. 14 (cont)

Thursday, June 13, 2002 3:42 PM
GD2407 pLNBLV-YFP Map.MPD (1 > 7010) Site and Sequence

```
AAGGATCTTACCGCTGTTGAGATCCAGTTCGATGTAACCCACTCGTGCACCCAACTGATCTTCAGCATCTTTTACTTTCA
---------+---------+---------+---------+---------+---------+---------+---------+ 6720
TTCCTAGAATGGCGACAACTCTAGGTCAAGCTACATTGGGTGAGCACGTGGGTTGACTAGAAGTCGTAGAAAATGAAAGT
Leu Ile Lys Gly Ser Asn Leu Asp Leu Glu Ile Tyr Gly Val Arg Ala Gly Leu Gln Asp Glu Ala Asp Lys Val Lys Val
-------------------------------b-Lactamse-------------------------------

CCAGCGTTTCTGGGTGAGCAAAAACAGGAAGGCAAAATGCCGCAAAAAAGGGAATAAGGGCGACACGGAAATGTTGAATA
---------+---------+---------+---------+---------+---------+---------+---------+ 6800
GGTCGCAAAGACCCACTCGTTTTTGTCCTTCCGTTTTACGGCGTTTTTTCCCTTATTCCCGCTGTGCCTTTACAACTTAT
Leu Thr Glu Pro His Ala Phe Val Pro Leu Cys Phe Ala Ala Phe Phe Pro Ile Leu Ala Val Arg Phe His Gln Ile
-------------------------------b-Lactamse-------------------------------

                                                        BspHI
CTCATACTCTTCCTTTTTCAATATTATTGAAGCATTTATCAGGGTTATTGTCTCATGAGCGGATACATATTTGAATGTAT
---------+---------+---------+---------+---------+---------+---------+---------+ 6880
GAGTATGAGAAGGAAAAAGTTATAATAACTTCGTAAATAGTCCCAATAACAGAGTACTCGCCTATGTATAAACTTACATA
Ser Met
-b-Lac

                                                                              BspHI
TTAGAAAAATAAACAAATAGGGGTTCCGCGCACATTTCCCCGAAAAGTGCCACCTGACGTCTAAGAAACCATTATTATCA
---------+---------+---------+---------+---------+---------+---------+---------+ 6960
AATCTTTTTATTTGTTTATCCCCAAGGCGCGTGTAAAGGGGCTTTTCACGGTGGACTGCAGATTCTTTGGTAATAATAGT

TGACATTAACCTATAAAAATAGGCGTATCACGAGGCCCTTTCGTCTTCAA
---------+---------+---------+---------+---------> 7010
ACTGTAATTGGATATTTTTATCCGCATAGTGCTCCGGGAAAGCAGAAGTT
```

FIG. 16

Tuesday, July 02, 2002 2:11 PM
pLNHiv-YFP Map.MPD (1 > 7121) Site and Sequence
Enzymes : 36 of 538 enzymes (Filtered)
Settings : Circular, Certain Sites Only, Standard Genetic Code

```
GAATTAATTCATACCAGATCACCGAAAACTGTCCTCCAAATGTGTCCCCCTCACACTCCCAAATTCGCGGGCTTCTGCCT  80
CTTAATTAAGTATGGTCTAGTGGCTTTTGACAGGAGGTTTACACAGGGGGAGTGTGAGGGTTTAAGCGCCCGAAGACGGA

SacII
CTTAGACCACTCTACCCTATTCCCCACACTCACCGGAGCCAAAGCCGCGGCCCTTCCGTTTCTTTGCTTTTGAAAGACCC  160
GAATCTGGTGAGATGGGATAAGGGGTGTGAGTGGCCTCGGTTTCGGCGCCGGGAAGGCAAAGAAACGAAAACTTTCTGGG
5' LTR

NheI
CACCCGTAGGTGGCAAGCTAGCTTAAGTAACGCCACTTTGCAAGGCATGGAAAAATACATAACTGAGAATAGAAAAGTTC  240
GTGGGCATCCACCGTTCGATCGAATTCATTGCGGTGAAACGTTCCGTACCTTTTTATGTATTGACTCTTATCTTTTCAAG
5' LTR

PvuII EcoRV
AGATCAAGGTCAGGAACAAAGAAACAGCTGAATACCAAACAGGATATCTGTGGTAAGCGGTTCCTGCCCCGGCTCAGGGC  320
TCTAGTTCCAGTCCTTGTTTCTTTGTCGACTTATGGTTTGTCCTATAGACACCATTCGCCAAGGACGGGGCCGAGTCCCG
5' LTR

PvuII EcoRV
CAAGAACAGATGAGACAGCTGAGTGATGGGCCAAACAGGATATCTGTGGTAAGCAGTTCCTGCCCCGGCTCGGGGCCAAG  400
GTTCTTGTCTACTCTGTCGACTCACTACCCGGTTTGTCCTATAGACACCATTCGTCAAGGACGGGGCCGAGCCCCGGTTC
5' LTR

AACAGATGGTCCCCAGATGCGGTCCAGCCCTCAGCAGTTTCTAGTGAATCATCAGATGTTTCCAGGGTGCCCCAAGGACC  480
TTGTCTACCAGGGGTCTACGCCAGGTCGGGAGTCGTCAAAGATCACTTAGTAGTCTACAAAGGTCCCACGGGGTTCCTGG
5' LTR

TGAAAATGACCCTGTACCTTATTTGAACTAACCAATCAGTTCGCTTCTCGCTTCTGTTCGCGCGCTTCCGCTCTCCGAGC  560
ACTTTTACTGGGACATGGAATAAACTTGATTGGTTAGTCAAGCGAAGAGCGAAGACAAGCGCGCGAAGGCGAGAGGCTCG
5' LTR
```

FIG. 16 (cont)

Tuesday, July 02, 2002 2:11 PM
pLNHiv-YFP Map.MPD (1 > 7121) Site and Sequence

SacI AscI SmaI KpnI

TCAATAAAAGAGCCCACAACCCCTCACTCGGCGCGCCAGTCTTCCGATAGACTGCGTCGCCCGGGTACCCGTATTCCCAA 640
AGTTATTTTCTCGGGTGTTGGGGAGTGAGCCGCGCGGTCAGAAGGCTATCTGACGCAGCGGGCCCATGGGCATAAGGGTT

5' LTR

TAAAGCCTCTTGCTGTTTGCATCCGAATCGTGGTCTCGCTGTTCCTTGGGAGGGTCTCCTCTGAGTGATTGACTACCCAC 720
ATTTCGGAGAACGACAAACGTAGGCTTAGCACCAGAGCGACAAGGAACCCTCCCAGAGGAGACTCACTAACTGATGGGTG

5' LTR

GACGGGGGTCTTTCATTTGGGGGCTCGTCCGGGATTTGGAGACCCCTGCCCAGGGACCACCGACCCACCACCGGGAGGTA 800
CTGCCCCCAGAAAGTAAACCCCCGAGCAGGCCCTAAACCTCTGGGGACGGGTCCCTGGTGGCTGGGTGGTGGCCCTCCAT

5' LTR

SpeI

AGCTGGCCAGCAACTTATCTGTGTCTGTCCGATTGTCTAGTGTCTATGTTTGATGTTATGCGCCTGCGTCTGTACTAGTT 880
TCGACCGGTCGTTGAATAGACACAGACAGGCTAACAGATCACAGATACAAACTACAATACGCGGACGCAGACATGATCAA

Extended Packaging Region

AGCTAACTAGCTCTGTATCTGGCGGACCCGTGGTGGAACTGACGAGTTCTGAACACCCGGCCGCAACCCTGGGAGACGTC 960
TCGATTGATCGAGACATAGACCGCCTGGGCACCACCTTGACTGCTCAAGACTTGTGGGCCGGCGTTGGGACCCTCTGCAG

Extended Packaging Region

CCAGGGACTTTGGGGGCCGTTTTTGTGGCCCGACCTGAGGAAGGGAGTCGATGTGGAATCCGACCCCGTCAGGATATGTG 1040
GGTCCCTGAAACCCCCGGCAAAAACACCGGGCTGGACTCCTTCCCTCAGCTACACCTTAGGCTGGGGCAGTCCTATACAC

Extended Packaging Region

GTTCTGGTAGGAGACGAGAACCTAAAACAGTTCCCGCCTCCGTCTGAATTTTTGCTTTCGGTTTGGAACCGAAGCCGCGC 1120
CAAGACCATCCTCTGCTCTTGGATTTTGTCAAGGGCGGAGGCAGACTTAAAAACGAAAGCCAAACCTTGGCTTCGGCGCG

Extended Packaging Region

PstI PstI

GTCTTGTCTGCTGCAGCGCTGCAGCATCGTTCTGTGTTGTCTCTGTCTGACTGTGTTTCTGTATTTGTCTGAAAATTAGG 1200
CAGAACAGACGACGTCGCGACGTCGTAGCAAGACACAACAGAGACAGACTGACACAAAGACATAAACAGACTTTTAATCC

Extended Packaging Region

FIG. 16 (cont)

Tuesday, July 02, 2002 2:11 PM
pLNHiv-YFP Map.MPD (1 > 7121) Site and Sequence

```
GCCAGACTGTTACCACTCCCTTAAGTTTGACCTTAGGTCACTGGAAAGATGTCGAGCGGATCGCTCACAACCAGTCGGTA 1280
CGGTCTGACAATGGTGAGGGAATTCAAACTGGAATCCAGTGACCTTTCTACAGCTCGCCTAGCGAGTGTTGGTCAGCCAT
Extended Packaging Region

                                           PstI
GATGTCAAGAAGAGACGTTGGGTTACCTTCTGCTCTGCAGAATGGCCAACCTTTAACGTCGGATGGCCGCGAGACGGCAC 1360
CTACAGTTCTTCTCTGCAACCCAATGGAAGACGAGACGTCTTACCGGTTGGAAATTGCAGCCTACCGGCGCTCTGCCGTG
Extended Packaging Region

CTTTAACCGAGACCTCATCACCCAGGTTAAGATCAAGGTCTTTTCACCTGGCCCGCATGGACACCCAGACCAGGTCCCCT 1440
GAAATTGGCTCTGGAGTAGTGGGTCCAATTCTAGTTCCAGAAAAGTGGACCGGGCGTACCTGTGGGTCTGGTCCAGGGGA
Extended Packaging Region

ACATCGTGACCTGGGAAGCCTTGGCTTTTGACCCCCCTCCCTGGGTCAAGCCCTTTGTACACCCTAAGCCTCCGCCTCCT 1520
TGTAGCACTGGACCCTTCGGAACCGAAAACTGGGGGGAGGGACCCAGTTCGGGAAACATGTGGGATTCGGAGGCGGAGGA
Extended Packaging Region

CTTCCTCCATCCGCCCCGTCTCTCCCCCTTGAACCTCCTCGTTCGACCCCGCCTCGATCCTCCCTTTATCCAGCCCTCAC 1600
GAAGGAGGTAGGCGGGGCAGAGAGGGGGAACTTGGAGGAGCAAGCTGGGGCGGAGCTAGGAGGGAAATAGGTCGGGAGTG
Extended Packaging Region

         NarI    EcoRI          BclI
TCCTTCTCTAGGCGCCGGAATTCCGATCTGATCAAGAGACAGGATGAGGATCGTTTCGCATGATTGAACAAGATGGATTG 1680
AGGAAGAGATCCGCGGCCTTAAGGCTAGACTAGTTCTCTGTCCTACTCCTAGCAAAGCGTACTAACTTGTTCTACCTAAC
· Extended Packaging                                            Met Ile Glu Gln Asp Gly Leu
                                                                NEO

CACGCAGGTTCTCCGGCCGCTTGGGTGGAGAGGCTATTCGGCTATGACTGGGCACAACAGACAATCGGCTGCTCTGATGC 1760
GTGCGTCCAAGAGGCCGGCGAACCCACCTCTCCGATAAGCCGATACTGACCCGTGTTGTCTGTTAGCCGACGAGACTACG
His Ala Gly Ser Pro Ala Ala Trp Val Glu Arg Leu Phe Gly Tyr Asp Trp Ala Gln Gln Thr Ile Gly Cys Ser Asp Ala
NEO

                                      NarI
CGCCGTGTTCCGGCTGTCAGCGCAGGGGCGCCCGGTTCTTTTTGTCAAGACCGACCTGTCCGGTGCCCTGAATGAACTGC 1840
GCGGCACAAGGCCGACAGTCGCGTCCCCGCGGGCCAAGAAAAACAGTTCTGGCTGGACAGGCCACGGGACTTACTTGACG
Ala Val Phe Arg Leu Ser Ala Gln Gly Arg Pro Val Leu Phe Val Lys Thr Asp Leu Ser Gly Ala Leu Asn Glu Leu
NEO
```

FIG. 16 (cont)

Tuesday, July 02, 2002 2:11 PM
pLNHiv-YFP Map.MPD (1 > 7121) Site and Sequence

```
PstI                                                     FspI PvuII
AGGACGAGGCAGCGCGGCTATCGTGGCTGGCCACGACGGGCGTTCCTTGCGCAGCTGTGCTCGACGTTGTCACTGAAGCG  1920
TCCTGCTCCGTCGCGCCGATAGCACCGACCGGTGCTGCCCGCAAGGAACGCGTCGACACGAGCTGCAACAGTGACTTCGC
Gln Asp Glu Ala Ala Arg Leu Ser Trp Leu Ala Thr Thr Gly Val Pro Cys Ala Ala Val Leu Asp Val Val Thr Glu Ala
NEO

GGAAGGGACTGGCTGCTATTGGGCGAAGTGCCGGGGCAGGATCTCCTGTCATCTCACCTTGCTCCTGCCGAGAAAGTATC  2000
CCTTCCCTGACCGACGATAACCCGCTTCACGGCCCCGTCCTAGAGGACAGTAGAGTGGAACGAGGACGGCTCTTTCATAG
Gly Arg Asp Trp Leu Leu Leu Gly Glu Val Pro Gly Gln Asp Leu Leu Ser Ser His Leu Ala Pro Ala Glu Lys Val Ser
NEO

CATCATGGCTGATGCAATGCGGCGGCTGCATACGCTTGATCCGGCTACCTGCCCATTCGACCACCAAGCGAAACATCGCA  2080
GTAGTACCGACTACGTTACGCCGCCGACGTATGCGAACTAGGCCGATGGACGGGTAAGCTGGTGGTTCGCTTTGTAGCGT
Ile Met Ala Asp Ala Met Arg Arg Leu His Thr Leu Asp Pro Ala Thr Cys Pro Phe Asp His Gln Ala Lys His Arg
NEO

TCGAGCGAGCACGTACTCGGATGGAAGCCGGTCTTGTCGATCAGGATGATCTGGACGAAGAGCATCAGGGGCTCGCGCCA  2160
AGCTCGCTCGTGCATGAGCCTACCTTCGGCCAGAACAGCTAGTCCTACTAGACCTGCTTCTCGTAGTCCCCGAGCGCGGT
Ile Glu Arg Ala Arg Thr Arg Met Glu Ala Gly Leu Val Asp Gln Asp Asp Leu Asp Glu Glu His Gln Gly Leu Ala Pro
NEO

                                       SphI                      NcoI
GCCGAACTGTTCGCCAGGCTCAAGGCGCGCATGCCCGACGGCGAGGATCTCGTCGTGACCCATGGCGATGCCTGCTTGCC  2240
CGGCTTGACAAGCGGTCCGAGTTCCGCGCGTACGGGCTGCCGCTCCTAGAGCAGCACTGGGTACCGCTACGGACGAACGG
Ala Glu Leu Phe Ala Arg Leu Lys Ala Arg Met Pro Asp Gly Glu Asp Leu Val Val Thr His Gly Asp Ala Cys Leu Pro
NEO

                                                         NaeI
GAATATCATGGTGGAAAATGGCCGCTTTTCTGGATTCATCGACTGTGGCCGGCTGGGTGTGGCGGACCGCTATCAGGACA  2320
CTTATAGTACCACCTTTTACCGGCGAAAAGACCTAAGTAGCTGACACCGGCCGACCCACACCGCCTGGCGATAGTCCTGT
Asn Ile Met Val Glu Asn Gly Arg Phe Ser Gly Phe Ile Asp Cys Gly Arg Leu Gly Val Ala Asp Arg Tyr Gln Asp
NEO

TAGCGTTGGCTACCCGTGATATTGCTGAAGAGCTTGGCGGCGAATGGGCTGACCGCTTCCTCGTGCTTTACGGTATCGCC  2400
ATCGCAACCGATGGGCACTATAACGACTTCTCGAACCGCCGCTTACCCGACTGGCGAAGGAGCACGAAATGCCATAGCGG
Ile Ala Leu Ala Thr Arg Asp Ile Ala Glu Glu Leu Gly Gly Glu Trp Ala Asp Arg Phe Leu Val Leu Tyr Gly Ile Ala
NEO

GCTCCCGATTCGCAGCGCATCGCCTTCTATCGCCTTCTTGACGAGTTCTTCTGAGCGGGACTCTGGGGTTCGAAATGACC  2480
CGAGGGCTAAGCGTCGCGTAGCGGAAGATAGCGGAAGAACTGCTCAAGAAGACTCGCCCTGAGACCCCAAGCTTTACTGG
Ala Pro Asp Ser Gln Arg Ile Ala Phe Tyr Arg Leu Leu Asp Glu Phe Phe •
NEO
```

FIG. 16 (cont)

Tuesday, July 02, 2002 2:11 PM
pLNHiv-YFP Map.MPD (1 > 7121) Site and Sequence

```
GACCAAGCGACGCCCAACCTGCCATCACGAGATTTCGATTCCACCGCCGCCTTCTATGAAAGGTTGGGCTTCGGAATCGT
---------+---------+---------+---------+---------+---------+---------+---------+ 2560
CTGGTTCGCTGCGGGTTGGACGGTAGTGCTCTAAAGCTAAGGTGGCGGCGGAAGATACTTTCCAACCCGAAGCCTTAGCA

                 NaeI                                                       SmaI
TTTCCGGGACGCCGGCTGGATGATCCTCCAGCGCGGGGATCTCATGCTGGAGTTCTTCGCCCACCCCGGGCTCGATCCCC
---------+---------+---------+---------+---------+---------+---------+---------+ 2640
AAAGGCCCTGCGGCCGACCTACTAGGAGGTCGCGCCCCTAGAGTACGACCTCAAGAAGCGGGTGGGGCCCGAGCTAGGGG

  NruI              PvuII
TCGCGAGTTGGTTCAGCTGCTGCCTGAGGCTGGACGACCTCGCGGAGTTCTACCGGCAGTGCAAATCCGTCGGCATCCAG
---------+---------+---------+---------+---------+---------+---------+---------+ 2720
AGCGCTCAACCAAGTCGACGACGGACTCCGACCTGCTGGAGCGCCTCAAGATGGCCGTCACGTTTAGGCAGCCGTAGGTC

                                           PstI
GAAACCAGCAGCGGCTATCCGCGCATCCATGCCCCCGAACTGCAGGAGTGGGGAGGCACGATGGCCGCTTTGGTCGAGGC
---------+---------+---------+---------+---------+---------+---------+---------+ 2800
CTTTGGTCGTCGCCGATAGGCGCGTAGGTACGGGGGCTTGACGTCCTCACCCCTCCGTGCTACCGGCGAAACCAGCTCCG

 BamHI
GGATCCTGGAAGGGCTAATTTGGTCCCAAAGAAGACAAGAGATCCTTGATCTGTGGATCTACCACACACAAGGCTACTTC
---------+---------+---------+---------+---------+---------+---------+---------+ 2880
CCTAGGACCTTCCCGATTAAACCAGGGTTTCTTCTGTTCTCTAGGAACTAGACACCTAGATGGTGTGTGTTCCGATGAAG
                              HIV-1 Promoter

                                            EcoRV
CCTGATTGGCAGAATTACACACCAGGGCCAGGGATCAGATATCCACTGACCTTTGGATGGTGCTTCAAGCTAGTACCAGT
---------+---------+---------+---------+---------+---------+---------+---------+ 2960
GGACTAACCGTCTTAATGTGTGGTCCCGGTCCCTAGTCTATAGGTGACTGGAAACCTACCACGAAGTTCGATCATGGTCA
                              HIV-1 Promoter

TGAGCCAGAGAAGGTAGAAGAGGCCAATGAAGGAGAGAACAACAGCTTGTTACACCCTATGAGCCTGCATGGGATGGAGG
---------+---------+---------+---------+---------+---------+---------+---------+ 3040
ACTCGGTCTCTTCCATCTTCTCCGGTTACTTCCTCTCTTGTTGTCGAACAATGTGGGATACTCGGACGTACCCTACCTCC
                              HIV-1 Promoter

ACGCGGAGAAAGAAGTGTTAGTGTGGAGGTTTGACAGCAAACTAGCATTTCATCACATGGCCCGAGAGCTGCATCCGGAG
---------+---------+---------+---------+---------+---------+---------+---------+ 3120
TGCGCCTCTTTCTTCACAATCACACCTCCAAACTGTCGTTTGATCGTAAAGTAGTGTACCGGGCTCTCGACGTAGGCCTC
                              HIV-1 Promoter

TACTACAAAGACTGCTGACATCGAGCTTTCTACAAGGGACTTTCCGCTGGGGACTTTCCAGGGAGGCGTGGCCTGGGCGG
---------+---------+---------+---------+---------+---------+---------+---------+ 3200
ATGATGTTTCTGACGACTGTAGCTCGAAAGATGTTCCCTGAAAGGCGACCCCTGAAAGGTCCCTCCGCACCGGACCCGCC
                              HIV-1 Promoter
```

Tuesday, July 02, 2002 2:11 PM
pLNHiv-YFP Map.MPD (1 > 7121) Site and Sequence

FIG. 16 (cont)

Tuesday, July 02, 2002 2:11 PM
pLNHiv-YFP Map.MPD (1 > 7121) Site and Sequence

```
CTTCAAGATCCGCCACAACATCGAGGACGGCAGCGTGCAGCTCGCCGACCACTACCAGCAGAACACCCCCATCGGCGACG  3920
GAAGTTCTAGGCGGTGTTGTAGCTCCTGCCGTCGCACGTCGAGCGGCTGGTGATGGTCGTCTTGTGGGGGTAGCCGCTGC
 Phe Lys Ile Arg His Asn Ile Glu Asp Gly Ser Val Gln Leu Ala Asp His Tyr Gln Gln Asn Thr Pro Ile Gly Asp
                                        YFP

GCCCCGTGCTGCTGCCCGACAACCACTACCTGAGCTACCAGTCCGCCCTGAGCAAAGACCCCAACGAGAAGCGCGATCAC  4000
CGGGGCACGACGACGGGCTGTTGGTGATGGACTCGATGGTCAGGCGGGACTCGTTTCTGGGGTTGCTCTTCGCGCTAGTG
Gly Pro Val Leu Leu Pro Asp Asn His Tyr Leu Ser Tyr Gln Ser Ala Leu Ser Lys Asp Pro Asn Glu Lys Arg Asp His
                                        YFP

                                                                    NotI      XhoI
ATGGTCCTGCTGGAGTTCGTGACCGCCGCCGGGATCACTCTCGGCATGGACGAGCTGTACAAGTAAAGCGGCCGCACTCG  4080
TACCAGGACGACCTCAAGCACTGGCGGCGGCCCTAGTGAGAGCCGTACCTGCTCGACATGTTCATTTCGCCGGCGTGAGC
Met Val Leu Leu Glu Phe Val Thr Ala Ala Gly Ile Thr Leu Gly Met Asp Glu Leu Tyr Lys  •
                                   YFP

  EcoRV
   XbaI                                         ClaI
AGATATCTAGACCCAGCTTTCTTGTACAAAGTGGTGATAACATCGATAAAATAAAAGATTTTATTTAGTCTCCAGAAAAA  4160
TCTATAGATCTGGGTCGAAAGAACATGTTTCACCACTATTGTAGCTATTTTATTTTCTAAAATAAATCAGAGGTCTTTTT
                  att B2

                                           NheI
GGGGGGAATGAAAGACCCCACCTGTAGGTTTGGCAAGCTAGCTTAAGTAACGCCATTTTGCAAGGCATGGAAAAATACAT  4240
CCCCCCTTACTTTCTGGGGTGGACATCCAAACCGTTCGATCGAATTCATTGCGGTAAAACGTTCCGTACCTTTTTATGTA
                                 3' LTR

                                                    PvuII              EcoRV
AACTGAGAATAGAGAAGTTCAGATCAAGGTCAGGAACAGATGGAACAGCTGAATATGGGCCAAACAGGATATCTGTGGTA  4320
TTGACTCTTATCTCTTCAAGTCTAGTTCCAGTCCTTGTCTACCTTGTCGACTTATACCCGGTTTGTCCTATAGACACCAT
                                 3' LTR

                                               PvuII              EcoRV
AGCAGTTCCTGCCCCGGCTCAGGGCCAAGAACAGATGGAACAGCTGAATATGGGCCAAACAGGATATCTGTGGTAAGCAG  4400
TCGTCAAGGACGGGGCCGAGTCCCGGTTCTTGTCTACCTTGTCGACTTATACCCGGTTTGTCCTATAGACACCATTCGTC
                                 3' LTR
```

FIG. 16 (cont)

Tuesday, July 02, 2002 2:11 PM
pLNHiv-YFP Map.MPD (1 > 7121) Site and Sequence

```
                                                                                         XbaI
TTCCTGCCCCGGCTCAGGGCCAAGAACAGATGGTCCCCAGATGCGGTCCAGCCCTCAGCAGTTTCTAGAGAACCATCAGA 4480
AAGGACGGGGCCGAGTCCCGGTTCTTGTCTACCAGGGGTCTACGCCAGGTCGGGAGTCGTCAAAGATCTCTTGGTAGTCT
                                    3' LTR

TGTTTCCAGGGTGCCCCAAGGACCTGAAATGACCCTGTGCCTTATTTGAACTAACCAATCAGTTCGCTTCTCGCTTCTGT 4560
ACAAAGGTCCCACGGGGTTCCTGGACTTTACTGGGACACGGAATAAACTTGATTGGTTAGTCAAGCGAAGAGCGAAGACA
                                    3' LTR

                        SacI                             NarI
TCGCGCGCTTCTGCTCCCCGAGCTCAATAAAAGAGCCCACAACCCCTCACTCGGGGCGCCAGTCCTCCGATTGACTGAGT 4640
AGCGCGCGAAGACGAGGGGCTCGAGTTATTTTCTCGGGTGTTGGGGAGTGAGCCCCGCGGTCAGGAGGCTAACTGACTCA
                                    3' LTR

    SmaI  KpnI
CGCCCGGGTACCCGTGTATCCAATAAACCCTCTTGCAGTTGCATCCGACTTGTGGTCTCGCTGTTCCTTGGGAGGGTCTC 4720
GCGGGCCCATGGGCACATAGGTTATTTGGGAGAACGTCAACGTAGGCTGAACACCAGAGCGACAAGGAACCCTCCCAGAG
                                    3' LTR

CTCTGAGTGATTGACTACCCGTCAGCGGGGGTCTTTCATTTGGGGGCTCGTCCGGGATCGGGAGACCCCTGCCCAGGGAC 4800
GAGACTCACTAACTGATGGGCAGTCGCCCCCAGAAAGTAAACCCCCGAGCAGGCCCTAGCCCTCTGGGGACGGGTCCCTG
                 3' LTR

CACCGACCCACCACCGGGAGGTAAGCTGGCTGCCTCGCGCGTTTCGGTGATGACGGTGAAAACCTCTGACACATGCAGCT 4880
GTGGCTGGGTGGTGGCCCTCCATTCGACCGACGGAGCGCGCAAAGCCACTACTGCCACTTTTGGAGACTGTGTACGTCGA

CCCGGAGACGGTCACAGCTTGTCTGTAAGCGGATGCCGGGAGCAGACAAGCCCGTCAGGGCGCGTCAGCGGGTGTTGGCG 4960
GGGCCTCTGCCAGTGTCGAACAGACATTCGCCTACGGCCCTCGTCTGTTCGGGCAGTCCCGCGCAGTCGCCCACAACCGC

GGTGTCGGGGCGCAGCCATGACCCAGTCACGTAGCGATAGCGGAGTGTATACTGGCTTAACTATGCGGCATCAGAGCAGA 5040
CCACAGCCCCGCGTCGGTACTGGGTCAGTGCATCGCTATCGCCTCACATATGACCGAATTGATACGCCGTAGTCTCGTCT

                  NdeI
TTGTACTGAGAGTGCACCATATGCGGTGTGAAATACCGCACAGATGCGTAAGGAGAAAATACCGCATCAGGCGCTCTTCC 5120
AACATGACTCTCACGTGGTATACGCCACACTTTATGGCGTGTCTACGCATTCCTCTTTTATGGCGTAGTCCGCGAGAAGG
```

FIG. 16 (cont)

Tuesday, July 02, 2002 2:11 PM
pLNHiv-YFP Map.MPD (1 > 7121) Site and Sequence

```
GCTTCCTCGCTCACTGACTCGCTGCGCTCGGTCGTTCGGCTGCGGCGAGCGGTATCAGCTCACTCAAAGGCGGTAATACG
-------------------------------------------------------------------------------- 5200
CGAAGGAGCGAGTGACTGAGCGACGCGAGCCAGCAAGCCGACGCCGCTCGCCATAGTCGAGTGAGTTTCCGCCATTATGC

GTTATCCACAGAATCAGGGGATAACGCAGGAAAGAACATGTGAGCAAAAGGCCAGCAAAAGGCCAGGAACCGTAAAAAGG
-------------------------------------------------------------------------------- 5280
CAATAGGTGTCTTAGTCCCCTATTGCGTCCTTTCTTGTACACTCGTTTTCCGGTCGTTTTCCGGTCCTTGGCATTTTTCC

CCGCGTTGCTGGCGTTTTTCCATAGGCTCCGCCCCCCTGACGAGCATCACAAAAATCGACGCTCAAGTCAGAGGTGGCGA
-------------------------------------------------------------------------------- 5360
GGCGCAACGACCGCAAAAAGGTATCCGAGGCGGGGGGACTGCTCGTAGTGTTTTTAGCTGCGAGTTCAGTCTCCACCGCT

AACCCGACAGGACTATAAAGATACCAGGCGTTTCCCCCTGGAAGCTCCCTCGTGCGCTCTCCTGTTCCGACCCTGCCGCT
-------------------------------------------------------------------------------- 5440
TTGGGCTGTCCTGATATTTCTATGGTCCGCAAAGGGGGACCTTCGAGGGAGCACGCGAGAGGACAAGGCTGGGACGGCGA

TACCGGATACCTGTCCGCCTTTCTCCCTTCGGGAAGCGTGGCGCTTTCTCATAGCTCACGCTGTAGGTATCTCAGTTCGG
-------------------------------------------------------------------------------- 5520
ATGGCCTATGGACAGGCGGAAAGAGGGAAGCCCTTCGCACCGCGAAAGAGTATCGAGTGCGACATCCATAGAGTCAAGCC

TGTAGGTCGTTCGCTCCAAGCTGGGCTGTGTGCACGAACCCCCCGTTCAGCCCGACCGCTGCGCCTTATCCGGTAACTAT
-------------------------------------------------------------------------------- 5600
ACATCCAGCAAGCGAGGTTCGACCCGACACACGTGCTTGGGGGGCAAGTCGGGCTGGCGACGCGGAATAGGCCATTGATA

CGTCTTGAGTCCAACCCGGTAAGACACGACTTATCGCCACTGGCAGCAGCCACTGGTAACAGGATTAGCAGAGCGAGGTA
-------------------------------------------------------------------------------- 5680
GCAGAACTCAGGTTGGGCCATTCTGTGCTGAATAGCGGTGACCGTCGTCGGTGACCATTGTCCTAATCGTCTCGCTCCAT

TGTAGGCGGTGCTACAGAGTTCTTGAAGTGGTGGCCTAACTACGGCTACACTAGAAGGACAGTATTTGGTATCTGCGCTC
-------------------------------------------------------------------------------- 5760
ACATCCGCCACGATGTCTCAAGAACTTCACCACCGGATTGATGCCGATGTGATCTTCCTGTCATAAACCATAGACGCGAG

TGCTGAAGCCAGTTACCTTCGGAAAAAGAGTTGGTAGCTCTTGATCCGGCAAACAAACCACCGCTGGTAGCGGTGGTTTT
-------------------------------------------------------------------------------- 5840
ACGACTTCGGTCAATGGAAGCCTTTTTCTCAACCATCGAGAACTAGGCCGTTTGTTTGGTGGCGACCATCGCCACCAAAA

TTTGTTTGCAAGCAGCAGATTACGCGCAGAAAAAAAGGATCTCAAGAAGATCCTTTGATCTTTTCTACGGGGTCTGACGC
-------------------------------------------------------------------------------- 5920
AAACAAACGTTCGTCGTCTAATGCGCGTCTTTTTTTCCTAGAGTTCTTCTAGGAAACTAGAAAAGATGCCCCAGACTGCG

                                    BspHI                                      DraI
                                    |                                          |
TCAGTGGAACGAAAACTCACGTTAAGGGATTTTGGTCATGAGATTATCAAAAAGGATCTTCACCTAGATCCTTTTAAATT
-------------------------------------------------------------------------------- 6000
AGTCACCTTGCTTTTGAGTGCAATTCCCTAAAACCAGTACTCTAATAGTTTTTCCTAGAAGTGGATCTAGGAAAATTTAA

              DraI
              |
AAAAATGAAGTTTTAAATCAATCTAAAGTATATATGAGTAAACTTGGTCTGACAGTTACCAATGCTTAATCAGTGAGGCA
-------------------------------------------------------------------------------- 6080
TTTTTACTTCAAAATTTAGTTAGATTTCATATATACTCATTTGAACCAGACTGTCAATGGTTACGAATTAGTCACTCCGT

                                                          • Trp His Lys Ile Leu Ser Ala
                                                          L---------AMP-----------------
```

FIG. 16 (cont)

Tuesday, July 02, 2002 2:11 PM
pLNHiv-YFP Map.MPD (1 > 7121) Site and Sequence

```
CCTATCTCAGCGATCTGTCTATTTCGTTCATCCATAGTTGCCTGACTCCCCGTCGTGTAGATAACTACGATACGGGAGGG
---------+---------+---------+---------+---------+---------+---------+---------+ 6160
GGATAGAGTCGCTAGACAGATAAAGCAAGTAGGTATCAACGGACTGAGGGGCAGCACATCTATTGATGCTATGCCCTCCC
Gly Ile Glu Ala Ile Gln Arg Asn Arg Glu Asp Met Thr Ala Gln Ser Gly Thr Thr Tyr Ile Val Val Ile Arg Ser Pro
AMP

CTTACCATCTGGCCCCAGTGCTGCAATGATACCGCGAGACCCACGCTCACCGGCTCCAGATTTATCAGCAATAAACCAGC
---------+---------+---------+---------+---------+---------+---------+---------+ 6240
GAATGGTAGACCGGGGTCACGACGTTACTATGGCGCTCTGGGTGCGAGTGGCCGAGGTCTAAATAGTCGTTATTTGGTCG
Lys Gly Asp Pro Gly Leu Ala Ala Ile Ile Gly Arg Ser Gly Arg Glu Gly Ala Gly Ser Lys Asp Ala Ile Phe Trp Gly
AMP

CAGCCGGAAGGGCCGAGCGCAGAAGTGGTCCTGCAACTTTATCCGCCTCCATCCAGTCTATTAATTGTTGCCGGGAAGCT
---------+---------+---------+---------+---------+---------+---------+---------+ 6320
GTCGGCCTTCCCGGCTCGCGTCTTCACCAGGACGTTGAAATAGGCGGAGGTAGGTCAGATAATTAACAACGGCCCTTCGA
Ala Pro Leu Ala Ser Arg Leu Leu Pro Gly Ala Val Lys Asp Ala Glu Met Trp Asp Ile Leu Gln Gln Arg Ser Ala
AMP

                               FspI                     PstI
AGAGTAAGTAGTTCGCCAGTTAATAGTTTGCGCAACGTTGTTGCCATTGCTGCAGGCATCGTGGTGTCACGCTCGTCGTT
---------+---------+---------+---------+---------+---------+---------+---------+ 6400
TCTCATTCATCAAGCGGTCAATTATCAAACGCGTTGCAACAACGGTAACGACGTCCGTAGCACCACAGTGCGAGCAGCAA
Leu Thr Leu Leu Glu Gly Thr Leu Leu Lys Arg Leu Thr Thr Ala Met Ala Ala Pro Met Thr Thr Asp Arg Glu Asp Asn
AMP

TGGTATGGCTTCATTCAGCTCCGGTTCCCAACGATCAAGGCGAGTTACATGATCCCCCATGTTGTGCAAAAAAGCGGTTA
---------+---------+---------+---------+---------+---------+---------+---------+ 6480
ACCATACCGAAGTAAGTCGAGGCCAAGGGTTGCTAGTTCCGCTCAATGTACTAGGGGGTACAACACGTTTTTTCGCCAAT
Pro Ile Ala Glu Asn Leu Glu Pro Glu Trp Arg Asp Leu Arg Thr Val His Asp Gly Met Asn His Leu Phe Ala Thr Leu
AMP

                    PvuI
GCTCCTTCGGTCCTCCGATCGTTGTCAGAAGTAAGTTGGCCGCAGTGTTATCACTCATGGTTATGGCAGCACTGCATAAT
---------+---------+---------+---------+---------+---------+---------+---------+ 6560
CGAGGAAGCCAGGAGGCTAGCAACAGTCTTCATTCAACCGGCGTCACAATAGTGAGTACCAATACCGTCGTGACGTATTA
Glu Lys Pro Gly Gly Ile Thr Thr Leu Leu Leu Asn Ala Ala Thr Asn Asp Ser Met Thr Ile Ala Ala Ser Cys Leu
AMP

TCTCTTACTGTCATGCCATCCGTAAGATGCTTTTCTGTGACTGGTGAGTACTCAACCAAGTCATTCTGAGAATAGTGTAT
---------+---------+---------+---------+---------+---------+---------+---------+ 6640
AGAGAATGACAGTACGGTAGGCATTCTACGAAAAGACACTGACCACTCATGAGTTGGTTCAGTAAGACTCTTATCACATA
Glu Arg Val Thr Met Gly Asp Thr Leu His Lys Glu Thr Val Pro Ser Tyr Glu Val Leu Asp Asn Gln Ser Tyr His Ile
AMP

                                                                    DraI
GCGGCGACCGAGTTGCTCTTGCCCGGCGTCAACACGGGATAATACCGCGCCACATAGCAGAACTTTAAAAGTGCTCATCA
---------+---------+---------+---------+---------+---------+---------+---------+ 6720
CGCCGCTGGCTCAACGAGAACGGGCCGCAGTTGTGCCCTATTATGGCGCGGTGTATCGTCTTGAAATTTTCACGAGTAGT
Arg Arg Gly Leu Gln Glu Gln Gly Ala Asp Val Arg Ser Leu Val Ala Gly Cys Leu Leu Val Lys Phe Thr Ser Met Met
AMP
```

FIG. 16 (cont)

Tuesday, July 02, 2002 2:11 PM
pLNHiv-YFP Map.MPD (1 > 7121) Site and Sequence

```
TTGGAAAACGTTCTTCGGGGCGAAAACTCTCAAGGATCTTACCGCTGTTGAGATCCAGTTCGATGTAACCCACTCGTGCA
---------+---------+---------+---------+---------+---------+---------+---------+ 6800
AACCTTTTGCAAGAAGCCCCGCTTTTGAGAGTTCCTAGAATGGCGACAACTCTAGGTCAAGCTACATTGGGTGAGCACGT
 Pro Phe Arg Glu Glu Pro Arg Phe Ser Glu Leu Ile Lys Gly Ser Asn Leu Asp Leu Glu Ile Tyr Gly Val Arg Ala
------------------------------------AMP-----------------------------------------

CCCAACTGATCTTCAGCATCTTTTACTTTCACCAGCGTTTCTGGGTGAGCAAAAACAGGAAGGCAAAATGCCGCAAAAAA
---------+---------+---------+---------+---------+---------+---------+---------+ 6880
GGGTTGACTAGAAGTCGTAGAAAATGAAAGTGGTCGCAAAGACCCACTCGTTTTTGTCCTTCCGTTTTACGGCGTTTTTT
Gly Leu Gln Asp Glu Ala Asp Lys Val Lys Val Leu Thr Glu Pro His Ala Phe Val Pro Leu Cys Phe Ala Ala Phe Phe
------------------------------------AMP-----------------------------------------

GGGAATAAGGGCGACACGGAAATGTTGAATACTCATACTCTTCCTTTTTCAATATTATTGAAGCATTTATCAGGGTTATT
---------+---------+---------+---------+---------+---------+---------+---------+ 6960
CCCTTATTCCCGCTGTGCCTTTACAACTTATGAGTATGAGAAGGAAAAAGTTATAATAACTTCGTAAATAGTCCCAATAA
 Pro Ile Leu Ala Val Arg Phe His Gln Ile Ser Met
---------------AMP---------------|

    BspHI

GTCTCATGAGCGGATACATATTTGAATGTATTTAGAAAAATAAACAAATAGGGGTTCCGCGCACATTTCCCCGAAAAGTG
---------+---------+---------+---------+---------+---------+---------+---------+ 7040
CAGAGTACTCGCCTATGTATAAACTTACATAAATCTTTTTATTTGTTTATCCCCAAGGCGCGTGTAAAGGGGCTTTTCAC

                             BspHI
                             |
CCACCTGACGTCTAAGAAACCATTATTATCATGACATTAACCTATAAAAATAGGCGTATCACGAGGCCCTTTCGTCTTCA
---------+---------+---------+---------+---------+---------+---------+---------+ 7120
GGTGGACTGCAGATTCTTTGGTAATAATAGTACTGTAATTGGATATTTTTATCCGCATAGTGCTCCGGGAAAGCAGAAGT

A
> 7121
T
```

INDUCIBLE PROTEIN EXPRESSION SYSTEM

RELATED APPLICATION

This application claims priority to U.S. Provisional Patent Application No. 60/442,103, filed on Jan. 23, 2003 and titled "Tax Inducible Expression System" by Jerome S. Harms, et al., its entire disclosure is incorporated by reference.

GOVERNMENT SUPPORT

This invention was made partially with government support under Grant No CA88752-03 awarded by the National Institute of Health. The Government has certain rights in the invention.

FIELD OF THE INVENTION

The present invention relates to gene expression. In particular, the present invention relates to inducible gene expression systems and a method thereof.

BACKGROUND OF THE INVENTION

The advent of recombinant DNA technology has made it possible to produce foreign proteins in mammalian cells through the introduction of foreign DNA encoding such proteins. Mammalian expression systems are available in which the foreign protein is constitutively expressed from an active promoter. This results in the continual expression of the foreign gene. Viral promoters are commonly used as regulatory elements in gene therapy vectors due to their strong activity in various cell lines in vitro. A widely used promoter in expression systems is the human cytomegalovirus immediate-early gene (CMV) promoter. The CMV promoter induces high-level constitutive expression in a variety of cell lines (Fitzsimons et al., Methods. 28:227 [2002]).

Frequently, the abundant presence of the foreign protein is toxic to the host cell. As a result of constitutive expression, the host cell population may become moribund and perish. Furthermore, the abundant presence of the toxic protein exerts selective pressures on the host cells which can result in the emergence of a cell population containing mutated versions of the foreign DNA, which express grossly modified protein or which have deleted the foreign gene. As a result, commercially useful levels of constitutive expression may never be maintained in the recombinant cell population.

Efforts to combat this shortcoming have resulted in the development of inducible mammalian expression systems that control the expression of the foreign protein. Inducible expression can be achieved by using promoters that are controlled by the presence or absence of a specific regulator. Another means of controlling foreign gene expression involves the use of a promoter that becomes more active in the presence of a specific activator protein. A foreign gene under the control of such a promoter is expressed at high levels only following the induction of synthesis of the activator. However, many of these inducible systems currently available suffer from decreased levels of expression and "leaky" control of expression (i.e., unwanted, low-level protein expression). A more ideal inducible system would have 1) low basal expression levels; 2) high induced expression; and 3) inducer-specific, modulated expression (Xu et al., Gene. 309:145 [2003]).

Accordingly, it would be desirable to provide a tightly regulated and highly inducible protein expression system that would overcome the aforementioned and other disadvantages.

SUMMARY OF THE INVENTION

A first aspect of the invention provides an inducible gene expression system. The system includes a first inducible gene expression system including a first vector comprising at least one retroviral promoter and at least one factor to induce the retroviral promoter. At least one gene product is expressed in proportion to retroviral promoter induction.

A second aspect of the invention provides a method of gene expression. The method includes providing a first vector comprising at least one retroviral promoter and providing at least one factor corresponding to the retroviral promoter. The retroviral promoter is induced with the at least one factor. At least one protein is expressed based on the induction of the retroviral promoter.

A third aspect of the invention provides an inducible gene expression system. The system includes first vector means comprising at least one retroviral promoter. Means for inducing the retroviral promoter are provided. Further included are means for expressing at least one protein based on the induction of the retroviral promoter.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DESCRIPTION OF THE FIGURES

FIG. 2 shows the nucleic acid sequence of the BLV promoter (SEQ ID NO:1);

FIG. 3 shows the nucleic acid (SEQ ID NO:2) and amino acid (SEQ ID NO:3) sequence of BLV Tax;

FIG. 4 shows the nucleic acid sequence of the HTLV promoter (SEQ ID NO:6);

FIG. 5 shows the nucleic acid (SEQ ID NO:4) and the amino acid (SEQ ID NO:5) of HTLV Tax;

FIG. 6 shows the nucleic acid sequence of the HIV promoter (SEQ ID NO:7);

FIG. 7 shows the nucleic acid (SEQ ID NO:8) and amino acid (SEQ ID NO:9) of HIV Tat;

DETAILED DESCRIPTION OF THE INVENTION

Figure 1:
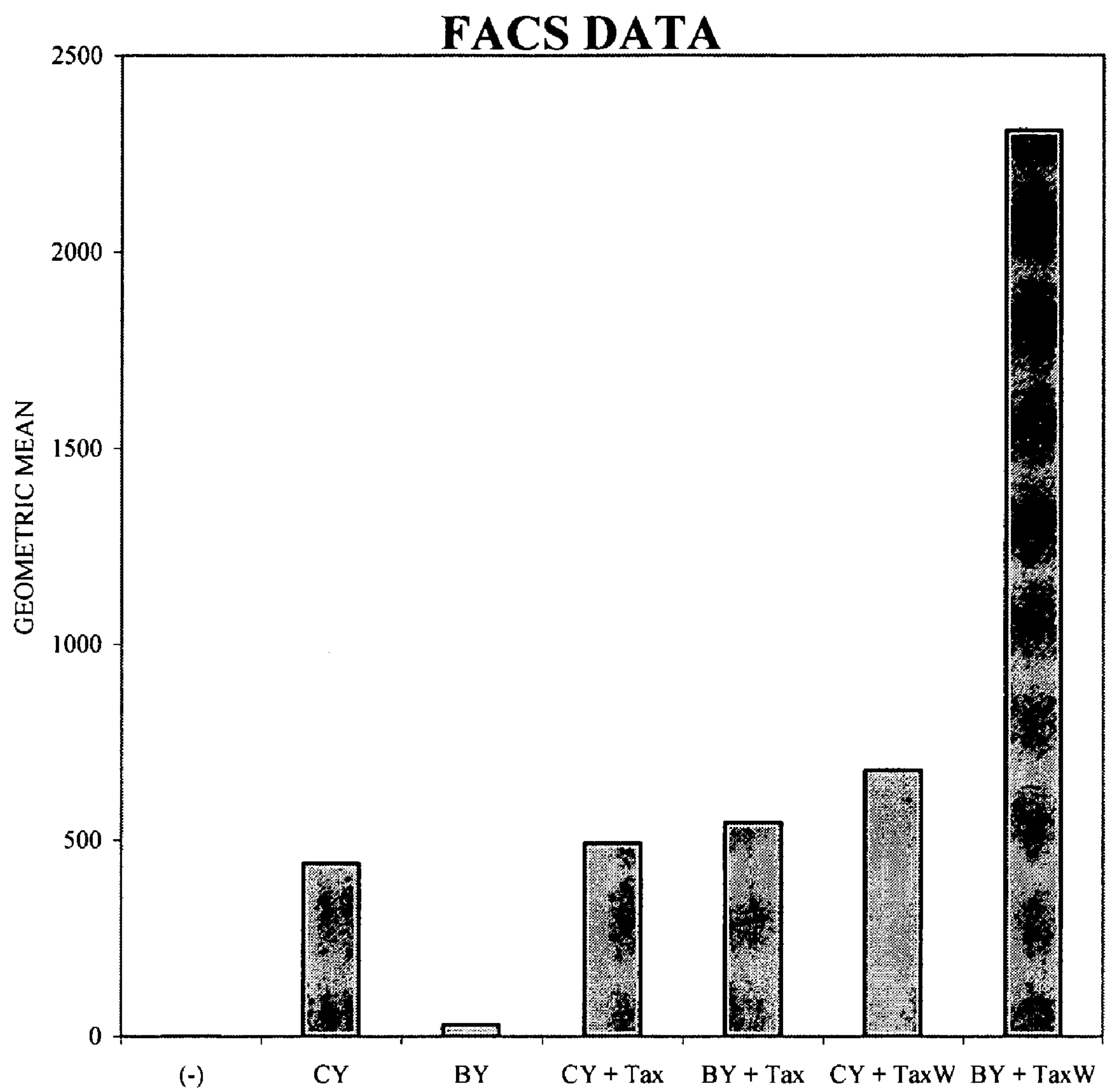
FIG. 1 shows the FACS data comparing expression constructs used in some embodiments of the present invention.
Figure 8:
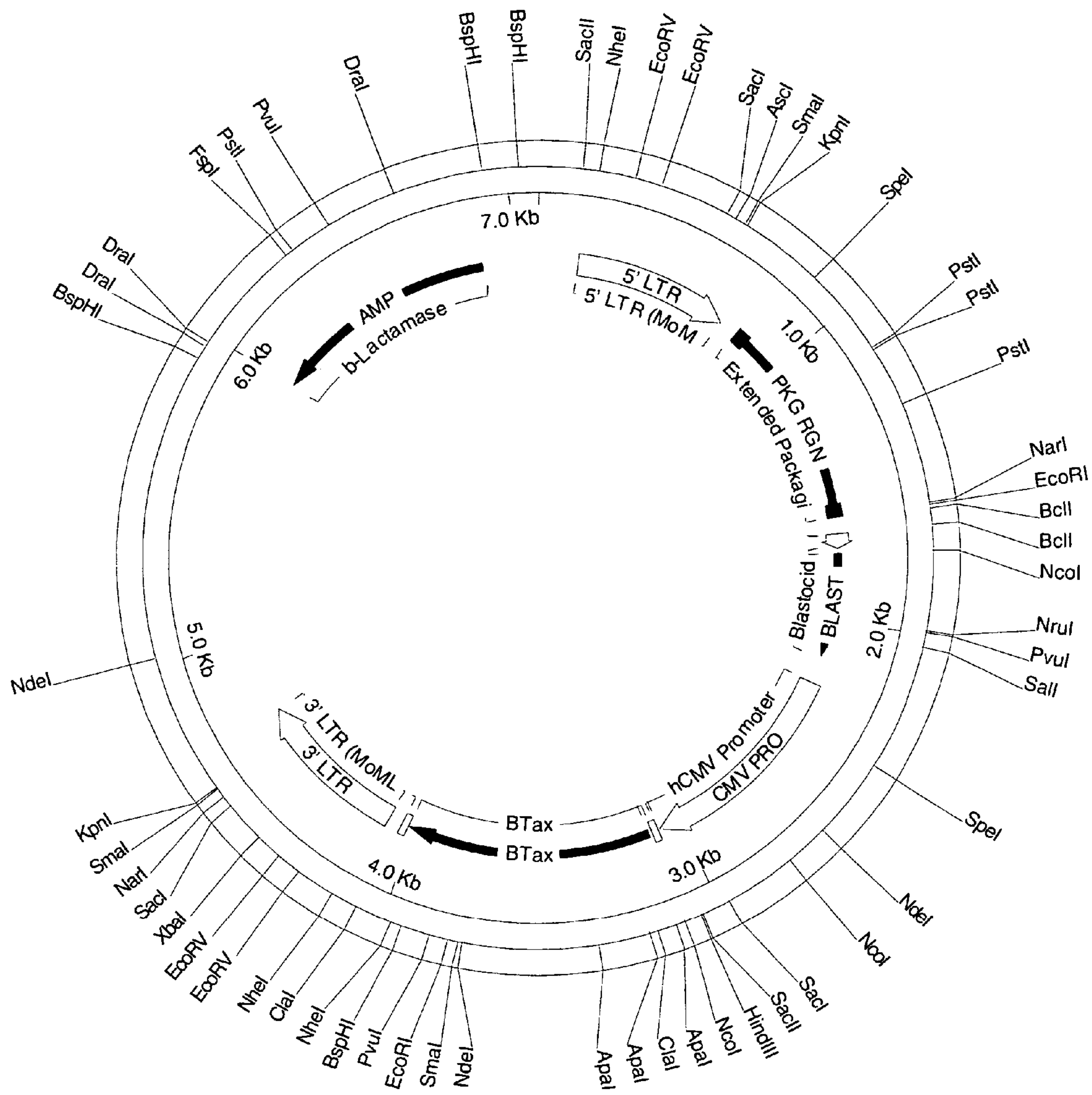
FIG. 8 shows a map of pLBC-BTax.

In some embodiments, the present invention provides eukaryotic gene expression vectors, systems, and methods based on inducible retroviral promoters. For example, in some embodiments, the present invention provides Tax inducible expression vectors utilizing the bovine leukemia virus (BLV) promoter. The BLV, a C-type retrovirus, is the cause of enzootic bovine leukemia (Miller and Olson. 1987. p. 87-90. In A. Burny and M. Mammerickx (eds). Enzootic Bovine Leukosis and Bovine Leukemia Virus. Martinus Nijhoff Publishing, Boston). The BLV promoter alone does not typically produce very high levels of gene expression. However, the BLV promoter is transactivated by Tax (Kiermer et al., J. Virol. 72:5526 [1998]), a transcriptional activator of the BLV long terminal repeat that influences the expression of many BLV genes (Jeang et al., J. Virol. 71:6277 [1997]).

The vectors of the present invention may provide several advantages over currently available expression systems. The inducible vectors of the present invention may provide tight on/off regulation of expression. Unlike many currently available systems, background, or leaky, expression of the gene in the absence of the inducer is extremely low. The promoters of the present invention, however, may offer higher inducible levels and faster response times. The vectors of the present invention may further offer high absolute expression levels. Maximum expression levels may be higher than expression levels obtained from constitutive promoters such as the CMV promoter. One particular advantage of the present design relates to the utilization of transcriptional activation, rather than repression to control expression.

I. Expression Vectors

In some embodiments, the present invention may provide retroviral expression vectors comprising retroviral promoters including an inducible element, a gene of interest, as well as other components necessary for expression of the gene of interest. In some embodiments, the inducer is provided separately from the gene of interest. As used herein, the term "vector" refers to any genetic element, such as a plasmid, phage, transposon, cosmid, chromosome, retrovirus, virion, etc., which is capable of replication when associated with the proper control elements and which can transfer gene sequences between cells. Thus, the term includes cloning and expression vehicles, as well as viral vectors. Further, the term "nucleotide sequence of interest" refers to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences, or portions thereof, of structural genes (e.g., reporter genes, selection marker genes, oncogenes, drug resistance genes, growth factors, etc.), and non-coding regulatory sequences that do not encode an mRNA or protein product (e.g., promoter sequence, polyadenylation sequence, termination sequence, enhancer sequence, etc.).

A. Promoters

In some embodiments, the present invention provides expression vectors comprising a retroviral vector comprising an inducible element. In some embodiments, the retroviral vector promoter is a Bovine leukemia virus (BLV) promoter (SEQ ID NO:1). The BLV promoter may include an inducer-responsive element (e.g., a Tax responsive element). The present invention, however, is not limited to the BLV promoter. Other suitable inducible retroviral promoters are contemplated including, but not limited to, the human immunodeficiency viruses (HIV-1 and HIV-2) promoters, feline immunodeficiency virus (FIV) promoter, simian immunodeficiency virus (SIV) promoter, caprine virus, human foamy virus and the human T-lymphocyte leukemia viruses (HTLV-1, HTLV-2, and HTLV-3) promoters.

B. RNA Export Elements

In other embodiments, the vectors may be modified by incorporating an RNA export element (See, e.g., U.S. Pat. Nos. 5,914,267; 6,136,597; and 5,686,120; and WO99/14310) either 3' or 5' to the nucleic acid sequence encoding the protein of interest. It is contemplated that the use of RNA export elements may allow high levels of expression of the protein of interest without incorporating splice signals or introns in the nucleic acid sequence encoding the protein of interest.

In certain embodiments, the vector additionally may include a RNA transport signal from woodchuck hepatitis virus response element (WPRE). The woodchuck hepatitis virus post transcriptional enhancer may enhance the cytoplasmic levels of RNA as well as the translation of the target protein. Experiments have demonstrated that inclusion of the WPRE can increase the expression of a reporter gene expression under the control of the BLV promoter activated by BLV Tax.

C. Vectors

The present invention is not limited to any particular vector. Indeed, the use of a variety of vectors is contemplated, including, but not limited to plasmids, cosmids, bacterial artificial chromosomes, yeast artificial chromosomes, adeno-associated virus vectors, and adenovirus vectors. Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as they are replicable and viable in the host. In some embodiments of the present invention, mammalian expression vectors comprise an origin of replication, a suitable promoter and enhancer (e.g., BLV and Tax), and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In some embodiments of the present invention, recombinant expression vectors include origins of replication and selectable markers permitting transformation of the host cell (e.g., dihydrofolate reductase or neomycin resistance for eukaryotic cell culture, or tetracycline or ampicillin resistance in *E. coli*). As used herein, the term "host cell" refers to any eukaryotic cell (e.g., mammalian cells, avian cells, amphibian cells, plant cells, fish cells, and insect cells), whether located in vitro or in vivo (e.g., in a transgenic organism). Further, the term "selectable marker" refers to a gene that encodes an enzymatic activity that confers the ability to grow in medium lacking what would otherwise be an essential nutrient (e.g., the HIS3 gene in yeast cells); in addition, a selectable marker may confer resistance to an antibiotic or drug upon the cell in which the selectable marker is expressed.

In other embodiments, the expression vector may also contain a ribosome binding site for translation initiation and a transcription terminator. In still other embodiments, the vector may include appropriate sequences for amplifying expression.

In some embodiments, the vector is a retroviral vector. Retroviruses (i.e., family Retroviridae) are divided into three groups: the spumaviruses (e.g., human foamy virus); the lentiviruses (e.g., human immunodeficiency virus and sheep visna virus) and the oncoviruses (e.g., MLV, Rous sarcoma virus).

Retroviruses are enveloped (i.e., surrounded by a host cell-derived lipid bilayer membrane) single-stranded RNA viruses, which infect animal cells. When a retrovirus infects a cell, its RNA genome is converted into a double-stranded linear DNA form (i.e., it is reverse transcribed). The DNA form of the virus is then integrated into the host cell genome as a provirus. The provirus serves as a template for the production of additional viral genomes and viral mRNAs. Mature viral particles containing two copies of genomic RNA bud from the surface of the infected cell. The viral particle comprises the genomic RNA, reverse transcriptase and other pol gene products inside the viral capsid (which contains the viral gag gene products), which is surrounded by a lipid bilayer membrane derived from the host cell containing the viral envelope glycoproteins (also referred to as membrane-associated proteins).

The organization of the genomes of numerous retroviruses is well known to the art and this has allowed the adaptation of the retroviral genome to produce retroviral vectors. The production of a recombinant retroviral vector carrying a gene of interest is typically achieved in two stages.

First, the gene of interest is inserted into a retroviral vector that contains: the sequences necessary for the efficient expression of the gene of interest (including promoter and/or enhancer elements which may be provided by the viral long terminal repeats (LTRs) or by an internal promoter/enhancer and relevant splicing signals); sequences required for the efficient packaging of the viral RNA into infectious virions (e.g., the packaging signal (Psi), the tRNA primer binding site (−PBS) the 3' regulatory sequences required for reverse transcription (+PBS)); and the viral LTRs. The LTRs contain sequences required for the association of viral genomic RNA, reverse transcriptase and integrase functions, and sequences involved in directing the expression of the genomic RNA to be packaged in viral particles. For safety reasons, many recombinant retroviral vectors lack functional copies of the genes that are essential for viral replication (these essential genes are either deleted or disabled); therefore, the resulting virus is said to be replication defective.

Second, following the construction of the recombinant vector, the vector DNA may be introduced into a packaging cell line. Packaging cell lines provide proteins required in trans for the packaging of the viral genomic RNA into viral particles having the desired host range (i.e., the viral-encoded gag, pol and env proteins). The host range is controlled, in part, by the type of envelope gene product expressed on the surface of the viral particle. Packaging cell lines may express ecotrophic, amphotropic or xenotropic envelope gene products. Alternatively, the packaging cell line may lack sequences encoding a viral envelope (env) protein. In this case the packaging cell line will package the viral genome into particles that lack a membrane-associated protein (e.g., an env protein). To produce viral particles containing a membrane associated protein that will permit entry of the virus into a cell, the packaging cell line containing the retroviral sequences may be transfected with sequences encoding a membrane-associated protein (e.g., the G protein of vesicular stomatitis virus (VSV)). The transfected packaging cell may then produce viral particles that contain the membrane-associated protein expressed by the transfected packaging cell line. These viral particles, which contain viral genomic RNA derived from one virus encapsulated by the envelope proteins of another virus, are said to be pseudotyped virus particles.

The retroviral vectors of the present invention may further be modified to include additional regulatory sequences (e.g., inducible promoters of the present invention). In other embodiments, where secretion of the protein of interest is desired, the vectors may be modified by including a signal peptide sequence in operable association with the protein of interest. The sequences of several suitable signal peptides are known to those in the art, including, but not limited to, those derived from tissue plasminogen activator, human growth hormone, lactoferrin, alpha-casein, and alpha-lactalbumin.

In still other embodiments, the vector may further comprise at least one internal ribosome entry site (IRES) sequence. The sequences of several suitable IRES's are available, including, but not limited to, those derived from foot and mouth disease virus (FDV), encephalomyocarditis virus, and poliovirus. The IRES sequence can be interposed between two transcriptional units (e.g., nucleic acids encoding different proteins of interest or subunits of a multisubunit protein such as an antibody) to form a polycistronic sequence so that the two transcriptional units are transcribed from the same promoter.

The retroviral vectors of the present invention may also further comprise a selectable marker allowing selection of transformed cells. A number of selectable markers may be implemented in the present invention, including, but not limited to: the bacterial aminoglycoside 3' phosphotransferase gene (also referred to as the neo gene) that confers resistance to the drug G418 in mammalian cells; the bacterial hygromycin G phosphotransferase (hyg) gene that confers resistance to the antibiotic hygromycin; and the bacterial xanthine-guanine phosphoribosyl transferase gene (also referred to as the gpt gene) that confers the ability to grow in the presence of mycophenolic acid. In some embodiments, the selectable marker gene may be provided as part of polycistronic sequence that also encodes the protein of interest.

Viral vectors, including recombinant retroviral vectors, may provide a more efficient means of transferring genes into cells as compared to other techniques such as calcium phosphate-DNA co-precipitation or DEAE-dextran-mediated transfection, electroporation or microinjection of nucleic acids. It is believed that the efficiency of viral transfer is due in part to the fact that the transfer of nucleic acid is a receptor-mediated process (i.e., the virus binds to a specific receptor protein on the surface of the cell to be infected). In addition, the virally transferred nucleic acid once inside a cell integrates in controlled manner in contrast to the integration of nucleic acids which are not virally transferred; nucleic acids transferred by other means such as calcium phosphate-DNA co-precipitation may be subject to rearrangement and degradation.

The most commonly used recombinant retroviral vectors are typically derived from the amphotropic Moloney murine leukemia virus (MOMLV) (See e.g., Miller and Baltimore Mol. Cell. Biol. 6:2895 [1986]). The MOMLV system has several advantages: 1) this specific retrovirus can infect many different cell types, 2) the established packaging cell lines are available for the production of recombinant MOMLV viral particles and 3) the transferred genes are permanently integrated into the target cell chromosome. The established MOMLV vector systems comprise a DNA vector containing a small portion of the retroviral sequence (e.g., the viral long terminal repeat or "LTR" and the packaging or "psi" signal) and a packaging cell line. The gene to be transferred is inserted into the DNA vector. The viral sequences present on the DNA vector provide the signals necessary for the insertion or packaging of the vector RNA into the viral particle and for the expression of the inserted gene. The packaging cell line provides the proteins required for particle assembly (Markowitz et al., J. Virol. 62:1120 [1988]).

The low titer and inefficient infection of certain cell types by MoMLV-based vectors has been overcome by the use of pseudotyped retroviral vectors that contain the G protein of VSV as the membrane associated protein. Unlike retroviral envelope proteins, which bind to a specific cell surface protein receptor to gain entry into a cell, the VSV G protein interacts with a phospholipid component of the plasma membrane (Mastromarino et al., J. Gen. Virol. 68:2359 [1977]). Because entry of VSV into a cell is not dependent upon the presence of specific protein receptors, VSV has an extremely broad host range. Pseudotyped retroviral vectors bearing the VSV G protein have an altered host range characteristic of VSV (i.e., they can infect almost all species of vertebrate, invertebrate and insect cells). Importantly, VSV G-pseudotyped retroviral vectors can be concentrated 2000-fold or more by ultracentrifugation without significant loss of infectivity (Burns et al. Proc. Natl. Acad. Sci. USA 90:8033 [1993]).

The present invention is not limited to the use of the VSV G protein when a viral G protein is employed as the heterologous membrane-associated protein within a viral particle (See, e.g., U.S. Pat. No. 5,512,421). The G proteins of viruses in the Vesiculovirus genera other than VSV, such as the Piry and Chandipura viruses, are highly homologous to the VSV G protein and, like the VSV G protein, contain covalently linked palmitic acid (Brun et al. Intervirol. 38:274 [1995] and Masters et al., Virol. 171:285 (1990]). Thus, the G protein of the Piry and Chandipura viruses may be used in place of the VSV G protein for the pseudotyping of viral particles. In addition, the VSV G proteins of viruses within the Lyssa virus genera such as Rabies and Mokola viruses show a high degree of conservation (amino acid sequence as well as functional conservation) with the VSV G proteins. For example, the Mokola virus G protein has been shown to function in a manner similar to the VSV G protein (i.e., to mediate membrane fusion) and therefore may be used in place of the VSV G protein for the pseudotyping of viral particles (Mebatsion et al., J. Virol. 69:1444 [1995]). Viral particles may be pseudotyped using either the Piry, Chandipura or Mokola G protein, with the exception that a plasmid containing sequences encoding either the Piry, Chandipura or Mokola G protein under the transcriptional control of a suitable promoter element (e.g., the CMV intermediate-early promoter; numerous expression vectors containing the CMV IE promoter are available, such as the pcDNA3.1 vectors (Invitrogen)) is used in place of pHCMV-G. Sequences encoding other G proteins derived from other members of the Rhabdoviridae family may be used; sequences encoding numerous rhabdoviral G proteins are available from the GenBank database.

The majority of retroviruses may transfer or integrate a double-stranded linear form of the virus (the provirus) into the genome of the recipient cell only if the recipient cell is cycling (i.e., dividing) at the time of infection. Retroviruses which have been shown to infect dividing cells exclusively, or more efficiently, include MLV, spleen necrosis virus, Rous sarcoma virus and human immunodeficiency virus (HIV; while HIV infects dividing cells more efficiently, HIV can infect non-dividing cells).

It has been demonstrated that the integration of MLV virus DNA depends upon the host cell's progression through mitosis and it has been postulated that the dependence upon mitosis reflects a requirement for the breakdown of the nuclear envelope in order for the viral integration complex to gain entry into the nucleus (Roe et al., EMBO J. 12:2099 [1993]). However, as integration does not occur in cells arrested in metaphase, the breakdown of the nuclear envelope alone may not be sufficient to permit viral integration; there may be additional requirements such as the state of condensation of the genomic DNA (Roe et al., supra).

For example, in one such embodiment, the construct backbone may comprise: 1) the Murine Sarcoma Virus 5' LTR; 2) extended viral packaging signal ($\psi$); 3) a selectable marker (e.g., neo); 4) an inducible promoter with an appropriate cloning site (e.g., the native BLV U3 promoter); and 5) the 3' Murine Leukemia Virus 3' LTR. In some embodiments, a post-transcriptional enhancer element may be added to the retroviral vector backbone construct to optimize the transport of the message from the nucleus to the cytoplasm.

Figure 11:
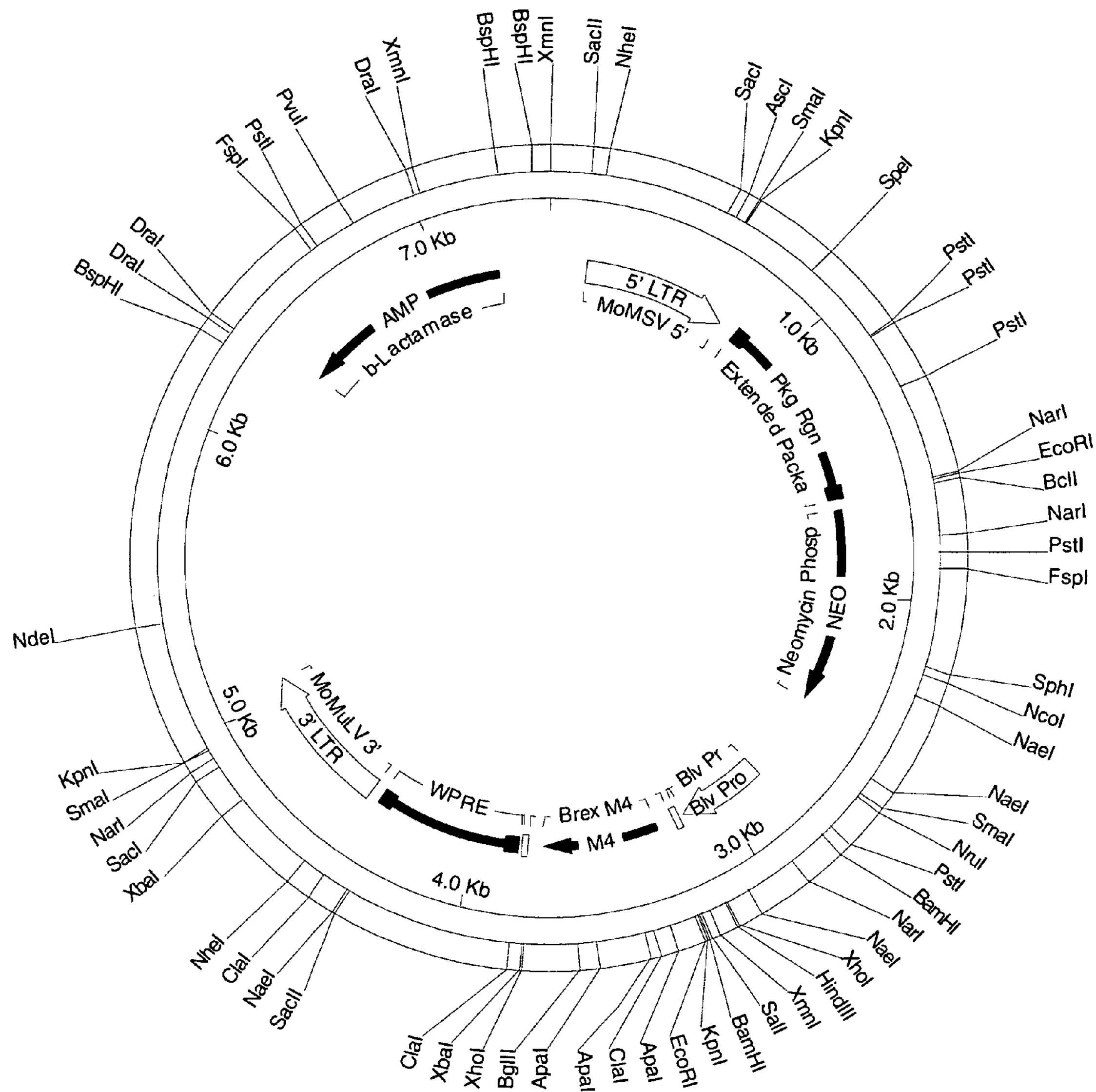
FIG. 11 shows a map of pLNBLV-M4W.
Figure 12:
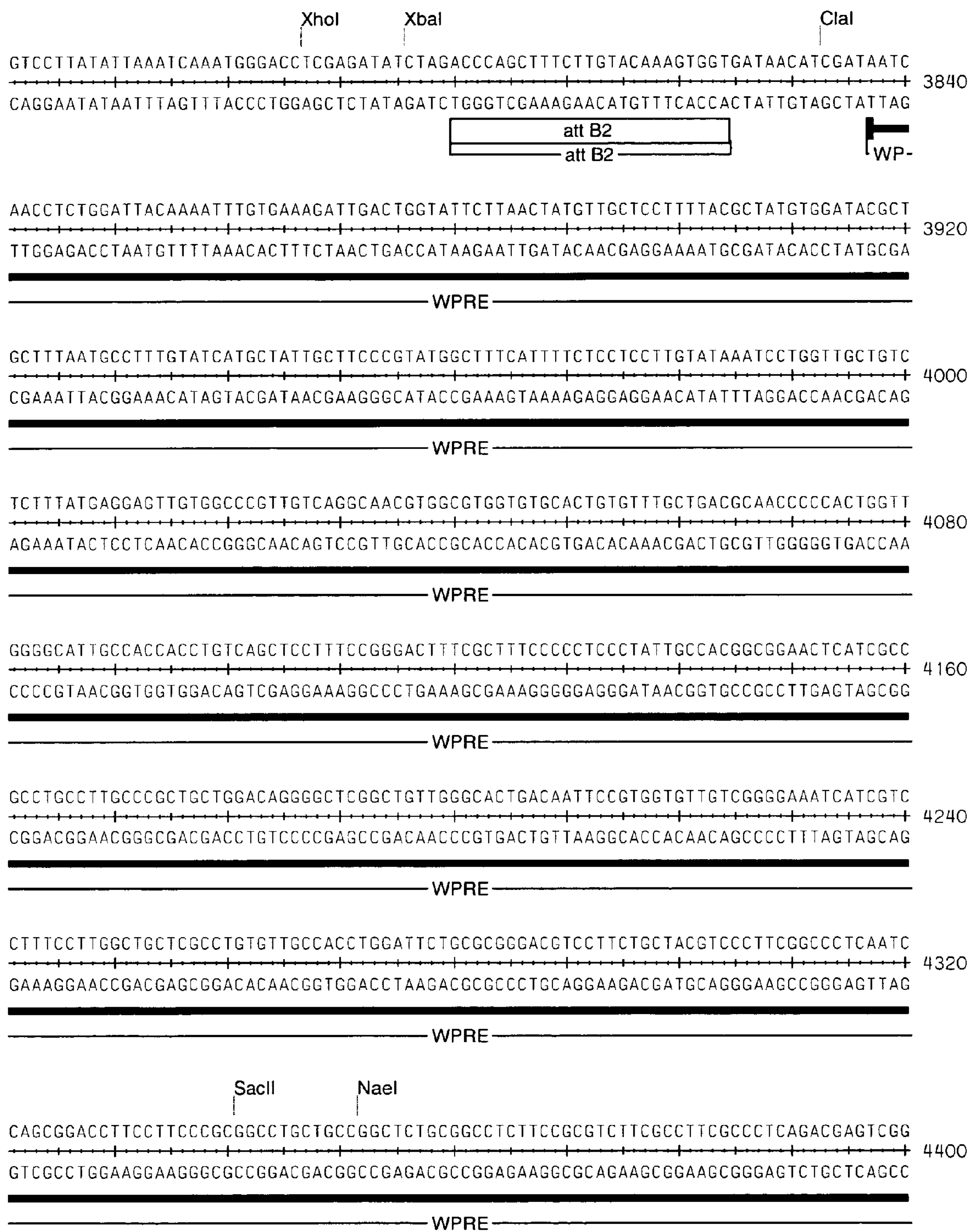
FIG. 12 shows the nucleic acid sequence of pLNBLV-M4W (SEQ ID NO: 15 for the upper strand and SEQ ID NO: 18 for the lower strand) and the three amino acid seciuences labeled as Neomycin Phosphotransferase, Brex M4, and b-Lactamase are provided in the sequence listing as SEQ ID NO:16, SEQ ID NO:17, and SEQ ID NO:19, respectively.
Figure 13:
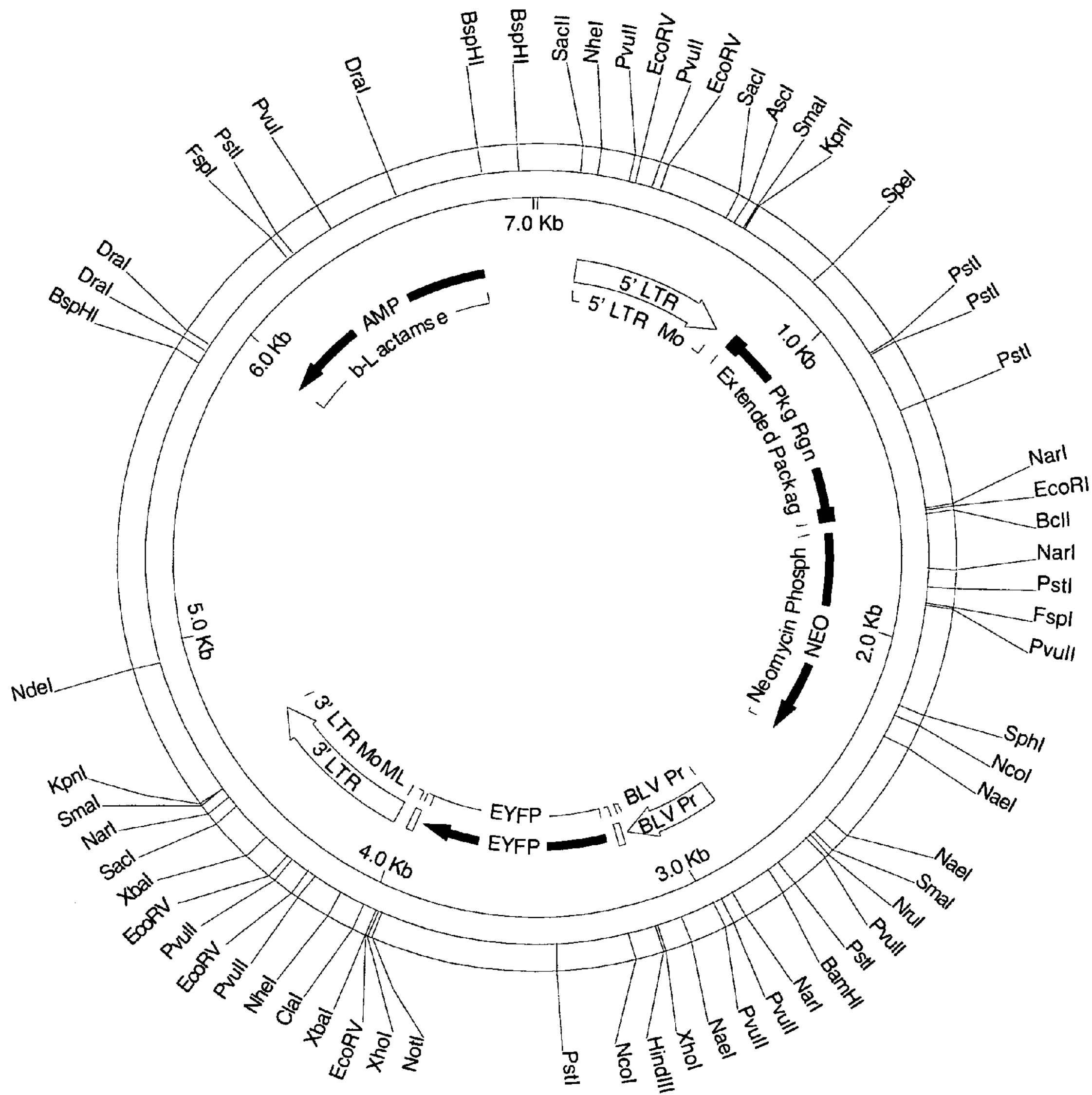
FIG. 13 shows a map of pLNBlv-YFP.
Figure 14:
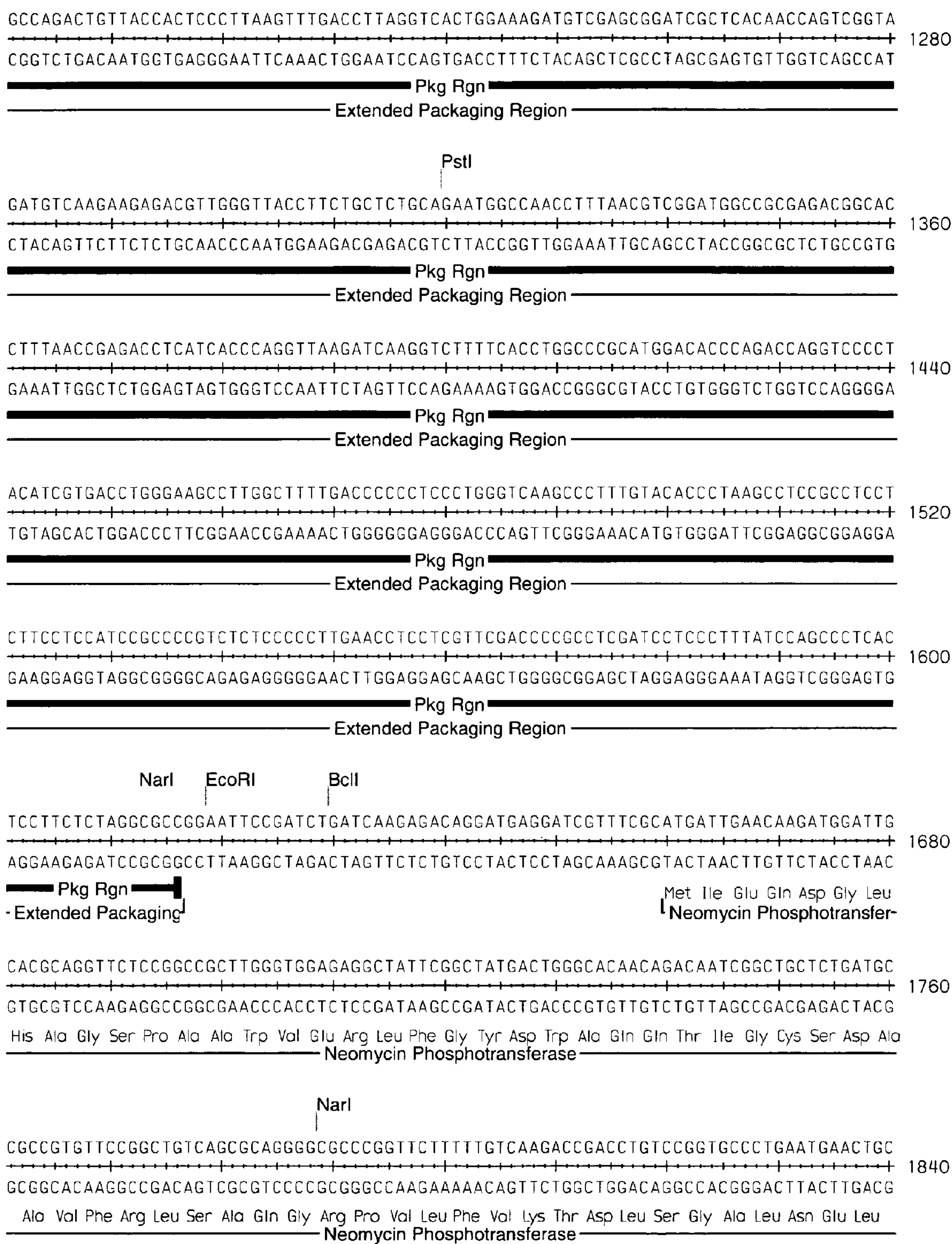
FIG. 14 shows the nucleic acid sequence of pLNBIv-YFP (SEQ ID NO:20 for the upper strand and SEQ ID NO:23 for the lower strand) and the three amino acid sequences labeled as Neomycin Phosphotransferase, EYFP, and b-Lactamse are provided in the sequence listing as SEQ ID NO:21, SEQ ID NO:22, and SEQ ID NO:24, respectively.
Figure 15:
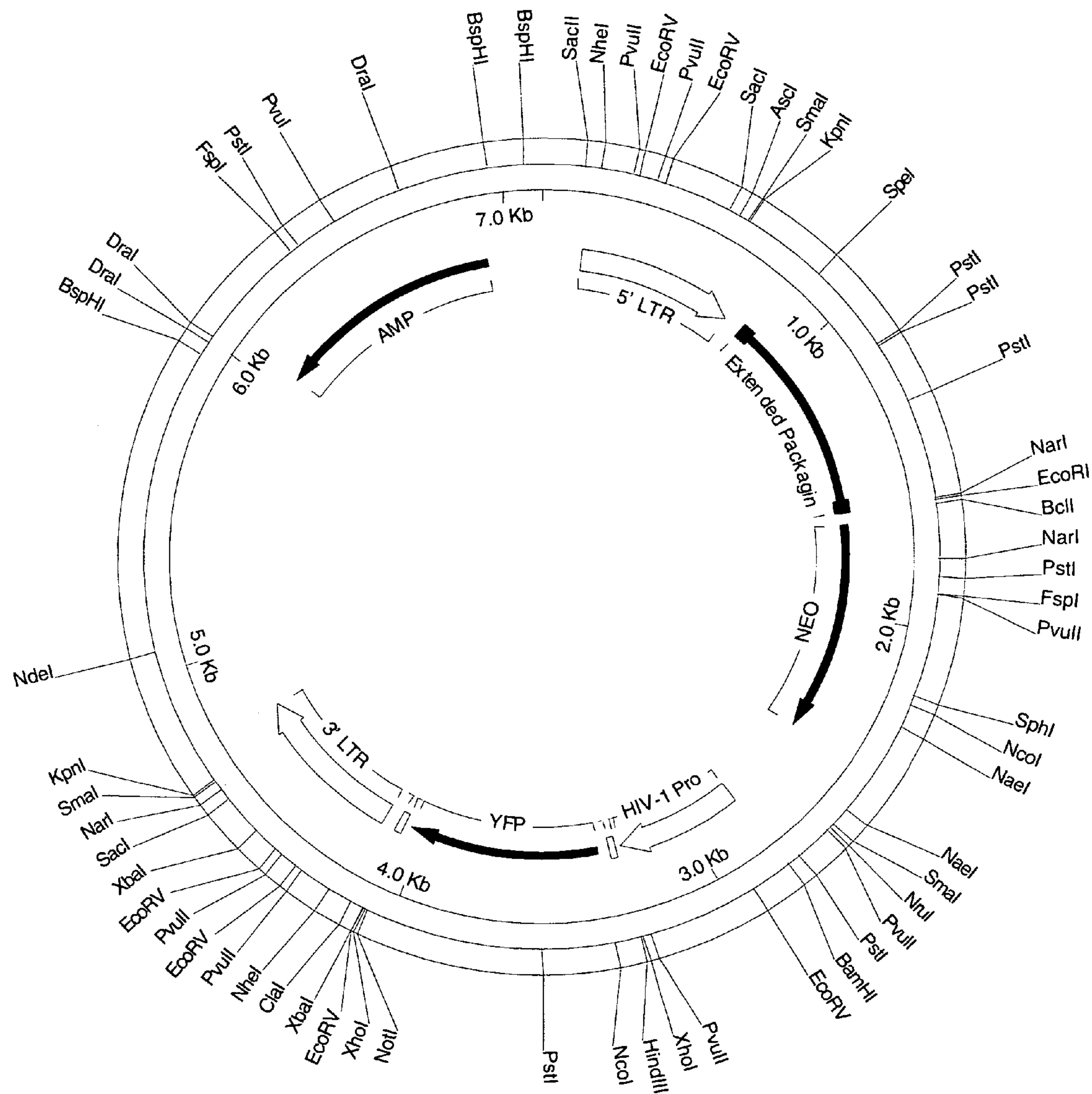
FIG. 15 shows a map of pLNHiv-YFP.
Figure 16:
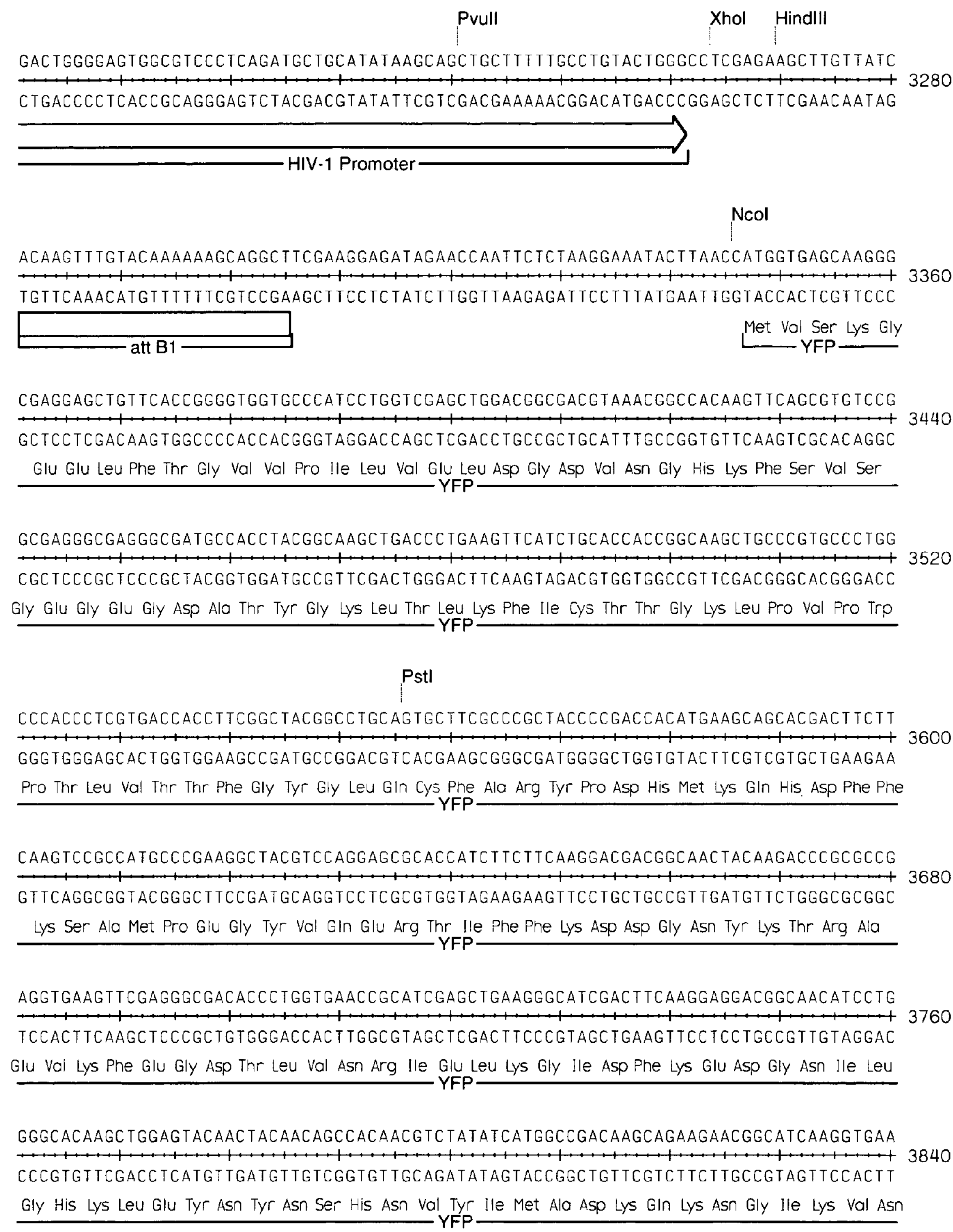
FIG. 16 shows the nucleic acid sequence of pLNHiv-YFP (SEQ ID NO:25 for the upper strand and SEQ ID NO:28 for the lower strand) and the three amino acid sequences labeled as NEO, YFP. and AMP are provided in the seciuence listing as SEQ ID NO:26, SEQ ID NO:27, and SEQ ID NO:29, respectively.

In some embodiments, the vectors may utilize the following items: 5' LTR (e.g., MoMSV); extended packaging region; NEO; retroviral promoter (e.g., BLV); gene of Interest; 3' LTR (e.g., MoMuLV). Exemplary vectors of the present invention comprising YFP (yellow fluorescent protein) or M4 as an exemplary gene of interest are shown in FIGS. 11-16 (SEQ ID NOs: 15, 20, and 25). FIG. 11 shows a map of a construct that further comprises a WPRE element.

The present invention also provides the use of lentiviral vectors to generate high copy number cell lines. The lentiviruses (e.g., equine infectious anemia virus, caprine arthritis-encephalitis virus, human immunodeficiency virus) are a subfamily of retroviruses that are able to integrate into non-dividing cells. The lentiviral genome and the proviral DNA have the three genes found in all retroviruses: gag, pol, and env, which are flanked by two LTR sequences. The gag gene encodes the internal structural proteins (e.g., matrix, capsid, and nucleocapsid proteins); the pol gene encodes the reverse transcriptase, protease, and integrase proteins; and the pol gene encodes the viral envelope glycoproteins. The 5' and 3' LTRs control transcription and polyadenylation of the viral RNAs. Additional genes in the lentiviral genome include the vif, vpr, tat, rev, vpu, nef, and vpx genes.

A variety of lentiviral vectors and packaging cell lines are known in the art and find use in the present invention (See, e.g., U.S. Pat. Nos. 5,994,136 and 6,013,516). Furthermore, the VSV G protein has also been used to pseudotype retroviral vectors based upon the human immunodeficiency virus (HIV) (Naldini et al., Science 272:263 [1996]). Thus, the VSV G protein may be used to generate a variety of pseudotyped retroviral vectors and is not limited to vectors based on MoMLV. The lentiviral vectors may also be modified as described above to contain various regulatory sequences (e.g., signal peptide sequences, RNA export elements, and IRES's). After the lentiviral vectors are produced, they may be used to transfect host cells as described above for retroviral vectors.

The present invention is not limited to the use of retroviral expression vectors. Any suitable expression vector for the expression of a gene of interest using the inducible promoters of the present invention may be utilized. Exemplary expression vectors include, but are not limited to cosmids, plasmids, adenoviral, and adeno-associated viral vectors. For example, in some embodiments, plasmids may be utilized for the expression of a gene of interest in a prokaryotic or eukaryotic cell. Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene) pSVK3, pBPV, pMSG, pSVL (Pharmacia). Any other plasmid or vector may be used as long as it is replicable and viable in the host.

In some embodiments, mammalian expression vectors may comprise an origin of replication, a suitable promoter (e.g., the inducible promoters of the present invention) and enhancer, and also any necessary ribosome binding sites, polyadenylation sites, splice donor and acceptor sites, transcriptional termination sequences, and 5' flanking non-transcribed sequences. In other embodiments, DNA sequences derived from the SV40 splice, and polyadenylation sites may be used to provide the required non-transcribed genetic elements.

In certain embodiments, the DNA sequence in the expression vector may be operatively linked to an appropriate expression control sequence(s) (promoter) to direct mRNA synthesis. Inducible promoters useful in the present invention may include, but are not limited to, those described above. In other embodiments, recombinant expression vectors may include origins of replication and selectable markers permitting transformation of the host cell (e.g., dihydrofolate reductase or neomycin resistance for eukaryotic cell culture, or tetracycline or ampicillin resistance in *E. coli*).

In some embodiments, transcription of the DNA encoding the polypeptides of the present invention by higher eukaryotes may be increased by inserting an enhancer sequence into the vector. Enhancers are cis-acting elements of DNA, usually about from 10 to 300 bp that act on a promoter to increase its transcription. Enhancers useful in the present invention include, but are not limited to, the SV40 enhancer on the late side of the replication origin bp 100 to 270, a cytomegalovirus early promoter enhancer, the polyoma enhancer on the late side of the replication origin, and adenovirus enhancers.

In other embodiments, the expression vector may also contain a ribosome binding site for translation initiation and a transcription terminator. In still other embodiments, the vector may also include appropriate sequences for amplifying expression.

In still other embodiments, adenoviral and adeno-associated viral vectors may be utilized as expression vectors (See e.g., WO 00/12738 and WO 00/09675 and U.S. Pat. Nos. 6,033,908, 6,019,978, 6,001,557, 5,994,132, 5,994,128, 5,994,106, 5,981,225, 5,885,808, 5,872,154, 5,830,730, and 5,824,544).

D. Host Cells

The present invention is not limited to a particular type of host cell. Numerous host cells that the vectors of the present invention are able to replicate and produce protein in may be adapted for use therewith. In preferred embodiments, eukaryotic host cells are utilized. In particularly preferred embodiments, mammalian host cells are utilized. A number of mammalian host cell lines are known in the art. In general, these host cells are capable of growth and survival when placed in either monolayer culture or in suspension culture in a medium containing the appropriate nutrients and growth factors, as is described in more detail below. Typically, the cells are capable of expressing and secreting large quantities of a particular protein of interest into the culture medium. Examples of suitable mammalian host cells include, but are not limited to, Chinese hamster ovary cells (CHO-K1, ATCC CCI-61); bovine mammary epithelial cells (ATCC CRL 10274; bovine mammary epithelial cells); monkey kidney CV1 line transformed by SV40 (COS-7, ATCC CRL 1651); human embryonic kidney line (293 or 293 cells subcloned for growth in suspension culture; see, e.g., Graham et al., J. Gen Virol., 36:59 [1977]); baby hamster kidney cells (BHK, ATCC CCL 10); mouse sertoli cells (TM4, Mather, Biol. Reprod. 23:243-251 [1980]); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68 [1982]); MRC 5 cells; FS4 cells; rat fibroblasts (208F cells); MDBK cells (bovine kidney cells); and a human hepatoma line (Hep G2).

The inventors also contemplate the use of amphibian and insect host cell lines. Examples of suitable insect host cell lines include, but are not limited to, mosquito cell lines (e.g., ATCC CRL-1660). Examples of suitable amphibian host cell lines include, but are not limited to, toad cell lines (e.g., ATCC CCL-102).

II. Inducers

The expression vectors and systems of the present invention may utilize inducers (e.g., transactivators). In preferred embodiments, the inducers are specific for the activation domain of the promoter chosen. For example, in some embodiments, the BLV promoter is activated with the BLV Tax inducer protein (SEQ ID NO:3). In other embodiments, the HTLV-1 promoter (SEQ ID NO:6) is activated by HTLV Tax protein (SEQ ID NO:5) and the HIV promoter (SEQ ID NO:7) is activated by the HIV Tat inducer protein (SEQ ID NO:9). In some embodiments, the HIV Tat protein is engineered to activate the BLV promoter (e.g., via site directed mutagenesis; See e.g., below discussion of engineered mutants).

The inducers of the present invention may be provided by any suitable method. In preferred embodiments, inducers are provided when expression of the gene of interest is desired (i.e., the expression of the gene of interest is regulated by the presence of inducer protein). In some embodiments, purified inducer protein is added to cells in culture. In other embodiments, a second expression vector encoding the inducer protein is included in the host cell comprising the retroviral expression vector of the present invention as known in the art.

A. Direct Administration

Accordingly, in some embodiments, purified inducer protein is provided directly to cells growing in culture. For example, in some embodiments, cells comprising a vector of the present invention are grown to the desired level of confluency for induction of protein expression and the inducer protein (e.g., Tax) is added to the culture. In preferred embodiments, one or more additional agents or delivery techniques designed to aid in the ability of the inducer to cross the cell membrane are utilized. Exemplary administration techniques include, but are not limited to, electroporation, lipid encapsulation, and the fusion of a protein transduction sequence to the inducer protein.

Accordingly, in some embodiments, inducer proteins are administered via electroporation (See e.g., Sambrook et al., supra). In electroporation, a brief electrical charge is administered to a sample of cells in culture, briefly allowing proteins to pass through the cell membrane. Apparatuses for administering the charge are commercially available.

In other embodiments, inducer proteins are encapsulated in lipids to allow for their movement through cell membranes. Several commercially available reagents are available for use in lipid encapsulation (e.g., including, but not limited to, Promega Corp., Madison, Wis., Mirus Corp., Madison, Wis.; EquiBio, Middlesex, UK; Roche Applied Science, Indianapolis, Ind.; and Stratagene, La Jolla, Calif.).

B. Expression of an Inducer Gene

In other embodiments, inducer proteins are provided via a second vector in the cell of interest. In preferred embodiments, the second vector only expresses the inducer protein when it is desired to induce expression of the gene of interest. For example, in some embodiments, the vector comprising the inducer gene is introduced to the cell containing the expression vector comprising the gene of interest only when it is desired to induce expression of the gene of interest. In other embodiments, the second vector comprising the gene expressing the inducer gene is present at all times but is under the control of an inducible promoter. In still further embodiments, both a first vector comprising the gene of interest under control of an inducible retroviral vector and a second vector comprising an inducer gene under the control of a promoter (e.g., a constitutive promoter) are introduced into a cell at the same time.

Figure 9:
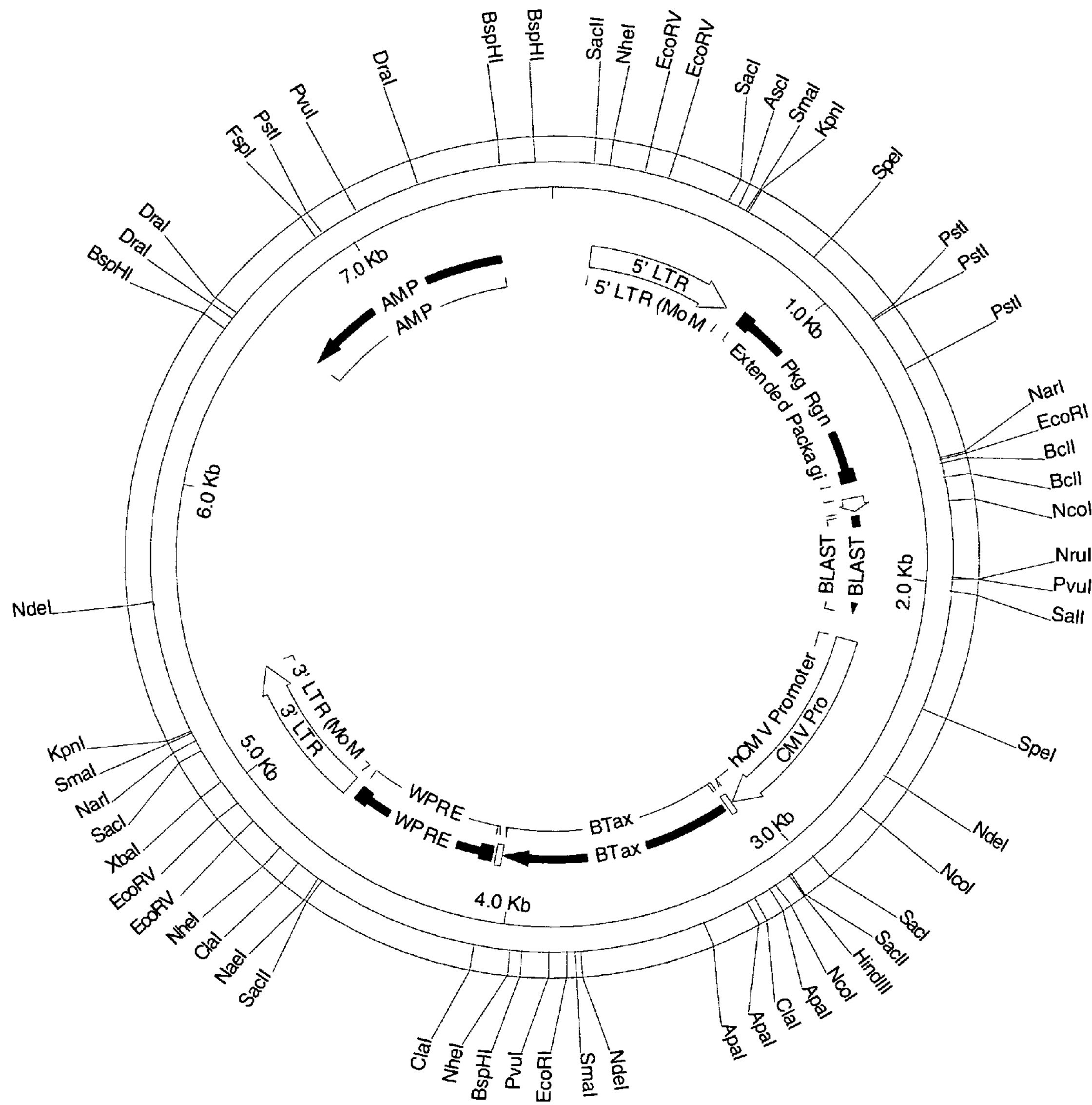
FIG. 9 shows a map of pLBC-BTaxW.
Figure 10:
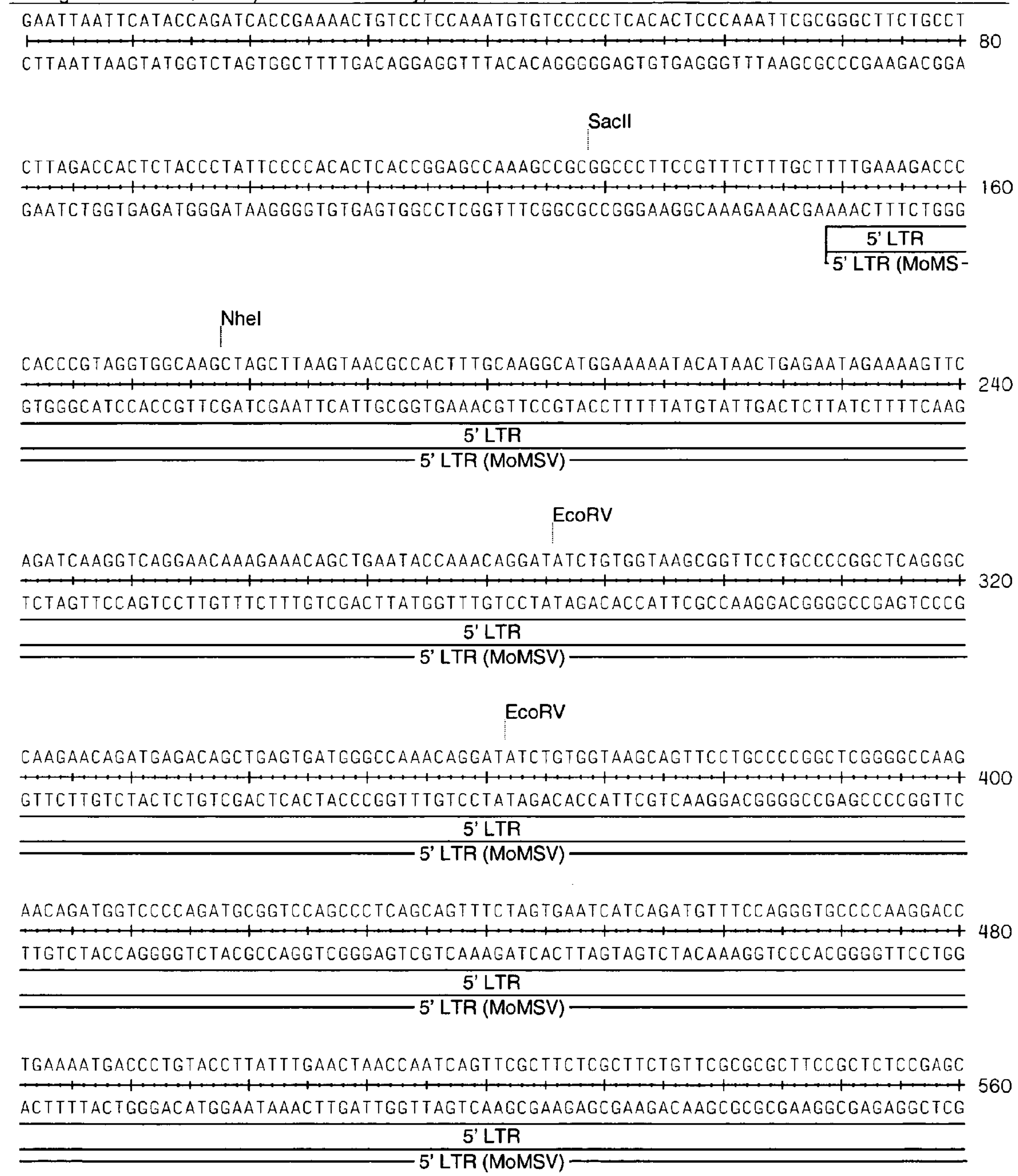
FIG. 10 shows the nucleic acid sequence of pLBC-BTaxW (SEQ ID NO:10 for the upper strand and SEQ ID NO: 13 for the lower strand) and the three amino acid seciuences labeled as BLAST, BTax, and AMP are provided in the sequence listing as SEQ ID NO: 11, SEQ ID NO:12, and SEQ ID NO:14, respectively.
Figure 10:
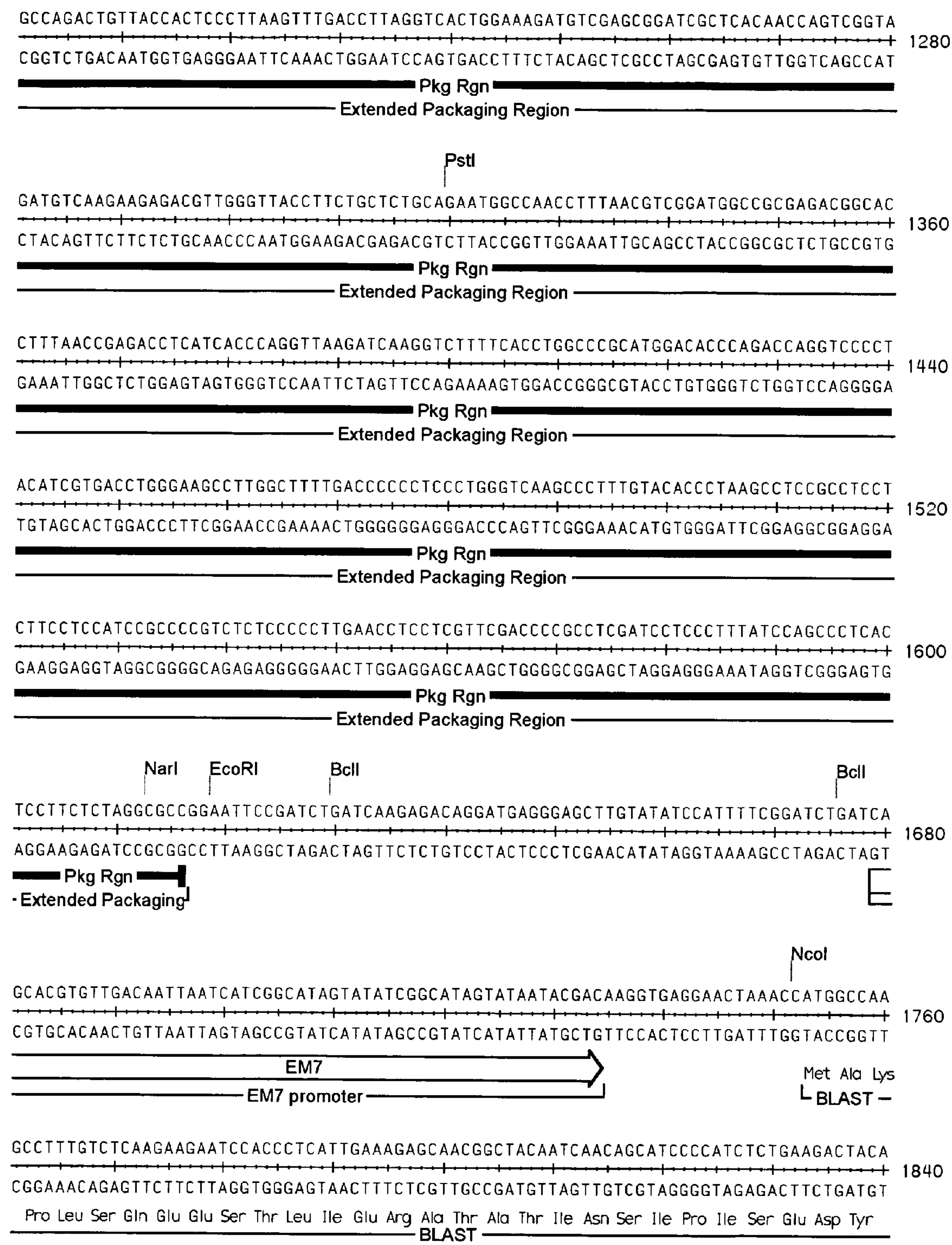
Figure 10:
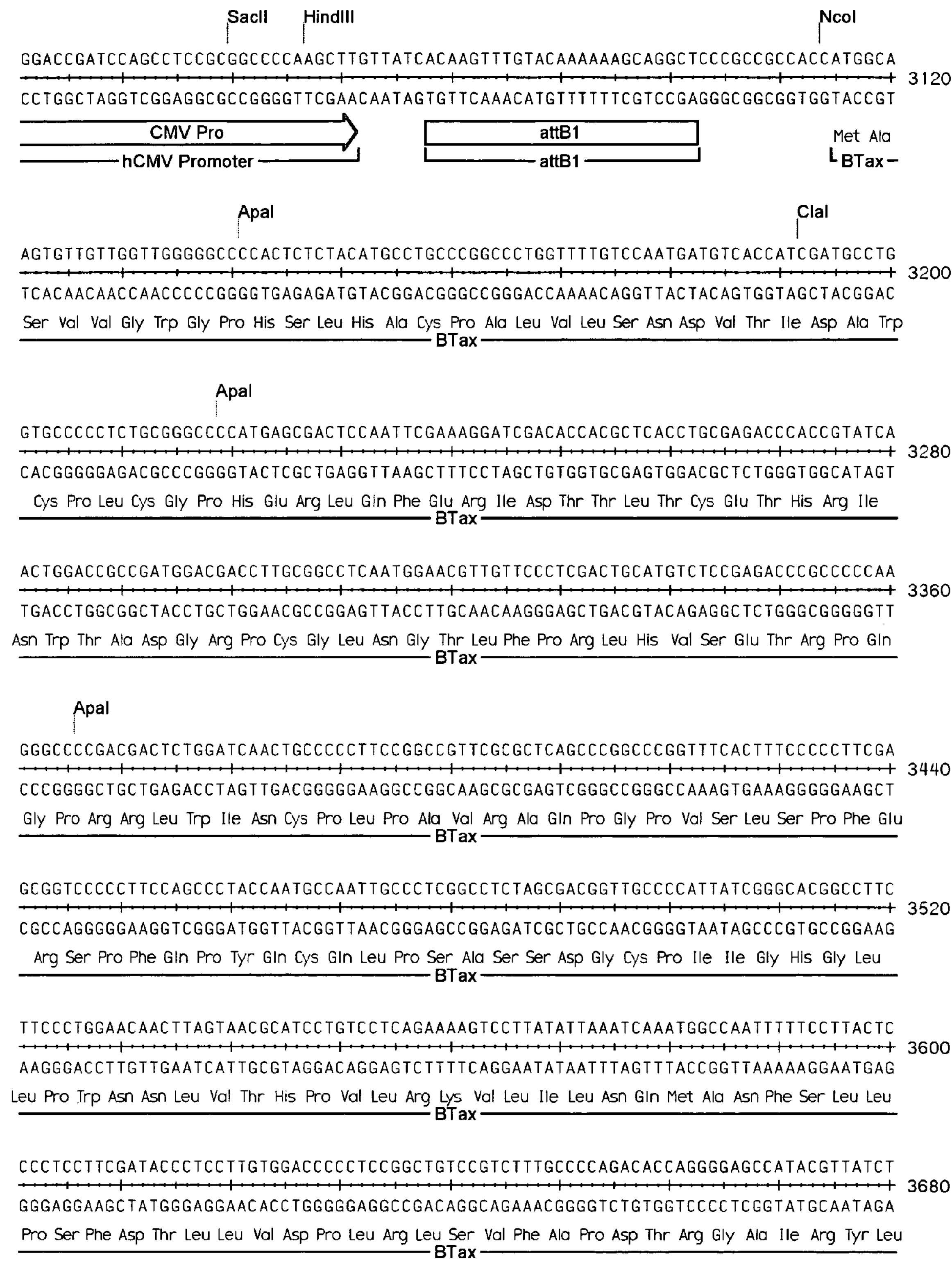

FIGS. 9 and 10 show an exemplary vector for the expression of Tax inducer protein (SEQ ID NO:10) comprising a WPRE element. The present invention is not limited to the particular constructs shown in FIGS. 9 and 10. Additional vectors for the expression of inducer proteins may be utilized (See e.g., above description of vectors).

C. Engineered Inducers

In some embodiments, inducer polypeptides (e.g., Tax) are engineered to make them more able to pass through cell membranes. For example, in some embodiments, inducer proteins are generated as a fusion protein with an additional polypeptide sequence (e.g., a protein transduction sequence) that allows them to pass through cell membranes unaided. In some embodiments, inducer proteins are fused to the HIV vp22 protein translocation sequence (See e.g., U.S. Pat. Nos. 6,358,739 and 6,251,398).

In other embodiments, inducer polypeptides such as Tax are generated as fusion proteins with the membrane translocation region of the HIV-1 Tat protein. The HIV Tat protein is known to cross cell membranes unaided (See e.g., U.S. Pat. No. 6,358,739; Vives et al., J. Biol. Chem. 272:16010 [1997]; Futaki et al., J. Biol. Chem. 276:5839 [2000]). The region of Tat known to direct translocation across cell membranes (i.e., the protein translocation domain) has been characterized (See e.g., Vives et al., supra; Futaki et al., supra). Proteins fused to the protein translocation domain of Tat have been shown to cross cell membranes (See e.g., Schwarze et al., Science 285:1569 [1999]; Bhorade et al., Bioconjug chem. 11:301 [2000]). Accordingly, in some embodiments, the protein translocation domain of Tat (e.g., amino acids 48-60) is fused to an inducer protein of the present invention (e.g., BLV or HTLV Tax).

In still further embodiments, an inducer protein of the present invention may be engineered to comprise an HIV Tat protein translocation domain internally. In preferred embodiments, the corresponding region of BLV or HTLV Tax (e.g., as determined by protein homology searches) may be substituted with the protein translocation domain of Tat.

III. Kits

In some embodiments, the inducible gene expression system(s) of the present invention may be provided as a kit for the expression of a protein of interest. Such expression kits may include the essential reagents required for the inducible expression methods of the present invention. In some embodiments, the kit may include a vessel containing an expression vector (e.g., a retroviral vector, plasmid, cosmid, adeno-associated viral vector, or an adenoviral vector) comprising an inducible promoter and a site for cloning an exogenous gene of interest such that the gene of interest is placed under the control of the inducible promoter. In some embodiments, the expression vector may further include an RNA export element (e.g., a WPRE element).

In some embodiments, the kit may further include a purified inducer protein or source of inducer protein (e.g., a vector for the expression of inducer protein) provided in a separate vessel. In the case of kits comprising a second expression vector for expression of the inducer protein, the kit may include all the reagents necessary for transfer of the second expression vector into a host cell and expression of the inducer protein.

The concentration of inducer protein may vary depending on the inducer protein and promoter, which may be determined experimentally. The kits according to the present invention may comprise a vessel containing excess amounts of inducer protein, such that the level can be optimized by the end user. The inducer protein provided in the kit may be at a high enough concentration such that only a small volume of inducer is required for inducing expression from the promoters.

In some embodiments, the kits may further include a separate vessel comprising host cells for expression of the gene of interest. The exact type of host cell, concentration of host cells, and storage conditions, are dependent on the type of expression vector chosen (e.g., plasmid or viral vector; eukaryotic or prokaryotic host cells).

The reagents may be provided in containers and be of a concentration suitable for direct use or use after dilution. A control may also be provided to allow for control of gene expression results. The kit may further include buffer for performing cloning and/or expression of the inducer protein. The kit may be packaged in a single enclosure including instructions for performing the expression methods. The instructions provided with the kit are specific to the type of expression vector and host cell provided with the kit. For example, separate kits may be provided for either viral or plasmid expression vectors.

EXPERIMENTAL

The following examples serve to illustrate certain preferred embodiments and aspects of the present invention and are not to be construed as limiting the scope thereof.

In the experimental disclosure which follows, the following abbreviations apply: M (molar); mM (millimolar); μM (micromolar); nM (nanomolar); mol (moles); mmol (millimoles); μmol (micromoles); nmol (nanomoles); gm (grams); mg (milligrams); μg (micrograms); pg (picograms); L (liters); ml (milliliters); μl (microliters); cm (centimeters); mm (millimeters); μm (micrometers); nm (nanometers); and ° C. (degrees Centigrade).

Example 1

Tax Inducible Gene Expression

Two different promoter constructs were analyzed in this example. Table 1 shows the constructs utilized in the experiments below and the geometric mean brightness values from FACS analysis. The BLV promoter was compared to the immediate early promoter of cytomegalovirus (CMV), a known strong promoter for mammalian expression systems. Two reporter constructs were used, LNBIv-YFP (FIG. 13), which contains the gene for yellow fluorescent protein (YFP) under the control of the BLV promoter, and LNC-YFP, which contains the gene for YFP under the control of the CMV promoter. The reporter constructs utilize the Neo selectable marker. Two inducer constructs were used, LBC-BTax (FIG. 9), which contains the gene for BLV Tax under control of the CMV promoter, and LBC-BTaxW, which is the same as LBC-BTax, with the addition of the WPRE in the 3' UTR of the BTax gene. The addition of the WPRE sequence to the Tax message is contemplated to increase Tax protein expression and lead to higher induction of the BLV promoter. D17 (canine osteogenic sarcoma) cells were then transduced with these vectors in the combinations shown in Table 1. Promoter strength was qualitatively and quantitatively evaluated by fluorescence activated cell sorting (FACS) and Western blot analysis, respectively, measuring yellow fluorescent protein (YFP) expression in cells transfected with the various vectors. The amount of YFP expression observed was directly proportional to promoter strength and, therefore, gene expression levels.

TABLE 1

| Cell Line (All D17) | Transduced With Retroviral Vector(s) | Geometric Mean Brightness (FACS) | | |
|---|---|---|---|---|
| (−) | None (negative control) | 1.17 | | |
| BY | LNBlv-YFP | 29.55 | | |
| CY | LNC-YFP | 441.52 | | |
| | | Unsorted | Bright | Dim |
| BY + Tax | LNBlv-YFP + LBC-BTax | 324.18 | 545.79 | 31.55 |
| BY + TaxW | LNBlv-YFP + LBC-BTaxW | 59.65 | 2310.02 | 29.93 |
| CY + Tax | LNC-YFP + LBC-BTax | 492.65 | | |
| CY + TaxW | LNC-YFP + LBC-BTaxW | 678.83 | | |

For the FACS analysis, propidium iodide (PI) was first added to the cells as an indicator of dead cells. The cells were gated according to PI signal such that only live cells were analyzed. Non-transfected D17 cells were used as a control for no YFP expression. The YFP expression of BY, CY, BY+Tax, CY+Tax, BY+TaxW, and CY+TaxW cells was measured and compared to non-transduced D17 cells [(−) in Table 1]. For each sample, YFP expression was quantified as amplitude of YFP. The YFP amplitude was on a logarithmic scale; therefore, YFP expression was measured as a geometric mean. The geometric mean data were organized into histograms that showed the distribution of YFP expression across a population of 10,000 cells. For the BY+Tax and BY+TaxW cells, the cell sorter was used to characterize the cells into Bright and Dim populations, as well as the whole population (Unsorted). With TaxW, a majority of the cells showed weak YFP expression, however about 20% of the cells showed extreme brightness.

FACS analysis was used to investigate the differences in YFP expression and, therefore, gene expression between the CMV and the BLV promoter with and without the Tax inducer. In the absence of Tax, the CMV promoter gave good expression of YFP, which was similar when the Tax or TaxW inducer protein was co-expressed (FIG. 1, Table 1). For the BLV promoter, YFP expression in the absence of Tax or TaxW was weak (BY FIG. 1 and Table 1)—barely detectable by FACS sorting. Adding the Tax inducer protein (in the absence of WPRE, "BY+Tax" in FIG. 1 and Table 1), increased YFP expression to levels comparable to YFP expression driven from the CMV promoter. When the WPRE was added to the Tax message, presumably increasing levels of Tax inducer protein, a subpopulation of cells showed extremely bright fluorescence. The Green Fluorescent Protein and its derivatives (YFP) are known to be toxic to cells when expressed at high levels. Thus, it is contemplated that very high expression led to selection of cells with low expression (the majority of cells—Dim) with a subpopulation expressing at full induction of the BLV promoter (Bright cells). In this case, the BY+TaxW cells (bright) showed levels of YFP expression 4-5 fold higher than CMV promoter driven YFP cells as judged by geometric mean fluorescence (FIG. 1, Table 1).

Quantitative western blot analysis was also performed on the six transfected cell types. The cells were first lysed using the M-PER (Pierce Biotechnology, Rockford, Ill.) mammalian protein extraction reagent. Cell lysates were then loaded onto a 12.5% SDS polyacrylamide gel electrophoresis system along with YPF sample standards of various concentrations. Following separation, the gel was transferred to a nitrocellulose membrane using the CRITERION gel blotting system (BioRad, Hercules, Calif.). The nitrocellulose membrane with the proteins attached was then treated in a blocking solution, followed by the primary murine anti-YFP specific and secondary dye-labeled rabbit anti-murine antibodies, and finally treatment with chemiluminescent reagent. The YFP treated with the chemiluminescent reagent was then exposed to x-ray film and developed. The bands produced on the film corresponded to YFP expression. Using the Un-Scan-It software program (available at the internet web site of ScienceDownload.com), the amount of YFP expression was quantitatively measured in terms of pixels on the film. Using the YFP standards, a standard curve was produced correlating the mass of YFP in the sample with pixels enumerated. From the standard curve, the mass of YFP in the BY, CY, BY+Tax, CY+Tax, BY+TaxW, and CY+TaxW samples was extrapolated. As with the FACS data, BLV promoter driven expression of YFP was very low in the absence of the Tax inducer. The co-expression of Tax increased BLV promoter driven YFP expression to a level similar to YFP expression from the CMV promoter.

TABLE 2

Quantitative Western

| | YFP Expression ngs +/− (StDev) |
|---|---|
| BY | not detected |
| BY + Tax | 43.1 (7.4) |
| BY + TaxW | 42.7 (0.8) |
| CY | 79.2 (12.0) |
| CY + Tax | 66.9 (21.5) |
| CY + TaxW | 76.3 (18.7) |

Example 2

Figure 17:
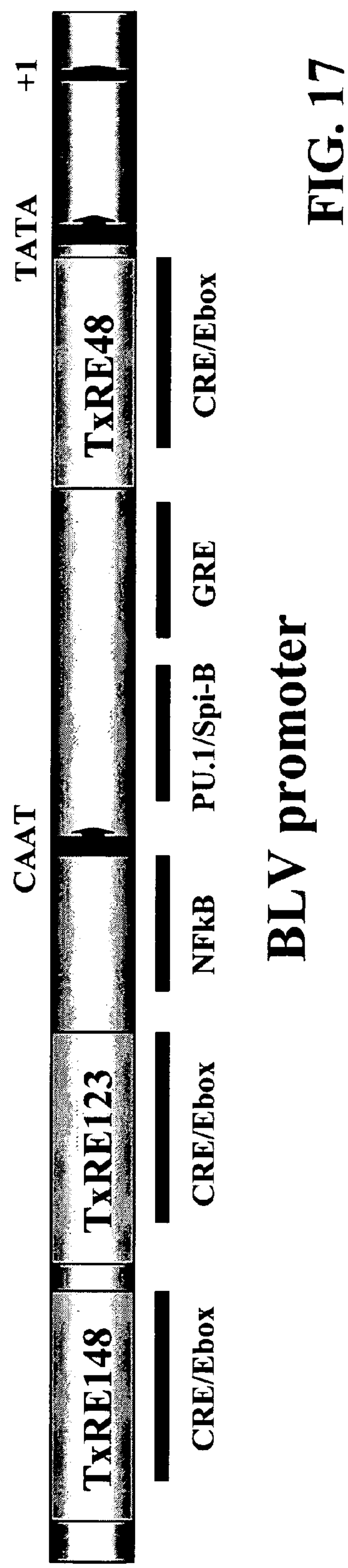
FIG. 17 shows a schematic representation of BLV promoter used in comparison studies. The BLV promoter (BLVp) consisting of the U3 region of the 5'LTR of BLV includes the basic elements of transcription start site (+1), CAAT (nt −97/−92) and TATA (nt 43/−37) boxes as shown. Unique to the BLVp are the three imperfectly conserved 21 bp sequences known as the Tax Responsive Elements (TxRE). The numbers following the TxRE designation represent its position relative to the transcription start site. Each TxRE contains a consensus E box-binding motif overlapping an imperfect cyclic AMP responsive element motif (CRE/Ebox). Additionally, the BLVp contains a glucocorticoid responsive element (GRE), Nuclear Factor Kappa Binding motif (NFkB), and B cell specific PU.1 or Spi-B transactivator binding motif (PU.1/Spi-B). The transcription elements are not drawn to scale.

Comparison of BLV and CMV Promoter-Driven Reporter Gene Expression in BLV-Infected and Non-Infected Cells A commercially available retroviral system was used with its standard CMV promoter (CMVp) or replaced with the BLV promoter (BLVp). FIG. 17 shows a schematic of the BLV promoter used in this experiment with its unique regulatory elements. The luciferase reporter gene was used to compare promoter expression strength within different cell lines and treatments. The WPRE was also incorporated to enhance transgene expression within these retroviral vectors. WPRE has been reported to significantly stimulate expression of transgenes in a promoter-independent fashion. Retroviral vectors were used because of the ease of stable cell line establishment, and because of its prominent use in transgenics and gene therapy. Cells of several different tissues and species were used in our studies and are listed in Table 3.

TABLE 3

Cells Used in Promoter Comparison Studies

| Name | Description | Reference |
|---|---|---|
| D17 | Dog Osteosarcoma | ATCC CCL-183; (Boris-Lawrie et al., J. Virol. 71: 1514 [1997]) |
| FLK | Sheep Kidney Cell Line; BLV expresser | (Tajima et al., J. Virol. 77: 1984 [2003]) |
| BL3.1 | Cow B-Lymphosarcoma; BLV expresser | ATCC CRL-2306; (Harms et al., Hum. Gene Ther. 6: 1291 [1996]) |
| B-Cell | Primary Cow B cell | Isolated as previously described (Harms et al., Hum. Immunol. 44: 50 [1995]) washed, and magnetically separated as known in the art. |

It was established through experimentation that the BLV promoter may be as strong as the CMV promoter depending on the host cell. Mammalian expression vector promoters have complex cis elements that bind diverse cellular trans factors resulting in varied levels of trans-gene expression depending on the host cell. Although the CMV promoter induces high-level constitutive trans-gene expression in most cells, absolute levels of expression vary greatly from cell line to cell line. In several cell lines (Harms et al., Hum. Immunopathology. 51:39 [1996]), the D17 cell line may produce the greatest level of trans-gene product through the CMV promoter. In contrast to the constitutive expression of the CMV promoter, the BLV promoter has cis elements that are dependent on BLV Tax for transgene expression (Tajima et al., J. Virol. 77:1984 [2003]). It was hypothesized therefore that in a cell line such as D17, the BLV promoter would have little or no activity compared to the CMV promoter. Conversely, in a cell line expressing the BLV Tax transactivator such as the BLV-producing FLK cell line, the BLV promoter would have similar activity compared to the CMV promoter. This theory was tested with luciferase as the transgene.

Figure 18B:
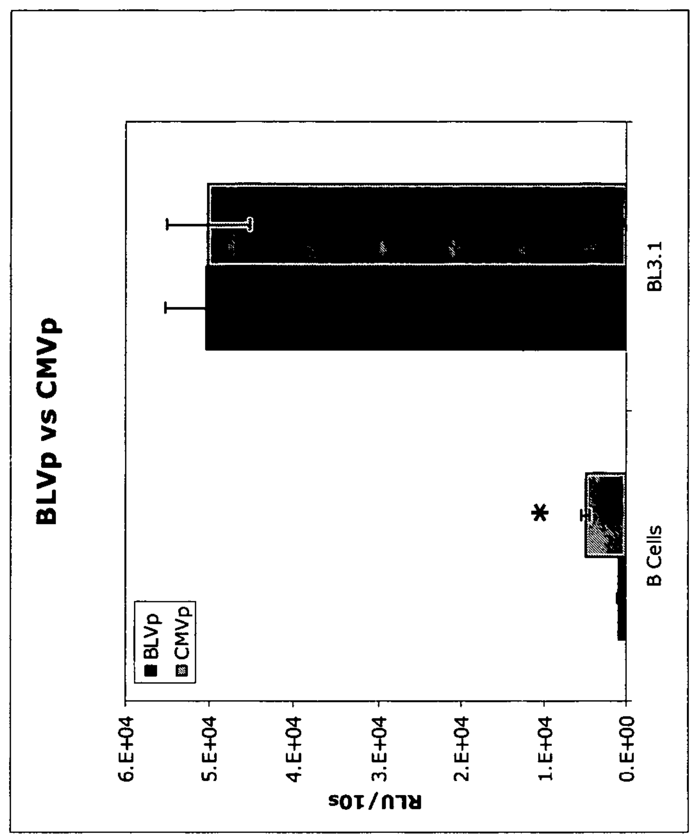
FIGS. 18A and 18B show BLVp and CMVp activity comparison in D17, FLK, primary cow B cells, and BL3.1. Relative light units (RLU) of luciferase activity driven by either the BLV promoter (BLVp) or CMV promoter (CMVp) of $1\times10^6$ stably transduced cells was measured during a 10 s period. Bars represent the arithmetic mean and variance of 10 experiments. *P<0.05; **P<0.001 determined by T-test.
Figure 18A:
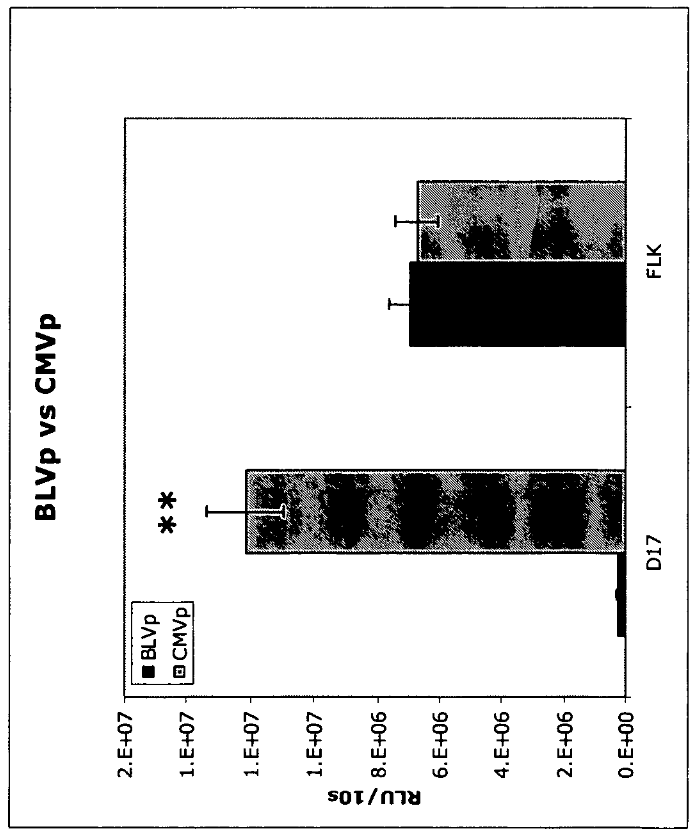

It was determined that the BLV promoter activity was about 50-fold less than CMV promoter activity in D17 cells but was about equal in FLK cells (FIG. 18A). As shown in FIG. 1, the BLVp also has a cis element that is B cell specific (PU.1/Spi-B). The strengths of BLV and CMV promoters were compared in primary B cells and a BLV infected B cell line hypothesizing that BLVp expression would be comparable to CMVp activity. BLVp activity was still less than CMVp activity in primary B cells but by only about a 5-fold difference (FIG. 18B). In the BLV infected BL3.1 cell line, BLVp activity was about equal to CMVp activity, analogous to results using the BLV infected FLK cell line. Thus, the BLV promoter may be as strong as the CMV promoter under appropriate conditions (e.g., BLV infection/Tax expression).

Example 3

Figure 19:
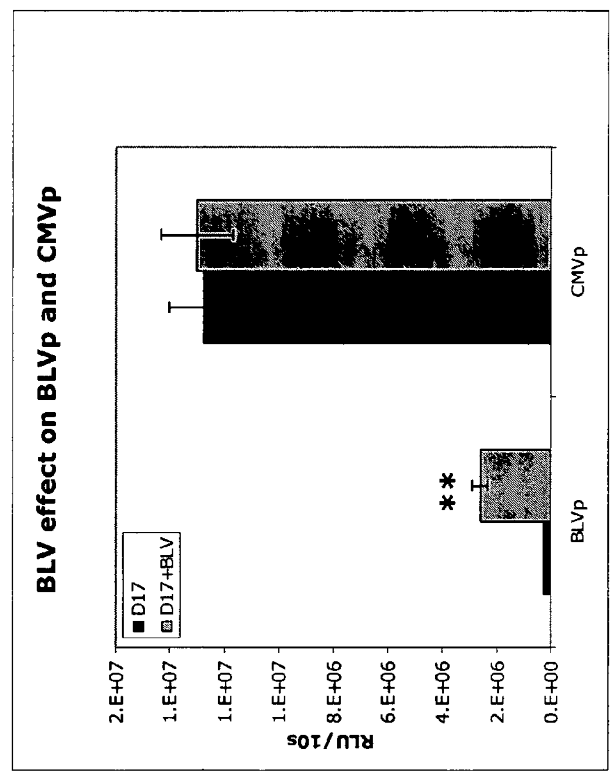
FIG. 19 shows that BLV infection enhances BLVp activity but has no effect on CMVp activity. D17 cells or D17 cells infected with and productively expressing BLV (D17+BLV) were transduced with luciferase expression vectors. Relative light units (RLU) of luciferase activity driven by either the BLV promoter (BLVp) or CMV promoter (CMVp) of $1\times10^6$ stably transduced cells was measured during a 10 s period. Bars represent the arithmetic mean and variance of 10 experiments. P<0.001 determined by T-test.

BLV Infection Enhances BLV Promoter Expression but Has No Measurable Effect on the CMV Promoter BLV promoter activity was greater than CMV promoter activity in the BLV infected FLK cell line but minimal compared to CMV promoter activity in the non-BLV infected D17 cell line. A determination was made as to whether BLV infection of D17 cells would enhance BLVp and/or suppress CMVp expression. The dog derived D17 cell line can be infected with BLV albeit not very efficiently (Boris-Lawrie et al., J. Virol. 71:1514 [1997]). D17 cells were infected with concentrated BLV from FLK cells, then clonally selected for BLV expression using pol RT-PCR and BLV reverse transcriptase assay of the supernatant. Luciferase assays demonstrated that BLV promoter activity in infected D17 cells was about 10-fold greater than BLV promoter activity in non-infected D17 cells (FIG. 19). CMV promoter activity remained unchanged.

The CMV promoter activity was still about 5-fold greater than BLV promoter activity in the BLV infected D17 cells compared to the relatively equal activity of the CMV promoter versus BLV promoter in BLV infected FLK cells. However, FLK cells are thought to contain four copies of the BLV provirus whereas BLV infected D17 cells contain a single copy of the provirus. Thus, there may be relatively greater expression of Tax in FLK cells effecting greater activity of the BLV promoter. Quantitative levels of Tax in BLV infected D17 or FLK cells were not measured.

Example 4

Figure 20B:
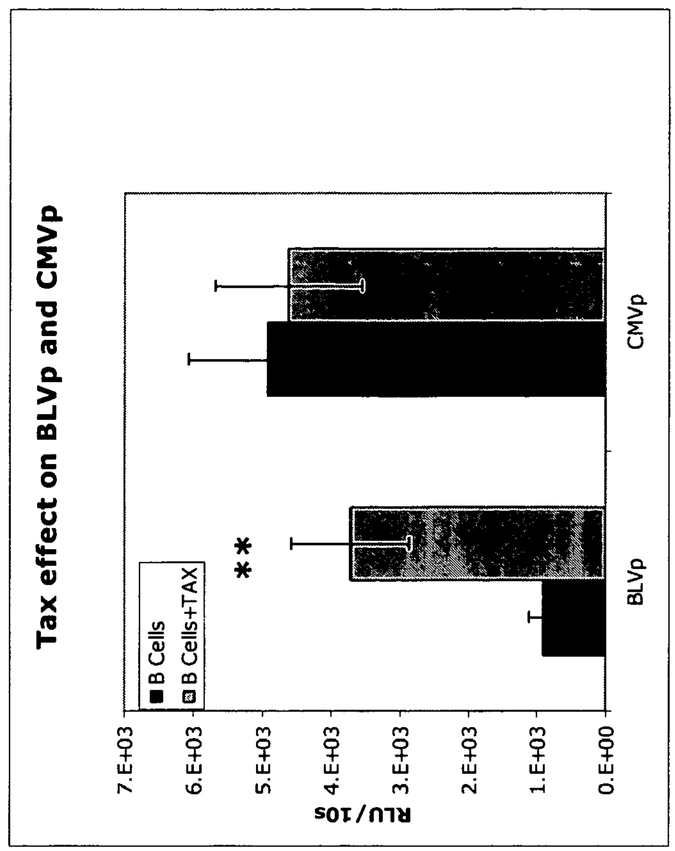
FIGS. 20A and 20B show that BLV Tax expression significantly enhances BLVp activity but has no effect on CMVp activity. D17 cells and primary bovine B cells (D17; B cells), or D17 cells and primary bovine B cells stably transduced with a BLV Tax expression vector (D17+TAX; B cells+TAX), were assayed. Relative light units (RLU) of luciferase activity driven by either the BLV promoter (BLVp) or CMV promoter (CMVp) of $1\times10^6$ stably transduced cells were measured during a 10 s period. Bars represent the arithmetic mean and variance of 10 experiments. P<0.001 determined by T-test.
Figure 20A:
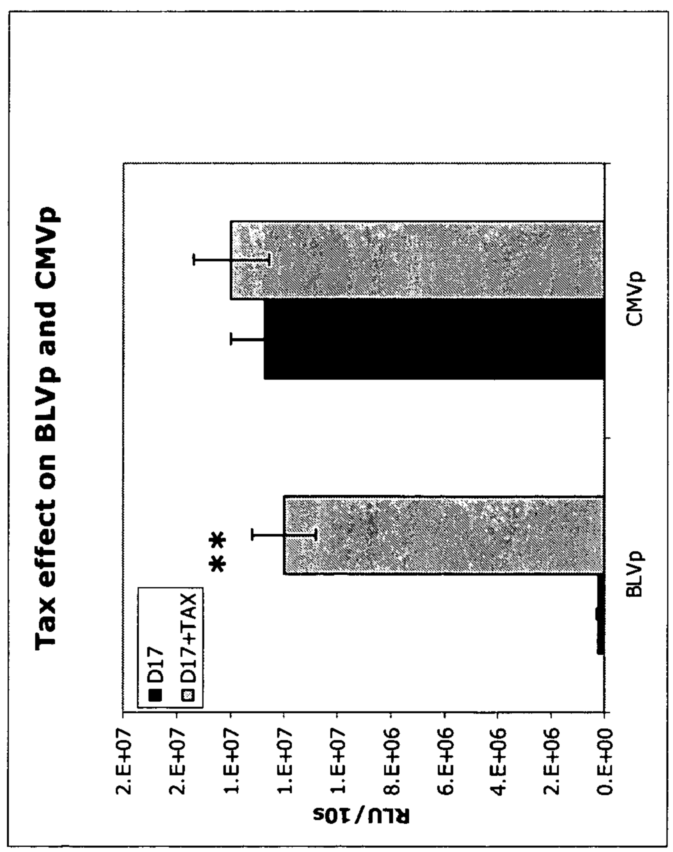

BLV Tax Enhances BLV Promoter Expression but Has No Measurable Effect on the CMV Promoter The BLV provirus encodes Tax within the X region located between the env gene and the 3' long terminal repeat (LTR). Within the provirus, Tax is subject to complex transcriptional and posttranscriptional regulation necessary for BLV expression and infectivity (Van Den Broeke et al., J. Virol. 731:1054 [1999]). Non-Tax regulatory factors encoded by BLV may affect the host and directly or indirectly, BLV promoter expression (Kerkhofs et al., J. Virol. 72:255 [1998]). To assess directly the effect of constitutive Tax expression on the BLV promoter and CMV promoter, BLV Tax was provided as a trans-gene to cells. As expected, Tax significantly enhanced BLV promoter activity but had no measurable effect on CMV promoter activity (FIGS. 20A/B) inducing BLVp activity about 48-fold in D17 cells. When BLV infected cells were transduced with the Tax transgene, the resulting increase in BLV promoter activity was a greater-than-additive enhancement of BLV infection and Tax transgene (Table 4). This effect could likely be caused by Tax up-regulating its expression within the BLV provirus. The effect on the CMV promoter was not significant.

TABLE 4

| | Percent of Basal Luciferase Expression | | |
|---|---|---|---|
| Promoter | D17 + Tax | D17 + BLV | D17 + Tax + BLV |
| BLVp | 115 ± 7 | 1226 ± 15 | 2038 ± 202 |
| CMVp | 96 ± 5 | 130 ± 23 | 118 ± 14 |

It should be noted that throughout the aforementioned studies of Examples 2, 3, and 4, expression vectors were assayed with and without the WPRE. WPRE enhanced transgene expression in all cell lines used, and in a promoter-independent fashion (about 2-fold greater for BLVp and CMVp in D17 cells). All data provided relating to Examples 2, 3, and 4 include vectors containing WPRE.

Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in material science, chemistry, and molecular biology or related fields are intended to be within the scope of the following claims.

The invention claimed is:

1. An inducible gene expression system comprising: a first vector comprising at least one retroviral promoter; at least one factor to induce the retroviral promoter, the at least one factor comprising a Tax polypeptide that comprises amino acids 48-60 of an HIV Tat protein; and at least one gene product expressed in proportion to retroviral promoter induction.

2. The system of claim 1 wherein the first vector is provided in a host cell.

3. The system of claim 1 wherein the first vector is selected from a retroviral vector, a plasmid, a cosmid, an adeno-associated viral vector, and an adenoviral vector.

4. The system of claim 1 wherein the first vector further comprises an RNA export element.

5. The system of claim 1 wherein the first vector comprises a retroviral promoter selected from a bovine leukemia virus promoter, a human T-lymphocyte virus promoter, a simian immunodeficiency virus promoter, and a caprine virus promoter.

6. The system of claim 1 wherein the Tax polypeptide comprises a polypeptide selected from a bovine leukemia virus Tax polypeptide, a human T-lymphocyte virus Tax polypeptide, a simian immunodeficiency virus Tax polypeptide, and a caprine virus Tax polypeptide.

7. The system of claim 1 wherein the Tax polypeptide comprises the amino acids 48-60 of the HIV Tat protein fused to a terminus of said Tax polypeptide.

8. The system of claim 1 wherein the Tax polypeptide comprises the amino acids 48-60 of the HIV Tat protein substituted for the corresponding amino acids of said Tax polypeptide.

9. The system of claim 1 wherein the at least one factor is provided exogenously.

10. The system of claim 1 wherein the Tax polypeptide that comprises amino acids 48-60 of an HIV Tat protein is produced from an encoding nucleic acid sequence provided in a second vector.

11. The system of claim 1 wherein the first vector comprises a bovine leukemia virus promoter and the Tax polypeptide that comprises amino acids 48-60 of an HIV Tat protein is a bovine leukemia virus Tax polypeptide that comprises amino acids 48-60 of an HIV Tat protein.

12. The system of claim 3 wherein the first vector comprises a pseudo-type retroviral vector.

13. The system of claim 4 wherein the RNA export element comprises a woodchuck mRNA processing enhancer.

* * * * *

UNITED STATES PATENT AND TRADEMARK OFFICE

CERTIFICATE OF CORRECTION

PATENT NO. : 7,297,536 B2
APPLICATION NO. : 10/763976
DATED : November 20, 2007
INVENTOR(S) : Jerome S. Harms et al.

It is certified that error appears in the above-identified patent and that said Letters Patent is hereby corrected as shown below:

In the Specification

Column 2, line 57 "seciuences" should be --sequences--

Column 2, line 64 "seciuences" should be --sequences--

Column 3, line 12 "seciuence" should be --sequence--

Column 7, line 59 "MOMLV" should be --MoMLV--

Column 7, line 60 "MOMLV" should be --MoMLV--

Column 7, line 64 "MOMLV" should be --MoMLV--

Column 7, line 66 "MOMLV" should be --MoMLV--

Signed and Sealed this
Fourth Day of February, 2014

Michelle K. Lee

Michelle K. Lee
*Deputy Director of the United States Patent and Trademark Office*

SEQUENCE LISTING

```
<160> NUMBER OF SEQ ID NOS: 65

<210> SEQ ID NO 1
<211> LENGTH: 576
<212> TYPE: DNA
<213> ORGANISM: Artificial
<220> FEATURE:
<223> OTHER INFORMATION: Engineered Sequence from virus and plasmid
<220> FEATURE:
<221> NAME/KEY: Promoter
<222> LOCATION: (87)..(432)
<223> OTHER INFORMATION: BLV Promoter

<400> SEQUENCE: 1

aggaaaccag cagcggctat ccgcgcatcc atgcccccga actgcaggag tggggaggca     60
```

-continued

```
cgatggccgc tttggtcgag gcggatccta gcagaaaaat aagacttgat tccccctttaa    120

aattacaact gctagaaaat gaatggctct cccgcctttt ttgaggggga atcatttgta    180

tgaaagatca tgccgaccta ggcgccgcca ccgccccgta aaccagacag agacgtcagc    240

tgccagaaaa gctggtgacg gcagctggtg gctagaatcc ccgtacctcc ccaacttccc    300

ctttcccgaa aaatccacac cctgagctgc tgacctcacc tgctgataaa ttaataaaat    360

gccggccctg tcgagttagc ggcaccagaa gcgttcttct cctgagaccc tcgtgctcag    420

ctctcggtcc tgcctcgaga agcttgttat cacaagtttg tacaaaaaag ctgaacgaga    480

aacgtaaaat gatataaata tcaatatatt aaattagatt ttgcataaaa aacagactac    540

ataatactgt aaaacacaac atatccagtc actatg                              576


<210> SEQ ID NO 2
<211> LENGTH: 930
<212> TYPE: DNA
<213> ORGANISM: Bovine leukemia virus
<220> FEATURE:
<221> NAME/KEY: CDS
<222> LOCATION: (1)..(930)

<400> SEQUENCE: 2

atg gca agt gtt gtt ggt tgg ggg ccc cac tct cta cat gcc tgc ccg       48
Met Ala Ser Val Val Gly Trp Gly Pro His Ser Leu His Ala Cys Pro
1               5                   10                  15

gcc ctg gtt ttg tcc aat gac gtc acc atc gat gcc tgg tgc ccc ctc       96
Ala Leu Val Leu Ser Asn Asp Val Thr Ile Asp Ala Trp Cys Pro Leu
            20                  25                  30

tgc ggg ccc cat gag cga ctc caa ttc gaa agg atc gac acc acg cac      144
Cys Gly Pro His Glu Arg Leu Gln Phe Glu Arg Ile Asp Thr Thr His
        35                  40                  45

acc tgc gag acc cac cgt atc acc tgg acc gcc gat gga cga cct ttc      192
Thr Cys Glu Thr His Arg Ile Thr Trp Thr Ala Asp Gly Arg Pro Phe
    50                  55                  60

ggc ctc aat gga gcg ctg ttc cct cga ctg cat gtc tcc aga gac ccg      240
Gly Leu Asn Gly Ala Leu Phe Pro Arg Leu His Val Ser Arg Asp Pro
65                  70                  75                  80

gcc cca agg gcc cga cga ctc tgg atc aac tgc ccc ctt ccg gcc gtt      288
Ala Pro Arg Ala Arg Arg Leu Trp Ile Asn Cys Pro Leu Pro Ala Val
                85                  90                  95

cgc gct cag ccc ggc ccg gtt tca ctt tcc ccc ttc gag cgg tcc ccc      336
Arg Ala Gln Pro Gly Pro Val Ser Leu Ser Pro Phe Glu Arg Ser Pro
            100                 105                 110

ttc cag ccc tac caa tgc caa ttg ccc tcg gcc tct agc gac ggt tgc      384
Phe Gln Pro Tyr Gln Cys Gln Leu Pro Ser Ala Ser Ser Asp Gly Cys
        115                 120                 125

ccc gtc atc ggg cac ggc ctt ctt ccc tgg aac aac tta gta acg cat      432
Pro Val Ile Gly His Gly Leu Leu Pro Trp Asn Asn Leu Val Thr His
    130                 135                 140

cct tgt cct cgg aaa gtc ctt ata tta aat caa atg gcc aat ttt tcc      480
Pro Cys Pro Arg Lys Val Leu Ile Leu Asn Gln Met Ala Asn Phe Ser
145                 150                 155                 160

tta ctc ccc ccc ttc aat acc ctc ctt gtg gac ccc ctc cgg ttg tcc      528
Leu Leu Pro Pro Phe Asn Thr Leu Leu Val Asp Pro Leu Arg Leu Ser
                165                 170                 175

gtc ttt gcc cca gac acc agg gga gcc ata cgt tat ctc tcc acc ctt      576
Val Phe Ala Pro Asp Thr Arg Gly Ala Ile Arg Tyr Leu Ser Thr Leu
            180                 185                 190

ttg acg cta tgc cca gct act tgt att cta ccc ctc ggc gag ccc ttc      624
```

-continued

```
Leu Thr Leu Cys Pro Ala Thr Cys Ile Leu Pro Leu Gly Glu Pro Phe
        195                 200                 205

tct cct aat gtc ccc ata tgt cgc ttt ccc cgg gac tcc aat gaa ccc      672
Ser Pro Asn Val Pro Ile Cys Arg Phe Pro Arg Asp Ser Asn Glu Pro
    210                 215                 220

ccc ctt tca gaa ttc gag ctg ccc ctt atc caa acg ccc ggc ctg tct      720
Pro Leu Ser Glu Phe Glu Leu Pro Leu Ile Gln Thr Pro Gly Leu Ser
225                 230                 235                 240

tgg tct gtc ccc gcg atc gac cta ttc cta acc ggc ccc cct tcc cca      768
Trp Ser Val Pro Ala Ile Asp Leu Phe Leu Thr Gly Pro Pro Ser Pro
                245                 250                 255

tgc gac cgg tta cac gta tgg tcc agt cct cag gcc tta cag cgc ttc      816
Cys Asp Arg Leu His Val Trp Ser Ser Pro Gln Ala Leu Gln Arg Phe
            260                 265                 270

ctc cat gac cct acg cta acc tgg tca gaa ttg gtt gct agc agg aaa      864
Leu His Asp Pro Thr Leu Thr Trp Ser Glu Leu Val Ala Ser Arg Lys
        275                 280                 285

cta aga ctt gat tca ccc tta aaa tta caa ctg tta gaa aat gaa tgg      912
Leu Arg Leu Asp Ser Pro Leu Lys Leu Gln Leu Leu Glu Asn Glu Trp
    290                 295                 300

ctc tcc cgc ctt ttt tga                                              930
Leu Ser Arg Leu Phe
305


<210> SEQ ID NO 3
<211> LENGTH: 309
<212> TYPE: PRT
<213> ORGANISM: Bovine leukemia virus

<400> SEQUENCE: 3

Met Ala Ser Val Val Gly Trp Gly Pro His Ser Leu His Ala Cys Pro
1               5                   10                  15

Ala Leu Val Leu Ser Asn Asp Val Thr Ile Asp Ala Trp Cys Pro Leu
            20                  25                  30

Cys Gly Pro His Glu Arg Leu Gln Phe Glu Arg Ile Asp Thr Thr His
        35                  40                  45

Thr Cys Glu Thr His Arg Ile Thr Trp Thr Ala Asp Gly Arg Pro Phe
    50                  55                  60

Gly Leu Asn Gly Ala Leu Phe Pro Arg Leu His Val Ser Arg Asp Pro
65                  70                  75                  80

Ala Pro Arg Ala Arg Arg Leu Trp Ile Asn Cys Pro Leu Pro Ala Val
                85                  90                  95

Arg Ala Gln Pro Gly Pro Val Ser Leu Ser Pro Phe Glu Arg Ser Pro
            100                 105                 110

Phe Gln Pro Tyr Gln Cys Gln Leu Pro Ser Ala Ser Ser Asp Gly Cys
        115                 120                 125

Pro Val Ile Gly His Gly Leu Leu Pro Trp Asn Asn Leu Val Thr His
    130                 135                 140

Pro Cys Pro Arg Lys Val Leu Ile Leu Asn Gln Met Ala Asn Phe Ser
145                 150                 155                 160

Leu Leu Pro Pro Phe Asn Thr Leu Leu Val Asp Pro Leu Arg Leu Ser
                165                 170                 175

Val Phe Ala Pro Asp Thr Arg Gly Ala Ile Arg Tyr Leu Ser Thr Leu
            180                 185                 190

Leu Thr Leu Cys Pro Ala Thr Cys Ile Leu Pro Leu Gly Glu Pro Phe
        195                 200                 205

Ser Pro Asn Val Pro Ile Cys Arg Phe Pro Arg Asp Ser Asn Glu Pro
```

-continued

```
    210                 215                 220

Pro Leu Ser Glu Phe Glu Leu Pro Leu Ile Gln Thr Pro Gly Leu Ser
225                 230                 235                 240

Trp Ser Val Pro Ala Ile Asp Leu Phe Leu Thr Gly Pro Pro Ser Pro
                245                 250                 255

Cys Asp Arg Leu His Val Trp Ser Ser Pro Gln Ala Leu Gln Arg Phe
            260                 265                 270

Leu His Asp Pro Thr Leu Thr Trp Ser Glu Leu Val Ala Ser Arg Lys
        275                 280                 285

Leu Arg Leu Asp Ser Pro Leu Lys Leu Gln Leu Leu Glu Asn Glu Trp
    290                 295                 300

Leu Ser Arg Leu Phe
305


<210> SEQ ID NO 4
<211> LENGTH: 1062
<212> TYPE: DNA
<213> ORGANISM: Human T-cell lymphotropic virus type 1
<220> FEATURE:
<221> NAME/KEY: promoter
<222> LOCATION: (1)..(353)

<400> SEQUENCE: 4

atggcccact tcccagggtt tggacagagt cttcttttcg gatacccagt ctacgtgttt      60

ggagacggcg actggtgccc ctgtgtacaa atctctgggg gactatgttc ggcccgccta     120

catcgtcacg ccctactggc cacctgtcca gagcatcaga tcacctggga ccccatcgat     180

ggacgcgtta tcggctcagc tctacagttc cttatccctc gactcccctc cttccccacc     240

cagagaacct ctaagaccct caaggtcctt accccgccaa tcactcatac aacccccaac     300

attccaccct ccttcctcca ggccatgcgc aaatactccc ccttccgaaa tggatacatg     360

gaacccaccc ttgggcagca cctcccaacc ctgtcttttc cagaccccgg actccggccc     420

caaaacctgt acaccctctg gggaggctcc gttgtctgca tgtacctcta ccagctttcc     480

ccccccatca cctggcccct cctgccccac gtgatttttt gccaccccgg ccagctcggg     540

gccttcctca ccaatgttcc ctacaagcga atagaagaac tcctctataa aatttccctt     600

accacagggg ccctaataat tctacccgaa gactgtttgc ccaccaccct tttccagcct     660

gttagggcac ccgtcacgct aacagcctgg caaaacggcc tccttccgtt ccactcaacc     720

ctcaccactc caggccttat ttggacattt accgatggca cgcctatgat ttccgggccc     780

tgccctaaag atggccagcc atctttagta ctacagtcct cctcctttat atttcacaaa     840

tttcaaacca aggcctacca cccctcattt ctactctcac acggcctcat acagtactct     900

tcctttcata atttacatct cctgtttgaa gaatacacca acatccccat ttctctactt     960

tttaacaaaa aagaggcaga tgacaatgac catgagcccc aaatatcccc cggggggctta    1020

gagcctccca gtgaaaaaca tttccgcgaa acagaagtct ga                       1062


<210> SEQ ID NO 5
<211> LENGTH: 353
<212> TYPE: DNA
<213> ORGANISM: Human T-cell lymphotropic virus type 1

<400> SEQUENCE: 5

tgacaatgac catgagcccc aaatatcccc cggggggctta gagcctctca gtgaaaaaca      60

tttccgtgaa acagaagtct gagaaggtca gggcccagaa taaggctctg acgtctcccc     120
```

-continued

```
ccggaggaca gctcagcacc agctcaggct aggccctgac gtgtcccccct aaagacaaat    180

cataagctca gacctccggg aagccaccgg gaaccaccca tttcctcccc atgtttgtca    240

agccgtcctc aggcgttgac gacaacccct cacctcaaaa aacttttcat ggcacgcata    300

cggctcaata aaataacagg agtctataaa agcgtgggga cagttcagga ggg           353


<210> SEQ ID NO 6
<211> LENGTH: 456
<212> TYPE: DNA
<213> ORGANISM: Human immunodeficiency virus type 1
<220> FEATURE:
<221> NAME/KEY: CDS
<222> LOCATION: (1)..(456)

<400> SEQUENCE: 6

ctg gaa ggg cta att tgg tcc caa aga aga caa gag atc ctt gat ctg       48
Leu Glu Gly Leu Ile Trp Ser Gln Arg Arg Gln Glu Ile Leu Asp Leu
1               5                   10                  15

tgg atc tac cac aca caa ggc tac ttc cct gat tgg cag aat tac aca       96
Trp Ile Tyr His Thr Gln Gly Tyr Phe Pro Asp Trp Gln Asn Tyr Thr
            20                  25                  30

cca ggg cca ggg atc aga tat cca ctg acc ttt gga tgg tgc ttc aag      144
Pro Gly Pro Gly Ile Arg Tyr Pro Leu Thr Phe Gly Trp Cys Phe Lys
        35                  40                  45

cta gta cca gtt gag cca gag aag gta gaa gag gcc aat gaa gga gag      192
Leu Val Pro Val Glu Pro Glu Lys Val Glu Glu Ala Asn Glu Gly Glu
    50                  55                  60

aac aac agc ttg tta cac cct atg agc ctg cat ggg atg gag gac gcg      240
Asn Asn Ser Leu Leu His Pro Met Ser Leu His Gly Met Glu Asp Ala
65                  70                  75                  80

gag aaa gaa gtg tta gtg tgg agg ttt gac agc aaa cta gca ttt cat      288
Glu Lys Glu Val Leu Val Trp Arg Phe Asp Ser Lys Leu Ala Phe His
                85                  90                  95

cac atg gcc cga gag ctg cat ccg gag tac tac aaa gac tgc tga cat      336
His Met Ala Arg Glu Leu His Pro Glu Tyr Tyr Lys Asp Cys     His
            100                 105                 110

cga gct ttc tac aag gga ctt tcc gct ggg gac ttt cca ggg agg cgt      384
Arg Ala Phe Tyr Lys Gly Leu Ser Ala Gly Asp Phe Pro Gly Arg Arg
            115                 120                 125

ggc ctg ggc ggg act ggg gag tgg cgt ccc tca gat gct gca tat aag      432
Gly Leu Gly Gly Thr Gly Glu Trp Arg Pro Ser Asp Ala Ala Tyr Lys
        130                 135                 140

cag ctg ctt ttt gcc tgt act ggg                                      456
Gln Leu Leu Phe Ala Cys Thr Gly
    145                 150


<210> SEQ ID NO 7
<211> LENGTH: 110
<212> TYPE: PRT
<213> ORGANISM: Human immunodeficiency virus type 1

<400> SEQUENCE: 7

Leu Glu Gly Leu Ile Trp Ser Gln Arg Arg Gln Glu Ile Leu Asp Leu
1               5                   10                  15

Trp Ile Tyr His Thr Gln Gly Tyr Phe Pro Asp Trp Gln Asn Tyr Thr
            20                  25                  30

Pro Gly Pro Gly Ile Arg Tyr Pro Leu Thr Phe Gly Trp Cys Phe Lys
        35                  40                  45

Leu Val Pro Val Glu Pro Glu Lys Val Glu Glu Ala Asn Glu Gly Glu
    50                  55                  60
```

```
Asn Asn Ser Leu Leu His Pro Met Ser Leu His Gly Met Glu Asp Ala
65                  70                  75                  80

Glu Lys Glu Val Leu Val Trp Arg Phe Asp Ser Lys Leu Ala Phe His
                85                  90                  95

His Met Ala Arg Glu Leu His Pro Glu Tyr Tyr Lys Asp Cys
            100                 105                 110


<210> SEQ ID NO 8
<211> LENGTH: 41
<212> TYPE: PRT
<213> ORGANISM: Human immunodeficiency virus type 1

<400> SEQUENCE: 8

His Arg Ala Phe Tyr Lys Gly Leu Ser Ala Gly Asp Phe Pro Gly Arg
1               5                   10                  15

Arg Gly Leu Gly Gly Thr Gly Glu Trp Arg Pro Ser Asp Ala Ala Tyr
            20                  25                  30

Lys Gln Leu Leu Phe Ala Cys Thr Gly
        35                  40


<210> SEQ ID NO 9
<211> LENGTH: 306
<212> TYPE: DNA
<213> ORGANISM: Human immunodeficiency virus type 1
<220> FEATURE:
<221> NAME/KEY: CDS
<222> LOCATION: (1)..(303)

<400> SEQUENCE: 9

atg gag cca gta gat cct aat cta gag ccc tgg aag cat cca gga agt       48
Met Glu Pro Val Asp Pro Asn Leu Glu Pro Trp Lys His Pro Gly Ser
1               5                   10                  15

cag cct agg act gct tgt aac aat tgc tat tgt aaa aag tgt tgc ttt       96
Gln Pro Arg Thr Ala Cys Asn Asn Cys Tyr Cys Lys Lys Cys Cys Phe
            20                  25                  30

cat tgc tac gcg tgt ttc aca aga aaa ggc tta ggc atc tcc tat ggc      144
His Cys Tyr Ala Cys Phe Thr Arg Lys Gly Leu Gly Ile Ser Tyr Gly
        35                  40                  45

agg aag aag cgg aga cag cga cga aga gct cct cag gac agt cag act      192
Arg Lys Lys Arg Arg Gln Arg Arg Arg Ala Pro Gln Asp Ser Gln Thr
    50                  55                  60

cat caa gct tct cta tca aag caa ccc gcc tcc cag tcc cga ggg gac      240
His Gln Ala Ser Leu Ser Lys Gln Pro Ala Ser Gln Ser Arg Gly Asp
65                  70                  75                  80

ccg aca ggc ccg acg gaa tcg aag aag aag gtg gag aga gag aca gag      288
Pro Thr Gly Pro Thr Glu Ser Lys Lys Lys Val Glu Arg Glu Thr Glu
                85                  90                  95

aca gat ccg ttc gat tag                                              306
Thr Asp Pro Phe Asp
            100


<210> SEQ ID NO 10
<211> LENGTH: 101
<212> TYPE: PRT
<213> ORGANISM: Human immunodeficiency virus type 1

<400> SEQUENCE: 10

Met Glu Pro Val Asp Pro Asn Leu Glu Pro Trp Lys His Pro Gly Ser
1               5                   10                  15

Gln Pro Arg Thr Ala Cys Asn Asn Cys Tyr Cys Lys Lys Cys Cys Phe
            20                  25                  30
```

-continued

```
His Cys Tyr Ala Cys Phe Thr Arg Lys Gly Leu Gly Ile Ser Tyr Gly
        35                  40                  45

Arg Lys Lys Arg Arg Gln Arg Arg Arg Ala Pro Gln Asp Ser Gln Thr
    50                  55                  60

His Gln Ala Ser Leu Ser Lys Gln Pro Ala Ser Gln Ser Arg Gly Asp
65                  70                  75                  80

Pro Thr Gly Pro Thr Glu Ser Lys Lys Lys Val Glu Arg Glu Thr Glu
                85                  90                  95

Thr Asp Pro Phe Asp
            100


<210> SEQ ID NO 11
<211> LENGTH: 309
<212> TYPE: PRT
<213> ORGANISM: Bovine leukemia virus

<400> SEQUENCE: 11

Met Ala Ser Val Val Gly Trp Gly Pro His Ser Leu His Ala Cys Pro
1               5                   10                  15

Ala Leu Val Leu Ser Asn Asp Val Thr Ile Asp Ala Trp Cys Pro Leu
            20                  25                  30

Cys Gly Pro His Glu Arg Leu Gln Phe Glu Arg Ile Asp Thr Thr His
        35                  40                  45

Thr Cys Glu Thr His Arg Ile Thr Trp Thr Ala Asp Gly Arg Pro Phe
    50                  55                  60

Gly Leu Asn Gly Ala Leu Phe Pro Arg Leu His Val Ser Arg Asp Pro
65                  70                  75                  80

Ala Pro Arg Ala Arg Arg Leu Trp Ile Asn Cys Pro Leu Pro Ala Val
                85                  90                  95

Arg Ala Gln Pro Gly Pro Val Ser Leu Ser Pro Phe Glu Arg Ser Pro
            100                 105                 110

Phe Gln Pro Tyr Gln Cys Gln Leu Pro Ser Ala Ser Ser Asp Gly Cys
        115                 120                 125

Pro Val Ile Gly His Gly Leu Leu Pro Trp Asn Asn Leu Val Thr His
    130                 135                 140

Pro Cys Pro Arg Lys Val Leu Ile Leu Asn Gln Met Ala Asn Phe Ser
145                 150                 155                 160

Leu Leu Pro Pro Phe Asn Thr Leu Leu Val Asp Pro Leu Arg Leu Ser
                165                 170                 175

Val Phe Ala Pro Asp Thr Arg Gly Ala Ile Arg Tyr Leu Ser Thr Leu
            180                 185                 190

Leu Thr Leu Cys Pro Ala Thr Cys Ile Leu Pro Leu Gly Glu Pro Phe
        195                 200                 205

Ser Pro Asn Val Pro Ile Cys Arg Phe Pro Arg Asp Ser Asn Glu Pro
    210                 215                 220

Pro Leu Ser Glu Phe Glu Leu Pro Leu Ile Gln Thr Pro Gly Leu Ser
225                 230                 235                 240

Trp Ser Val Pro Ala Ile Asp Leu Phe Leu Thr Gly Pro Pro Ser Pro
                245                 250                 255

Cys Asp Arg Leu His Val Trp Ser Ser Pro Gln Ala Leu Gln Arg Phe
            260                 265                 270

Leu His Asp Pro Thr Leu Thr Trp Ser Glu Leu Val Ala Ser Arg Lys
        275                 280                 285

Leu Arg Leu Asp Ser Pro Leu Lys Leu Gln Leu Leu Glu Asn Glu Trp
    290                 295                 300
```

```
Leu Ser Arg Leu Phe
305


<210> SEQ ID NO 12
<211> LENGTH: 353
<212> TYPE: PRT
<213> ORGANISM: Human T-cell lymphotropic virus type 1

<400> SEQUENCE: 12

Met Ala His Phe Pro Gly Phe Gly Gln Ser Leu Leu Phe Gly Tyr Pro
1               5                   10                  15

Val Tyr Val Phe Gly Asp Cys Val Gln Gly Asp Trp Cys Pro Ile Ser
            20                  25                  30

Gly Gly Leu Cys Ser Ala Arg Leu His Arg His Ala Leu Leu Ala Thr
        35                  40                  45

Cys Pro Glu His Gln Ile Thr Trp Asp Pro Ile Asp Gly Arg Val Ile
    50                  55                  60

Gly Ser Ala Leu Gln Phe Leu Ile Pro Arg Leu Pro Ser Phe Pro Thr
65                  70                  75                  80

Gln Arg Thr Ser Lys Thr Leu Lys Val Leu Thr Pro Pro Ile Thr His
                85                  90                  95

Thr Thr Pro Asn Ile Pro Pro Ser Phe Leu Gln Ala Met Arg Lys Tyr
            100                 105                 110

Ser Pro Phe Arg Asn Gly Tyr Met Glu Pro Thr Leu Gly Gln His Leu
        115                 120                 125

Pro Thr Leu Ser Phe Pro Asp Pro Gly Leu Arg Pro Gln Asn Leu Tyr
    130                 135                 140

Thr Leu Trp Gly Gly Ser Val Val Cys Met Tyr Leu Tyr Gln Leu Ser
145                 150                 155                 160

Pro Pro Ile Thr Trp Pro Leu Leu Pro His Val Ile Phe Cys His Pro
                165                 170                 175

Gly Gln Leu Gly Ala Phe Leu Thr Asn Val Pro Tyr Lys Arg Ile Glu
            180                 185                 190

Glu Leu Leu Tyr Lys Ile Ser Leu Thr Thr Gly Ala Leu Ile Ile Leu
        195                 200                 205

Pro Glu Asp Cys Leu Pro Thr Thr Leu Phe Gln Pro Val Arg Ala Pro
    210                 215                 220

Val Thr Leu Thr Ala Trp Gln Asn Gly Leu Leu Pro Phe His Ser Thr
225                 230                 235                 240

Leu Thr Thr Pro Gly Leu Ile Trp Thr Phe Thr Asp Gly Thr Pro Met
                245                 250                 255

Ile Ser Gly Pro Cys Pro Lys Asp Gly Gln Pro Ser Leu Val Leu Gln
            260                 265                 270

Ser Ser Ser Phe Ile Phe His Lys Phe Gln Thr Lys Ala Tyr His Pro
        275                 280                 285

Ser Phe Leu Leu Ser His Gly Leu Ile Gln Tyr Ser Ser Phe His Asn
    290                 295                 300

Leu His Leu Leu Phe Glu Glu Tyr Thr Asn Ile Pro Ile Ser Leu Leu
305                 310                 315                 320

Phe Asn Lys Lys Glu Ala Asp Asp Asn Asp His Glu Pro Gln Ile Ser
                325                 330                 335

Pro Gly Gly Leu Glu Pro Pro Ser Glu Lys His Phe Arg Glu Thr Glu
            340                 345                 350

Val
```

```
<210> SEQ ID NO 13
<211> LENGTH: 101
<212> TYPE: PRT
<213> ORGANISM: Human T-cell lymphotropic virus type 1

<400> SEQUENCE: 13

Met Glu Pro Val Asp Pro Asn Leu Glu Pro Trp Lys His Pro Gly Ser
1               5                   10                  15

Gln Pro Arg Thr Ala Cys Asn Asn Cys Tyr Cys Lys Lys Cys Cys Phe
            20                  25                  30

His Cys Tyr Ala Cys Phe Thr Arg Lys Gly Leu Gly Ile Ser Tyr Gly
        35                  40                  45

Arg Lys Lys Arg Arg Gln Arg Arg Arg Ala Pro Gln Asp Ser Gln Thr
    50                  55                  60

His Gln Ala Ser Leu Ser Lys Gln Pro Ala Ser Gln Ser Arg Gly Asp
65                  70                  75                  80

Pro Thr Gly Pro Thr Glu Ser Lys Lys Lys Val Glu Arg Glu Thr Glu
                85                  90                  95

Thr Asp Pro Phe Asp
            100


<210> SEQ ID NO 14
<211> LENGTH: 7685
<212> TYPE: DNA
<213> ORGANISM: Artificial
<220> FEATURE:
<223> OTHER INFORMATION: Engineered Sequence from virus and plasmid
<220> FEATURE:
<221> NAME/KEY: LTR
<222> LOCATION: (149)..(737)
<223> OTHER INFORMATION: 5' MoMuSVLTR
<220> FEATURE:
<221> NAME/KEY: CDS
<222> LOCATION: (1753)..(2148)
<223> OTHER INFORMATION: Blasticidin Resistance
<220> FEATURE:
<221> NAME/KEY: promoter
<222> LOCATION: (2257)..(3074)
<223> OTHER INFORMATION: CMV IE promoter
<220> FEATURE:
<221> NAME/KEY: misc_recomb
<222> LOCATION: (3078)..(3102)
<223> OTHER INFORMATION: attB1
<220> FEATURE:
<221> NAME/KEY: CDS
<222> LOCATION: (3115)..(4041)
<223> OTHER INFORMATION: BLV Tax
<220> FEATURE:
<221> NAME/KEY: misc_recomb
<222> LOCATION: (4046)..(4070)
<223> OTHER INFORMATION: attB2
<220> FEATURE:
<221> NAME/KEY: misc_signal
<222> LOCATION: (4082)..(4674)
<223> OTHER INFORMATION: WPRE; woodchuck hepatitis virus
      post-transcriptional regulatory element
<220> FEATURE:
<221> NAME/KEY: LTR
<222> LOCATION: (4720)..(5313)
<223> OTHER INFORMATION: 3' MoMuLvLTR
<220> FEATURE:
<221> NAME/KEY: CDS
<222> LOCATION: (6616)..(7476)
<223> OTHER INFORMATION: Ampicillin Resistance

<400> SEQUENCE: 14

gaattaattc ataccagatc accgaaaact gtcctccaaa tgtgtccccc tcacactccc     60
```

-continued

```
aaattcgcgg gcttctgcct cttagaccac tctaccctat tccccacact caccggagcc    120

aaagccgcgg cccttccgtt tctttgcttt tgaaagaccc cacccgtagg tggcaagcta    180

gcttaagtaa cgccactttg caaggcatgg aaaaatacat aactgagaat agaaaagttc    240

agatcaaggt caggaacaaa gaaacagctg aataccaaac aggatatctg tggtaagcgg    300

ttcctgcccc ggctcagggc caagaacaga tgagacagct gagtgatggg ccaaacagga    360

tatctgtggt aagcagttcc tgccccggct cggggccaag aacagatggt ccccagatgc    420

ggtccagccc tcagcagttt ctagtgaatc atcagatgtt tccagggtgc cccaaggacc    480

tgaaaatgac cctgtacctt atttgaacta accaatcagt tcgcttctcg cttctgttcg    540

cgcgcttccg ctctccgagc tcaataaaag agcccacaac ccctcactcg gcgcgccagt    600

cttccgatag actgcgtcgc ccgggtaccc gtattcccaa taaagcctct tgctgtttgc    660

atccgaatcg tggtctcgct gttccttggg agggtctcct ctgagtgatt gactacccac    720

gacgggggtc tttcatttgg gggctcgtcc gggatttgga gacccctgcc cagggaccac    780

cgacccacca ccgggaggta agctggccag caacttatct gtgtctgtcc gattgtctag    840

tgtctatgtt tgatgttatg cgcctgcgtc tgtactagtt agctaactag ctctgtatct    900

ggcggacccg tggtggaact gacgagttct gaacacccgg ccgcaaccct gggagacgtc    960

ccagggactt tgggggccgt ttttgtggcc cgacctgagg aagggagtcg atgtggaatc   1020

cgaccccgtc aggatatgtg gttctggtag gagacgagaa cctaaaacag ttcccgcctc   1080

cgtctgaatt tttgctttcg gtttggaacc gaagccgcgc gtcttgtctg ctgcagcgct   1140

gcagcatcgt tctgtgttgt ctctgtctga ctgtgtttct gtatttgtct gaaaattagg   1200

gccagactgt taccactccc ttaagtttga ccttaggtca ctggaaagat gtcgagcgga   1260

tcgctcacaa ccagtcggta gatgtcaaga agagacgttg ggttaccttc tgctctgcag   1320

aatggccaac ctttaacgtc ggatggccgc gagacggcac ctttaaccga gacctcatca   1380

cccaggttaa gatcaaggtc ttttcacctg gcccgcatgg acacccagac caggtcccct   1440

acatcgtgac ctgggaagcc ttggcttttg acccccctcc ctgggtcaag ccctttgtac   1500

accctaagcc tccgcctcct cttcctccat ccgccccgtc tctcccccttt gaacctcctc  1560

gttcgacccc gcctcgatcc tccctttatc cagccctcac tccttctcta ggcgccggaa   1620

ttccgatctg atcaagagac aggatgaggg agcttgtata tccattttcg gatctgatca   1680

gcacgtgttg acaattaatc atcggcatag tatatcggca tagtataata cgacaaggtg   1740

aggaactaaa cc atg gcc aag cct ttg tct caa gaa gaa tcc acc ctc att   1791
              Met Ala Lys Pro Leu Ser Gln Glu Glu Ser Thr Leu Ile
              1               5                   10

gaa aga gca acg gct aca atc aac agc atc ccc atc tct gaa gac tac     1839
Glu Arg Ala Thr Ala Thr Ile Asn Ser Ile Pro Ile Ser Glu Asp Tyr
    15                  20                  25

agc gtc gcc agc gca gct ctc tct agc gac ggc cgc atc ttc act ggt     1887
Ser Val Ala Ser Ala Ala Leu Ser Ser Asp Gly Arg Ile Phe Thr Gly
30                  35                  40                  45

gtc aat gta tat cat ttt act ggg gga cct tgt gca gaa ctc gtg gtg     1935
Val Asn Val Tyr His Phe Thr Gly Gly Pro Cys Ala Glu Leu Val Val
                50                  55                  60

ctg ggc act gct gct gct gcg gca gct ggc aac ctg act tgt atc gtc     1983
Leu Gly Thr Ala Ala Ala Ala Ala Ala Gly Asn Leu Thr Cys Ile Val
            65                  70                  75

gcg atc gga aat gag aac agg ggc atc ttg agc ccc tgc gga cgg tgt     2031
Ala Ile Gly Asn Glu Asn Arg Gly Ile Leu Ser Pro Cys Gly Arg Cys
        80                  85                  90
```

```
cga cag gtg ctt ctc gat ctg cat cct ggg atc aaa gcg ata gtg aag     2079
Arg Gln Val Leu Leu Asp Leu His Pro Gly Ile Lys Ala Ile Val Lys
    95                  100                 105

gac agt gat gga cag ccg acg gca gtt ggg att cgt gaa ttg ctg ccc     2127
Asp Ser Asp Gly Gln Pro Thr Ala Val Gly Ile Arg Glu Leu Leu Pro
110                 115                 120                 125

tct ggt tat gtg tgg gag ggc taagcacttc gtggccgagg agcaggactg        2178
Ser Gly Tyr Val Trp Glu Gly
                130

acacgtgcta cgagatttcg attccaccgc cgccttctat gaaaggttgg gcttcggaat   2238

cgttttccgg gacgccgatc cggccattag ccatattatt cattggttat atagcataaa   2298

tcaatattgg ctattggcca ttgcatacgt tgtatccata tcataatatg tacatttata   2358

ttggctcatg tccaacatta ccgccatgtt gacattgatt attgactagt tattaatagt   2418

aatcaattac ggggtcatta gttcatagcc catatatgga gttccgcgtt acataactta   2478

cggtaaatgg cccgcctggc tgaccgccca acgacccccg cccattgacg tcaataatga   2538

cgtatgttcc catagtaacg ccaataggga ctttccattg acgtcaatgg gtggagtatt   2598

tacggtaaac tgcccacttg gcagtacatc aagtgtatca tatgccaagt acgcccccta   2658

ttgacgtcaa tgacggtaaa tggcccgcct ggcattatgc ccagtacatg accttatggg   2718

actttcctac ttggcagtac atctacgtat tagtcatcgc tattaccatg gtgatgcggt   2778

tttggcagta catcaatggg cgtggatagc ggtttgactc acggggattt ccaagtctcc   2838

accccattga cgtcaatggg agtttgtttt ggcaccaaaa tcaacgggac tttccaaaat   2898

gtcgtaacaa ctccgcccca ttgacgcaaa tgggcggtag gcatgtacgg tgggaggtct   2958

atataagcag agctcgttta gtgaaccgtc agatcgcctg gagacgccat ccacgctgtt   3018

ttgacctcca tagaagacac cgggaccgat ccagcctccg cggccccaag cttgttatca   3078

caagtttgta caaaaaagca ggctcccgcc gccacc atg gca agt gtt gtt ggt     3132
                                        Met Ala Ser Val Val Gly
                                                    135

tgg ggg ccc cac tct cta cat gcc tgc ccg gcc ctg gtt ttg tcc aat     3180
Trp Gly Pro His Ser Leu His Ala Cys Pro Ala Leu Val Leu Ser Asn
    140                 145                 150

gat gtc acc atc gat gcc tgg tgc ccc ctc tgc ggg ccc cat gag cga     3228
Asp Val Thr Ile Asp Ala Trp Cys Pro Leu Cys Gly Pro His Glu Arg
155                 160                 165                 170

ctc caa ttc gaa agg atc gac acc acg ctc acc tgc gag acc cac cgt     3276
Leu Gln Phe Glu Arg Ile Asp Thr Thr Leu Thr Cys Glu Thr His Arg
                175                 180                 185

atc aac tgg acc gcc gat gga cga cct tgc ggc ctc aat gga acg ttg     3324
Ile Asn Trp Thr Ala Asp Gly Arg Pro Cys Gly Leu Asn Gly Thr Leu
            190                 195                 200

ttc cct cga ctg cat gtc tcc gag acc cgc ccc caa ggg ccc cga cga     3372
Phe Pro Arg Leu His Val Ser Glu Thr Arg Pro Gln Gly Pro Arg Arg
        205                 210                 215

ctc tgg atc aac tgc ccc ctt ccg gcc gtt cgc gct cag ccc ggc ccg     3420
Leu Trp Ile Asn Cys Pro Leu Pro Ala Val Arg Ala Gln Pro Gly Pro
    220                 225                 230

gtt tca ctt tcc ccc ttc gag cgg tcc ccc ttc cag ccc tac caa tgc     3468
Val Ser Leu Ser Pro Phe Glu Arg Ser Pro Phe Gln Pro Tyr Gln Cys
235                 240                 245                 250

caa ttg ccc tcg gcc tct agc gac ggt tgc ccc att atc ggg cac ggc     3516
Gln Leu Pro Ser Ala Ser Ser Asp Gly Cys Pro Ile Ile Gly His Gly
                255                 260                 265
```

-continued

```
ctt ctt ccc tgg aac aac tta gta acg cat cct gtc ctc aga aaa gtc      3564
Leu Leu Pro Trp Asn Asn Leu Val Thr His Pro Val Leu Arg Lys Val
            270                 275                 280

ctt ata tta aat caa atg gcc aat ttt tcc tta ctc ccc tcc ttc gat      3612
Leu Ile Leu Asn Gln Met Ala Asn Phe Ser Leu Leu Pro Ser Phe Asp
        285                 290                 295

acc ctc ctt gtg gac ccc ctc cgg ctg tcc gtc ttt gcc cca gac acc      3660
Thr Leu Leu Val Asp Pro Leu Arg Leu Ser Val Phe Ala Pro Asp Thr
    300                 305                 310

agg gga gcc ata cgt tat ctc tcc acc ctt ttg acg cta tgc ccg gct      3708
Arg Gly Ala Ile Arg Tyr Leu Ser Thr Leu Leu Thr Leu Cys Pro Ala
315                 320                 325                 330

act tgt att cta ccc cta ggc gag ccc ttc tct cct aat gtc ccc ata      3756
Thr Cys Ile Leu Pro Leu Gly Glu Pro Phe Ser Pro Asn Val Pro Ile
                335                 340                 345

tgc cgc ttt ccc cgg gac tcc aat gaa ccc ccc ctt tca gaa ttc gag      3804
Cys Arg Phe Pro Arg Asp Ser Asn Glu Pro Pro Leu Ser Glu Phe Glu
            350                 355                 360

ctg ccc ctt atc caa acg ccc ggc ctg tct tgg tct gtc ccc gcg atc      3852
Leu Pro Leu Ile Gln Thr Pro Gly Leu Ser Trp Ser Val Pro Ala Ile
        365                 370                 375

gac cta ttc cta acc ggt ccc cct tcc cca tgc gac cgg tta cac gta      3900
Asp Leu Phe Leu Thr Gly Pro Pro Ser Pro Cys Asp Arg Leu His Val
    380                 385                 390

tgg tcc agt cct cag gcc tta cag cgc ttc ctt cat gac cct acg cta      3948
Trp Ser Ser Pro Gln Ala Leu Gln Arg Phe Leu His Asp Pro Thr Leu
395                 400                 405                 410

acc tgg tcc gaa tta gtt gct agc aga aaa ata aga ctt gat tcc ccc      3996
Thr Trp Ser Glu Leu Val Ala Ser Arg Lys Ile Arg Leu Asp Ser Pro
                415                 420                 425

tta aaa tta caa ctg cta gaa aat gaa tgg ctc tcc cgc ctt ttt          4041
Leu Lys Leu Gln Leu Leu Glu Asn Glu Trp Leu Ser Arg Leu Phe
            430                 435                 440

tgagacccag ctttcttgta caaagtggtg ataacatcga taatcaacct ctggattaca    4101

aaatttgtga aagattgact ggtattctta actatgttgc tccttttacg ctatgtggat    4161

acgctgcttt aatgcctttg tatcatgcta ttgcttcccg tatggctttc attttctcct    4221

ccttgtataa atcctggttg ctgtctcttt atgaggagtt gtggcccgtt gtcaggcaac    4281

gtggcgtggt gtgcactgtg tttgctgacg caacccccac tggttggggc attgccacca    4341

cctgtcagct cctttccggg actttcgctt tccccctccc tattgccacg gcggaactca    4401

tcgccgcctg ccttgcccgc tgctggacag gggctcggct gttgggcact gacaattccg    4461

tggtgttgtc ggggaaatca tcgtcctttc cttggctgct cgcctgtgtt gccacctgga    4521

ttctgcgcgg gacgtccttc tgctacgtcc cttcggccct caatccagcg gaccttcctt    4581

cccgcggcct gctgccggct ctgcggcctc ttccgcgtct tcgccttcgc cctcagacga    4641

gtcggatctc cctttgggcc gcctccccgc ctgatcgata aaataaaaga ttttatttag    4701

tctccagaaa aaggggggaa tgaaagaccc cacctgtagg tttggcaagc tagcttaagt    4761

aacgccattt tgcaaggcat ggaaaaatac ataactgaga atagagaagt tcagatcaag    4821

gtcaggaaca gatggaacag ctgaatatgg gccaaacagg atatctgtgg taagcagttc    4881

ctgccccggc tcagggccaa gaacagatgg aacagctgaa tatgggccaa acaggatatc    4941

tgtggtaagc agttcctgcc ccggctcagg gccaagaaca gatggtcccc agatgcggtc    5001

cagccctcag cagtttctag agaaccatca gatgtttcca gggtgcccca aggacctgaa    5061

atgaccctgt gccttatttg aactaaccaa tcagttcgct tctcgcttct gttcgcgcgc    5121
```

-continued

```
ttctgctccc cgagctcaat aaaagagccc acaacccctc actcggggcg ccagtcctcc   5181

gattgactga gtcgcccggg tacccgtgta tccaataaac cctcttgcag ttgcatccga   5241

cttgtggtct cgctgttcct tgggagggtc tcctctgagt gattgactac ccgtcagcgg   5301

gggtctttca tttttccatt gggggctcgt ccgggatcgg gagacccctg cccagggacc   5361

accgacccac caccgggagg taagctggct gcctcgcgcg tttcggtgat gacggtgaaa   5421

acctctgaca catgcagctc ccggagacgg tcacagcttg tctgtaagcg gatgccggga   5481

gcagacaagc ccgtcagggc gcgtcagcgg gtgttggcgg gtgtcggggc gcagccatga   5541

cccagtcacg tagcgatagc ggagtgtata ctggcttaac tatgcggcat cagagcagat   5601

tgtactgaga gtgcaccata tgcggtgtga aataccgcac agatgcgtaa ggagaaaata   5661

ccgcatcagg cgctcttccg cttcctcgct cactgactcg ctgcgctcgg tcgttcggct   5721

gcggcgagcg gtatcagctc actcaaaggc ggtaatacgg ttatccacag aatcagggga   5781

taacgcagga aagaacatgt gagcaaaagg ccagcaaaag gccaggaacc gtaaaaaggc   5841

cgcgttgctg gcgtttttcc ataggctccg cccccctgac gagcatcaca aaaatcgacg   5901

ctcaagtcag aggtggcgaa acccgacagg actataaaga taccaggcgt ttccccctgg   5961

aagctccctc gtgcgctctc ctgttccgac cctgccgctt accggatacc tgtccgcctt   6021

tctcccttcg ggaagcgtgg cgctttctca tagctcacgc tgtaggtatc tcagttcggt   6081

gtaggtcgtt cgctccaagc tgggctgtgt gcacgaaccc cccgttcagc ccgaccgctg   6141

cgccttatcc ggtaactatc gtcttgagtc caacccggta agacacgact tatcgccact   6201

ggcagcagcc actggtaaca ggattagcag agcgaggtat gtaggcggtg ctacagagtt   6261

cttgaagtgg tggcctaact acggctacac tagaaggaca gtatttggta tctgcgctct   6321

gctgaagcca gttaccttcg gaaaaagagt tggtagctct tgatccggca aacaaaccac   6381

cgctggtagc ggtggttttt ttgtttgcaa gcagcagatt acgcgcagaa aaaaaggatc   6441

tcaagaagat cctttgatct tttctacggg gtctgacgct cagtggaacg aaaactcacg   6501

ttaagggatt ttggtcatga gattatcaaa aaggatcttc acctagatcc ttttaaatta   6561
aaaatgaagt tttaaatcaa tctaaagtat atatgagtaa acttggtctg acag tta     6618
                                                            Leu

cca atg ctt aat cag tga ggc acc tat ctc agc gat ctg tct att tcg     6666
Pro Met Leu Asn Gln     Gly Thr Tyr Leu Ser Asp Leu Ser Ile Ser
        445                     450                 455

ttc atc cat agt tgc ctg act ccc cgt cgt gta gat aac tac gat acg     6714
Phe Ile His Ser Cys Leu Thr Pro Arg Arg Val Asp Asn Tyr Asp Thr
        460                 465                 470

gga ggg ctt acc atc tgg ccc cag tgc tgc aat gat acc gcg aga ccc     6762
Gly Gly Leu Thr Ile Trp Pro Gln Cys Cys Asn Asp Thr Ala Arg Pro
    475                 480                 485

acg ctc acc ggc tcc aga ttt atc agc aat aaa cca gcc agc cgg aag     6810
Thr Leu Thr Gly Ser Arg Phe Ile Ser Asn Lys Pro Ala Ser Arg Lys
490                 495                 500                 505

ggc cga gcg cag aag tgg tcc tgc aac ttt atc cgc ctc cat cca gtc     6858
Gly Arg Ala Gln Lys Trp Ser Cys Asn Phe Ile Arg Leu His Pro Val
                510                 515                 520

tat taa ttg ttg ccg gga agc tag agt aag tag ttc gcc agt taa tag     6906
Tyr     Leu Leu Pro Gly Ser     Ser Lys     Phe Ala Ser
                525                     530

ttt gcg caa cgt tgt tgc cat tgc tgc agg cat cgt ggt gtc acg ctc     6954
Phe Ala Gln Arg Cys Cys His Cys Cys Arg His Arg Gly Val Thr Leu
        535                 540                 545
```

-continued

```
gtc gtt tgg tat ggc ttc att cag ctc cgg ttc cca acg atc aag gcg     7002
Val Val Trp Tyr Gly Phe Ile Gln Leu Arg Phe Pro Thr Ile Lys Ala
    550                 555                 560

agt tac atg atc ccc cat gtt gtg caa aaa agc ggt tag ctc ctt cgg     7050
Ser Tyr Met Ile Pro His Val Val Gln Lys Ser Gly     Leu Leu Arg
565                 570                 575

tcc tcc gat cgt tgt cag aag taa gtt ggc cgc agt gtt atc act cat     7098
Ser Ser Asp Arg Cys Gln Lys     Val Gly Arg Ser Val Ile Thr His
580                 585                 590

ggt tat ggc agc act gca taa ttc tct tac tgt cat gcc atc cgt aag     7146
Gly Tyr Gly Ser Thr Ala     Phe Ser Tyr Cys His Ala Ile Arg Lys
595                 600                 605

atg ctt ttc tgt gac tgg tga gta ctc aac caa gtc att ctg aga ata     7194
Met Leu Phe Cys Asp Trp     Val Leu Asn Gln Val Ile Leu Arg Ile
610                 615                 620

gtg tat gcg gcg acc gag ttg ctc ttg ccc ggc gtc aac acg gga taa     7242
Val Tyr Ala Ala Thr Glu Leu Leu Leu Pro Gly Val Asn Thr Gly
625                 630                 635

tac cgc gcc aca tag cag aac ttt aaa agt gct cat cat tgg aaa acg     7290
Tyr Arg Ala Thr     Gln Asn Phe Lys Ser Ala His His Trp Lys Thr
640                 645                 650

ttc ttc ggg gcg aaa act ctc aag gat ctt acc gct gtt gag atc cag     7338
Phe Phe Gly Ala Lys Thr Leu Lys Asp Leu Thr Ala Val Glu Ile Gln
655                 660                 665                 670

ttc gat gta acc cac tcg tgc acc caa ctg atc ttc agc atc ttt tac     7386
Phe Asp Val Thr His Ser Cys Thr Gln Leu Ile Phe Ser Ile Phe Tyr
                675                 680                 685

ttt cac cag cgt ttc tgg gtg agc aaa aac agg aag gca aaa tgc cgc     7434
Phe His Gln Arg Phe Trp Val Ser Lys Asn Arg Lys Ala Lys Cys Arg
            690                 695                 700

aaa aaa ggg aat aag ggc gac acg gaa atg ttg aat act cat             7476
Lys Lys Gly Asn Lys Gly Asp Thr Glu Met Leu Asn Thr His
        705                 710                 715

actcttcctt tttcaatatt attgaagcat ttatcagggt tattgtctca tgagcggata   7536

catatttgaa tgtatttaga aaaataaaca aataggggtt ccgcgcacat ttccccgaaa   7596

agtgccacct gacgtctaag aaaccattat tatcatgaca ttaacctata aaaataggcg   7656

tatcacgagg ccctttcgtc ttcaagaat                                     7685


<210> SEQ ID NO 15
<211> LENGTH: 132
<212> TYPE: PRT
<213> ORGANISM: Artificial
<220> FEATURE:
<223> OTHER INFORMATION: Synthetic Construct

<400> SEQUENCE: 15

Met Ala Lys Pro Leu Ser Gln Glu Glu Ser Thr Leu Ile Glu Arg Ala
1               5                   10                  15

Thr Ala Thr Ile Asn Ser Ile Pro Ile Ser Glu Asp Tyr Ser Val Ala
            20                  25                  30

Ser Ala Ala Leu Ser Ser Asp Gly Arg Ile Phe Thr Gly Val Asn Val
        35                  40                  45

Tyr His Phe Thr Gly Gly Pro Cys Ala Glu Leu Val Val Leu Gly Thr
    50                  55                  60

Ala Ala Ala Ala Ala Ala Gly Asn Leu Thr Cys Ile Val Ala Ile Gly
65                  70                  75                  80

Asn Glu Asn Arg Gly Ile Leu Ser Pro Cys Gly Arg Cys Arg Gln Val
                85                  90                  95
```

```
Leu Leu Asp Leu His Pro Gly Ile Lys Ala Ile Val Lys Asp Ser Asp
            100                 105                 110

Gly Gln Pro Thr Ala Val Gly Ile Arg Glu Leu Leu Pro Ser Gly Tyr
        115                 120                 125

Val Trp Glu Gly
    130


<210> SEQ ID NO 16
<211> LENGTH: 309
<212> TYPE: PRT
<213> ORGANISM: Artificial
<220> FEATURE:
<223> OTHER INFORMATION: Synthetic Construct

<400> SEQUENCE: 16

Met Ala Ser Val Val Gly Trp Gly Pro His Ser Leu His Ala Cys Pro
1               5                   10                  15

Ala Leu Val Leu Ser Asn Asp Val Thr Ile Asp Ala Trp Cys Pro Leu
            20                  25                  30

Cys Gly Pro His Glu Arg Leu Gln Phe Glu Arg Ile Asp Thr Thr Leu
        35                  40                  45

Thr Cys Glu Thr His Arg Ile Asn Trp Thr Ala Asp Gly Arg Pro Cys
    50                  55                  60

Gly Leu Asn Gly Thr Leu Phe Pro Arg Leu His Val Ser Glu Thr Arg
65                  70                  75                  80

Pro Gln Gly Pro Arg Arg Leu Trp Ile Asn Cys Pro Leu Pro Ala Val
                85                  90                  95

Arg Ala Gln Pro Gly Pro Val Ser Leu Ser Pro Phe Glu Arg Ser Pro
            100                 105                 110

Phe Gln Pro Tyr Gln Cys Gln Leu Pro Ser Ala Ser Ser Asp Gly Cys
        115                 120                 125

Pro Ile Ile Gly His Gly Leu Leu Pro Trp Asn Asn Leu Val Thr His
    130                 135                 140

Pro Val Leu Arg Lys Val Leu Ile Leu Asn Gln Met Ala Asn Phe Ser
145                 150                 155                 160

Leu Leu Pro Ser Phe Asp Thr Leu Leu Val Asp Pro Leu Arg Leu Ser
                165                 170                 175

Val Phe Ala Pro Asp Thr Arg Gly Ala Ile Arg Tyr Leu Ser Thr Leu
            180                 185                 190

Leu Thr Leu Cys Pro Ala Thr Cys Ile Leu Pro Leu Gly Glu Pro Phe
        195                 200                 205

Ser Pro Asn Val Pro Ile Cys Arg Phe Pro Arg Asp Ser Asn Glu Pro
    210                 215                 220

Pro Leu Ser Glu Phe Glu Leu Pro Leu Ile Gln Thr Pro Gly Leu Ser
225                 230                 235                 240

Trp Ser Val Pro Ala Ile Asp Leu Phe Leu Thr Gly Pro Pro Ser Pro
                245                 250                 255

Cys Asp Arg Leu His Val Trp Ser Ser Pro Gln Ala Leu Gln Arg Phe
            260                 265                 270

Leu His Asp Pro Thr Leu Thr Trp Ser Glu Leu Val Ala Ser Arg Lys
        275                 280                 285

Ile Arg Leu Asp Ser Pro Leu Lys Leu Gln Leu Leu Glu Asn Glu Trp
    290                 295                 300

Leu Ser Arg Leu Phe
305
```

<210> SEQ ID NO 17
<211> LENGTH: 6
<212> TYPE: PRT
<213> ORGANISM: Artificial
<220> FEATURE:
<223> OTHER INFORMATION: Synthetic Construct

<400> SEQUENCE: 17

```
Leu Pro Met Leu Asn Gln
1               5
```

<210> SEQ ID NO 18
<211> LENGTH: 75
<212> TYPE: PRT
<213> ORGANISM: Artificial
<220> FEATURE:
<223> OTHER INFORMATION: Synthetic Construct

<400> SEQUENCE: 18

```
Gly Thr Tyr Leu Ser Asp Leu Ser Ile Ser Phe Ile His Ser Cys Leu
1               5                   10                  15

Thr Pro Arg Arg Val Asp Asn Tyr Asp Thr Gly Gly Leu Thr Ile Trp
            20                  25                  30

Pro Gln Cys Cys Asn Asp Thr Ala Arg Pro Thr Leu Thr Gly Ser Arg
        35                  40                  45

Phe Ile Ser Asn Lys Pro Ala Ser Arg Lys Gly Arg Ala Gln Lys Trp
    50                  55                  60

Ser Cys Asn Phe Ile Arg Leu His Pro Val Tyr
65                  70                  75
```

<210> SEQ ID NO 19
<211> LENGTH: 5
<212> TYPE: PRT
<213> ORGANISM: Artificial
<220> FEATURE:
<223> OTHER INFORMATION: Synthetic Construct

<400> SEQUENCE: 19

```
Leu Leu Pro Gly Ser
1               5
```

<210> SEQ ID NO 20
<211> LENGTH: 44
<212> TYPE: PRT
<213> ORGANISM: Artificial
<220> FEATURE:
<223> OTHER INFORMATION: Synthetic Construct

<400> SEQUENCE: 20

```
Phe Ala Gln Arg Cys Cys His Cys Cys Arg His Arg Gly Val Thr Leu
1               5                   10                  15

Val Val Trp Tyr Gly Phe Ile Gln Leu Arg Phe Pro Thr Ile Lys Ala
            20                  25                  30

Ser Tyr Met Ile Pro His Val Val Gln Lys Ser Gly
        35                  40
```

<210> SEQ ID NO 21
<211> LENGTH: 10
<212> TYPE: PRT
<213> ORGANISM: Artificial
<220> FEATURE:
<223> OTHER INFORMATION: Synthetic Construct

<400> SEQUENCE: 21

```
Leu Leu Arg Ser Ser Asp Arg Cys Gln Lys
1               5                   10
```

<210> SEQ ID NO 22
<211> LENGTH: 14
<212> TYPE: PRT
<213> ORGANISM: Artificial
<220> FEATURE:
<223> OTHER INFORMATION: Synthetic Construct

<400> SEQUENCE: 22

```
Val Gly Arg Ser Val Ile Thr His Gly Tyr Gly Ser Thr Ala
1               5                   10
```

<210> SEQ ID NO 23
<211> LENGTH: 15
<212> TYPE: PRT
<213> ORGANISM: Artificial
<220> FEATURE:
<223> OTHER INFORMATION: Synthetic Construct

<400> SEQUENCE: 23

```
Phe Ser Tyr Cys His Ala Ile Arg Lys Met Leu Phe Cys Asp Trp
1               5                   10                  15
```

<210> SEQ ID NO 24
<211> LENGTH: 24
<212> TYPE: PRT
<213> ORGANISM: Artificial
<220> FEATURE:
<223> OTHER INFORMATION: Synthetic Construct

<400> SEQUENCE: 24

```
Val Leu Asn Gln Val Ile Leu Arg Ile Val Tyr Ala Ala Thr Glu Leu
1               5                   10                  15

Leu Leu Pro Gly Val Asn Thr Gly
            20
```

<210> SEQ ID NO 25
<211> LENGTH: 4
<212> TYPE: PRT
<213> ORGANISM: Artificial
<220> FEATURE:
<223> OTHER INFORMATION: Synthetic Construct

<400> SEQUENCE: 25

```
Tyr Arg Ala Thr
1
```

<210> SEQ ID NO 26
<211> LENGTH: 73
<212> TYPE: PRT
<213> ORGANISM: Artificial
<220> FEATURE:
<223> OTHER INFORMATION: Synthetic Construct

<400> SEQUENCE: 26

```
Gln Asn Phe Lys Ser Ala His His Trp Lys Thr Phe Phe Gly Ala Lys
1               5                   10                  15

Thr Leu Lys Asp Leu Thr Ala Val Glu Ile Gln Phe Asp Val Thr His
            20                  25                  30

Ser Cys Thr Gln Leu Ile Phe Ser Ile Phe Tyr Phe His Gln Arg Phe
        35                  40                  45
```

-continued

```
Trp Val Ser Lys Asn Arg Lys Ala Lys Cys Arg Lys Lys Gly Asn Lys
    50                  55                  60

Gly Asp Thr Glu Met Leu Asn Thr His
65                  70
```

<210> SEQ ID NO 27
<211> LENGTH: 7430
<212> TYPE: DNA
<213> ORGANISM: Artificial
<220> FEATURE:
<223> OTHER INFORMATION: Engineered Sequence from virus and plasmid
<220> FEATURE:
<221> NAME/KEY: LTR
<222> LOCATION: (1)..(589)
<223> OTHER INFORMATION: 5' MoMuSVLTR
<220> FEATURE:
<221> NAME/KEY: CDS
<222> LOCATION: (1512)..(2306)
<223> OTHER INFORMATION: neomycin resistance
<220> FEATURE:
<221> NAME/KEY: misc_feature
<222> LOCATION: (3023)..(3047)
<223> OTHER INFORMATION: attB1
<220> FEATURE:
<221> NAME/KEY: CDS
<222> LOCATION: (3120)..(3590)
<223> OTHER INFORMATION: trans-dominant BLV Rex (M4)
<220> FEATURE:
<221> NAME/KEY: misc_feature
<222> LOCATION: (3653)..(4282)
<223> OTHER INFORMATION: attB2
<220> FEATURE:
<221> NAME/KEY: misc_signal
<222> LOCATION: (3690)..(4282)
<223> OTHER INFORMATION: WPRE; woodchuck hepatitis virus
      post-transcriptional regulatory element
<220> FEATURE:
<221> NAME/KEY: LTR
<222> LOCATION: (4328)..(4921)
<223> OTHER INFORMATION: 3' MoMuLVLTR
<220> FEATURE:
<221> NAME/KEY: CDS
<222> LOCATION: (6217)..(7077)
<223> OTHER INFORMATION: ampicillin resistance

<400> SEQUENCE: 27

```
tttgaaagac cccacccgta ggtggcaagc tagcttaagt aacgccactt tgcaaggcat     60

ggaaaaatac ataactgaga atagaaaagt tcagatcaag gtcaggaaca aagaaacagc    120

tgaataccaa acaggatatc tgtggtaagc ggttcctgcc ccggctcagg gccaagaaca    180

gatgagacag ctgagtgatg ggccaaacag gatatctgtg gtaagcagtt cctgccccgg    240

ctcggggcca agaacagatg gtccccagat gcggtccagc cctcagcagt ttctagtgaa    300

tcatcagatg tttccagggt gccccaagga cctgaaaatg accctgtacc ttatttgaac    360

taaccaatca gttcgcttct cgcttctgtt cgcgcgcttc cgctctccga gctcaataaa    420

agagcccaca acccctcact cggcgcgcca gtcttccgat agactgcgtc gcccgggtac    480

ccgtattccc aataaagcct cttgctgttt gcatccgaat cgtggtctcg ctgttccttg    540

ggagggtctc ctctgagtga ttgactaccc acgacggggg tctttcattt gggggctcgt    600

ccgggatttg gagacccctg cccagggacc accgacccac caccgggagg taagctggcc    660

agcaacttat ctgtgtctgt ccgattgtct agtgtctatg tttgatgtta tgcgcctgcg    720

tctgtactag ttagctaact agctctgtat ctggcggacc cgtggtggaa ctgacgagtt    780

ctgaacaccc ggccgcaacc ctgggagacg tcccagggac tttgggggcc gtttttgtgg    840

cccgacctga ggaagggagt cgatgtggaa tccgaccccg tcaggatatg tggttctggt    900
```

-continued

```
aggagacgag aacctaaaac agttcccgcc tccgtctgaa tttttgcttt cggtttggaa    960

ccgaagccgc gcgtcttgtc tgctgcagcg ctgcagcatc gttctgtgtt gtctctgtct   1020

gactgtgttt ctgtatttgt ctgaaaatta gggccagact gttaccactc ccttaagttt   1080

gaccttaggt cactggaaag atgtcgagcg gatcgctcac aaccagtcgg tagatgtcaa   1140

gaagagacgt tgggttacct tctgctctgc agaatggcca acctttaacg tcggatggcc   1200

gcgagacggc acctttaacc gagacctcat cacccaggtt aagatcaagg tcttttcacc   1260

tggcccgcat ggacacccag accaggtccc ctacatcgtg acctgggaag ccttggcttt   1320

tgaccccccct ccctgggtca agccctttgt acaccctaag cctccgcctc ctcttcctcc   1380

atccgccccg tctctccccc ttgaacctcc tcgttcgacc ccgcctcgat cctcccttta   1440

tccagccctc actccttctc taggcgccgg aattccgatc tgatcaagag acaggatgag   1500

gatcgtttcg c atg att gaa caa gat gga ttg cac gca ggt tct ccg gcc    1550
             Met Ile Glu Gln Asp Gly Leu His Ala Gly Ser Pro Ala
             1               5                   10

gct tgg gtg gag agg cta ttc ggc tat gac tgg gca caa cag aca atc     1598
Ala Trp Val Glu Arg Leu Phe Gly Tyr Asp Trp Ala Gln Gln Thr Ile
    15                  20                  25

ggc tgc tct gat gcc gcc gtg ttc cgg ctg tca gcg cag ggg cgc ccg     1646
Gly Cys Ser Asp Ala Ala Val Phe Arg Leu Ser Ala Gln Gly Arg Pro
30                  35                  40                  45

gtt ctt ttt gtc aag acc gac ctg tcc ggt gcc ctg aat gaa ctg cag     1694
Val Leu Phe Val Lys Thr Asp Leu Ser Gly Ala Leu Asn Glu Leu Gln
                50                  55                  60

gac gag gca gcg cgg cta tcg tgg ctg gcc acg acg ggc gtt cct tgc     1742
Asp Glu Ala Ala Arg Leu Ser Trp Leu Ala Thr Thr Gly Val Pro Cys
            65                  70                  75

gca gct gtg ctc gac gtt gtc act gaa gcg gga agg gac tgg ctg cta     1790
Ala Ala Val Leu Asp Val Val Thr Glu Ala Gly Arg Asp Trp Leu Leu
        80                  85                  90

ttg ggc gaa gtg ccg ggg cag gat ctc ctg tca tct cac ctt gct cct     1838
Leu Gly Glu Val Pro Gly Gln Asp Leu Leu Ser Ser His Leu Ala Pro
    95                  100                 105

gcc gag aaa gta tcc atc atg gct gat gca atg cgg cgg ctg cat acg     1886
Ala Glu Lys Val Ser Ile Met Ala Asp Ala Met Arg Arg Leu His Thr
110                 115                 120                 125

ctt gat ccg gct acc tgc cca ttc gac cac caa gcg aaa cat cgc atc     1934
Leu Asp Pro Ala Thr Cys Pro Phe Asp His Gln Ala Lys His Arg Ile
                130                 135                 140

gag cga gca cgt act cgg atg gaa gcc ggt ctt gtc gat cag gat gat     1982
Glu Arg Ala Arg Thr Arg Met Glu Ala Gly Leu Val Asp Gln Asp Asp
            145                 150                 155

ctg gac gaa gag cat cag ggg ctc gcg cca gcc gaa ctg ttc gcc agg     2030
Leu Asp Glu Glu His Gln Gly Leu Ala Pro Ala Glu Leu Phe Ala Arg
        160                 165                 170

ctc aag gcg cgc atg ccc gac ggc gag gat ctc gtc gtg acc cat ggc     2078
Leu Lys Ala Arg Met Pro Asp Gly Glu Asp Leu Val Val Thr His Gly
    175                 180                 185

gat gcc tgc ttg ccg aat atc atg gtg gaa aat ggc cgc ttt tct gga     2126
Asp Ala Cys Leu Pro Asn Ile Met Val Glu Asn Gly Arg Phe Ser Gly
190                 195                 200                 205

ttc atc gac tgt ggc cgg ctg ggt gtg gcg gac cgc tat cag gac ata     2174
Phe Ile Asp Cys Gly Arg Leu Gly Val Ala Asp Arg Tyr Gln Asp Ile
                210                 215                 220

gcg ttg gct acc cgt gat att gct gaa gag ctt ggc ggc gaa tgg gct     2222
Ala Leu Ala Thr Arg Asp Ile Ala Glu Glu Leu Gly Gly Glu Trp Ala
            225                 230                 235
```

```
gac cgc ttc ctc gtg ctt tac ggt atc gcc gct ccc gat tcg cag cgc     2270
Asp Arg Phe Leu Val Leu Tyr Gly Ile Ala Ala Pro Asp Ser Gln Arg
        240                 245                 250

atc gcc ttc tat cgc ctt ctt gac gag ttc ttc tga gcgggactct          2316
Ile Ala Phe Tyr Arg Leu Leu Asp Glu Phe Phe
    255                 260

ggggttcgaa atgaccgacc aagcgacgcc caacctgcca tcacgagatt tcgattccac   2376

cgccgccttc tatgaaaggt tgggcttcgg aatcgttttc cgggacgccg gctggatgat   2436

cctccagcgc ggggatctca tgctggagtt cttcgcccac cccgggctcg atcccctcgc   2496

gagttggttc agctgctgcc tgaggctgga cgacctcgcg gagttctacc ggcagtgcaa   2556

atccgtcggc atccaggaaa ccagcagcgg ctatccgcgc atccatgccc ccgaactgca   2616

ggagtgggga ggcacgatgg ccgctttggt cgaggcggat cctagcagaa aaataagact   2676

tgattccccc ttaaaattac aactgctaga aaatgaatgg ctctcccgcc ttttttgagg   2736

gggaatcatt tgtatgaaag atcatgccga cctaggcgcc gccaccgccc cgtaaaccag   2796

acagagacgt cagctgccag aaaagctggt gacggcagct ggtggctaga atccccgtac   2856

ctccccaact tccccttccc cgaaaaatcc acaccctgag ctgctgacct cacctgctga   2916

taaattaata aaatgccggc cctgtcgagt tagcggcacc agaagcgttc ttctcctgag   2976

accctcgtgc tcagctctcg gtcctgcctc gagaagcttg ttatcaacaa gtttgtacaa   3036

aaaagcaggc ttcgaaggag atagaaccaa ttctctaagg aaatacttaa cgtcgactgg   3096

atccggtacc gaattcgatc cac atg cct aaa aaa cga cgg tcc cga aga cgc   3149
                          Met Pro Lys Lys Arg Arg Ser Arg Arg Arg
                          265                 270

cca caa ccg atc atc aga tgg caa gtg ttg ttg gtt ggg ggc ccc act     3197
Pro Gln Pro Ile Ile Arg Trp Gln Val Leu Leu Val Gly Gly Pro Thr
275                 280                 285                 290

ctc tac atg cct gcc cgg ccc tgg ttt tgt cca atg atg tca cca tcg     3245
Leu Tyr Met Pro Ala Arg Pro Trp Phe Cys Pro Met Met Ser Pro Ser
                295                 300                 305

atg cct ggt gcc ccc tct gcg ggc ccc atg agc gac tcc aat tcg aaa     3293
Met Pro Gly Ala Pro Ser Ala Gly Pro Met Ser Asp Ser Asn Ser Lys
            310                 315                 320

gga tcg aca cca cgc tca cct gcg aga ccc acc gta tca act gga ccg     3341
Gly Ser Thr Pro Arg Ser Pro Ala Arg Pro Thr Val Ser Thr Gly Pro
        325                 330                 335

ccg atg gac gac ctt gcg gcc tca atg gaa cgt tgt tcc ctc gac tgc     3389
Pro Met Asp Asp Leu Ala Ala Ser Met Glu Arg Cys Ser Leu Asp Cys
    340                 345                 350

atg tct ccg aga ccc gcc ccc aag ggc ccc gac gac tct gga tca act     3437
Met Ser Pro Arg Pro Ala Pro Lys Gly Pro Asp Asp Ser Gly Ser Thr
355                 360                 365                 370

gcc ccc ttc cgg ccg ttc gcg ctc agc ccg gcc cgg tta gat ctt ccc     3485
Ala Pro Phe Arg Pro Phe Ala Leu Ser Pro Ala Arg Leu Asp Leu Pro
                375                 380                 385

cct tcg agc ggt ccc cct tcc agc cct acc aat gcc aat tgc cct cgg     3533
Pro Ser Ser Gly Pro Pro Ser Ser Pro Thr Asn Ala Asn Cys Pro Arg
            390                 395                 400

cct cta gcg acg gtt gcc cca tta tcg ggc acg gcc ttc ttc cct gga     3581
Pro Leu Ala Thr Val Ala Pro Leu Ser Gly Thr Ala Phe Phe Pro Gly
        405                 410                 415

aca act tag taacgcatcc tgtcctcaga aaagtcctta tattaaatca             3630
Thr Thr
    420
```

-continued

```
aatgggacct cgagatatct agacccagct ttcttgtaca aagtggttga taacatcgat   3690
aatcaacctc tggattacaa aatttgtgaa agattgactg gtattcttaa ctatgttgct   3750
ccttttacgc tatgtggata cgctgcttta atgcctttgt atcatgctat tgcttcccgt   3810
atggctttca ttttctcctc cttgtataaa tcctggttgc tgtctcttta tgaggagttg   3870
tggcccgttg tcaggcaacg tggcgtggtg tgcactgtgt ttgctgacgc aacccccact   3930
ggttggggca ttgccaccac ctgtcagctc ctttccggga ctttcgcttt ccccctccct   3990
attgccacgg cggaactcat cgccgcctgc cttgcccgct gctggacagg ggctcggctg   4050
ttgggcactg acaattccgt ggtgttgtcg gggaaatcat cgtcctttcc ttggctgctc   4110
gcctgtgttg ccacctggat tctgcgcggg acgtccttct gctacgtccc ttcggccctc   4170
aatccagcgg accttccttc ccgcggcctg ctgccggctc tgcggcctct tccgcgtctt   4230
cgccttcgcc ctcagacgag tcggatctcc ctttgggccg cctccccgcc tgatcgataa   4290
aataaaagat tttatttagt ctccagaaaa aggggggaat gaaagacccc acctgtaggt   4350
ttggcaagct agcttaagta acgccatttt gcaaggcatg gaaaaataca taactgagaa   4410
tagagaagtt cagatcaagg tcaggaacag atggaacagc tgaatatggg ccaaacagga   4470
tatctgtggt aagcagttcc tgccccggct cagggccaag aacagatgga acagctgaat   4530
atgggccaaa caggatatct gtggtaagca gttcctgccc cggctcaggg ccaagaacag   4590
atggtcccca gatgcggtcc agccctcagc agtttctaga gaaccatcag atgtttccag   4650
ggtgccccaa ggacctgaaa tgaccctgtg ccttatttga actaaccaat cagttcgctt   4710
ctcgcttctg ttcgcgcgct tctgctcccc gagctcaata aaagagccca caacccctca   4770
ctcggggcgc cagtcctccg attgactgag tcgcccgggt acccgtgtat ccaataaacc   4830
ctcttgcagt tgcatccgac ttgtggtctc gctgttcctt gggagggtct cctctgagtg   4890
attgactacc cgtcagcggg ggtctttcat ttgggggctc gtccgggatc gggagacccc   4950
tgcccaggga ccaccgaccc accaccggga ggtaagctgg ctgcctcgcg cgtttcggtg   5010
atgacggtga aaacctctga cacatgcagc tcccggagac ggtcacagct tgtctgtaag   5070
cggatgccgg gagcagacaa gcccgtcagg gcgcgtcagc gggtgttggc gggtgtcggg   5130
gcgcagccat gacccagtca cgtagcgata gcggagtgta tactggctta actatgcggc   5190
atcagagcag attgtactga gagtgcacca tatgcggtgt gaaataccgc acagatgcgt   5250
aaggagaaaa taccgcatca ggcgctcttc cgcttcctcg ctcactgact cgctgcgctc   5310
ggtcgttcgg ctgcggcgag cggtatcagc tcactcaaag gcggtaatac ggttatccac   5370
agaatcaggg gataacgcag gaaagaacat gtgagcaaaa ggccagcaaa aggccaggaa   5430
ccgtaaaaag gccgcgttgc tggcgttttt ccataggctc cgcccccctg acgagcatca   5490
caaaaatcga cgctcaagtc agaggtggcg aaacccgaca ggactataaa gataccaggc   5550
gtttccccct ggaagctccc tcgtgcgctc tcctgttccg accctgccgc ttaccggata   5610
cctgtccgcc tttctccctt cgggaagcgt ggcgctttct catagctcac gctgtaggta   5670
tctcagttcg gtgtaggtcg ttcgctccaa gctgggctgt gtgcacgaac cccccgttca   5730
gcccgaccgc tgcgccttat ccggtaacta tcgtcttgag tccaacccgg taagacacga   5790
cttatcgcca ctggcagcag ccactggtaa caggattagc agagcgaggt atgtaggcgg   5850
tgctacagag ttcttgaagt ggtggcctaa ctacggctac actagaagga cagtatttgg   5910
tatctgcgct ctgctgaagc cagttacctt cggaaaaaga gttggtagct cttgatccgg   5970
caaacaaacc accgctggta gcggtggttt ttttgtttgc aagcagcaga ttacgcgcag   6030
```

```
aaaaaaagga tctcaagaag atcctttgat cttttctacg gggtctgacg ctcagtggaa   6090

cgaaaactca cgttaaggga ttttggtcat gagattatca aaaaggatct tcacctagat   6150

ccttttaaat taaaaatgaa gttttaaatc aatctaaagt atatatgagt aaacttggtc   6210

tgacag tta cca atg ctt aat cag tga ggc acc tat ctc agc gat ctg     6258
       Leu Pro Met Leu Asn Gln     Gly Thr Tyr Leu Ser Asp Leu
                           425                 430

tct att tcg ttc atc cat agt tgc ctg act ccc cgt cgt gta gat aac     6306
Ser Ile Ser Phe Ile His Ser Cys Leu Thr Pro Arg Arg Val Asp Asn
    435                 440                 445

tac gat acg gga ggg ctt acc atc tgg ccc cag tgc tgc aat gat acc     6354
Tyr Asp Thr Gly Gly Leu Thr Ile Trp Pro Gln Cys Cys Asn Asp Thr
450                 455                 460                 465

gcg aga ccc acg ctc acc ggc tcc aga ttt atc agc aat aaa cca gcc     6402
Ala Arg Pro Thr Leu Thr Gly Ser Arg Phe Ile Ser Asn Lys Pro Ala
                470                 475                 480

agc cgg aag ggc cga gcg cag aag tgg tcc tgc aac ttt atc cgc ctc     6450
Ser Arg Lys Gly Arg Ala Gln Lys Trp Ser Cys Asn Phe Ile Arg Leu
            485                 490                 495

cat cca gtc tat taa ttg ttg ccg gga agc tag agt aag tag ttc gcc     6498
His Pro Val Tyr     Leu Leu Pro Gly Ser     Ser Lys     Phe Ala
        500                 505                             510

agt taa tag ttt gcg caa cgt tgt tgc cat tgc tgc agg cat cgt ggt     6546
Ser         Phe Ala Gln Arg Cys Cys His Cys Cys Arg His Arg Gly
                        515                 520

gtc acg ctc gtc gtt tgg tat ggc ttc att cag ctc cgg ttc cca acg     6594
Val Thr Leu Val Val Trp Tyr Gly Phe Ile Gln Leu Arg Phe Pro Thr
525                 530                 535                 540

atc aag gcg agt tac atg atc ccc cat gtt gtg caa aaa agc ggt tag     6642
Ile Lys Ala Ser Tyr Met Ile Pro His Val Val Gln Lys Ser Gly
                545                 550                 555

ctc ctt cgg tcc tcc gat cgt tgt cag aag taa gtt ggc cgc agt gtt     6690
Leu Leu Arg Ser Ser Asp Arg Cys Gln Lys     Val Gly Arg Ser Val
                560                 565                 570

atc act cat ggt tat ggc agc act gca taa ttc tct tac tgt cat gcc     6738
Ile Thr His Gly Tyr Gly Ser Thr Ala     Phe Ser Tyr Cys His Ala
                575                 580                 585

atc cgt aag atg ctt ttc tgt gac tgg tga gta ctc aac caa gtc att     6786
Ile Arg Lys Met Leu Phe Cys Asp Trp     Val Leu Asn Gln Val Ile
                590                 595                 600

ctg aga ata gtg tat gcg gcg acc gag ttg ctc ttg ccc ggc gtc aac     6834
Leu Arg Ile Val Tyr Ala Ala Thr Glu Leu Leu Leu Pro Gly Val Asn
                605                 610                 615

acg gga taa tac cgc gcc aca tag cag aac ttt aaa agt gct cat cat     6882
Thr Gly     Tyr Arg Ala Thr     Gln Asn Phe Lys Ser Ala His His
                620                 625                 630

tgg aaa acg ttc ttc ggg gcg aaa act ctc aag gat ctt acc gct gtt     6930
Trp Lys Thr Phe Phe Gly Ala Lys Thr Leu Lys Asp Leu Thr Ala Val
                635                 640                 645

gag atc cag ttc gat gta acc cac tcg tgc acc caa ctg atc ttc agc     6978
Glu Ile Gln Phe Asp Val Thr His Ser Cys Thr Gln Leu Ile Phe Ser
            650                 655                 660

atc ttt tac ttt cac cag cgt ttc tgg gtg agc aaa aac agg aag gca     7026
Ile Phe Tyr Phe His Gln Arg Phe Trp Val Ser Lys Asn Arg Lys Ala
        665                 670                 675

aaa tgc cgc aaa aaa ggg aat aag ggc gac acg gaa atg ttg aat act     7074
Lys Cys Arg Lys Lys Gly Asn Lys Gly Asp Thr Glu Met Leu Asn Thr
    680                 685                 690
```

-continued

```
cat actcttcctt tttcaatatt attgaagcat ttatcagggt tattgtctca         7127
His
695

tgagcggata catatttgaa tgtatttaga aaaataaaca aataggggtt ccgcgcacat   7187

ttccccgaaa agtgccacct gacgtctaag aaaccattat tatcatgaca ttaacctata   7247

aaaataggcg tatcacgagg ccctttcgtc ttcaagaatt aattcatacc agatcaccga   7307

aaactgtcct ccaaatgtgt ccccctcaca ctcccaaatt cgcgggcttc tgcctcttag   7367

accactctac cctattcccc acactcaccg gagccaaagc cgcggccctt ccgtttcttt   7427

gct                                                                 7430


<210> SEQ ID NO 28
<211> LENGTH: 264
<212> TYPE: PRT
<213> ORGANISM: Artificial
<220> FEATURE:
<223> OTHER INFORMATION: Synthetic Construct

<400> SEQUENCE: 28

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260


<210> SEQ ID NO 29
```

-continued

<211> LENGTH: 156
<212> TYPE: PRT
<213> ORGANISM: Artificial
<220> FEATURE:
<223> OTHER INFORMATION: Synthetic Construct

<400> SEQUENCE: 29

```
Met Pro Lys Lys Arg Arg Ser Arg Arg Arg Pro Gln Pro Ile Ile Arg
1               5                   10                  15

Trp Gln Val Leu Leu Val Gly Gly Pro Thr Leu Tyr Met Pro Ala Arg
            20                  25                  30

Pro Trp Phe Cys Pro Met Met Ser Pro Ser Met Pro Gly Ala Pro Ser
        35                  40                  45

Ala Gly Pro Met Ser Asp Ser Asn Ser Lys Gly Ser Thr Pro Arg Ser
    50                  55                  60

Pro Ala Arg Pro Thr Val Ser Thr Gly Pro Pro Met Asp Asp Leu Ala
65                  70                  75                  80

Ala Ser Met Glu Arg Cys Ser Leu Asp Cys Met Ser Pro Arg Pro Ala
                85                  90                  95

Pro Lys Gly Pro Asp Asp Ser Gly Ser Thr Ala Pro Phe Arg Pro Phe
            100                 105                 110

Ala Leu Ser Pro Ala Arg Leu Asp Leu Pro Pro Ser Ser Gly Pro Pro
        115                 120                 125

Ser Ser Pro Thr Asn Ala Asn Cys Pro Arg Pro Leu Ala Thr Val Ala
    130                 135                 140

Pro Leu Ser Gly Thr Ala Phe Phe Pro Gly Thr Thr
145                 150                 155
```

<210> SEQ ID NO 30
<211> LENGTH: 6
<212> TYPE: PRT
<213> ORGANISM: Artificial
<220> FEATURE:
<223> OTHER INFORMATION: Synthetic Construct

<400> SEQUENCE: 30

```
Leu Pro Met Leu Asn Gln
1               5
```

<210> SEQ ID NO 31
<211> LENGTH: 75
<212> TYPE: PRT
<213> ORGANISM: Artificial
<220> FEATURE:
<223> OTHER INFORMATION: Synthetic Construct

<400> SEQUENCE: 31

```
Gly Thr Tyr Leu Ser Asp Leu Ser Ile Ser Phe Ile His Ser Cys Leu
1               5                   10                  15

Thr Pro Arg Arg Val Asp Asn Tyr Asp Thr Gly Gly Leu Thr Ile Trp
            20                  25                  30

Pro Gln Cys Cys Asn Asp Thr Ala Arg Pro Thr Leu Thr Gly Ser Arg
        35                  40                  45

Phe Ile Ser Asn Lys Pro Ala Ser Arg Lys Gly Arg Ala Gln Lys Trp
    50                  55                  60

Ser Cys Asn Phe Ile Arg Leu His Pro Val Tyr
65                  70                  75
```

<210> SEQ ID NO 32
<211> LENGTH: 5

<212> TYPE: PRT
<213> ORGANISM: Artificial
<220> FEATURE:
<223> OTHER INFORMATION: Synthetic Construct

<400> SEQUENCE: 32

Leu Leu Pro Gly Ser
1               5

<210> SEQ ID NO 33
<211> LENGTH: 44
<212> TYPE: PRT
<213> ORGANISM: Artificial
<220> FEATURE:
<223> OTHER INFORMATION: Synthetic Construct

<400> SEQUENCE: 33

Phe Ala Gln Arg Cys Cys His Cys Cys Arg His Arg Gly Val Thr Leu
1               5                   10                  15

Val Val Trp Tyr Gly Phe Ile Gln Leu Arg Phe Pro Thr Ile Lys Ala
            20                  25                  30

Ser Tyr Met Ile Pro His Val Val Gln Lys Ser Gly
        35                  40

<210> SEQ ID NO 34
<211> LENGTH: 10
<212> TYPE: PRT
<213> ORGANISM: Artificial
<220> FEATURE:
<223> OTHER INFORMATION: Synthetic Construct

<400> SEQUENCE: 34

Leu Leu Arg Ser Ser Asp Arg Cys Gln Lys
1               5                   10

<210> SEQ ID NO 35
<211> LENGTH: 14
<212> TYPE: PRT
<213> ORGANISM: Artificial
<220> FEATURE:
<223> OTHER INFORMATION: Synthetic Construct

<400> SEQUENCE: 35

Val Gly Arg Ser Val Ile Thr His Gly Tyr Gly Ser Thr Ala
1               5                   10

<210> SEQ ID NO 36
<211> LENGTH: 15
<212> TYPE: PRT
<213> ORGANISM: Artificial
<220> FEATURE:
<223> OTHER INFORMATION: Synthetic Construct

<400> SEQUENCE: 36

Phe Ser Tyr Cys His Ala Ile Arg Lys Met Leu Phe Cys Asp Trp
1               5                   10                  15

<210> SEQ ID NO 37
<211> LENGTH: 24
<212> TYPE: PRT
<213> ORGANISM: Artificial
<220> FEATURE:
<223> OTHER INFORMATION: Synthetic Construct

<400> SEQUENCE: 37

Val Leu Asn Gln Val Ile Leu Arg Ile Val Tyr Ala Ala Thr Glu Leu

-continued

```
1               5                   10                  15

Leu Leu Pro Gly Val Asn Thr Gly
            20


<210> SEQ ID NO 38
<211> LENGTH: 4
<212> TYPE: PRT
<213> ORGANISM: Artificial
<220> FEATURE:
<223> OTHER INFORMATION: Synthetic Construct

<400> SEQUENCE: 38

Tyr Arg Ala Thr
1


<210> SEQ ID NO 39
<211> LENGTH: 73
<212> TYPE: PRT
<213> ORGANISM: Artificial
<220> FEATURE:
<223> OTHER INFORMATION: Synthetic Construct

<400> SEQUENCE: 39

Gln Asn Phe Lys Ser Ala His His Trp Lys Thr Phe Phe Gly Ala Lys
1               5                   10                  15

Thr Leu Lys Asp Leu Thr Ala Val Glu Ile Gln Phe Asp Val Thr His
            20                  25                  30

Ser Cys Thr Gln Leu Ile Phe Ser Ile Phe Tyr Phe His Gln Arg Phe
        35                  40                  45

Trp Val Ser Lys Asn Arg Lys Ala Lys Cys Arg Lys Lys Gly Asn Lys
    50                  55                  60

Gly Asp Thr Glu Met Leu Asn Thr His
65                  70


<210> SEQ ID NO 40
<211> LENGTH: 7010
<212> TYPE: DNA
<213> ORGANISM: Artificial
<220> FEATURE:
<223> OTHER INFORMATION: Engineered Sequence from virus and plasmid
<220> FEATURE:
<221> NAME/KEY: LTR
<222> LOCATION: (149)..(737)
<223> OTHER INFORMATION: 5' MoMuSVLTR
<220> FEATURE:
<221> NAME/KEY: CDS
<222> LOCATION: (1660)..(2454)
<223> OTHER INFORMATION: neomycin resistance
<220> FEATURE:
<221> NAME/KEY: promoter
<222> LOCATION: (2806)..(3150)
<223> OTHER INFORMATION: BLV promoter
<220> FEATURE:
<221> NAME/KEY: misc_feature
<222> LOCATION: (3170)..(3194)
<223> OTHER INFORMATION: attb1
<220> FEATURE:
<221> NAME/KEY: CDS
<222> LOCATION: (3236)..(3955)
<223> OTHER INFORMATION: EYFP; enhanced yellow florescent protein
<220> FEATURE:
<221> NAME/KEY: misc_feature
<222> LOCATION: (3980)..(4004)
<223> OTHER INFORMATION: attb2
<220> FEATURE:
<221> NAME/KEY: LTR
<222> LOCATION: (4056)..(4649)
<223> OTHER INFORMATION: 3' MoMuSVLTR
<220> FEATURE:
```

```
<221> NAME/KEY: CDS
<222> LOCATION: (5945)..(6805)
<223> OTHER INFORMATION: ampicillin resistance

<400> SEQUENCE: 40

gaattaattc ataccagatc accgaaaact gtcctccaaa tgtgtccccc tcacactccc     60

aaattcgcgg gcttctgcct cttagaccac tctaccctat tccccacact caccggagcc    120

aaagccgcgg cccttccgtt tctttgcttt tgaaagaccc cacccgtagg tggcaagcta    180

gcttaagtaa cgccactttg caaggcatgg aaaaatacat aactgagaat agaaaagttc    240

agatcaaggt caggaacaaa gaaacagctg aataccaaac aggatatctg tggtaagcgg    300

ttcctgcccc ggctcagggc caagaacaga tgagacagct gagtgatggg ccaaacagga    360

tatctgtggt aagcagttcc tgccccggct cggggccaag aacagatggt ccccagatgc    420

ggtccagccc tcagcagttt ctagtgaatc atcagatgtt tccagggtgc cccaaggacc    480

tgaaaatgac cctgtacctt atttgaacta accaatcagt tcgcttctcg cttctgttcg    540

cgcgcttccg ctctccgagc tcaataaaag agcccacaac ccctcactcg gcgcgccagt    600

cttccgatag actgcgtcgc ccgggtaccc gtattcccaa taaagcctct tgctgtttgc    660

atccgaatcg tggtctcgct gttccttggg agggtctcct ctgagtgatt gactacccac    720

gacgggggtc tttcatttgg gggctcgtcc gggatttgga gacccctgcc cagggaccac    780

cgacccacca ccgggaggta agctggccag caacttatct gtgtctgtcc gattgtctag    840

tgtctatgtt tgatgttatg cgcctgcgtc tgtactagtt agctaactag ctctgtatct    900

ggcggacccg tggtggaact gacgagttct gaacacccgg ccgcaaccct gggagacgtc    960

ccagggactt tgggggccgt ttttgtggcc cgacctgagg aagggagtcg atgtggaatc   1020

cgaccccgtc aggatatgtg gttctggtag gagacgagaa cctaaaacag ttcccgcctc   1080

cgtctgaatt tttgctttcg gtttggaacc gaagccgcgc gtcttgtctg ctgcagcgct   1140

gcagcatcgt tctgtgttgt ctctgtctga ctgtgtttct gtatttgtct gaaaattagg   1200

gccagactgt taccactccc ttaagtttga ccttaggtca ctggaaagat gtcgagcgga   1260

tcgctcacaa ccagtcggta gatgtcaaga agagacgttg ggttaccttc tgctctgcag   1320

aatggccaac ctttaacgtc ggatggccgc gagacggcac ctttaaccga gacctcatca   1380

cccaggttaa gatcaaggtc ttttcacctg gcccgcatgg acacccagac caggtcccct   1440

acatcgtgac ctgggaagcc ttggcttttg acccccctcc ctgggtcaag ccctttgtac   1500

accctaagcc tccgcctcct cttcctccat ccgccccgtc tctcccccctt gaacctcctc   1560

gttcgacccc gcctcgatcc tccctttatc cagccctcac tccttctcta ggcgccggaa   1620

ttccgatctg atcaagagac aggatgagga tcgtttcgc atg att gaa caa gat      1674
                                           Met Ile Glu Gln Asp
                                           1               5

gga ttg cac gca ggt tct ccg gcc gct tgg gtg gag agg cta ttc ggc     1722
Gly Leu His Ala Gly Ser Pro Ala Ala Trp Val Glu Arg Leu Phe Gly
                10                  15                  20

tat gac tgg gca caa cag aca atc ggc tgc tct gat gcc gcc gtg ttc     1770
Tyr Asp Trp Ala Gln Gln Thr Ile Gly Cys Ser Asp Ala Ala Val Phe
            25                  30                  35

cgg ctg tca gcg cag ggg cgc ccg gtt ctt ttt gtc aag acc gac ctg     1818
Arg Leu Ser Ala Gln Gly Arg Pro Val Leu Phe Val Lys Thr Asp Leu
        40                  45                  50

tcc ggt gcc ctg aat gaa ctg cag gac gag gca gcg cgg cta tcg tgg     1866
Ser Gly Ala Leu Asn Glu Leu Gln Asp Glu Ala Ala Arg Leu Ser Trp
    55                  60                  65
```

-continued

```
ctg gcc acg acg ggc gtt cct tgc gca gct gtg ctc gac gtt gtc act     1914
Leu Ala Thr Thr Gly Val Pro Cys Ala Ala Val Leu Asp Val Val Thr
70                  75                  80                  85

gaa gcg gga agg gac tgg ctg cta ttg ggc gaa gtg ccg ggg cag gat     1962
Glu Ala Gly Arg Asp Trp Leu Leu Leu Gly Glu Val Pro Gly Gln Asp
                90                  95                  100

ctc ctg tca tct cac ctt gct cct gcc gag aaa gta tcc atc atg gct     2010
Leu Leu Ser Ser His Leu Ala Pro Ala Glu Lys Val Ser Ile Met Ala
            105                 110                 115

gat gca atg cgg cgg ctg cat acg ctt gat ccg gct acc tgc cca ttc     2058
Asp Ala Met Arg Arg Leu His Thr Leu Asp Pro Ala Thr Cys Pro Phe
        120                 125                 130

gac cac caa gcg aaa cat cgc atc gag cga gca cgt act cgg atg gaa     2106
Asp His Gln Ala Lys His Arg Ile Glu Arg Ala Arg Thr Arg Met Glu
    135                 140                 145

gcc ggt ctt gtc gat cag gat gat ctg gac gaa gag cat cag ggg ctc     2154
Ala Gly Leu Val Asp Gln Asp Asp Leu Asp Glu Glu His Gln Gly Leu
150                 155                 160                 165

gcg cca gcc gaa ctg ttc gcc agg ctc aag gcg cgc atg ccc gac ggc     2202
Ala Pro Ala Glu Leu Phe Ala Arg Leu Lys Ala Arg Met Pro Asp Gly
                170                 175                 180

gag gat ctc gtc gtg acc cat ggc gat gcc tgc ttg ccg aat atc atg     2250
Glu Asp Leu Val Val Thr His Gly Asp Ala Cys Leu Pro Asn Ile Met
            185                 190                 195

gtg gaa aat ggc cgc ttt tct gga ttc atc gac tgt ggc cgg ctg ggt     2298
Val Glu Asn Gly Arg Phe Ser Gly Phe Ile Asp Cys Gly Arg Leu Gly
        200                 205                 210

gtg gcg gac cgc tat cag gac ata gcg ttg gct acc cgt gat att gct     2346
Val Ala Asp Arg Tyr Gln Asp Ile Ala Leu Ala Thr Arg Asp Ile Ala
    215                 220                 225

gaa gag ctt ggc ggc gaa tgg gct gac cgc ttc ctc gtg ctt tac ggt     2394
Glu Glu Leu Gly Gly Glu Trp Ala Asp Arg Phe Leu Val Leu Tyr Gly
230                 235                 240                 245

atc gcc gct ccc gat tcg cag cgc atc gcc ttc tat cgc ctt ctt gac     2442
Ile Ala Ala Pro Asp Ser Gln Arg Ile Ala Phe Tyr Arg Leu Leu Asp
                250                 255                 260

gag ttc ttc tga gcgggactct ggggttcgaa atgaccgacc aagcgacgcc         2494
Glu Phe Phe

caacctgcca tcacgagatt tcgattccac cgccgccttc tatgaaaggt tgggcttcgg   2554

aatcgttttc cgggacgccg gctggatgat cctccagcgc ggggatctca tgctggagtt   2614

cttcgcccac cccgggctcg atcccctcgc gagttggttc agctgctgcc tgaggctgga   2674

cgacctcgcg gagttctacc ggcagtgcaa atccgtcggc atccaggaaa ccagcagcgg   2734

ctatccgcgc atccatgccc ccgaactgca ggagtgggga ggcacgatgg ccgctttggt   2794

cgaggcggat cctagcagaa aaataagact tgattccccc ttaaaattac aactgctaga   2854

aaatgaatgg ctctcccgcc ttttttgagg gggaatcatt tgtatgaaag atcatgccga   2914

cctaggcgcc gccaccgccc cgtaaaccag acagagacgt cagctgccag aaaagctggt   2974

gacggcagct ggtggctaga atccccgtac ctccccaact tcccctttcc cgaaaaatcc   3034

acaccctgag ctgctgacct cacctgctga taaattaata aaatgccggc cctgtcgagt   3094

tagcggcacc agaagcgttc ttctcctgag accctcgtgc tcagctctcg gtcctgcctc   3154

gagaagcttg ttatcacaag tttgtacaaa aaagcaggct tcgaaggaga tagaaccaat   3214

tctctaagga aatacttaac c atg gtg agc aag ggc gag gag ctg ttc acc     3265
                        Met Val Ser Lys Gly Glu Glu Leu Phe Thr
                        265                 270
```

-continued

```
ggg gtg gtg ccc atc ctg gtc gag ctg gac ggc gac gta aac ggc cac     3313
Gly Val Val Pro Ile Leu Val Glu Leu Asp Gly Asp Val Asn Gly His
275                 280                 285                 290

aag ttc agc gtg tcc ggc gag ggc gag ggc gat gcc acc tac ggc aag     3361
Lys Phe Ser Val Ser Gly Glu Gly Glu Gly Asp Ala Thr Tyr Gly Lys
                295                 300                 305

ctg acc ctg aag ttc atc tgc acc acc ggc aag ctg ccc gtg ccc tgg     3409
Leu Thr Leu Lys Phe Ile Cys Thr Thr Gly Lys Leu Pro Val Pro Trp
            310                 315                 320

ccc acc ctc gtg acc acc ttc ggc tac ggc ctg cag tgc ttc gcc cgc     3457
Pro Thr Leu Val Thr Thr Phe Gly Tyr Gly Leu Gln Cys Phe Ala Arg
        325                 330                 335

tac ccc gac cac atg aag cag cac gac ttc ttc aag tcc gcc atg ccc     3505
Tyr Pro Asp His Met Lys Gln His Asp Phe Phe Lys Ser Ala Met Pro
    340                 345                 350

gaa ggc tac gtc cag gag cgc acc atc ttc ttc aag gac gac ggc aac     3553
Glu Gly Tyr Val Gln Glu Arg Thr Ile Phe Phe Lys Asp Asp Gly Asn
355                 360                 365                 370

tac aag acc cgc gcc gag gtg aag ttc gag ggc gac acc ctg gtg aac     3601
Tyr Lys Thr Arg Ala Glu Val Lys Phe Glu Gly Asp Thr Leu Val Asn
                375                 380                 385

cgc atc gag ctg aag ggc atc gac ttc aag gag gac ggc aac atc ctg     3649
Arg Ile Glu Leu Lys Gly Ile Asp Phe Lys Glu Asp Gly Asn Ile Leu
            390                 395                 400

ggg cac aag ctg gag tac aac tac aac agc cac aac gtc tat atc atg     3697
Gly His Lys Leu Glu Tyr Asn Tyr Asn Ser His Asn Val Tyr Ile Met
        405                 410                 415

gcc gac aag cag aag aac ggc atc aag gtg aac ttc aag atc cgc cac     3745
Ala Asp Lys Gln Lys Asn Gly Ile Lys Val Asn Phe Lys Ile Arg His
    420                 425                 430

aac atc gag gac ggc agc gtg cag ctc gcc gac cac tac cag cag aac     3793
Asn Ile Glu Asp Gly Ser Val Gln Leu Ala Asp His Tyr Gln Gln Asn
435                 440                 445                 450

acc ccc atc ggc gac ggc ccc gtg ctg ctg ccc gac aac cac tac ctg     3841
Thr Pro Ile Gly Asp Gly Pro Val Leu Leu Pro Asp Asn His Tyr Leu
                455                 460                 465

agc tac cag tcc gcc ctg agc aaa gac ccc aac gag aag cgc gat cac     3889
Ser Tyr Gln Ser Ala Leu Ser Lys Asp Pro Asn Glu Lys Arg Asp His
            470                 475                 480

atg gtc ctg ctg gag ttc gtg acc gcc gcc ggg atc act ctc ggc atg     3937
Met Val Leu Leu Glu Phe Val Thr Ala Ala Gly Ile Thr Leu Gly Met
        485                 490                 495

gac gag ctg tac aag taa agcggccgca ctcgagatat ctagacccag            3985
Asp Glu Leu Tyr Lys
    500

ctttcttgta caaagtggtg ataacatcga taaaataaaa gattttattt agtctccaga   4045

aaaagggggg aatgaaagac cccacctgta ggtttggcaa gctagcttaa gtaacgccat   4105

tttgcaaggc atggaaaaat acataactga gaatagagaa gttcagatca aggtcaggaa   4165

cagatggaac agctgaatat gggccaaaca ggatatctgt ggtaagcagt tcctgccccg   4225

gctcagggcc aagaacagat ggaacagctg aatatgggcc aaacaggata tctgtggtaa   4285

gcagttcctg ccccggctca gggccaagaa cagatggtcc ccagatgcgg tccagccctc   4345

agcagtttct agagaaccat cagatgtttc cagggtgccc caaggacctg aaatgaccct   4405

gtgccttatt tgaactaacc aatcagttcg cttctcgctt ctgttcgcgc gcttctgctc   4465

cccgagctca ataaaagagc ccacaacccc tcactcgggg cgccagtcct ccgattgact   4525
```

-continued

```
gagtcgcccg ggtacccgtg tatccaataa accctcttgc agttgcatcc gacttgtggt   4585

ctcgctgttc cttgggaggg tctcctctga gtgattgact acccgtcagc gggggtcttt   4645

catttggggg ctcgtccggg atcgggagac ccctgcccag ggaccaccga cccaccaccg   4705

ggaggtaagc tggctgcctc gcgcgtttcg gtgatgacgg tgaaaacctc tgacacatgc   4765

agctcccgga gacggtcaca gcttgtctgt aagcggatgc cgggagcaga caagcccgtc   4825

agggcgcgtc agcgggtgtt ggcgggtgtc ggggcgcagc catgacccag tcacgtagcg   4885

atagcggagt gtatactggc ttaactatgc ggcatcagag cagattgtac tgagagtgca   4945

ccatatgcgg tgtgaaatac cgcacagatg cgtaaggaga aaataccgca tcaggcgctc   5005

ttccgcttcc tcgctcactg actcgctgcg ctcggtcgtt cggctgcggc gagcggtatc   5065

agctcactca aaggcggtaa tacggttatc cacagaatca ggggataacg caggaaagaa   5125

catgtgagca aaaggccagc aaaaggccag gaaccgtaaa aaggccgcgt tgctggcgtt   5185

tttccatagg ctccgccccc ctgacgagca tcacaaaaat cgacgctcaa gtcagaggtg   5245

gcgaaacccg acaggactat aaagatacca ggcgtttccc cctggaagct ccctcgtgcg   5305

ctctcctgtt ccgaccctgc cgcttaccgg atacctgtcc gcctttctcc cttcgggaag   5365

cgtggcgctt tctcatagct cacgctgtag gtatctcagt tcggtgtagg tcgttcgctc   5425

caagctgggc tgtgtgcacg aaccccccgt tcagcccgac cgctgcgcct tatccggtaa   5485

ctatcgtctt gagtccaacc cggtaagaca cgacttatcg ccactggcag cagccactgg   5545

taacaggatt agcagagcga ggtatgtagg cggtgctaca gagttcttga agtggtggcc   5605

taactacggc tacactagaa ggacagtatt tggtatctgc gctctgctga agccagttac   5665

cttcggaaaa agagttggta gctcttgatc cggcaaacaa accaccgctg gtagcggtgg   5725

tttttttgtt tgcaagcagc agattacgcg cagaaaaaaa ggatctcaag aagatccttt   5785

gatcttttct acggggtctg acgctcagtg gaacgaaaac tcacgttaag ggattttggt   5845

catgagatta tcaaaaagga tcttcaccta gatcctttta aattaaaaat gaagttttaa   5905

atcaatctaa agtatatatg agtaaacttg gtctgacag tta cca atg ctt aat      5959
                                           Leu Pro Met Leu Asn
                                                   505

cag tga ggc acc tat ctc agc gat ctg tct att tcg ttc atc cat agt     6007
Gln     Gly Thr Tyr Leu Ser Asp Leu Ser Ile Ser Phe Ile His Ser
        510                 515                 520

tgc ctg act ccc cgt cgt gta gat aac tac gat acg gga ggg ctt acc     6055
Cys Leu Thr Pro Arg Arg Val Asp Asn Tyr Asp Thr Gly Gly Leu Thr
    525                 530                 535

atc tgg ccc cag tgc tgc aat gat acc gcg aga ccc acg ctc acc ggc     6103
Ile Trp Pro Gln Cys Cys Asn Asp Thr Ala Arg Pro Thr Leu Thr Gly
540                 545                 550                 555

tcc aga ttt atc agc aat aaa cca gcc agc cgg aag ggc cga gcg cag     6151
Ser Arg Phe Ile Ser Asn Lys Pro Ala Ser Arg Lys Gly Arg Ala Gln
                560                 565                 570

aag tgg tcc tgc aac ttt atc cgc ctc cat cca gtc tat taa ttg ttg     6199
Lys Trp Ser Cys Asn Phe Ile Arg Leu His Pro Val Tyr     Leu Leu
            575                 580                 585

ccg gga agc tag agt aag tag ttc gcc agt taa tag ttt gcg caa cgt     6247
Pro Gly Ser     Ser Lys     Phe Ala Ser         Phe Ala Gln Arg
                590                             595

tgt tgc cat tgc tgc agg cat cgt ggt gtc acg ctc gtc gtt tgg tat     6295
Cys Cys His Cys Cys Arg His Arg Gly Val Thr Leu Val Val Trp Tyr
    600                 605                 610

ggc ttc att cag ctc cgg ttc cca acg atc aag gcg agt tac atg atc     6343
```

-continued

```
Gly Phe Ile Gln Leu Arg Phe Pro Thr Ile Lys Ala Ser Tyr Met Ile
615                 620                 625                 630

ccc cat gtt gtg caa aaa agc ggt tag ctc ctt cgg tcc tcc gat cgt     6391
Pro His Val Val Gln Lys Ser Gly     Leu Leu Arg Ser Ser Asp Arg
                635                 640                 645

tgt cag aag taa gtt ggc cgc agt gtt atc act cat ggt tat ggc agc     6439
Cys Gln Lys     Val Gly Arg Ser Val Ile Thr His Gly Tyr Gly Ser
                650                 655                 660

act gca taa ttc tct tac tgt cat gcc atc cgt aag atg ctt ttc tgt     6487
Thr Ala     Phe Ser Tyr Cys His Ala Ile Arg Lys Met Leu Phe Cys
                665                 670                 675

gac tgg tga gta ctc aac caa gtc att ctg aga ata gtg tat gcg gcg     6535
Asp Trp     Val Leu Asn Gln Val Ile Leu Arg Ile Val Tyr Ala Ala
                680                 685                 690

acc gag ttg ctc ttg ccc ggc gtc aac acg gga taa tac cgc gcc aca     6583
Thr Glu Leu Leu Leu Pro Gly Val Asn Thr Gly     Tyr Arg Ala Thr
                695                 700                 705

tag cag aac ttt aaa agt gct cat cat tgg aaa acg ttc ttc ggg gcg     6631
    Gln Asn Phe Lys Ser Ala His His Trp Lys Thr Phe Phe Gly Ala
                710                 715                 720

aaa act ctc aag gat ctt acc gct gtt gag atc cag ttc gat gta acc     6679
Lys Thr Leu Lys Asp Leu Thr Ala Val Glu Ile Gln Phe Asp Val Thr
                725                 730                 735

cac tcg tgc acc caa ctg atc ttc agc atc ttt tac ttt cac cag cgt     6727
His Ser Cys Thr Gln Leu Ile Phe Ser Ile Phe Tyr Phe His Gln Arg
            740                 745                 750

ttc tgg gtg agc aaa aac agg aag gca aaa tgc cgc aaa aaa ggg aat     6775
Phe Trp Val Ser Lys Asn Arg Lys Ala Lys Cys Arg Lys Lys Gly Asn
        755                 760                 765

aag ggc gac acg gaa atg ttg aat act cat actcttcctt tttcaatatt      6825
Lys Gly Asp Thr Glu Met Leu Asn Thr His
    770                 775

attgaagcat ttatcagggt tattgtctca tgagcggata catatttgaa tgtatttaga   6885

aaaataaaca aataggggtt ccgcgcacat ttccccgaaa agtgccacct gacgtctaag   6945

aaaccattat tatcatgaca ttaacctata aaaataggcg tatcacgagg ccctttcgtc   7005

ttcaa                                                               7010


<210> SEQ ID NO 41
<211> LENGTH: 264
<212> TYPE: PRT
<213> ORGANISM: Artificial
<220> FEATURE:
<223> OTHER INFORMATION: Synthetic Construct

<400> SEQUENCE: 41

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95
```

-continued

```
Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

<210> SEQ ID NO 42
<211> LENGTH: 239
<212> TYPE: PRT
<213> ORGANISM: Artificial
<220> FEATURE:
<223> OTHER INFORMATION: Synthetic Construct

<400> SEQUENCE: 42

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190
```

```
Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 43
<211> LENGTH: 6
<212> TYPE: PRT
<213> ORGANISM: Artificial
<220> FEATURE:
<223> OTHER INFORMATION: Synthetic Construct

<400> SEQUENCE: 43

Leu Pro Met Leu Asn Gln
1               5


<210> SEQ ID NO 44
<211> LENGTH: 75
<212> TYPE: PRT
<213> ORGANISM: Artificial
<220> FEATURE:
<223> OTHER INFORMATION: Synthetic Construct

<400> SEQUENCE: 44

Gly Thr Tyr Leu Ser Asp Leu Ser Ile Ser Phe Ile His Ser Cys Leu
1               5                   10                  15

Thr Pro Arg Arg Val Asp Asn Tyr Asp Thr Gly Gly Leu Thr Ile Trp
            20                  25                  30

Pro Gln Cys Cys Asn Asp Thr Ala Arg Pro Thr Leu Thr Gly Ser Arg
        35                  40                  45

Phe Ile Ser Asn Lys Pro Ala Ser Arg Lys Gly Arg Ala Gln Lys Trp
    50                  55                  60

Ser Cys Asn Phe Ile Arg Leu His Pro Val Tyr
65                  70                  75


<210> SEQ ID NO 45
<211> LENGTH: 5
<212> TYPE: PRT
<213> ORGANISM: Artificial
<220> FEATURE:
<223> OTHER INFORMATION: Synthetic Construct

<400> SEQUENCE: 45

Leu Leu Pro Gly Ser
1               5


<210> SEQ ID NO 46
<211> LENGTH: 44
<212> TYPE: PRT
<213> ORGANISM: Artificial
<220> FEATURE:
<223> OTHER INFORMATION: Synthetic Construct

<400> SEQUENCE: 46

Phe Ala Gln Arg Cys Cys His Cys Cys Arg His Arg Gly Val Thr Leu
1               5                   10                  15

Val Val Trp Tyr Gly Phe Ile Gln Leu Arg Phe Pro Thr Ile Lys Ala
            20                  25                  30

Ser Tyr Met Ile Pro His Val Val Gln Lys Ser Gly
        35                  40
```

```
<210> SEQ ID NO 47
<211> LENGTH: 10
<212> TYPE: PRT
<213> ORGANISM: Artificial
<220> FEATURE:
<223> OTHER INFORMATION: Synthetic Construct

<400> SEQUENCE: 47

Leu Leu Arg Ser Ser Asp Arg Cys Gln Lys
1               5                   10


<210> SEQ ID NO 48
<211> LENGTH: 14
<212> TYPE: PRT
<213> ORGANISM: Artificial
<220> FEATURE:
<223> OTHER INFORMATION: Synthetic Construct

<400> SEQUENCE: 48

Val Gly Arg Ser Val Ile Thr His Gly Tyr Gly Ser Thr Ala
1               5                   10


<210> SEQ ID NO 49
<211> LENGTH: 15
<212> TYPE: PRT
<213> ORGANISM: Artificial
<220> FEATURE:
<223> OTHER INFORMATION: Synthetic Construct

<400> SEQUENCE: 49

Phe Ser Tyr Cys His Ala Ile Arg Lys Met Leu Phe Cys Asp Trp
1               5                   10                  15


<210> SEQ ID NO 50
<211> LENGTH: 24
<212> TYPE: PRT
<213> ORGANISM: Artificial
<220> FEATURE:
<223> OTHER INFORMATION: Synthetic Construct

<400> SEQUENCE: 50

Val Leu Asn Gln Val Ile Leu Arg Ile Val Tyr Ala Ala Thr Glu Leu
1               5                   10                  15

Leu Leu Pro Gly Val Asn Thr Gly
            20


<210> SEQ ID NO 51
<211> LENGTH: 4
<212> TYPE: PRT
<213> ORGANISM: Artificial
<220> FEATURE:
<223> OTHER INFORMATION: Synthetic Construct

<400> SEQUENCE: 51

Tyr Arg Ala Thr
1


<210> SEQ ID NO 52
<211> LENGTH: 73
<212> TYPE: PRT
<213> ORGANISM: Artificial
<220> FEATURE:
<223> OTHER INFORMATION: Synthetic Construct

<400> SEQUENCE: 52

Gln Asn Phe Lys Ser Ala His His Trp Lys Thr Phe Phe Gly Ala Lys
```

-continued

```
1               5                   10                  15

Thr Leu Lys Asp Leu Thr Ala Val Glu Ile Gln Phe Asp Val Thr His
            20                  25                  30

Ser Cys Thr Gln Leu Ile Phe Ser Ile Phe Tyr Phe His Gln Arg Phe
        35                  40                  45

Trp Val Ser Lys Asn Arg Lys Ala Lys Cys Arg Lys Lys Gly Asn Lys
    50                  55                  60

Gly Asp Thr Glu Met Leu Asn Thr His
65                  70


<210> SEQ ID NO 53
<211> LENGTH: 7121
<212> TYPE: DNA
<213> ORGANISM: Artificial
<220> FEATURE:
<223> OTHER INFORMATION: Engineered Sequence from virus and plasmid
<220> FEATURE:
<221> NAME/KEY: LTR
<222> LOCATION: (149)..(737)
<223> OTHER INFORMATION: 5' MoMuSVLTR
<220> FEATURE:
<221> NAME/KEY: CDS
<222> LOCATION: (1660)..(2454)
<223> OTHER INFORMATION: neomycin resistance
<220> FEATURE:
<221> NAME/KEY: promoter
<222> LOCATION: (2806)..(3261)
<223> OTHER INFORMATION: HIV promoter
<220> FEATURE:
<221> NAME/KEY: misc_feature
<222> LOCATION: (3281)..(3305)
<223> OTHER INFORMATION: attB1
<220> FEATURE:
<221> NAME/KEY: CDS
<222> LOCATION: (3347)..(4066)
<223> OTHER INFORMATION: EYFP; enhanced yellow florescent protein
<220> FEATURE:
<221> NAME/KEY: misc_feature
<222> LOCATION: (4091)..(4115)
<223> OTHER INFORMATION: attB2
<220> FEATURE:
<221> NAME/KEY: LTR
<222> LOCATION: (4167)..(4760)
<223> OTHER INFORMATION: 3' MoMuLVLTR
<220> FEATURE:
<221> NAME/KEY: CDS
<222> LOCATION: (6056)..(6916)
<223> OTHER INFORMATION: ampicillin resistance

<400> SEQUENCE: 53

gaattaattc ataccagatc accgaaaact gtcctccaaa tgtgtccccc tcacactccc      60

aaattcgcgg gcttctgcct cttagaccac tctaccctat tccccacact caccggagcc     120

aaagccgcgg cccttccgtt tctttgcttt tgaaagaccc cacccgtagg tggcaagcta     180

gcttaagtaa cgccactttg caaggcatgg aaaaatacat aactgagaat agaaaagttc     240

agatcaaggt caggaacaaa gaaacagctg aataccaaac aggatatctg tggtaagcgg     300

ttcctgcccc ggctcagggc caagaacaga tgagacagct gagtgatggg ccaaacagga     360

tatctgtggt aagcagttcc tgccccggct cggggccaag aacagatggt ccccagatgc     420

ggtccagccc tcagcagttt ctagtgaatc atcagatgtt tccagggtgc cccaaggacc     480

tgaaaatgac cctgtacctt atttgaacta accaatcagt tcgcttctcg cttctgttcg     540

cgcgcttccg ctctccgagc tcaataaaag agcccacaac ccctcactcg gcgcgccagt     600

cttccgatag actgcgtcgc ccgggtaccc gtattcccaa taaagcctct tgctgtttgc     660

atccgaatcg tggtctcgct gttccttggg agggtctcct ctgagtgatt gactacccac     720
```

-continued

```
gacgggggtc tttcatttgg gggctcgtcc gggatttgga gacccctgcc cagggaccac    780

cgacccacca ccgggaggta agctggccag caacttatct gtgtctgtcc gattgtctag    840

tgtctatgtt tgatgttatg cgcctgcgtc tgtactagtt agctaactag ctctgtatct    900

ggcggacccg tggtggaact gacgagttct gaacacccgg ccgcaaccct gggagacgtc    960

ccagggactt tgggggccgt ttttgtggcc cgacctgagg aagggagtcg atgtggaatc   1020

cgaccccgtc aggatatgtg gttctggtag gagacgagaa cctaaaacag ttcccgcctc   1080

cgtctgaatt tttgctttcg gtttggaacc gaagccgcgc gtcttgtctg ctgcagcgct   1140

gcagcatcgt tctgtgttgt ctctgtctga ctgtgtttct gtatttgtct gaaaattagg   1200

gccagactgt taccactccc ttaagtttga ccttaggtca ctggaaagat gtcgagcgga   1260

tcgctcacaa ccagtcggta gatgtcaaga agagacgttg ggttaccttc tgctctgcag   1320

aatggccaac ctttaacgtc ggatggccgc gagacggcac ctttaaccga gacctcatca   1380

cccaggttaa gatcaaggtc ttttcacctg gcccgcatgg acacccagac caggtcccct   1440

acatcgtgac ctgggaagcc ttggcttttg acccccctcc ctgggtcaag ccctttgtac   1500

accctaagcc tccgcctcct cttcctccat ccgccccgtc tctccccctt gaacctcctc   1560

gttcgacccc gcctcgatcc tccctttatc cagccctcac tccttctcta ggcgccggaa   1620

ttccgatctg atcaagagac aggatgagga tcgtttcgc atg att gaa caa gat      1674
                                           Met Ile Glu Gln Asp
                                           1               5

gga ttg cac gca ggt tct ccg gcc gct tgg gtg gag agg cta ttc ggc     1722
Gly Leu His Ala Gly Ser Pro Ala Ala Trp Val Glu Arg Leu Phe Gly
            10                  15                  20

tat gac tgg gca caa cag aca atc ggc tgc tct gat gcc gcc gtg ttc     1770
Tyr Asp Trp Ala Gln Gln Thr Ile Gly Cys Ser Asp Ala Ala Val Phe
            25                  30                  35

cgg ctg tca gcg cag ggg cgc ccg gtt ctt ttt gtc aag acc gac ctg     1818
Arg Leu Ser Ala Gln Gly Arg Pro Val Leu Phe Val Lys Thr Asp Leu
        40                  45                  50

tcc ggt gcc ctg aat gaa ctg cag gac gag gca gcg cgg cta tcg tgg     1866
Ser Gly Ala Leu Asn Glu Leu Gln Asp Glu Ala Ala Arg Leu Ser Trp
    55                  60                  65

ctg gcc acg acg ggc gtt cct tgc gca gct gtg ctc gac gtt gtc act     1914
Leu Ala Thr Thr Gly Val Pro Cys Ala Ala Val Leu Asp Val Val Thr
70                  75                  80                  85

gaa gcg gga agg gac tgg ctg cta ttg ggc gaa gtg ccg ggg cag gat     1962
Glu Ala Gly Arg Asp Trp Leu Leu Leu Gly Glu Val Pro Gly Gln Asp
            90                  95                  100

ctc ctg tca tct cac ctt gct cct gcc gag aaa gta tcc atc atg gct     2010
Leu Leu Ser Ser His Leu Ala Pro Ala Glu Lys Val Ser Ile Met Ala
            105                 110                 115

gat gca atg cgg cgg ctg cat acg ctt gat ccg gct acc tgc cca ttc     2058
Asp Ala Met Arg Arg Leu His Thr Leu Asp Pro Ala Thr Cys Pro Phe
        120                 125                 130

gac cac caa gcg aaa cat cgc atc gag cga gca cgt act cgg atg gaa     2106
Asp His Gln Ala Lys His Arg Ile Glu Arg Ala Arg Thr Arg Met Glu
    135                 140                 145

gcc ggt ctt gtc gat cag gat gat ctg gac gaa gag cat cag ggg ctc     2154
Ala Gly Leu Val Asp Gln Asp Asp Leu Asp Glu Glu His Gln Gly Leu
150                 155                 160                 165

gcg cca gcc gaa ctg ttc gcc agg ctc aag gcg cgc atg ccc gac ggc     2202
Ala Pro Ala Glu Leu Phe Ala Arg Leu Lys Ala Arg Met Pro Asp Gly
            170                 175                 180
```

-continued

```
gag gat ctc gtc gtg acc cat ggc gat gcc tgc ttg ccg aat atc atg     2250
Glu Asp Leu Val Val Thr His Gly Asp Ala Cys Leu Pro Asn Ile Met
            185                 190                 195

gtg gaa aat ggc cgc ttt tct gga ttc atc gac tgt ggc cgg ctg ggt     2298
Val Glu Asn Gly Arg Phe Ser Gly Phe Ile Asp Cys Gly Arg Leu Gly
        200                 205                 210

gtg gcg gac cgc tat cag gac ata gcg ttg gct acc cgt gat att gct     2346
Val Ala Asp Arg Tyr Gln Asp Ile Ala Leu Ala Thr Arg Asp Ile Ala
    215                 220                 225

gaa gag ctt ggc ggc gaa tgg gct gac cgc ttc ctc gtg ctt tac ggt     2394
Glu Glu Leu Gly Gly Glu Trp Ala Asp Arg Phe Leu Val Leu Tyr Gly
230                 235                 240                 245

atc gcc gct ccc gat tcg cag cgc atc gcc ttc tat cgc ctt ctt gac     2442
Ile Ala Ala Pro Asp Ser Gln Arg Ile Ala Phe Tyr Arg Leu Leu Asp
                250                 255                 260

gag ttc ttc tga gcgggactct ggggttcgaa atgaccgacc aagcgacgcc         2494
Glu Phe Phe

caacctgcca tcacgagatt tcgattccac cgccgccttc tatgaaaggt tgggcttcgg   2554

aatcgttttc cgggacgccg gctggatgat cctccagcgc ggggatctca tgctggagtt   2614

cttcgcccac ccgggctcg atcccctcgc gagttggttc agctgctgcc tgaggctgga    2674

cgacctcgcg gagttctacc ggcagtgcaa atccgtcggc atccaggaaa ccagcagcgg   2734

ctatccgcgc atccatgccc ccgaactgca ggagtgggga ggcacgatgg ccgctttggt   2794

cgaggcggat cctggaaggg ctaatttggt cccaaagaag acaagagatc cttgatctgt   2854

ggatctacca cacacaaggc tacttccctg attggcagaa ttacacacca gggccaggga   2914

tcagatatcc actgaccttt ggatggtgct tcaagctagt accagttgag ccagagaagg   2974

tagaagaggc caatgaagga gagaacaaca gcttgttaca ccctatgagc ctgcatggga   3034

tggaggacgc ggagaaagaa gtgttagtgt ggaggtttga cagcaaacta gcatttcatc   3094

acatggcccg agagctgcat ccggagtact acaaagactg ctgacatcga gctttctaca   3154

agggactttc cgctggggac tttccaggga ggcgtggcct gggcgggact ggggagtggc   3214

gtccctcaga tgctgcatat aagcagctgc tttttgcctg tactgggcct cgagaagctt   3274

gttatcacaa gtttgtacaa aaaagcaggc ttcgaaggag atagaaccaa ttctctaagg   3334

aaatacttaa cc atg gtg agc aag ggc gag gag ctg ttc acc ggg gtg gtg   3385
              Met Val Ser Lys Gly Glu Glu Leu Phe Thr Gly Val Val
              265                 270                 275

ccc atc ctg gtc gag ctg gac ggc gac gta aac ggc cac aag ttc agc     3433
Pro Ile Leu Val Glu Leu Asp Gly Asp Val Asn Gly His Lys Phe Ser
        280                 285                 290

gtg tcc ggc gag ggc gag ggc gat gcc acc tac ggc aag ctg acc ctg     3481
Val Ser Gly Glu Gly Glu Gly Asp Ala Thr Tyr Gly Lys Leu Thr Leu
    295                 300                 305

aag ttc atc tgc acc acc ggc aag ctg ccc gtg ccc tgg ccc acc ctc     3529
Lys Phe Ile Cys Thr Thr Gly Lys Leu Pro Val Pro Trp Pro Thr Leu
310                 315                 320                 325

gtg acc acc ttc ggc tac ggc ctg cag tgc ttc gcc cgc tac ccc gac     3577
Val Thr Thr Phe Gly Tyr Gly Leu Gln Cys Phe Ala Arg Tyr Pro Asp
                330                 335                 340

cac atg aag cag cac gac ttc ttc aag tcc gcc atg ccc gaa ggc tac     3625
His Met Lys Gln His Asp Phe Phe Lys Ser Ala Met Pro Glu Gly Tyr
            345                 350                 355

gtc cag gag cgc acc atc ttc ttc aag gac gac ggc aac tac aag acc     3673
Val Gln Glu Arg Thr Ile Phe Phe Lys Asp Asp Gly Asn Tyr Lys Thr
        360                 365                 370
```

-continued

```
cgc gcc gag gtg aag ttc gag ggc gac acc ctg gtg aac cgc atc gag      3721
Arg Ala Glu Val Lys Phe Glu Gly Asp Thr Leu Val Asn Arg Ile Glu
    375                 380                 385

ctg aag ggc atc gac ttc aag gag gac ggc aac atc ctg ggg cac aag      3769
Leu Lys Gly Ile Asp Phe Lys Glu Asp Gly Asn Ile Leu Gly His Lys
390                 395                 400                 405

ctg gag tac aac tac aac agc cac aac gtc tat atc atg gcc gac aag      3817
Leu Glu Tyr Asn Tyr Asn Ser His Asn Val Tyr Ile Met Ala Asp Lys
                410                 415                 420

cag aag aac ggc atc aag gtg aac ttc aag atc cgc cac aac atc gag      3865
Gln Lys Asn Gly Ile Lys Val Asn Phe Lys Ile Arg His Asn Ile Glu
            425                 430                 435

gac ggc agc gtg cag ctc gcc gac cac tac cag cag aac acc ccc atc      3913
Asp Gly Ser Val Gln Leu Ala Asp His Tyr Gln Gln Asn Thr Pro Ile
        440                 445                 450

ggc gac ggc ccc gtg ctg ctg ccc gac aac cac tac ctg agc tac cag      3961
Gly Asp Gly Pro Val Leu Leu Pro Asp Asn His Tyr Leu Ser Tyr Gln
    455                 460                 465

tcc gcc ctg agc aaa gac ccc aac gag aag cgc gat cac atg gtc ctg      4009
Ser Ala Leu Ser Lys Asp Pro Asn Glu Lys Arg Asp His Met Val Leu
470                 475                 480                 485

ctg gag ttc gtg acc gcc gcc ggg atc act ctc ggc atg gac gag ctg      4057
Leu Glu Phe Val Thr Ala Ala Gly Ile Thr Leu Gly Met Asp Glu Leu
                490                 495                 500
tac aag taa agcggccgca ctcgagatat ctagacccag ctttcttgta              4106
Tyr Lys

caaagtggtg ataacatcga taaaataaaa gattttattt agtctccaga aaaagggggg   4166

aatgaaagac cccacctgta ggtttggcaa gctagcttaa gtaacgccat tttgcaaggc   4226

atggaaaaat acataactga gaatagagaa gttcagatca aggtcaggaa cagatggaac   4286

agctgaatat gggccaaaca ggatatctgt ggtaagcagt tcctgccccg gctcagggcc   4346

aagaacagat ggaacagctg aatatgggcc aaacaggata tctgtggtaa gcagttcctg   4406

ccccggctca gggccaagaa cagatggtcc ccagatgcgg tccagccctc agcagtttct   4466

agagaaccat cagatgtttc cagggtgccc caaggacctg aaatgaccct gtgccttatt   4526

tgaactaacc aatcagttcg cttctcgctt ctgttcgcgc gcttctgctc cccgagctca   4586

ataaaagagc ccacaacccc tcactcgggg cgccagtcct ccgattgact gagtcgcccg   4646

ggtacccgtg tatccaataa accctcttgc agttgcatcc gacttgtggt ctcgctgttc   4706

cttgggaggg tctcctctga gtgattgact acccgtcagc gggggtcttt catttggggg   4766

ctcgtccggg atcgggagac ccctgcccag ggaccaccga cccaccaccg ggaggtaagc   4826

tggctgcctc gcgcgtttcg gtgatgacgg tgaaaacctc tgacacatgc agctcccgga   4886

gacggtcaca gcttgtctgt aagcggatgc cgggagcaga caagcccgtc agggcgcgtc   4946

agcgggtgtt ggcgggtgtc ggggcgcagc catgacccag tcacgtagcg atagcggagt   5006

gtatactggc ttaactatgc ggcatcagag cagattgtac tgagagtgca ccatatgcgg   5066

tgtgaaatac cgcacagatg cgtaaggaga aaataccgca tcaggcgctc ttccgcttcc   5126

tcgctcactg actcgctgcg ctcggtcgtt cggctgcggc gagcggtatc agctcactca   5186

aaggcggtaa tacggttatc cacagaatca ggggataacg caggaaagaa catgtgagca   5246

aaaggccagc aaaaggccag gaaccgtaaa aaggccgcgt tgctggcgtt tttccatagg   5306

ctccgccccc ctgacgagca tcacaaaaat cgacgctcaa gtcagaggtg gcgaaacccg   5366

acaggactat aaagatacca ggcgtttccc cctggaagct ccctcgtgcg ctctcctgtt   5426

ccgaccctgc cgcttaccgg atacctgtcc gcctttctcc cttcgggaag cgtggcgctt   5486
```

-continued

```
tctcatagct cacgctgtag gtatctcagt tcggtgtagg tcgttcgctc caagctgggc   5546

tgtgtgcacg aaccccccgt tcagcccgac cgctgcgcct tatccggtaa ctatcgtctt   5606

gagtccaacc cggtaagaca cgacttatcg ccactggcag cagccactgg taacaggatt   5666

agcagagcga ggtatgtagg cggtgctaca gagttcttga agtggtggcc taactacggc   5726

tacactagaa ggacagtatt tggtatctgc gctctgctga agccagttac cttcggaaaa   5786

agagttggta gctcttgatc cggcaaacaa accaccgctg gtagcggtgg tttttttgtt   5846

tgcaagcagc agattacgcg cagaaaaaaa ggatctcaag aagatccttt gatcttttct   5906

acggggtctg acgctcagtg gaacgaaaac tcacgttaag ggattttggt catgagatta   5966

tcaaaaagga tcttcaccta gatcctttta aattaaaaat gaagttttaa atcaatctaa   6026

agtatatatg agtaaacttg gtctgacag tta cca atg ctt aat cag tga ggc     6079
                                Leu Pro Met Leu Asn Gln     Gly
                                    505                     510

acc tat ctc agc gat ctg tct att tcg ttc atc cat agt tgc ctg act     6127
Thr Tyr Leu Ser Asp Leu Ser Ile Ser Phe Ile His Ser Cys Leu Thr
                515                 520                 525

ccc cgt cgt gta gat aac tac gat acg gga ggg ctt acc atc tgg ccc     6175
Pro Arg Arg Val Asp Asn Tyr Asp Thr Gly Gly Leu Thr Ile Trp Pro
            530                 535                 540

cag tgc tgc aat gat acc gcg aga ccc acg ctc acc ggc tcc aga ttt     6223
Gln Cys Cys Asn Asp Thr Ala Arg Pro Thr Leu Thr Gly Ser Arg Phe
        545                 550                 555

atc agc aat aaa cca gcc agc cgg aag ggc cga gcg cag aag tgg tcc     6271
Ile Ser Asn Lys Pro Ala Ser Arg Lys Gly Arg Ala Gln Lys Trp Ser
    560                 565                 570

tgc aac ttt atc cgc ctc cat cca gtc tat taa ttg ttg ccg gga agc     6319
Cys Asn Phe Ile Arg Leu His Pro Val Tyr     Leu Leu Pro Gly Ser
575                 580                     585

tag agt aag tag ttc gcc agt taa tag ttt gcg caa cgt tgt tgc cat     6367
    Ser Lys     Phe Ala Ser         Phe Ala Gln Arg Cys Cys His
    590                             595                 600

tgc tgc agg cat cgt ggt gtc acg ctc gtc gtt tgg tat ggc ttc att     6415
Cys Cys Arg His Arg Gly Val Thr Leu Val Val Trp Tyr Gly Phe Ile
            605                 610                 615

cag ctc cgg ttc cca acg atc aag gcg agt tac atg atc ccc cat gtt     6463
Gln Leu Arg Phe Pro Thr Ile Lys Ala Ser Tyr Met Ile Pro His Val
        620                 625                 630

gtg caa aaa agc ggt tag ctc ctt cgg tcc tcc gat cgt tgt cag aag     6511
Val Gln Lys Ser Gly     Leu Leu Arg Ser Ser Asp Arg Cys Gln Lys
    635                 640                 645

taa gtt ggc cgc agt gtt atc act cat ggt tat ggc agc act gca taa     6559
    Val Gly Arg Ser Val Ile Thr His Gly Tyr Gly Ser Thr Ala
        650                 655                 660

ttc tct tac tgt cat gcc atc cgt aag atg ctt ttc tgt gac tgg tga     6607
Phe Ser Tyr Cys His Ala Ile Arg Lys Met Leu Phe Cys Asp Trp
        665                 670                 675

gta ctc aac caa gtc att ctg aga ata gtg tat gcg gcg acc gag ttg     6655
Val Leu Asn Gln Val Ile Leu Arg Ile Val Tyr Ala Ala Thr Glu Leu
        680                 685                 690

ctc ttg ccc ggc gtc aac acg gga taa tac cgc gcc aca tag cag aac     6703
Leu Leu Pro Gly Val Asn Thr Gly     Tyr Arg Ala Thr     Gln Asn
    695                 700                 705

ttt aaa agt gct cat cat tgg aaa acg ttc ttc ggg gcg aaa act ctc     6751
Phe Lys Ser Ala His His Trp Lys Thr Phe Phe Gly Ala Lys Thr Leu
        710                 715                 720
```

-continued

```
aag gat ctt acc gct gtt gag atc cag ttc gat gta acc cac tcg tgc     6799
Lys Asp Leu Thr Ala Val Glu Ile Gln Phe Asp Val Thr His Ser Cys
    725                 730                 735

acc caa ctg atc ttc agc atc ttt tac ttt cac cag cgt ttc tgg gtg     6847
Thr Gln Leu Ile Phe Ser Ile Phe Tyr Phe His Gln Arg Phe Trp Val
740                 745                 750                 755

agc aaa aac agg aag gca aaa tgc cgc aaa aaa ggg aat aag ggc gac     6895
Ser Lys Asn Arg Lys Ala Lys Cys Arg Lys Lys Gly Asn Lys Gly Asp
                760                 765                 770

acg gaa atg ttg aat act cat actcttcctt tttcaatatt attgaagcat        6946
Thr Glu Met Leu Asn Thr His
            775

ttatcagggt tattgtctca tgagcggata catatttgaa tgtatttaga aaaataaaca   7006

aataggggtt ccgcgcacat ttccccgaaa agtgccacct gacgtctaag aaaccattat   7066

tatcatgaca ttaacctata aaaataggcg tatcacgagg ccctttcgtc ttcaa        7121


<210> SEQ ID NO 54
<211> LENGTH: 264
<212> TYPE: PRT
<213> ORGANISM: Artificial
<220> FEATURE:
<223> OTHER INFORMATION: Synthetic Construct

<400> SEQUENCE: 54

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255
```

```
Tyr Arg Leu Leu Asp Glu Phe Phe
            260


<210> SEQ ID NO 55
<211> LENGTH: 239
<212> TYPE: PRT
<213> ORGANISM: Artificial
<220> FEATURE:
<223> OTHER INFORMATION: Synthetic Construct

<400> SEQUENCE: 55

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Phe Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys
225                 230                 235


<210> SEQ ID NO 56
<211> LENGTH: 6
<212> TYPE: PRT
<213> ORGANISM: Artificial
<220> FEATURE:
<223> OTHER INFORMATION: Synthetic Construct

<400> SEQUENCE: 56

Leu Pro Met Leu Asn Gln
1               5


<210> SEQ ID NO 57
<211> LENGTH: 75
<212> TYPE: PRT
<213> ORGANISM: Artificial
<220> FEATURE:
<223> OTHER INFORMATION: Synthetic Construct
```

<400> SEQUENCE: 57

Gly Thr Tyr Leu Ser Asp Leu Ser Ile Ser Phe Ile His Ser Cys Leu
1               5                   10                  15

Thr Pro Arg Arg Val Asp Asn Tyr Asp Thr Gly Gly Leu Thr Ile Trp
            20                  25                  30

Pro Gln Cys Cys Asn Asp Thr Ala Arg Pro Thr Leu Thr Gly Ser Arg
        35                  40                  45

Phe Ile Ser Asn Lys Pro Ala Ser Arg Lys Gly Arg Ala Gln Lys Trp
    50                  55                  60

Ser Cys Asn Phe Ile Arg Leu His Pro Val Tyr
65                  70                  75

<210> SEQ ID NO 58
<211> LENGTH: 5
<212> TYPE: PRT
<213> ORGANISM: Artificial
<220> FEATURE:
<223> OTHER INFORMATION: Synthetic Construct

<400> SEQUENCE: 58

Leu Leu Pro Gly Ser
1               5

<210> SEQ ID NO 59
<211> LENGTH: 44
<212> TYPE: PRT
<213> ORGANISM: Artificial
<220> FEATURE:
<223> OTHER INFORMATION: Synthetic Construct

<400> SEQUENCE: 59

Phe Ala Gln Arg Cys Cys His Cys Cys Arg His Arg Gly Val Thr Leu
1               5                   10                  15

Val Val Trp Tyr Gly Phe Ile Gln Leu Arg Phe Pro Thr Ile Lys Ala
            20                  25                  30

Ser Tyr Met Ile Pro His Val Val Gln Lys Ser Gly
        35                  40

<210> SEQ ID NO 60
<211> LENGTH: 10
<212> TYPE: PRT
<213> ORGANISM: Artificial
<220> FEATURE:
<223> OTHER INFORMATION: Synthetic Construct

<400> SEQUENCE: 60

Leu Leu Arg Ser Ser Asp Arg Cys Gln Lys
1               5                   10

<210> SEQ ID NO 61
<211> LENGTH: 14
<212> TYPE: PRT
<213> ORGANISM: Artificial
<220> FEATURE:
<223> OTHER INFORMATION: Synthetic Construct

<400> SEQUENCE: 61

Val Gly Arg Ser Val Ile Thr His Gly Tyr Gly Ser Thr Ala
1               5                   10

<210> SEQ ID NO 62
<211> LENGTH: 15

-continued

```
<212> TYPE: PRT
<213> ORGANISM: Artificial
<220> FEATURE:
<223> OTHER INFORMATION: Synthetic Construct

<400> SEQUENCE: 62

Phe Ser Tyr Cys His Ala Ile Arg Lys Met Leu Phe Cys Asp Trp
1               5                   10                  15


<210> SEQ ID NO 63
<211> LENGTH: 24
<212> TYPE: PRT
<213> ORGANISM: Artificial
<220> FEATURE:
<223> OTHER INFORMATION: Synthetic Construct

<400> SEQUENCE: 63

Val Leu Asn Gln Val Ile Leu Arg Ile Val Tyr Ala Ala Thr Glu Leu
1               5                   10                  15

Leu Leu Pro Gly Val Asn Thr Gly
            20


<210> SEQ ID NO 64
<211> LENGTH: 4
<212> TYPE: PRT
<213> ORGANISM: Artificial
<220> FEATURE:
<223> OTHER INFORMATION: Synthetic Construct

<400> SEQUENCE: 64

Tyr Arg Ala Thr
1


<210> SEQ ID NO 65
<211> LENGTH: 73
<212> TYPE: PRT
<213> ORGANISM: Artificial
<220> FEATURE:
<223> OTHER INFORMATION: Synthetic Construct

<400> SEQUENCE: 65

Gln Asn Phe Lys Ser Ala His His Trp Lys Thr Phe Phe Gly Ala Lys
1               5                   10                  15

Thr Leu Lys Asp Leu Thr Ala Val Glu Ile Gln Phe Asp Val Thr His
            20                  25                  30

Ser Cys Thr Gln Leu Ile Phe Ser Ile Phe Tyr Phe His Gln Arg Phe
        35                  40                  45

Trp Val Ser Lys Asn Arg Lys Ala Lys Cys Arg Lys Lys Gly Asn Lys
    50                  55                  60

Gly Asp Thr Glu Met Leu Asn Thr His
65                  70
```